United States Patent
Borchardt et al.

(10) Patent No.: US 7,115,658 B2
(45) Date of Patent: Oct. 3, 2006

(54) INHIBITORS OF HEPATITIS C VIRUS RNA-DEPENDENT RNA POLYMERASE

(75) Inventors: Allen J. Borchardt, San Diego, CA (US); Peter Scott Dragovich, San Diego, CA (US); Javier Gonzalez, Oceanside, CA (US); Tanya Michelle Jewell, Encinitas, CA (US); Hui Li, Carlsbad, CA (US); Maria Angelica Linton, San Diego, CA (US); John Howard Tatlock, San Diego, CA (US); Ru Zhou, Carlsbad, CA (US); Thomas Jay Prins, Cardiff, CA (US); Melwyn A. Abreo, Jamul, CA (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 36 days.

(21) Appl. No.: 10/434,702

(22) Filed: May 9, 2003

(65) Prior Publication Data

US 2004/0023958 A1    Feb. 5, 2004

Related U.S. Application Data

(60) Provisional application No. 60/379,433, filed on May 10, 2002.

(51) Int. Cl.
*A61K 31/351*    (2006.01)

(52) U.S. Cl. .................. 514/460; 514/459; 514/336; 514/365; 514/452; 514/364; 514/378; 514/405; 514/326; 514/231.5; 514/422; 514/259.31; 514/384; 514/397; 514/262.1; 514/456; 514/258.1; 514/382; 514/255.05; 514/369; 514/274; 514/340; 514/363; 514/375; 514/254.1

(58) Field of Classification Search ............... 514/262
See application file for complete search history.

(56) References Cited

U.S. PATENT DOCUMENTS

| | | |
|---|---|---|
| 3,786,063 A | 1/1974 | Arnold |
| 4,326,058 A | 4/1982 | Okabe et al. |
| 4,489,077 A | 12/1984 | Sircar et al. |
| 4,591,583 A | 5/1986 | Helgstrand et al. |
| 5,504,104 A | 4/1996 | Ellsworth et al. |
| 5,789,440 A | 8/1998 | Ellsworth et al. |
| 5,808,062 A | 9/1998 | Domagala et al. |
| 5,834,506 A | 11/1998 | Boyer, Jr. et al. |
| 5,840,751 A | 11/1998 | Ellsworth et al. |
| 5,846,964 A | 12/1998 | Ozeki |
| 5,936,128 A | 8/1999 | Ellsworth et al. |
| 6,046,355 A | 4/2000 | Boyer, Jr. et al. |
| 6,174,868 B1 | 1/2001 | Anderson et al. |
| 6,512,006 B1 | 1/2003 | Boyer, Jr. et al. |
| 6,528,510 B1 | 3/2003 | Boyer, Jr. et al. |
| 2003/0171425 A1 | 9/2003 | Boyer, Jr., et al. |
| 2003/0195239 A1* | 10/2003 | Borchardt et al. .......... 514/365 |

FOREIGN PATENT DOCUMENTS

| | | |
|---|---|---|
| EP | 1 256 628 A2 | 11/2002 |
| WO | WO 94 11361 | 5/1994 |
| WO | WO 95 14011 | 5/1995 |
| WO | WO 95 14012 | 5/1995 |
| WO | WO 98 19997 | 5/1998 |
| WO | WO 00 15634 | 3/2000 |
| WO | WO 0015634 | 3/2000 |
| WO | WO 00 40237 | 7/2000 |

OTHER PUBLICATIONS

Allen, C.F., et al. "The Structure of Certain Polyazaindenes. III. 1,2,3a,7-and 1,3,3a,7-Tetrazaindenes," *J. Org. Chem*,1959, pp. 793-796, vol. 24.

Bergman, J., et al., "Synthesis of Chrysogine, a Metabolite of Penicillium Chrysogenum and Some Related 2-substituted 4-(3H)-Quinazolinones," *Tetrahedron*, 1990, pp. 1295-1310, vol. 46.

Burke, T.R., et al., "Conformationallly Constrained Phosphotyrosyl Mimetics Designed As Monomeric Src Homology 2 Domain Inhibitors," *J. Med. Chem.* 1995, pp. 1386-1396, vol. 38.

Carvalho, C.F., et al., "Naturally Occurring Dibenzofurans. Part 6. Synthesis Of Didymic Acid," *J. Chem Soc. Perkin Trans 1*, 1984, pp. 1621-1626.

Chavignon, O., et al., "Pyrrolization Processes Of Vinyl Substituted Imidazol[1,2-α]pyridine, Pyrimidine And 1,8-Naphthyridine," *J. Heterocyclic Chem.*, 1992, pp. 691-697, vol. 29.

Doria, G., et al, "7-Z-Trans-(2-Pyridylethenyl)-5H-Thiazolo[3,2-a] Pyrimidine-5-Ones: Synthesis and Pharmacological Activity," *Farmaco Ed. Sci.*, 1985, pp. 885-895.

Ellsworth, E.L., et al., "4 Hydroxy -5,6-Dihydro-2*H*-Pyran-2-ones. 3.Bicyclic and Hetero-Aromatic Ring Systems as 3-Position Scaffolds to Bind to $S_1$' and $S_2$' of the HIV-1 Protease Enzyme," *Biporg. Med. Chem. Lett.*, 1999, pp. 2019-2024, vol. 9, issue 14.

(Continued)

Primary Examiner—Phyllis G. Spivack
(74) *Attorney, Agent, or Firm*—Jeffrey H. Tidwell; Bryan C. Zielinski

(57) ABSTRACT

Compounds of formula I are hepatitis C virus (HCV) RNA-dependent RNA polymerase (RdRp) inhibitors, and are useful in therapeutic and prophylactic treatment of persons infected with hepatitis C virus

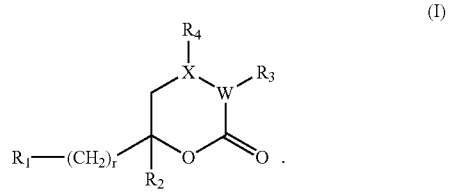

(I)

2 Claims, No Drawings

OTHER PUBLICATIONS

Halimorad et al., "Some observations on the Binding Properties of Alfalfa Mosaic Virus to Polystyrene and its Significance to Indirect ELISA," Arch. Virol., 1991, pp. 219-235, vol. 2.

Gerecke, M., et al, "New Tetracyclic Derivatives of Imidazo-[1,5-a][1,4]Benzodiazepines and of Imidazo [1,5-a]Thieno[3,2-f][1,4]Diazepines," Heterocycles, 1994, pp. 693-721, vol. 39, No. 2.

Hagen, S., et al., "Synthesis of 5,6-Dihydro-4-hydroxy-2-pyrones as HIV-1 Protease Inhibitors: The Profound Effect of Polarity on Antiviral Activity," J. Med Chem., 1997, pp. 3707-3711, vol. 40, issue 23.

Hénichart, J., et al., "A Convenient Method For The Preparation of ω-Di-Alkylaminoalkyl Isothiocyanates," Synthesis, 1980, pp. 311-312.

Ishizumi, K. et al., "Synthesis and Anxiolytic Activity of N-Substituted Cyclic Imides 91R*, 2S*,3R*, 4S*)-N-[4[4-(2-Pyrimidinyl)-1-Piperazinyl]butyl]-2,3-Bicyclo[2.2.1]Heptanedicarboximide (Tandospirone) And Related Compounds," Chem. Pharm Bull., 1991, pp. 2288-2300, vol. 39, No. 9.

Kuchar, M., et al., "The Synthesis of Arylpropionic Acids and The Quantitative Relationship Between the Structure and the Activation of Fibrinolysis," Collect. Czech. Chem. Commun, 1981, pp. 1173-1187, vol. 46.

Lee, Y.R., et al., "A New Route For The Synthesis of Furanoflavone and Furanochalcone Natural Products," Tetrahedron, 1995, pp. 4909-4922, vol. 51.

Moloney, G.P, et al., "Synthesis and Serotonergic Activity of 2-oxadiazolyl-5-substituted-N,N-dimethyltryptamines: Novel Antagonists for the Vascular 5-HT $_{1b}$-like Receptor" J. Chem. Soc Perkin, 1999, pp. 2725-2733, vol. 19.

Mylari, B.L., et al., "Potent, Orally Active Aldose Reductase Inhibitors Related to Zopolrestat: Surrogates For Benzothiazole Side Chain," J. Med. Chem., 1992, pp. 457-465, vol. 35, issue 3.

Palazzo, G, et al., "1,2,4-Oxadiazoles—IV. Synthesis and Pharmacological Properties of a Series of Substituted Aminoalkyl-1,2,4-oxadiazoles," J. Med. Pharm. Chem., 1961, pp. 351-367, vol. 4, issue 2.

Powell, M.T., et al, "Optically active $C^3$-Symmetric Triarylphosphines in Asymmetric Allylations," Tetrahedron, 2001, pp. 5027-5038, vol. 57.

Ren, R., et al., "Total Synthesis Of The Ocular Age Pigment A2-E: A Convergent Pathway," J. Am. Chem. Soc., 1997, pp. 3619-3620, vol. 119.

Selassie, C., et al., "QSAR For The Cytotoxicity of 2-Alkyl or 2,6-Dialkyl, 4-X-Phenols: The Nature of the Radical Reaction," J. Chem. Soc. Perkin Trans 2, 2002, pp. 1112-1117.

Shishoo, C. J., et al., "Reaction of Nitriles Under Acidic Conditions. Part III. A Facile Synthesis of Thienopyrimidin-4(3H)-ones," J. Heterocyclic Chem., 1984, pp. 375-380, vol. 21.

Szmuszkovicz, J., et al., "A Study Of The Inhibitory Effect Of Various Hydrazides On Monoamine Oxidase in vitro And in vivo," Journal Of Medicinal And Pharmaceutical Chemistry, 1961, pp. 259-296, vol. 4, No. 2.

Vara Prasad, J.V.N., et al., "Nonpeptidic HIV Protease Inhibitors: 6-Alkyl-5,6-Dihydropyran-2-Ones Possessing Achiral 3-(4-Amino/Carboxamide-2-t-Butyl, 5-Methylphenyl Thio) Moiety: Antiviral Activities and Pharmacokinetic Properties," Bioorg. Med. Chem. Lett., (Jul. 6, 1999), pp. 1481-1486, vol. 9, issue 11.

Vara Prasad, et al., "Nonpeptidic HIV Protease Inhibitors Processing Excellent Antiviral Activities and Therapeutic Indices. PD 178390: A Lead HIV Protease Inhibitor", Bioorganic Medicinal Chemistry Letters, 1999, pp. 2775-2800.

Baginski S., et al., "Mechanism of Action Of A Pestivirus Antiviral Compound" Proc. Natl. Acad. Sci. USA (2000) pp. 7981-7986, vol. 97.

Bagshawe, "Antibody-Directed Enzyme Prodrug Therapy: A Review", Drug Dev. Res., 1995, pp. 220-230, vol. 34.

Bartenschlager, et al., "Molecular Targets In Inhibition Of Hepatitis C Virus Replication" Antiviral Chemistry & Chemotherapy 1997, pp. 281-301, vol. 8, No. 4.

Bartenschlager, et al., "Nonstructural Protein 3 Of The Hepatitis C Virus Encodes A Serine-Type Proteinase Required For Cleavage At The NS3/4 And NS4/5 Junctions" Journal of Virology, Jul. 1993, pp. 3835-3844, vol. 67, No. 7.

Bertolini, et al., "A New Rational Hypothesis for the Pharmacophore of the Active Metabolite of Leflunomide, a Potent Immunosuppressive Drug", J. Med. Chem., 1997, pp. 2011-2016, vol. 40.

Bodor, "Novel Approaches to the Design of Safer Drugs: Soft Drugs and Site-Specific Chemical Delivery Systems", Advances in Drug Res., 1984, pp. 224-331, vol. 13.

Boyer, et al., 5,6-Dihydropyran-2-ones Possessing Various Sulfonyl Functionalities: Potent Nonpeptidic Inhibitors of HIV Protease, J. Med. Chem., 2000, pp. 843-858, vol. 43, No. 5.

Brown, et al., "Secondary Structure Of The 5'Nontranslated Regions of Hepatitis C Virus And Pestivirus Genomic RNAs" Nucleic Acids Research, 1992, pp. 5041-5045, vol. 20, No. 19.

Bukh, et al., "Sequence Analysis Of The 5' Noncoding Region Of Hepatitis C Virus" Proc. Natl. Acad. Sci. USA, Jun. 1992, pp. 4942-4946, vol. 89.

Bundgaard, Design of Prodrugs (Elsevier Press, 1985).

Choo, et al., "Isolation of a cDNA Clone Derived From A Blood-Borne Non-A, Non-B Viral Hepatitis Genome" Science, Apr. 21, 1989, pp. 359-362, vol. 244.

Cuthbert, J., "Hepatitis C: Progress and Problems" Clinical Microbiology Reviews, Oct. 1994, pp. 505-532, vol. 7, No. 4.

Dear, et al., "Mass Directed Peak Selection, an Efficient Method of Drug Metabolite Identification Using Directly Coupled Liquid Chromatography-Mass Spectrometry-Nuclear Magnetic Resonance Spectroscopy", J. Chromatogr. B, 2000, pp. 281-293, vol. 748.

Doyle, M. et al., "Macrocycle Formation By Catalytic Intramolecular Cyclopropanation. A New General Methodology For The Synthesis Of Macrolides" Journal of the American Chemical Society, 1997, pp. 8826-8837.

Earl, R., et al., "The Preparation of 2(1H)-Pyridinones And 2,3-Dihydro-5(1H)-Indolizinoes via Transition Metal Mediated Cocyclization Of Alkynes And Isocyanates. A Novel Construction Of The Antitumor Agent Camptothecin" Journal of Org. Chem., 1984, pp. 4786-4800, vol. 106.

Ferrari, et al., "Characterization Of Soluble Hepatitis C Virus RNA-Dependent RNA Polymerase Expressed in Escherichia coli" Journal of Virology, Feb. 1999 pp. 1649-1654, vol. 73, No. 2.

Grakoui, et al., "Expression And Identification Of Hepatitis C Virus Polyprotein Cleavage Products" Journal Of Virology, Mar. 1993, pp. 1385-1395, vol. 67, No. 3.

Hagen, et al., "4-Hydroxy-5,6-dihydropyrones as Inhibitors of HIV Protease: The Effect of Heterocyclic Substituents at C-6 on Antiviral Potency and Pharmacokinetic Parameters", J. Med. Chem. 2001, pp. 2319-2332, vol. 44, No. 14.

Hijikata, et al., "Gene Mapping Of The Putative Structural Region Of The Hepatitis C Virus Genome By In Vitro Processing Analysis" Proc. Natl. Acad. Sci. USA, Jul. 1991, pp. 5547-5551, vol. 88.

Hwang, et al., "Hepatitis C Virus NS5B Protein Is A Membrane-Associated Phosphoprotein With A Predominantly Preinuclear Localization," Virology, 1997, pp. 439-446, vol. 227.

Ishii, et al., "Expression of Hepatitis C Virus NS5B Protein: Characterization of Its RNA Polymerase Activity and RNA Binding", Hepatology, 1999, pp. 1227-1235, vol. 29.

Kim, et al., "Crystal Structure Of The Hepatitis C Virus NS3 Protease Domain Complexed With A Synthetic NS4A Cofactor Peptide" Cell, Oct. 18, 1996, pp. 343-355, vol. 87.

Kim, et al., "Hepatitis C Virus NS3 RNA Helicase Domain With A Bound Oligonucleotide: The Crystal Structure Provides Insights Into The Mode Of Unwinding" Structure, 1998, pp. 89-100, vol. 6, No. 1.

Kolykhalov, et al., "Identification Of A Highly Conserved Sequence Element At The 3' Terminus Of Hepatitis C Virus Genome RNA" Journal Of Virology, Jun. 1996, pp. 3363-3371.

Larsen, Design and Application of Prodrugs, Drug Design and Development, Krogsgaard-Larsen, et al. eds., Harwood Academic Publishers, 1991.

Lin, et al., "Processing In The Hepatitis C Virus E2-NS2 Region: Identification of p7 and Two Distinct E2-Specific Products With Different C Termini" *Journal of Virology*, Aug. 1994, pp. 5063-5073, vol. 68, No. 8.

Lohmann, et al., "Biochemical And Kinetic Analyses Of NS5B RNA-Dependent RNA Polymerase Of The Hepatitis C Virus" *Virology*, 1998, pp. 108-118, vol. 71, No. 11.

Lohmann, et al., "Biochemical Properties Of Hepatitis C Virus NS5B RNA-Dependent RNA Polymerase And Identification Of Amino Acid Sequence Motifs Essential For Enzymatic Activity," *Journal Of Virology*, Nov. 1997, pp. 8416-8428.

Lorentzen, R. et al., "Application Of The Benzene Sector And The Benzene Chirality Rules To Perhydrobenzoclycloalkenes And Related Compounds" *Journal Amer. Chem. Soc.*, 1992, pp. 2181-2187, vol. 114.

Love, et al., "The Crystal Structure Of Hepatitis C Virus NS3 Proteinase Reveals A Trypsin-Like Fold And A Structural Zinc Binding Site" *Cell*, 1996, pp. 331-342, vol. 87.

Marcellin, et al., "Long-Term Histologic Improvement And Loss Of Detectable Intrahepatic HCV RNA In Patients With Chronic Hepatitis C And Sustained Response To Interferon-alpha Therapy," *Ann. Inter. Med.*, Nov. 15, 1997, pp. 875-881, vol. 127.

Miller, et al., "Hepatitis C Virus Shares Amino Acid Sequence Similarity With Pestiviruses And Flaviviruses as Well As Members Of Two Plant Virus Supergroups," *Proc. Natl. Acad. Sci. USA*, Mar. 1990 pp. 2057-2061, vol. 87.

Poch, et al., "Identification Of Four Conserved Motifs Among The RNA-Dependent Polymerase Encoding Elements" *The EMBO Journal*, 1989, pp. 3867-3874, vol. 8, No. 12.

Prasad, et al., "Nonpeptidic HIV Protease Inhibitors Processing Excellent Antiviral Activities and Therapeutic Indices. PD 178390: A Lead HIV Protease Inhibitor", *Bioorganic Medicinal Chemistry Letters*, 1999 pp. 2775-2800.

Prox, et al., "Rapid Structure Elucidation of Drug Metabolites by Use of Stable Isotopes", *Xenobiotica*, 1973, pp. 103-112, vol. 3, No. 2.

Rin k, Hans, "Solid-Phase Synthesis Of Protected Peptide Fragments Using A Trialkoxy-Diphenyl-Methylester Resin." *Tetrahedron Letters*, 1987, pp. 3787-3790, vol. 28, No. 33.

Shan, D. et al., "Prodrug Strategies Based On Intramolecular Cyclization Reactions" *J. Pharm. Sci.* 1997, pp. 765-767 vol. 86, No. 7.

Simmonds, et al., "Classification Of Hepatitis C Virus Into Six Major Genotypes And A Series Of Subtypes By Phylogenetic Analysis Of The NS-5 Region" *Journal of General Virology*, 1993, pp. 2391-2399, vol. 74.

Smith, A. et al., "Photochemical Reactions of 1-Cyclopentenyl And 1-Cyclohexanyl Ketones" *Journal of American Chem. Soc.*, 1973, pp. 1961-1968.

Spraul, et al., "Liquid Chromatography Coupled with High-Field Proton NMR for Profiling Human Urine for Endogenous Compounds and Drug Metabolites", *J. Pharmaceutical & Biomedical Analysis*, 1992, pp. 601-605, vol. 10, No. 8.

Tanaka, et al., "Structure Of The 3' Terminus Of The Hepatitis C Virus Genome," *Journal of Virology*, May 1996, pp. 3307-3312, vol. 70, No. 5.

Tee, et al., "Kinetics and Mechanism of Bromination of 2-Pyridone and Related Derivatives in Aqueous Solution", J. Am. Chem. Soc., 1982, pp. 4142-4246.

Wang, et al., "Recent Advances In Prevention And Treatment of Hepatitis C Virus Infections," *Process in Drug Research*, 2000, pp. 1-32, vol. 55.

Weiner, et al., "Evidence For Immune Selection Of Hepatitis C Virus (HCV) Putative Envelope Glycoprotein Variants: Potential Role In Chronic HCV Infections," *Proc. Natl. Acad. Sci. USA*, Apr. 1992, pp. 3468-3472, vol. 89.

Weiner, et al., "Variable And Hypervariable Domains Are Found In The Regions Of HCV Corresponding To The Flavivirus Envelope And NS1 Proteins And The Pestivirus Envelope Glycoproteins" *Virology*, 1991, pp. 842-848, vol. 180.

World Health Organization, *The Lancet*, 1998, p. 1415, vol. 351.

Wyatt, et al., "Immunity In Chimpanzees Chroncially Infected With Hepatitis C Virus: Role Of Minor Quasispecies In Reinfection" *Journal Of Virology*, Mar. 1998, pp. 1725-1730, vol. 72, No. 3.

Yamashita, et al., "RNA-Dependent RNA Polymerase Activity Of The Soluble Recombinant Hepatitis C Virus NS5B Protein Truncated AT The C-Terminal Region" *The Journal Of Biological Chemistry*, Jun. 19, 1998, pp. 15479-15486, vol. 273, No. 25.

Zeuzem, et al., "Hepatitis C Virus Dynamics In Vivo: Effect Of Ribavirin And Interferon Alfa On Viral Turnover" *Hepatology*, 1998, pp. 245-252.

* cited by examiner

INHIBITORS OF HEPATITIS C VIRUS RNA-DEPENDENT RNA POLYMERASE

FIELD OF THE INVENTION

This application claims the benefit of U.S. Provisional Application Ser. No. 60/379,433, filed May 10, 2002.

The invention relates to agents that inhibit hepatitis C virus (HCV) RNA-dependent RNA polymerase (RdRp). The invention also relates to the use of such compounds in pharmaceutical compositions and therapeutic treatments useful for inhibition of HCV replication.

BACKGROUND OF THE INVENTION

Hepatitis C virus (HCV) is a member of the hepacivirus genus in the family Flaviviridae. It is the major causative agent of non-A, non-B viral hepatitis and is the major cause of transfusion-associated hepatitis and accounts for a significant proportion of hepatitis cases worldwide. Although acute HCV infection is often asymptomatic, nearly 80% of cases resolve to chronic hepatitis. The persistent property of the HCV infection has been explained by its ability to escape from the host immune surveillance through hypermutability of the exposed regions in the envelope protein E2 (Weiner et al., *Virology* 180:842–848 (1991); Weiner et al. *Proc. Natl. Acad. Sci. USA* 89:3468–3472 (1992). About 60% of patients develop liver disease with various clinical outcomes ranging from an asymptomatic carrier state to chronic active hepatitis and liver cirrhosis (occurring in about 20% of patients), which is strongly associated with the development of hepatocellular carcinoma (occurring in about 1–5% of patients) (for reviews, see Cuthbert, *Clin. Microbiol. Rev.* 7:505–532 (1994); World Health Organization, *Lancet* 351: 1415 (1998). The World Health Organization estimates that 170 million people are chronically infected with HCV, with an estimate of 4 million of these living in the United States.

HCV is an enveloped RNA virus containing a single-stranded positive-sense RNA genome approximately 9.5 kb in length (Choo et al., *Science* 244:359–362 (1989)). The RNA genome contains a 5'-nontranslated region (5' NTR) of 341 nucleotides (Brown et al., *Nucl. Acids Res.* 20:5041–5045 (1992); Bukh et al., *Proc. Natl. Acad. Sci. USA* 89:4942–4946 (1992)), a large open reading frame (ORF) encoding a single polypeptide of 3,010 to 3,040 amino acids (Choo et al. (1989), supra;), and a 3'-nontranslated region (3'-NTR) of variable length of about 230 nucleotides (Kolykhalov et al., *J. Virol.* 70:3363–3371 (1996); Tanaka et al., *J. Virol.* 70:3307–3312 (1996)). By analogy to other plus-strand RNA viruses, the 3' nontranslated region is assumed to play an important role in viral RNA synthesis. HCV is similar in amino acid sequence and genome organization to flaviviruses and pestiviruses (Miller et al., *Proc. Natl. Acad. Sci. USA* 87:2057–2061 (1990)), and therefore HCV has been classified as a third genus of the family Flaviviridae (Francki et al., *Arch. Virol.* 2:223–233 (1991).

Studies of HCV replication and the search for specific anti-HCV agents have been hampered by the lack of an efficient tissue culture system for HCV propagation, the absence of a suitable small-animal model for HCV infection, the low level of viral replication, and the considerable genetic heterogeneity associated with the virus (Bartenschlager, *Antivir. Chem. Chemother.* 8:281–301 (1997); Simmonds et al., *J. Gen. Virol.* 74:2391–2399 (1993)). The current understanding of the structures and functions of the HCV genome and encoded proteins is primarily derived from in vitro studies using various recombinant systems (Bartenschlager (1997), supra).

The 5' NTR is one of the most conserved regions of the viral genome and plays a pivotal role in the initiation of translation of the viral polyprotein (Bartenschlager (1997), supra). A single ORF encodes a polyprotein that is co- or post-translationally processed into structural (core, E1, and E2) and nonstructural (NS2, NS3, NS4A, NS4B, NS5A, and NS5B) viral proteins by either cellular or viral proteinases (Bartenschlager (1997), supra). The 3' NTR consists of three distinct regions: a variable region of about 38 nucleotides following the stop codon of the polyprotein, a polyuridine tract of variable length with interspersed substitutions of cystines, and 98 nucleotides (nt) at the very 3' end which are highly conserved among various HCV isolates. The order of the genes within the genome is: $NH_2$—C-E1-E2-p7-NS2-NS3-NS4A-NS4B-NS5A-NS5B—COOH (Grakoui et al., *J. Virol.* 67:1385–1395 (1993)).

Processing of the structural proteins core (C), envelope protein 1 and (E1, E2), and the p7 region is mediated by host signal peptidases. In contrast, maturation of the nonstructural (NS) region is accomplished by two viral enzymes. The HCV polyprotein is first cleaved by a host signal peptidase generating the structural proteins C/E1, E1/E2, E2/p7, and p7/NS2 (Hijikata et al., *Proc. Natl. Acad. Sci. USA* 88:5547–5551 (1991); Lin et al., *J. Virol.* 68:5063–5073 (1994)). The NS2–3 proteinase, which is a metalloprotease, then cleaves at the NS2/NS3 junction. The NS3/4A proteinase complex (NS3 serine protease/NS4A cofactor), then at all the remaining cleavage sites (Bartenschlager et al., *J. Virol.* 67:3835–3844 (1993); Bartenschlager (1997), supra). RNA helicase and NTPase activities have also been identified in the NS3 protein. The N-terminal one-third of the NS3 protein functions as a protease, and the remaining two-thirds of the molecule acts as a helicase/ATPase, which is thought to be involved in HCV replication (Bartenschlager (1997), supra). NS5A may be phosphorylated and act as a putative cofactor of NS5B. The fourth viral enzyme, NS5B, is an RNA-dependent RNA polymerase (RdRp) and a key component responsible for replication of the viral RNA genome (Lohmann et al., *J. Virol.* 71:8416–8428 (1997)). NS5B contains the "GDD" sequence motif, which is highly conserved among all RdRps characterized to date (Poch et al., *EMBO J.* 8:3867–3874 (1989)).

Replication of HCV is thought to occur in membrane-associated replication complexes. Within these, the genomic plus-strand RNA is transcribed into minus-strand RNA, which in turn can be used as a template for synthesis of progeny genomic plus strands. Two viral proteins appear to be involved in this reaction: the NS3 protein, which carries in the carboxy terminal two-thirds a nucleoside triphosphatase/RNA helicase, and the NS5B protein, which is a membrane-associated phosphoprotein with an RNA-dependent RNA polymerase activity (RdRp) (Hwang et al., *J. Virol.* 227:439–446 (1997)). While the role of NS3 in RNA replication is less clear, NS5B apparently is the key enzyme responsible for synthesis of progeny RNA strands. Using recombinant baculoviruses to express NS5B in insect cells and a synthetic nonviral RNA as a substrate, two enzymatic activities have been identified as being associated with NS5B. The two activities include a primer-dependent RdRp and a terminal transferase (TNTase) activity. NS5B's activity was confirmed and further-characterized through the use of the HCV RNA genome as a substrate (Lohmann et al., *Virology* 249: 108–118 (1998)). Recent studies have shown that NS5B with a C-terminal 21 amino-acid truncation expressed in *Escherichia coli* is also active for in vitro RNA synthesis (Ferrari et al., *J. Virol.* 73:1649–1654 (1999); Yamashita et al., *J. Biol. Chem.* 273:15479–15486 (1998)).

Since persistent infection of HCV is related to chronic hepatitis and eventually to hepatocarcinogenesis, HCV replication is one of the targets to eliminate HCV reproduction and to prevent hepatocellular carcinoma. Unfortunately, present treatment approaches for HCV infection are characterized by relatively poor efficacy and an unfavorable side-effect profile. Therefore, intensive effort is directed at the discovery of molecules to treat this disease. These new approaches include the development of prophylactic and therapeutic vaccines, the identification of interferons with improved pharmacokinetic characteristics, and the discovery of drugs designed to inhibit the function of the three major viral proteins, protease, helicase and polymerase. In addition, the HCV RNA genome itself, particularly the IRES element, is being explored as an antiviral target using antisense molecules and catalytic ribozymes. For a review, see Wang et al., *Prog. Drug Res.* 55:1–32 (2000).

Particular therapies for HCV infection include α-interferon alone and the combination of α-interferon with ribavirin. These therapies have been shown to be effective in a portion of patients with chronic HCV infection (Marcellin et al., *Ann. Intern. Med.* 127:875–881 (1997); Zeuzem et al., *Hepatology* 28:245–252 (1998)). Use of antisense oligonucleotides for treatment of HCV infection has also been proposed (Anderson et al., U.S. Pat. No. 6,174,868 (2001)), as well as use of free bile acids, e.g., ursodeoxycholic acid, chenodeoxycholic acid, or conjugated bile acids, e.g., tauroursodeoxycholic acid (Ozeki, U.S. Pat. No. 5,846,964 (1998)). Phosphonoformic acid esters have also been proposed to be useful in treating a number of viral infections including HCV (Helgstrand et al., U.S. Pat. No. 4,591,583 (1986)). However, the high degree of immune evasion and the lack of protection against reinfection, even with the same inoculum has hampered vaccine development (Wyatt et al., *J. Virol.* 72:1725–1730 (1998)).

The development of small-molecule inhibitors directed against specific viral targets has become a focus of anti-HCV research. The determination of crystal structures for NS3 protease (Kim et al., *Cell* 87:343–355 (1996); Love et al., *Cell* 87:331–342 (1996)) and NS3 RNA helicase (Kim et al., *Structure* 6:89–100 (1998)) has provided important structural insights for rational design of specific inhibitors.

NS5B, the RNA-dependent RNA polymerase, is also a useful viral target for small-molecule inhibitors. Studies with pestiviruses have shown that the small molecule VP32947 (3-[((2-dipropylamino)ethyl)thio]-5H-1,2,4-triazino[5,6-b]indole) is a potent inhibitor of pestivirus replication and may inhibit the NS5B enzyme (Baginski et al., *Proc. Natl. Acad. Sci. USA* 97:7981–7986 (2000)). Inhibition of RdRp activity by (-)β-L-2',3'-dideoxy-3'-thiacytidine 5'-triphosphate (3TC; lamivudine triphosphate) and phosphonoacetic acid also has been observed (Ishii et al., *Hepatology* 29:1227–1235 (1999)).

Nonetheless, there is still a need for non-peptide, small-molecule compounds that are HCV RdRp inhibitors and that have desirable or improved physical and chemical properties appropriate for pharmaceutical applications.

SUMMARY OF THE INVENTION

The present invention is directed to compounds that function as inhibitors to hepatitis C virus RNA-dependent RNA polymerase. The invention is also directed to the use of such compounds in pharmaceutical compositions and therapeutic treatments useful for inhibition of HCV replication.

In one of its aspects, the present invention relates to a method of inhibiting HCV polymerase activity comprising contacting an HCV polymerase with an effective amount of a compound represented by formula (I) or a salt, solvate, prodrug, or metabolite thereof:

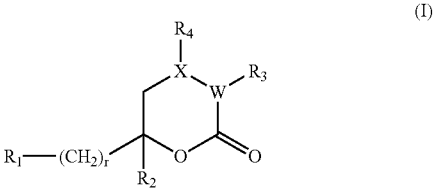

wherein r, $R_1$, $R_2$, $R_3$, $R_4$, and X—W are as defined below.
In one embodiment, $R_3$ is hydrogen. In another embodiment, $R_3$ is an optionally substituted —S—$(CH_2)_z$-aryl or —S—$(CH_2)_z$-heteroaryl group, wherein z is an integer from 0 to 4. In still another embodiment, $R_3$ is an optionally substituted amino. In yet another embodiment, $R_3$ is an optionally substituted —C(O)H group. In a further embodiment, $R_2$ is an isopropyl, phenyl, or an unsubstituted cyclopentyl or cyclohexyl group. In still a further embodiment, r is 2. In yet a further embodiment, $R_4$ is a =O, —OH, or —$OCH_3$ group. In another embodiment, $R_1$ is an optionally substituted phenyl group. In still another embodiment, $R_3$ is —Cl; =S or an optionally substituted —SH; —S-naphthyl; —S—$CH_2$-Phenyl; —$CH_2$-Phenyl; or halogen.

In another of its aspects, the present invention relates to a method of inhibiting HCV polymerase activity comprising contacting an HCV polymerase with an effective amount of a compound represented by formula (I) or a salt thereof:

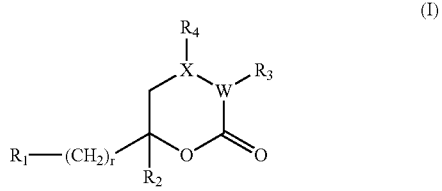

wherein r, $R_1$, $R_2$, $R_3$, $R_4$, and X—W are as defined below.
In still another of its aspects, the present invention relates to a method of inhibiting HCV polymerase activity in mammalian tissue comprising contacting said mammalian tissue with a compound represented by formula (I) or a salt, solvate, prodrug, or metabolite thereof:

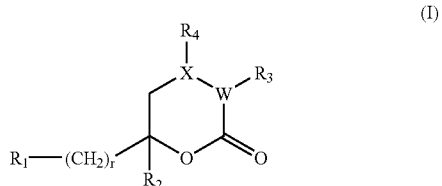

wherein r, $R_1$, $R_2$, $R_3$, $R_4$, and X—W are as defined below.
In one embodiment, the mammalian tissue is human tissue.

In yet another of its aspects, the present invention relates to a method of treating a condition that is mediated by HCV polymerase in a patient, comprising administering to said patient an effective amount of compound represented by formula (I) or a salt, solvate, prodrug, or metabolite thereof:

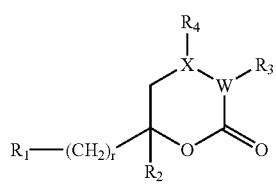

wherein r, $R_1$, $R_2$, $R_3$, $R_4$, and X—W are as defined below. In one embodiment, the compound, salt, solvate, prodrug, or metabolite is administered orally or intravenously.

Other features and advantages of the invention will be apparent from the description that follows, which illustrates the invention and its preferred embodiments.

DETAILED DESCRIPTION OF THE INVENTION AND PREFERRED EMBODIMENTS

HCV-Inhibiting Agents

As used herein, the terms "comprising" and "including" are used in their open, non-limiting sense.

In accordance with a convention used in the art, the symbol

is used in structural formulas herein to depict the bond that is the point of attachment of the moiety or substituent to the core or backbone structure. In accordance with another convention, in some structural formulae herein the carbon atoms and their bound hydrogen atoms are not explicitly depicted, e.g.,

represents a methyl group,

represents an ethyl group,

represents a cyclopentyl group, etc.

As used herein, the term "alkyl" means a branched- or straight-chained (linear) paraffinic hydrocarbon group (saturated aliphatic group) having from 1 to 12 carbon atoms in its chain, which may be generally represented by the formula $C_kH_{2k+1}$, where k is an integer of from 1 to 10. Examples of alkyl groups include methyl, ethyl, n-propyl, isopropyl, n-butyl, isobutyl, t-butyl, pentyl, n-pentyl, isopentyl, neopentyl, hexyl, and the like. A "lower alkyl" is intended to mean an alkyl group having from 1 to 4 carbon atoms in its chain. The term "heteroalkyl" refers to a straight- or branched-chain alkyl group having from 2 to 12 atoms in the chain, one or more of which is a heteroatom selected from S, O, and N. Exemplary heteroalkyls include alkyl ethers, secondary and tertiary amines, alkyl sulfides and the like.

The term "alkenyl" means a branched- or straight-chained olefinic hydrocarbon group (unsaturated aliphatic group having one or more double bonds) containing 2 to 12 carbons in its chain. Exemplary alkenyls include ethenyl, 1-propenyl, 2-propenyl, 1-butenyl, 2-butenyl, isobutenyl, and the like.

The term "alkynyl" means a branched or straight-chained hydrocarbon group having one or more carbon-carbon triple bonds, and having from 2 to 12 carbon atoms in its chain. Exemplary alkynyls include ethynyl, propynyl, 1-butynyl, 2-butynyl, 2-pentynyl, 2-methylbur-2-ynyl, and the like.

The term "carbocycle" refers to a saturated, partially saturated, unsaturated, or aromatic, monocyclic or fused or non-fused polycyclic, ring structure having only carbon ring atoms (no heteroatoms, i.e., non-carbon ring atoms). Exemplary carbocycles include cycloalkyl, aryl, and cycloalkyl-aryl groups.

The term "heterocycle" refers to a saturated, partially saturated, unsaturated, or aromatic, monocyclic or fused or non-fused polycyclic, ring structure having one or more heteroatoms selected from N, O, and S. Exemplary heterocycles include heterocycloalkyl, heteroaryl, and heterocycloalkyl-heteroaryl groups.

A "cycloalkyl group" is intended to mean a saturated or partially saturated, monocyclic, or fused or spiro polycyclic, ring structure having a total of from 3 to 18 carbon ring atoms (but no heteroatoms). Exemplary cycloalkyls include cyclopropyl, cyclobutyl, cyclopentyl, cyclopentenyl, cyclohexyl, cycloheptyl, adamantyl, and like groups.

A "heterocycloalkyl group" is intended to mean a monocyclic, or fused or spiro polycyclic, ring structure that is saturated or partially saturated, and has a total of from 3 to 18 ring atoms, including 1 to 5 heteroatoms selected from nitrogen, oxygen, and sulfur. Illustrative Examples of heterocycloalkyl groups include pyrrolidinyl, tetrahydrofuryl, piperidinyl, piperazinyl, morpholinyl, thiomorpholinyl, aziridinyl, and like groups.

The term "aryl" means an aromatic monocyclic or fused or spiro polycyclic ring structure having a total of from 4 to 18 ring carbon atoms (no heteroatoms). Exemplary aryl groups include phenyl, naphthyl, anthracenyl, and the like.

A "heteroaryl group" is intended to mean a monocyclic or fused or spiro polycyclic, aromatic ring structure having from 4 to 18 ring atoms, including from 1 to 5 heteroatoms selected from nitrogen, oxygen, and sulfur. Illustrative Examples of heteroaryl groups include pyrrolyl, thienyl, oxazolyl, pyrazolyl, thiazolyl, furyl, pyridinyl, pyrazinyl, triazolyl, tetrazolyl, indolyl, quinolinyl, quinoxalinyl, benzthiazolyl, benzodioxinyl, benzodioxolyl, benzooxazolyl, and the like.

The term "alkoxy" is intended to mean the radical —$OR_a$, where $R_a$ is an alkyl group. Exemplary alkoxy groups include methoxy, ethoxy, propoxy, and the like. "Lower alkoxy" groups have alkyl moieties having from 1 to 4 carbons.

The term "amino" is intended to mean the —NH$_2$ radical.

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents.

A "HCV-inhibiting agent" means a compound represented by formula I or a pharmaceutically acceptable salt, prodrug, active metabolite or solvate thereof.

A "prodrug" is a compound that may be converted under physiological conditions or by solvolysis to the specified compound or to a pharmaceutically acceptable salt of such compound. A prodrug may be a derivative of one of the compounds of the present invention that contains a moiety, such as for Example —CO$_2$R, —PO(OR)$_2$ or —C=NR, that may be cleaved under physiological conditions or by solvolysis. Any suitable R substituent may be used that provides a pharmaceutically acceptable solvolysis or cleavage product. A prodrug containing such a moiety may be prepared according to conventional procedures by treatment of a compound of this invention containing, for Example, an amido, carboxylic acid, or hydroxyl moiety with a suitable reagent. An "active metabolite" is a pharmacologically active product produced through metabolism in the body of a specified compound or salt thereof. Prodrugs and active metabolites of a compound may be identified using routine techniques known in the art. See, e.g., Bertolini et al., *J. Med. Chem.*, 40:2011–2016 (1997); Shan et al., *J. Pharm. Sci.*, 86 (7):765–767 (1997); Bagshawe, *Drug Dev. Res.*, 34:220–230 (1995); Bodor, *Advances in Drug Res.*, 13:224–331 (1984); Bundgaard, "Design of Prodrugs" (Elsevier Press, 1985); Larsen, *Design and Application of Prodrugs*, Drug Design and Development (Krogsgaard-Larsen et al. eds., Harwood Academic Publishers, 1991); Dear et al., *Chromatogr. B*, 748:281–293 (2000); Spraul et al., *J. Pharmaceutical & Biomedical Analysis*, 10 (8):601–605 (1992); and Prox et al., *Xenobiol*, 3(2):103–112 (1992).

A "solvate" is intended to mean a pharmaceutically acceptable solvate form of a specified compound that retains the biological effectiveness of such compound. Examples of solvates include compounds of the invention in combination with water, isopropanol, ethanol, methanol, DMSO, ethyl acetate, acetic acid, or ethanolamine. A "pharmaceutically acceptable salt" is intended to mean a salt that retains the biological effectiveness of the free acids and bases of the specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methane-sulfonates, propanesulfonates, naphthalene-1-sulfonates, naphthalene-2-sulfonates, and mandelates.

If an inventive compound is a base, a desired salt may be prepared by any suitable method known to the art, including treatment of the free base with an inorganic acid, such as hydrochloric acid; hydrobromic acid; sulfuric acid; nitric acid; phosphoric acid; and the like, or with an organic acid, such as acetic acid; maleic acid; succinic acid; mandelic acid; fumaric acid; malonic acid; pyruvic acid; oxalic acid; glycolic acid; salicylic acid; pyranosidyl acid, such as glucuronic acid or galacturonic acid; alpha-hydroxy acid, such as citric acid or tartaric acid; amino acid, such as aspartic acid or glutamic acid; aromatic acid, such as benzoic acid or cinnamic acid; sulfonic acid, such as p-toluenesulfonic acid or ethanesulfonic acid; and the like.

If an inventive compound is an acid, a desired salt may be prepared by any suitable method known to the art, including treatment of the free acid with an inorganic or organic base, such as an amine (primary, secondary, or tertiary); an alkali metal or alkaline earth metal hydroxide; or the like. Illustrative Examples of suitable salts include organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

In the case of compounds, prodrugs, salts, or solvates that are solids, it is understood by those skilled in the art that the inventive compounds, prodrugs, salts, and solvates may exist in different polymorph or crystal forms, all of which are intended to be within the scope of the present invention and specified formulas. In addition, the compounds, salts, prodrugs and solvates of the present invention may exist as tautomers, all of which are intended to be within the broad scope of the present invention.

In some cases, the inventive compounds will have chiral centers. When chiral centers are present, the inventive compounds may exist as single stereoisomers, racemates, and/or mixtures of enantiomers and/or diastereomers. All such single stereoisomers, racemates, and mixtures thereof are intended to be within the broad scope of the present invention.

As generally understood by those skilled in the art, an optically pure compound is one that is enantiomerically pure. As used herein, the term "optically pure" is intended to mean a compound comprising at least a sufficient activity. Preferably, an optically pure amount of a single enantiomer to yield a compound having the desired pharmacological pure compound of the invention comprises at least 90% of a single isomer (80% enantiomeric excess), more preferably at least 95% (90% e.e.), even more preferably at least 97.5% (95% e.e.), and most preferably at least 99% (98% e.e.).

The present invention is also directed to a method of inhibiting HCV RdRp activity, comprising contacting the protein with an effective amount of a compound of formula I, or a pharmaceutically acceptable salt, prodrug, pharmaceutically active metabolite, or solvate thereof. For Example, HCV activity may be inhibited in mammalian tissue by administering a HCV-inhibiting agent according to the invention.

"Treating" or "treatment" is intended to mean at least the mitigation of an injury or a disease condition in a mammal, such as a human, that is alleviated by the inhibition of HCV activity, and includes: (a) prophylactic treatment in a mammal, particularly when the mammal is found to be predisposed to having the disease condition but not yet diagnosed as having it; (b) inhibiting the disease condition; and/or (c) alleviating, in whole or in part, the disease condition.

The activity of the inventive compounds as inhibitors of HCV activity may be measured by any of the suitable methods available in the art, including in vivo and in vitro assays. An Example of a suitable assay for activity measurements is the HCV polymerase inhibition assay described herein.

Administration of the compounds of formula I and their pharmaceutically acceptable prodrugs, salts, active metabolites, and solvates may be performed according to any of the accepted modes of administration available to those skilled in the art. Illustrative Examples of suitable modes of administration include oral, nasal, parenteral, topical, transdermal, and rectal. Oral and intravenous deliveries are preferred.

An HCV-inhibiting agent may be administered as a pharmaceutical composition in any suitable pharmaceutical form. Suitable pharmaceutical forms include solid, semisolid, liquid, or lyopholized formulations, such as tablets, powders, capsules, suppositories, suspensions, liposomes, and aerosols. The HCV-inhibiting agent may be prepared as a solution using any of a variety of methodologies. For Example, the HCV-inhibiting agent can be dissolved with acid (e.g., 1 M HCl) and diluted with a sufficient volume of a solution of 5% dextrose in water (D5W) to yield the desired final concentration of HCV-inhibiting agent (e.g., about 15 mM). Alternatively, a solution of D5W containing about 15 mM HCl can be used to provide a solution of the HCV-inhibiting agent at the appropriate concentration. Further, the HCV-inhibiting agent can be prepared as a suspension using, for Example, a 1% solution of carboxymethylcellulose (CMC).

Acceptable methods of preparing suitable pharmaceutical forms of the pharmaceutical compositions are known or may be routinely determined by those skilled in the art. For Example, pharmaceutical preparations may be prepared following conventional techniques of the pharmaceutical chemist involving steps such as mixing, granulating, and compressing when necessary for tablet forms, or mixing, filling, and dissolving the ingredients as appropriate, to give the desired products for oral, parenteral, topical, intravaginal, intranasal, intrabronchial, intraocular, intraaural, and/or rectal administration.

Pharmaceutical compositions of the invention may also include suitable excipients, diluents, vehicles, and carriers, as well as other pharmaceutically active agents, depending upon the intended use. Solid or liquid pharmaceutically acceptable carriers, diluents, vehicles, or excipients may be employed in the pharmaceutical compositions. Illustrative solid carriers include starch, lactose, calcium sulfate dihydrate, terra alba, sucrose, talc, gelatin, pectin, acacia, magnesium stearate, and stearic acid. Illustrative liquid carriers include syrup, peanut oil, olive oil, saline solution, and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., solution), or a nonaqueous or aqueous liquid suspension.

A dose of the pharmaceutical composition contains at least a therapeutically effective amount of the HCV-inhibiting agent and preferably is made up of one or more pharmaceutical dosage units. The selected dose may be administered to a mammal, for Example, a human patient, in need of treatment mediated by inhibition of HCV activity, by any known or suitable method of administering the dose, including topically, for Example, as an ointment or cream; orally; rectally, for Example, as a suppository; parenterally by injection; intravenously; or continuously by intravaginal, intranasal, intrabronchial, intraaural, or intraocular infusion. When the composition is administered in conjunction with a cytotoxic drug, the composition can be administered before, with, and/or after introduction of the cytotoxic drug. However, when the composition is administered in conjunction with radiotherapy, the composition is preferably introduced before radiotherapy is commenced.

The phrases "therapeutically effective amount" and "effective amount" are intended to mean the amount of an inventive agent that, when administered to a mammal in need of treatment, is sufficient to effect treatment for injury or disease conditions alleviated by the inhibition of HCV activity, such as for potentiation of anti-cancer therapies or inhibition of neurotoxicity consequent to stroke, head trauma, and neurodegenerative diseases. The amount of a given compound of the invention that will be therapeutically effective will vary depending upon factors such as the particular compound, the disease condition and the severity thereof, the identity and characteristics of the mammal in need thereof, which amount may be routinely determined by artisans.

It will be appreciated that the actual dosages of the HCV-inhibiting agents used in the pharmaceutical compositions of this invention will be selected according to the properties of the particular agent being used, the particular composition formulated, the mode of administration and the particular site, and the host and condition being treated. Optimal dosages for a given set of conditions can be ascertained by those skilled in the art using conventional dosage-determination tests. For oral administration, e.g., a dose that may be employed is from about 0.001 to about 1000 mg/kg body weight, preferably from about 0.1 to about 100 mg/kg body weight, and even more preferably from about 1 to about 50 mg/kg body weight, with courses of treatment repeated at appropriate intervals.

EXAMPLES

Specific Examples of various compounds according to the invention may be advantageously prepared as set out in the Examples above.

The structures of the compounds of the following Examples were confirmed by one or more of the following: proton magnetic resonance spectroscopy, infrared spectroscopy, elemental microanalysis, mass spectrometry, thin layer chromatography, melting point, boiling point, and HPLC.

Proton magnetic resonance ($^1$H NMR) spectra were determined using a 300 megahertz Tech-Mag, Bruker Avance 300DPX, or Bruker Avance 500 DRX spectrometer operating at a field strength of 300 or 500 megahertz (MHz). Chemical shifts are reported in parts per million (ppm, $\delta$) downfield from an internal tetramethylsilane standard. Alternatively, $^1$H NMR spectra were referenced to residual protic solvent signals as follows: $CHCl_3$=7.26 ppm; DMSO=2.49 ppm; $C_6HD_5$=7.15 ppm. Peak multiplicities are designated as follows: s=singlet; d=doublet; dd=doublet of doublets; t=triplet; q=quartet; br=broad resonance; and m=multiplet. Coupling constants are given in Hertz. Infrared absorption (IR) spectra were obtained using a Perkin-Elmer 1600 series FTIR spectrometer. Elemental microanalyses were performed by Atlantic Microlab Inc. (Norcross, Ga.) and gave results for the elements stated within ±0.4% of the theoretical values. Flash column chromatography was performed using Silica gel 60 (Merck Art 9385). Analytical thin layer chromatography (TLC) was performed using precoated sheets of Silica 60 F$_{254}$ (Merck Art 5719). HPLC chromatographs were run on a Hewlett Packard Model 1100 system fitted with a Zorbax SB-C18 4.6 mm×150 mm column having 3.5 micron packing material. Unless otherwise stated, a ramp of 5% CH$_3$CN/H$_2$O to 95% CH$_3$CN/H$_2$O over 7.5 minutes then holding at 95% CH$_3$CN/H$_2$O minutes (both solvents contained 0.1% v/v TFA) at a flow of 1 mL/min was used. Retention times (Rt) are given in minutes. Semi-preparative HPLC samples were run on a Gilson LC3D system fitted with a 21.2 mm×250 mm C8 column. Ramps were optimized for each compound with a CH$_3$CN/H$_2$O solvent system. Melting points were determined on a Mel-Temp apparatus and are uncorrected. All reactions were performed in septum-sealed flasks under a slight positive pressure of argon, unless otherwise noted. All commercial reagents were used as received from their respective suppliers with the following exceptions: tetrahydrofuran (THF) was distilled from sodium-benzophenone ketyl prior to use; dichloromethane (CH$_2$Cl$_2$) was distilled from calcium hydride prior to use; anhydrous lithium chloride was prepared by heating at 110° C. under vacuum overnight. Mass spectra, both low and high resolution, were measured using either electrospray (EI) or fast atom bombardment (FAB) ionization techniques.

The following abbreviations are used herein: Et$_2$O (diethyl ether); DMF (N,N-dimethylformamide); DMSO (dimethylsulfoxide); MeOH (methanol); EtOH (ethanol); EtOAc (ethyl acetate); Ac (acetyl); Hex (hexane); Me (methyl); Et (ethyl); Ph (phenyl); DIEA (diisopropylethylamine); TFA (trifluoroacetic acid); DTT (dithiothreitol); and THF (tetrahydrofuran); and (precipitate); min. or min (minutes); h (hours).

Solid-phase syntheses were performed by immobilizing reagents with Rink amide linkers (Rink, *Tetrahedron Letters* (1987) 28:3787), which are standard acid-cleavable linkers that upon cleavage generate a free carboxamide group. Small-scale solid-phase syntheses, e.g., about 2–5 μmole, were performed using Chiron SynPhase® polystyrene O-series crowns (pins) derivatized with Fmoc-protected Rink amide linkers. For larger scale (e.g., greater than about 100 μmole) syntheses, the Rink amide linkages were formed to Argonaut Technologies Argogel® resin, a grafted polystyrene-poly(ethylene glycol) copolymer. Any suitable resin may be used as the solid phase, selected from resins that are physically resilient and that, other than with regard to the linking and cleavage reactions, are inert to the synthetic reaction conditions.

Example 1

6-Cyclopentyl-6-[2-(4-hydroxyphenyl)ethyl]dihydropyran-2,4-dione

Step 1: 3-(4-Hydroxyphenyl)propionic acid methyl ester

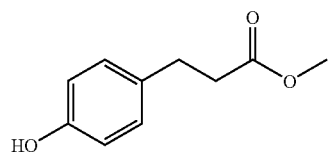

A solution of HCl in dioxane (4.0 M, 7.4 mL) was added to a solution of 4-hydroxyphenylpropionic acid (15.0 g, 90.3 mmol) in MeOH (500 mL). The reaction mixture was stirred overnight and then evaporated. The residue was evaporated from benzene (2×50 mL) to provide the product as an oil, which was used without further purification.

Step 2: 3-(4-Benzyloxyphenyl)propionic acid methyl ester

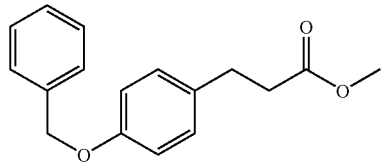

Benzyl bromide (12.9 mL, 108 mmol), K$_2$CO$_3$ (15.0 g, 109 mmol) and the 3-(4-hydroxyphenyl)propionic acid methyl ester from step 1 above were combined in acetone (300 mL) and refluxed 40 h. The crude reaction mixture was filtered and the cake washed with acetone (2×100 mL). The filtrate was evaporated and the residue was triturated with MeOH (50 mL, 6 mL, 4 mL) to provide the product as a solid, which was used without further purification.

Step 3: 3-(4-Benzyloxyphenyl)propionic acid

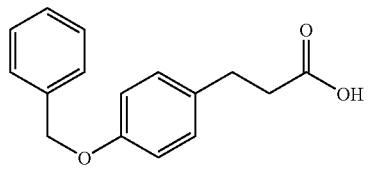

An aqueous solution of NaOH (1 M, 270 mL) was added to a mixture of the 3-(4-benzyloxyphenyl)propionic acid methyl ester from step 2 above in MeOH (600 mL), and the reaction was stirred overnight. The crystalline ppt was collected by filtration, air dried and then partitioned between EtOAc/Et$_2$O/1 M HCl (500 mL, 250 mL, 150 mL). The organic phases were dried over MgSO$_4$ and evaporated to give the product as a white solid (16.2 g, 70%, 3 steps). $^1$H NMR (CDCl$_3$): δ 2.61–2.68 (m, 2H), 2.86–2.93 (m, 2H), 5.03 (s, 2H), 6.88–6.93 (m, 2H), 7.10–7.15 (m, 2H), 7.28–7.45 (m, 5H).

Step 4: 3-(4-Benzyloxyphenyl)thiopropionic acid S-pyridin-2-yl ester

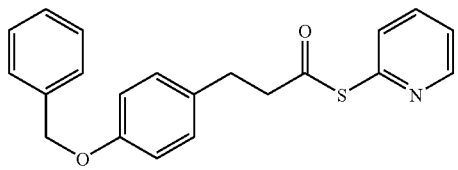

In this step, 3-(4-Benzyloxyphenyl)propionic acid (5.40 g, 21.1 mmol) from step 3 above, triphenylphosphine (7.18 g, 27.4 mmol) and 2,2'-dipyridyl disulfide (5.80 g, 26.3 mmol) were combined successively in CH$_2$Cl$_2$ (24 mL). The reaction mixture was stirred 1 h and then loaded directly onto a column for purification by flash chromatography (33% EtOAc in hexanes) to give a residue. This residue was washed with hexanes (20 mL) and the solid, partially crystalline material was collected by filtration and air dried to give the product (7.11 g, 97%). ¹H NMR (CDCl₃) δ 2.98 (s, 4H), 5.04 (s, 2H), 6.88–6.94 (m, 2H), 7.10–7.16 (m, 2H), 7.25–7.45 (m, 6H), 7.57–7.60 (m, 1H), 7.70–7.77 (m, 1H), 8.60–8.64 (m, 1H).

Step 5: 3-(4-Benzyloxyphenyl)-1-cyclopentylpropan-1-one

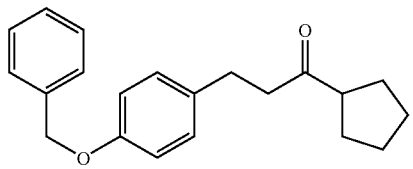

In this step, 3-(4-Benzyloxyphenyl)thiopropionic acid S-pyridin-2-yl ester (3.00 g, 8.58 mmol) from step 4 above was dissolved in dry THF (45 mL) and cooled to −78° C. A solution of cyclopentylmagnesium bromide in Et₂O (2.0 M, 4.51 mL, 9.02 mmol) was added dropwise along the sides of the reaction vessel. After stirring 35 min, the cooling bath was removed. The reaction mixture was quenched with saturated aq. NH₄Cl upon reaching ambient temperature and extracted with Et₂O (500 mL). The organic phase was washed with brine (50 mL), dried over MgSO₄ and evaporated. The residue was purified by flash column chromatography (10% EtOAc in hexanes) to give the product (2.22 g, 84%) as a white semi-crystalline material. ¹H NMR (CDCl₃): δ1.48–1.83 (m, 8H), 2.69–2.77 (m, 2H), 2.79–2.88 (m, 3H), 5.03 (s, 2H), 6.86–6.92 (m, 2H), 7.07–7.12 (m, 2H), 7.28–7.45 (m, 5H).

Step 6: 6-[2-(4-Benzyloxyphenyl)ethyl]-6-cyclopentyldihydropyran-2,4-dione

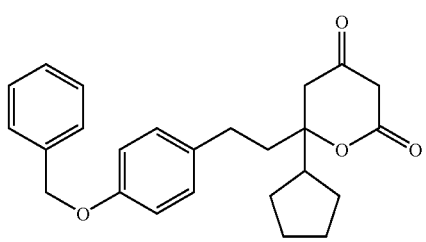

Methylacetoacetate (1.63 mL, 15.1 mmol) was dissolved in dry THF (42 mL) and cooled to 0° C. NaH (60% in mineral oil, 0.604 g, 15.1 mmol) was carefully added and the reaction mixture was stirred for 20 min. A solution of BuLi in hexanes (1.6 M, 9.44 mL, 15.1 mmol) was added dropwise and the resulting mixture was stirred an additional 20 min. A solution of 3-(4-benzyloxyphenyl)-1-cyclopentylpropan-1-one (2.33 g, 7.55 mmol) from step 5 above in THF (37 mL) was added dropwise. After stirring 1 hour (h), the reaction mixture was quenched with saturated aq NH₄Cl (100 mL) and extracted with Et₂O (600 mL). The organic phase was dried over MgSO₄ and evaporated. The residue was then stirred overnight in a mixture of 0.1 M NaOH (370 mL) and THF (37 mL). After the addition of an aq solution of 10% aq KHSO₄ (50 mL) the resulting mixture was stirred 30 min and then extracted with Et₂O (600 mL). The organic phase was washed with brine, dried over MgSO₄ and evaporated. The residue was purified by flash column chromatography (50% EtOAc in hexanes) to give the product (1.54 g, 52%) as a white foam. ¹H NMR (CDCl₃) δ 1.39–2.04 (m, 10H), 2.21–2.33 (m, 1H), 2.56–2.67 (m, 2H), 2.76 (s, 2H), 3.41 (s, 2H), 5.03 (s, 2H), 6.87–6.93 (m, 2H), 7.02–7.08 (m, 2H), 7.28–7.44 (m, 5H).

Step 7: 6-Cyclopentyl-6-[2-(4-hydroxyphenyl)ethyl]dihydropyran-2,4-dione

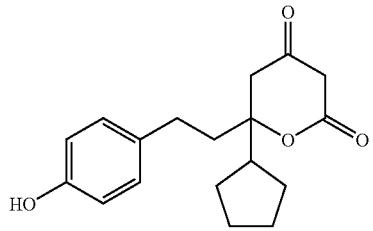

6-[2-(4-Benzyloxyphenyl)ethyl]-6-cyclopentyldihydropyran-2,4-dione (0.563 g, 1.43 mmol) from step 6 above and palladium (10% on activated carbon, 0.170 g) were combined in THF (20 mL) and stirred 16 h under an atmosphere of hydrogen. The reaction mixture was filtered and the filtrate evaporated to give a residue, which was purified by flash column chromatography (67% EtOAc in hexanes) to give the title compound (0.316 g, 73%) as a foam. ¹H NMR (CDCl₃): δ 1.42–2.00 (m, 10H), 2.23–2.32 (m, 1H), 2.52–2.70 (m, 2H), 2.77 (s, 2H), 3.42 (s, 2H), 5.88 (br s, 1H), 6.74–6.80 (m, 2H), 6.96–7.03 (m, 2H); HRMS calcd for C₁₈H₂₂O₄ (M+Na⁺) 325.1410. found 325.1404.

Example 2

6-Cyclopentyl-6-(2-napthalen-1-ylethyl)dihydropyran-2,4-dione

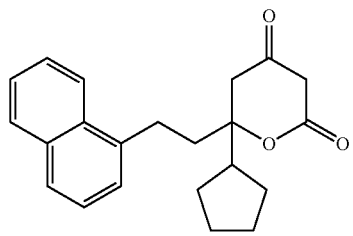

The title compound was prepared as described in steps 4, 5 and 6 of Example 1, ecept substituting cyclopentanecarboxylic acid for 3-(4-benzyloxyphenyl)-propionic acid in step 4 and 2-(1-napthyl)ethyl magnesium bromide for cyclopentylmagnesium bromide in step 5 of that Example. ¹H NMR (DMSO-d₆) (approx. 1:1 distribution of tautomers): δ 1.28–1.43 (m, 2H), 1.46–1.63 (m, 10H), 1.65–1.77 (m, 4H), 1.96–2.06 (m, 4H), 2.41–2.70 (m, 6H), 3.02–3.12 (m, 4H), 3.33 (s, 2H), 5.01 (s, 1H), 7.32–7.44 (m, 4H), 7.46–7.56 (m, 4H), 7.74–7.79 (m, 2H), 7.88–7.98 (m, 4H), 11.39 (s, 1H); HRMS calcd for C₂₂H₂₄O₃ (M+H⁺) 337.1804. found 337.1818.

Example 3

6-Cyclopentyl-6-[2-(4-hydroxyphenyl)ethyl]dihydropyran-2,4-dione

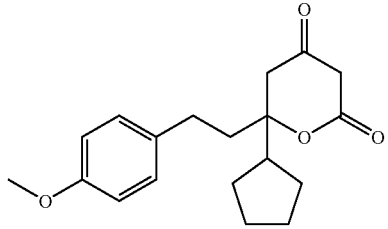

The title compound was prepared as described in steps 4, 5 and 6 of Example 1, except substituting 3-(4-methoxyphenyl)propionic acid for 3-(4-benzyloxyphenyl) propionic acid in step 4 of that Example. $^1$H NMR (DMSO-d$_6$) (approx. 1:1 distribution of tautomers): δ 1.25–1.70 (m, 16H), 1.82–1.91 (m, 4H), 2.25–2.38 (m, 2H), 2.39–2.61 (m, 8H), 3.33 (s, 2H), 3.69 (s, 6H), 4.97 (s, 1H), 6.79–6.85 (m, 4H), 7.04–7.11 (m, 4H), 11.32 (s, 1H); HRMS calcd for C$_{19}$H$_{24}$O$_4$ (M+H$^+$) 317.1753. found 317.1747.

Example 4

6-Cyclopentyl-6-[2-(2-methoxyphenyl)ethyl]dihydropyran-2,4-dione

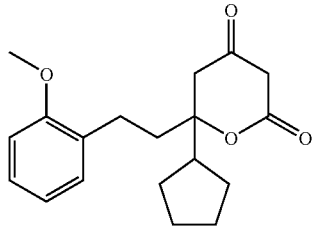

The title compound was prepared as described in steps 4, 5 and 6 of Example 1, except substituting 3-(2-methoxyphenyl)propionic acid for 3-(4-benzyloxyphenyl)propionic acid in step 4 of that Example. $^1$H NMR (CDCl$_3$): δ 1.37–1.50 (m, 1H), 1.53–2.05 (m, 9H), 2.30–2.42 (m, 1H), 2.55–2.74 (m, 2H), 2.73 (d, 1H, J=16.3), 2.80 (d, 1H, J=16.3), 3.41 (s, 2H), 3.80 (s, 3H), 6.81–6.91 (m, 2H), 7.06–7.10 (m, 1H), 7.16–7.24 (m, 1H); HRMS calcd for C$_{19}$H$_{24}$O$_4$ (M+H$^+$) 317.1753. found 317.1766.

Example 5

6-[2-(2-Allyloxymethylphenyl)ethyl]-6-cyclopentyldihydropyran-2,4-dione

Step 1: (2-Allyloxymethylphenyl)methanol

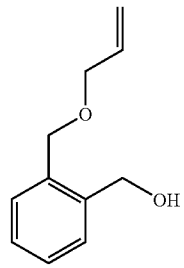

The title compound was prepared as described in the following reference: *Journal of the American Chemical Society*, 8826–8837 (1997).

Step 2: 1-Allyloxymethyl-2-bromomethylbenzene

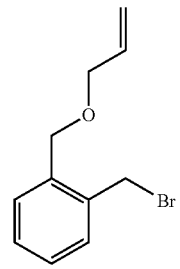

(2-Allyloxymethylphenyl)methanol (1.06 g, 5.95 mmol) from step 1 above, triphenylphosphine (1.87 g, 7.13 mmol) and carbon tetrabromide (2.37 g, 7.15 mmol) were combined successively in dry THF (27 mL) and stirred 1 h. Hexanes (27 mL) were added and the mixture was filtered. The filter cake was washed with hexanes (20 mL) and the combined filtrates were evaporated to provide a residue, which was purified by flash column chromatography (5% EtOAc in hexanes) to yield the product (1.15 g, 80%) as a clear, colorless liquid. $^1$H NMR (CDCl$_3$): δ 4.06–4.10 (m, 2H), 4.64 (s, 2H), 4.66 (s, 2H), 5.21–5.27 (m, 1H), 5.30–5.38 (m, 1H), 5.91–6.06 (m, 1H), 7.28–7.40 (m, 4H).

Step 3: 3-(2-Allyloxymethylphenyl)propionic acid tert-butyl ester

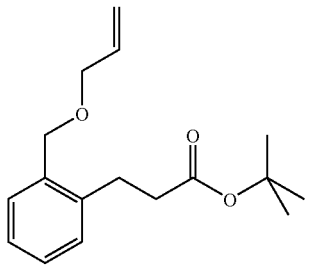

A solution of N-isopropylcyclohexylamine (0.606 mL, 3.68 mmol) in dry THF (22 mL) was cooled to −78° C. A solution of n-butyllithium (1.6 M in hexanes, 2.30 mL, 3.68 mmol) was added. The reaction mixture was stirred 45 min at −78° C. then allowed to warm to −10° C. for 2 min and then cooled again to −78° C. at which point tert-butyl acetate (0.496 mL, 3.68 mmol) was added. After stirring an additional 20 min, this reaction mixture was cannulated into a −78° C. solution of 1-allyloxymethyl-2-bromomethylbenzene (0.888 g, 3.68 mmol) from step 2 above in dry THF (10 mL). The resulting reaction mixture was maintained at −78° C. for 40 min and then quenched by the addition of aq. NH$_4$Cl (50 mL). The resulting mixture was extracted with MTBE (200 mL). The organic phase was washed with brine, dried over MgSO$_4$ and evaporated. The residue was purified by flash column chromatography (12% EtOAc in hexanes) to yield the product (0.700 g, 69%) as an oil. $^1$H NMR (CDCl$_3$) δ 1.43 (s, 9H), 2.50–2.58 (m, 2H), 2.92–2.99 (m, 2H), 4.04–4.07 (m, 2H), 4.54 (s, 2H), 5.18–5.24 (m, 1H), 5.28–5.36 (m, 1H), 5.90–6.04 (m, 1H), 7.16–7.36 (m, 4H). Anal. Calcd. For C$_{17}$H$_{24}$O$_3$: C, 73.88; H, 8.75. Found: C, 73.49; H, 8.76.

Step 4: 3-(2-Allyloxymethylphenyl)propionic acid

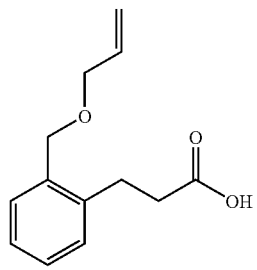

3-(2-Allyloxymethylphenyl)propionic acid tert-butyl ester (0.685 g, 2.48 mmol) from step 3 above was dissolved in a solution of TFA (7 mL) and CH$_2$Cl$_2$ (7 mL), then stirred overnight. After evaporation of the volatiles, the residue was evaporated from toluene to provide the product (0.545 g, 100%) as a partially crystalline solid which was used without further purification.

Step 5: 6-[2-(2-Allyloxymethylphenyl)ethyl]-6-cyclopentyldihydropyran-2,4-dione

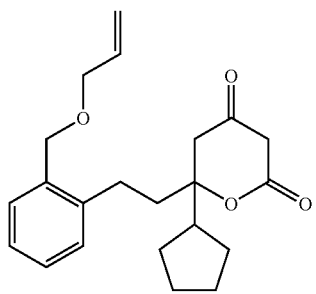

The title compound was prepared as described in steps 4, 5 and 6 of Example 1 using 3-(2-allyloxymethylphenyl) propionic acid from step 4 above for 3-(4-benzyloxyphenyl) propionic acid in step 4 of that Example. $^1$H NMR (CDCl$_3$) δ 1.41–2.07 (m, 10H), 2.27–2.40 (m, 1H), 2.71–2.80 (m, 4H), 3.39 (d, 1H, J=21.2), 3.49 (d, 1H, J=21.2), 4.00–4.04 (m, 2H), 4.44 (d, 1H, J=11.4), 4.52 (d, 1H, J=11.4), 5.19–5.24 (m, 1H), 5.26–5.34 (m, 1H), 5.88–6.02 (m, 1H), 7.12–7.32 (m, 4H). Anal. Calcd. For C$_{22}$H$_{28}$O$_4$.0.15 H$_2$O: C, 73.57; H, 7.94. Found: C, 73.54; H, 7.97.

Example 6

6-Cyclopentyl-6-[2-(2-hydroxymethylphenyl)ethyl]dihydropyran-2,4-dione

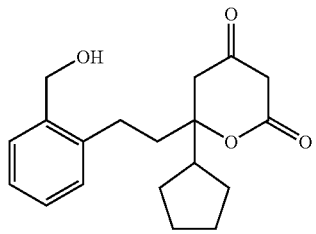

p-Toluenesulfinic acid (0.101 g, 0.647 mmol) was added to a solution of tetrakis(triphenylphosphine)palladium(0) (0.075 g, 0.065 mmol) and 6-[2-(2-allyloxymethylphenyl) ethyl]-6-cyclopentyldihydropyran-2,4-dione (0.154 g, 0.432 mmol) prepared as described in the final step of Example 5 in CH$_2$Cl$_2$ (7 mL). After stirring 40 min, the reaction mixture was loaded directly onto a column for purification by flash column chromatography (4% MeOH in CHCl$_3$) to yield the title compound (0.106 g, 77%) as faintly yellow foam. $^1$H NMR (CDCl$_3$) δ 1.37–2.09 (m, 11H), 2.31–2.44 (m, 1H), 2.68–2.86 (m, 4H), 3.38 (d, 1H, J=21.3), 3.49 (d, 1H, J=21.3), 4.63 (d, 1H, J=11.9), 4.69 (d, 1H, J=11.9), 7.12–7.33 (m, 4H). Anal. calcd. for C$_{19}$H$_{24}$O$_4$.0.7 H$_2$O: C, 69.36; H, 7.78. found: C, 69.12; H, 7.40.

Example 7

2-[2-(2-Cyclopentyl-4,6-dioxo-tetrahydro-pyran-2-yl)-ethyl]-5-methoxy-benzonitrile Step 1: 1-Cyclopentyl-3-trimethylsilanyl-propynone

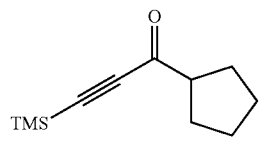

The title compound was prepared as described in the following reference: J. of Org. Chem., 106, 4786–4800 (1984). $^1$H NMR (CDCl$_3$): δ 0.24 (s, 9H), 1.63 (m, 4H), 1.90 (m, 4H), 2.92 (pentet, 1H, J=8.2 Hz).

Step 2: 1-Cyclopentyl-3-trimethylsflanyl-prop-2-yn-1-ol

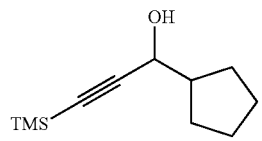

A solution of 1-cyclopentyl-3-trimethylsilanyl-propynone (1.20 g, 6.182 mmol) from step 1 above, CeCl$_3$.7H$_2$O (2.99 g, 8.037 mmol), and methanol (20 mL), were premixed for 15 minutes. To this solution, at room temperature, was added a solution of NaBH$_4$ (0.701 g, 18.546 mmol) dissolved in MeOH (20 mL), over 15 minutes. After stirring for 35 minutes at room temperature the reaction was complete by TLC (15% EtOAc/Hex; KMnO$_4$). The reaction was quenched with saturated NH$_4$Cl aq. (50 ml), acidified to pH 1 with 1N HCl aq., stripped of methanol, and extracted with Et$_2$O. The Et$_2$O layer was further extracted with 1N HCL aq., 1 N NaHCO$_3$, brine, dried with MgSO$_4$, giving 1.47 g of product that was used without further purification. $^1$H NMR (CDCl$_3$): δ 0.17 (s, 9H), 1.5.6 (m, 4H), 1.78 (m, 4H), 2.17 (m, 1H), 4.22 (d, 1H).

Step 3: 1-Cyclopentyl-prop-2-yn-1-olone

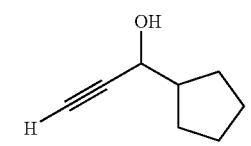

1-Cyclopentyl-3-trimethylsilanyl-prop-2-yn-1-ol (1.35 g, 7.04 mmol) from step 2 above, was added to a solution of K$_2$CO$_3$ (97 mg, 0.704 mmol) dissolved in 80 ml of 10% aq.

MeOH. After stirring overnight at room temperature, TLC (15% EtOAc/Hex; KMnO₄) showed product at 0.25 Rf. The reaction was concentrated, diluted with Et₂O, extracted with 1N HCL aq., 1N NaHCO₃, brine, dried with MgSO₄ giving 0.821 g (94% yield) of product that was used without further purification. ¹H NMR (CDCl₃): δ 1.45 (m, 2H), 1.60 (m, 4H), 1.81 (m, 2H), 2.19 (m, 1H), 2.43 (s, 1H), 4.24 (bs, 1H).

Step 4: 2-(3-Cyclopentyl-3-hydroxy-prop-1-ynyl)-5-methoxy-benzonitrile

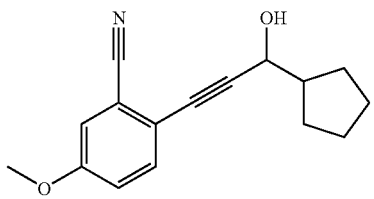

A 25 mL Schlenk tube under argon was charged with 2-bromo-5-methoxy-benzonitrile (210.92 mg, 1.00 mmol) from step 3 above, Pd(PhCN)₂Cl₂(II) (11.5 mg, 0.03 mmol), and CuI (3.8 mg, 0.02 mmol), vacuum flushed with argon (3×), then charged with 1-Cyclopentyl-prop-2-yn-1-olone (145.3 mg, 1.2 mmol), dioxane (1.0 mL; dry), P(t-Bu)₃ (250 μL of a 10% by weight solution in hexanes, 0.62 mmol), and diisopropylamine (170 μL, 1.2 mmol). The resulting mixture darkened immediately. After stirring overnight, TLC (25% EtOAc/Hex; KMnO₄) showed no starting material. The reaction was filtered through a plug of silica, eluted with EtOAc, then concentrated and chromatographed on silica using a gradient of 20% to 25% ethylacetate in hexanes. This product was further purified from a co-polar impurity by chromatographing on silica eluted with a gradient of 100% CH₂CL₂ to 7.5% CH₃CN/CH₂CL₂, giving 107 mg of product (42% yield for three steps). ¹H NMR (CDCl₃): δ 1.63 (m, 6H), 1.87 (m, 2H), 1.99 (d, 1H), 2.32 (m, 1H), 3.84 (s, 3H), 4.51 (t, 1H), 7.06 (dd, J=2.6, 8.7 Hz, 1H), 7.12 (d, J=2.6 Hz, 1H), 7.45 (d, J=8.6 Hz, 1H).

Step 5: 2-(3-Cyclopentyl-3-hydroxy-propyl)-5-methoxy-benzonitrile

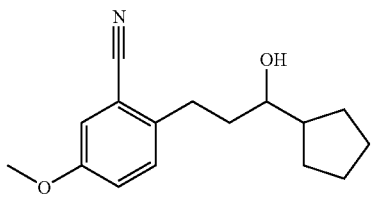

A solution of 2-(3-cyclopentyl-3-hydroxy-prop-1-ynyl)-5-methoxy-benzonitrile (296 mg, 1.161 mmol) from step 4 above was dissolved in EtOH (4.0 mL), placed under an argon atmosphere, charged with 10% Pd/C (120 mg), then vacuum flushed with hydrogen gas from a balloon. After stirring for 1 h TLC (25% EtOAc/Hex; UV or KMnO₄) showed clean conversion to the product. The reaction mixture was filtered through a fine frit, and concentrated to give 291 mg (97% mass recovery) of product that was used without further purification. ¹H NMR (CDCl₃): δ 1.18 (m, 1H), 1.34 (m, 1H), 1.45 to 1.97 (b m, 9H), 2.92 (m, 2H), 3.43 (bs, 1H), 2.32 (m, 1H), 3.81 (s, 3H), 7.04 (d, J=2.9 Hz, 1H), 7.08 (m, 1H), 7.25 (d, J=8.4 Hz, 1H). ESIMS (M+Na⁺): 282.2.

Step 6: 2-(3-Cyclopentyl-3-oxo-propyl)-5-methoxy-benzonitrile

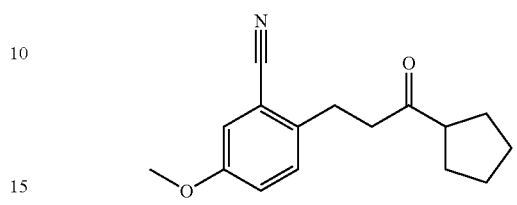

A solution of 2-(3-cyclopentyl-3-hydroxy-propyl)-5-methoxy-benzonitrile (277 mg, 1.07 mmol) from step 5 above, IBX (750 mg, 2.68 mmol), and DMSO (4.0 mL), were stirred in a 40° C. oil bath. After stirring for 6 h TLC (10% EtOAC/Hex; UV) showed no starting material. The reaction was diluted EtOAc (to precipitate IBX), filtered, extracted with water, and brine, then dried with MgSO₄, and concentrated. The resulting material was chromatographed (10% EtOAC/Hex), giving 239 mg of the product (88% yield). ¹H NMR (CDCl₃): δ 1.48 to 1.84 (bm, 8H), 2.81 (m, 3H), 3.05 (t, J=7.4 Hz, 2H), 3.80 (s, 3H), 7.04 (dd, J=2.8, 8.4 Hz, 1H), 7.09 (d, J=3.2 Hz, 1H), 7.25 (d, J=8.9 Hz, 1H). ESIMS (M+Na⁺): 280.1.

Step 7: 7-(2-Cyano-4-methoxy-phenyl)-5-cyclopentyl-5-hydroxy-3-oxo-heptanoic acid methyl ester

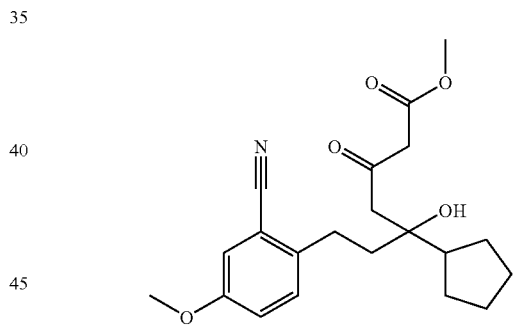

To a mixture of NaH (12 mg, 0.50 mmol), in THF (1.5 mL) at 0° C. under argon, was added methylacetoacetate (54, 0.50 mmol) slowly over 5 minutes. After stirring for an additional 5 min at 0° C., BuLi (0.2 mL, 0.50 mmol, 2.5 M in hexanes) was added dropwise over 5 minutes, then stirred for an additional 5 min. The resulting dianion was cooled to −78° C., where 2-(3-Cyclopentyl-3-oxo-propyl)-5-methoxy-benzonitrile (63.3 mg, 0.25 mmol) dissolved in THF (1.0 mL) was added dropwise over 2 minutes. After stirring for 1 h at −78° C., the reaction was quenched with saturated NH₄Cl at −35° C., then extracted with ethylacetate. The organic layer was washed with NaHCO₃, brine, and dried with MgSO₄. This material was used without further purification. ¹H NMR (CDCl₃): δ1.36 to 1.90 (bm, 9H), 1.97 (m, 2H), 2.34 (m, 1H), 2.80 (s, 2H), 2.87 (m, 2H), 3.46 (s, 2H), 3.81 (s, 3H), 7.07 (m, 2H), 7.19 (d, J=8.4 Hz, 1H). Anal. Calcd. For C₂₀H₂₃N₁O₄·0.45 H₂O: C, 68.73; H, 6.89; N, 4.01. Found: C, 68.70; H, 6.95; N, 3.71. ESIMS (M+Na⁺): 364.1.

Step 8: 2-[2-(2-Cyclopentyl-4,6-dioxo-tetrahydro-pyran-2-yl)-ethyl]-5-methoxy-benzonitrile

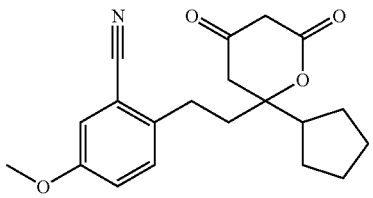

A solution of 7-(2-Cyano-4-methoxy-phenyl)-5-cyclopentyl-5-hydroxy-3-oxo-heptanoic acid methyl ester (75 mg, 0.20 mmol, from step 7 above), and bis(dibutylchlorotin)oxide (7.0 mg, 0.0125 mmol), dissolved in toluene (4.0 mL) were heated at reflux for 1 h, at which time TLC (50% ethyl acetate/hexanes) indicated that all starting material had been consumed. The resulting mixture was concentrated and purified by silica gel chromatography, giving 46 mg of product (54% yield, two steps). $^1$H NMR (CDCl$_3$): δ 1.36 to 1.90 (bm, 9H), 1.97 (m, 2H), 2.34 (m, 1H), 2.80 (s, 2H), 2.87 (m, 2H), 3.46 (s, 2H), 3.81 (s, 3H), 7.07 (m, 2H), 7.19 (d, J=8.4 Hz, 1H). Anal. Calcd. For C$_{20}$H$_{23}$N$_1$O$_4$.0.45 H$_2$O: C, 68.73; H, 6.89; N, 4.01. Found: C, 68.70; H, 6.95; N, 3.71. ESIMS (M+Na$^+$): 364.1.

Example 8

6-cyclopentyl-6-[2-(6-methoxypyridin-3-yl)ethyl]dihydro-2H-pyran-2,4(3H)-dione

Step 1: 6-[2-Cyclopentyl-2-hydroxy-4-(6-methoxy-pyridin-3-yl)-but-3-ynyl]-2,2-dimethyl-[1,3]dioxin-4-one

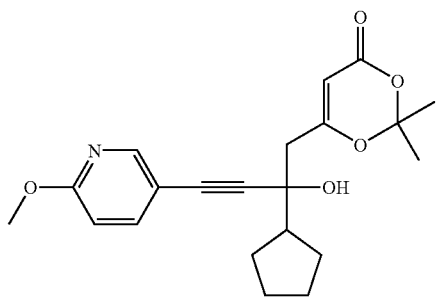

The title compound was prepared as described in to Example 84, except 5-Bromo-2-methoxy-pyridine was substituted for 4-bromoanisole in step 1 of that Example. ESIMS (M+Na$^+$): 394.43.

Step 2: 6-[2-Cyclopentyl-2-hydroxy-4-(6-methoxy-pyridin-3-yl)-butyl]-2,2-dimethyl-[1,3]dioxin-4-one To a solution of 6-[2-Cyclopentyl-2-hydroxy-4-(6-methoxy-pyridin-3-yl)-but-3-ynyl]-2,2-dimethyl-[1,3]dioxin-4-one (220 mg, 0.59 mmol), dissolved in ethanol (3.0 mL), under argon was added 10% Pd/C (70 mg). The resulting mixture was vacuum flushed with hydrogen, and then stirred under balloon pressure hydrogen for 1 hr. The reaction was vacuum flushed with argon, filtered, and purified by flash chromatography (40% EtOAc/Hex), yielding 145 mg of product (65% yield). ESIMS (M+Na$^+$): 398.20.

Step 3: 6-cyclopentyl-6-[2-(6-methoxypyridin-3-yl)ethyl]dihydro-2H-pyran-2,4(3H-dione

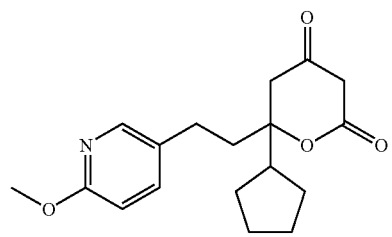

A solution of 6-[2-Cyclopentyl-2-hydroxy-4-(6-methoxy-pyridin-3-yl)-butyl]-2,2-dimethyl-[1,3]dioxin-4-one (125 mg, 0.333 mmol), and bis(dibutylchlorotin)oxide (17.5 mg, 0.033 mmol), dissolved toluene (2.0 mL), was heated in a 100° C. for 1.5 h. The resulting mixture was concentrated and purified by silica gel chromatography (40% to 60% EtOAc/hexanes gradient), giving the 80 mg of the product (76% yield). $^1$H NMR (CDCl$_3$): δ 1.41–1.84 (m, 4H), 1.95 (m, 2H), 2.23 (pentet, 1H, J=8.3 Hz), 2.73 (m, 2H), 3.57 (s, 2H), 4.02 (s, 3H), 6.88 (d, 1H, J=8.5 Hz), 7.68 (d, 1H, J=8.7 Hz), 8.21 (s, 1H). Anal Calcd. For C$_{18}$H$_{23}$N$_1$O$_4$.1.20 H$_2$O: C, 52.48; H, 5.53; N, 3.00. Found: C, 52.54; H, 5.70; N, 3.23. ESIMS (M–H$^-$): 316.1.

Example 9

6-Cyclopentyl-6-[2-(3-isopropyl-phenyl)-ethyl]-dihydro-pyran-2,4-dione

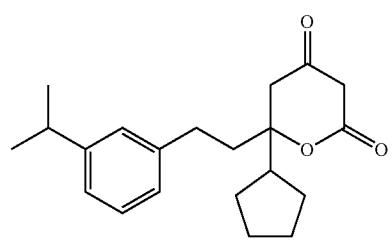

The title compound was prepared as described in Example 8, except 3-bromo-isopropyl-benzene was substituted for 5-Bromo-2-methoxy-pyridine in step 1 of that Example. $^1$H NMR (CDCl$_3$): δ 1.24 (d, 6H, J=8.5 Hz )1.40–1.75 (m, 4H), 1.99 (m, 2H), 2.29 (pentet, 1H, J=8.1 Hz), 2.66 (t, 2H, J=8.5 Hz), 2.78 (s, 2H), 2.87 (m, 1H), 3.42 (s, 3H), 6.97 (m, 2H), 7.10 (m, 1H), 7.22 (m, 1H). Anal. Calcd. For C$_{21}$H$_{28}$O$_3$.0.25 H$_2$O: C, 75.75; H, 8.63. Found: C, 75.68; H, 8.48. ESIMS (M–H$^-$): 327.2.

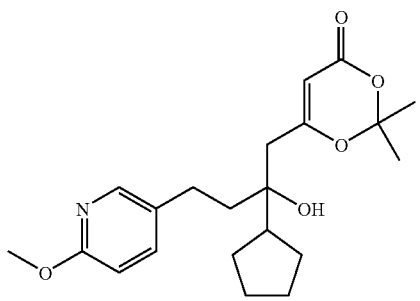

Example 10

{4-[2-(2-Cyclopentyl-4,6-dioxo-tetrahydro-pyran-2-yl)-ethyl]-phenyl}-acetic acid methyl ester

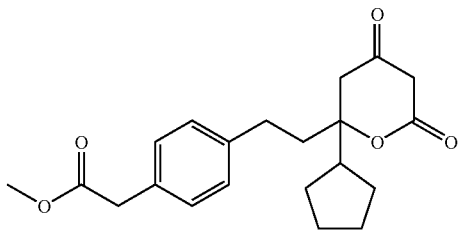

The title compound was prepared as described in Example 8, where (4-Bromo-phenyl)-acetic acid methyl ester was substituted for 5-Bromo-2-methoxy-pyridine in step 1 of that Example. $^1$H NMR (CDCl$_3$): δ 1.35–1.84 (m, 4H), 1.95 (m, 2H), 2.28 (m, 1H), 2.66 (t, 2H, J=8.7 Hz), 2.77 (s, 2H), 3.42 (s, 2H), 3.60 (s, 2H), 3.69 (s, 3H), 7.11 (d, 2H, J=7.9 Hz), 7.22 (d, 2H, J=7.9 Hz). Anal. Calcd. For C$_{21}$H$_{26}$O$_5$: C, 70.37; H, 7.31. Found: C, 70.14; H, 7.55. ESIMS (M–H$^-$): 357.2.

Example 11

6-[2-(3-tert-butyl-phenyl)-ethyl]-6-cyclopentyl-dihydro-pyran-2,4-dione

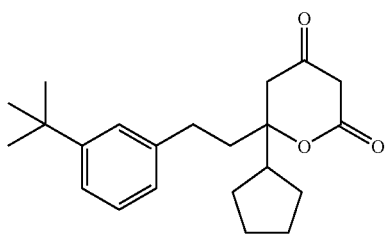

The title compound was prepared as described in Example 8, where trifluoro-methanesulfonic acid 3-tert-butyl-phenyl ester was substituted for 5-Bromo-2-methoxy-pyridine in step 1 of that Example. $^1$H NMR (CDCl$_3$): δ 1.31 (s, 9H), 1.35–1.81 (m, 4H), 1.97 (m, 2H), 2.29 (m, 1H), 2.68 (t, 2H, J=8.7 Hz), 2.78 (s, 2H), 2.86 (s, 2H), 3.42 (s, 2H), 4.08 (s, 2H), 6.96 (m, 1H), 7.15 (s, 1H), 7.23 (m, 2H). Anal. Calcd. For C$_{22}$H$_{30}$O$_3$.0.10 H$_2$O: C, 76.75; H, 8.84. Found: C, 76.89; H, 9.03. ESIMS (M–H$^-$): 341.2.

Example 12

6-Cyclopentyl-6-(2-thiazol-2-yl-ethyl)-dihydro-pyran-2,4-dione

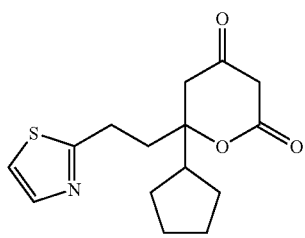

The title compound was prepared as described in Example 8, where 2-bromo-thiazole was substituted for 5-Bromo-2-methoxy-pyridine in step 1 of that Example. $^1$H NMR (CDCl$_3$): δ 1.35–1.81 (m, 4H), 2.27 (m, 3H), 2.74 (s, 2H), 3.16 (t, 2H, J=8.1 Hz), 3.46 (d, 2H, J=5.4 Hz), 7.22 (d, 1H, J=3.2 Hz), 7.67 (d, 1H, J=3.4 Hz). Anal. Calcd. For C$_{22}$H$_{30}$O$_3$.0.10 H$_2$O: C, 76.75; H, 8.84. Found: C, 76.89; H, 9.03. ESIMS (M–H$^-$): 292.1.

Example 13

2-{3-[2-(2-Cyclopentyl-4,6-dioxo-tetrahydro-pyran-2-yl)-ethyl]-phenyl}-2-methyl-propionitrile Step 1: 2-(3-Bromo-phenyl)-2-methyl-propionitrile

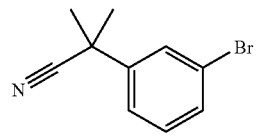

To a solution of NaH (5.06 g, 220 mmol), dissolved in DMF (200 mL) and THF (100 mL) at room temperature, was added (3-Bromo-phenyl)-acetonitrile (9.61 g, 100 mmol). The mixture became yellow, and gas was liberated as the anion formed. After 5 minutes it was necessary to cool the reaction with a room temperature water bath. After 15 minutes MeI was added slowly over 15 minutes, during which gas evolved and the reaction exothermed. The resulting mixture was stirred at room temperature for 4 hr, at which time it was quenched slowly with 1N HCl, then extracted into ether. The ether layer was washed with 1N NaHCO$_3$, brine, anddried with MgSO$_4$. The crude material was purified by high vacuum distillation, where the desired product was collected at 80° C. The mass of the product was 11.0 g (49% yield). $^1$H NMR (CDCl$_3$): δ 1.71 (s, 6H), 7.29 (m, 1H), 7.47 (m, 2H), 7.64 (s, 1H).

Step 2: 2-{3-[2-(2-Cyclopentyl-4,6-dioxo-tetrahydro-pyran-2-yl)-ethyl]-phenyl}-2-methyl-propionitrile

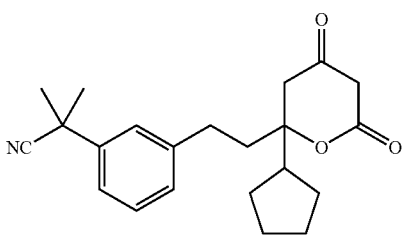

The title compound was prepared as described in Example 8, except 2-(3-Bromo-phenyl)-2-methyl-propionitrile (described above) was substituted for of 5-Bromo-2-methoxy-pyridine in step 1 of that Example. $^1$H NMR (CDCl$_3$): δ 1.35–1.81 (m, 4H), 1.72 (s, 6H), 1.97 (m, 2H), 2.29 (m, 1H), 2.72 (t, 2H, J=8.5 Hz), 2.78 (s, 2H), 3.44 (s, 2H), 7.11 (m, 1H), 7.25 (m, 2H), 7.31 (m, 2H). Anal. Calcd. For C$_{22}$H$_{27}$NO$_3$.0.90 H$_2$O: C, 71.48; H, 7.85; N, 3.79. Found: C, 71.88; H, 7.68; N, 3.25. ESIMS (M–H$^-$): 352.3.

Example 14

(2-{3-[2-(2-Cyclopentyl-4,6-dioxo-tetrahydro-pyran-2-yl)-ethyl]-phenyl}-2-methyl-propyl)-carbamic acid tert-butyl ester Step 1: [2-(3-Bromo-phenyl)-2-methyl-propyl]-carbamic acid tert-butyl ester

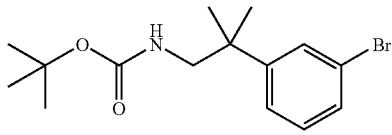

2-(3-Bromo-phenyl)-2-methyl-propionitrile (6.05 g, 48.8 mmol, described in step 1 of Example 13) was slowly added to a solution of lithium aluminum hydride (2.78 g, 73.2 mmol) slurried in THF (100 ml). The mixture was stirred for 48 h, and then treated with (BOC)$_2$O (12.8 g, 58.6 mmol), and stirred an additional 2 h at room temperature. The reaction was diluted with ether, then quenched with 1N HCl. The ether layer was extracted with 1N NaOH, dried with brine and MgSO$_4$, then purified by silica gel chromatography (10% to 12.5% EtOAc/hexanes), giving the product as an oil (2.78 g, 17%). $^1$H NMR (CDCl$_3$): δ 1.30 (s, 6H), 1.40 (s, 9H), 3.32 (d, 2H, J=6.4 Hz), 7.23 (m, 2H), 7.34 (m, 1H), 7.47 (s, 1H).

Step 2: (2-{3-[2-(2-Cyclopentyl-4,6-dioxo-tetrahydro-pyran-2-yl)-ethyl]-phenyl}-2-methyl-propyl)-carbamic acid tert-butyl ester

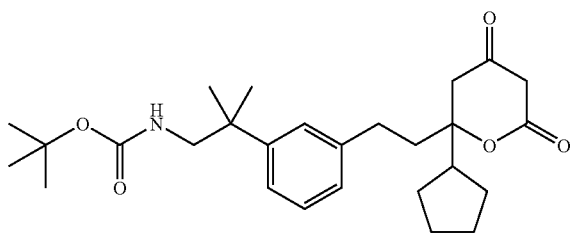

The title compound was prepared as described in Example 8, except [2-(3-Bromo-phenyl)-2-methyl-propyl]-carbamic acid tert-butyl ester (described above) was substituted for of 5-Bromo-2-methoxy-pyridine in step 1 of that Example. $^1$H NMR (CDCl$_3$): δ 1.30 (s, 6H), 1.39 (s, 9H), 1.40–1.80 (m, 4H), 2.00 (m, 2H), 2.29 (m, 1H), 2.68 (t, 2H, J=8.3 Hz), 2.78 (s, 2H), 3.331 (d, 2H J=6.3 Hz), 3.43 (s, 2H), 4.41 (bs, 1H), 6.99 (m, 1H), 7.11 (m, 1H), 7.21 (s, 1H), 7.24 (s, 1H). Anal. Calcd. For C$_{27}$H$_{39}$NO$_5$.0.50 H$_2$O: C, 69.50; H, 8.64; N, 3.00. Found: C, 69.65; H, 8.42; N, 3.02. ESIMS (M−H$^-$): 465.2.

Example 15

6-Cyclopentyl-4-hydroxy-6-indan-1-ylmethyl-5,6-dihydro-pyran-2-one

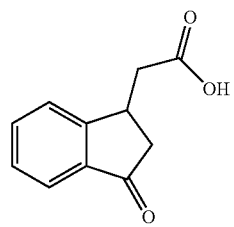

The title compound was prepared as described in the following reference: *J. Amer. Chem. Soc.*, 114, 2181–2187 (1992). $^1$H NMR (DMSO): δ 2.37–2.45 (m, 2H), 2.86–2.95 (m, 2H), 3.66–3.75 (m, 1H), 7.42–7.48 (m, 1H), 7.63–7.71 (m, 3H). IR (cm$^{-1}$) 3442, 1647.

Step 2: Indan-1-yl-acetic acid

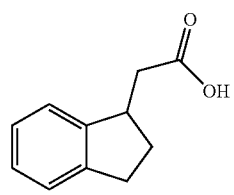

Zinc (20.40 g, 312 mmol) was shaken with HgCl$_2$ (2.12 g, 78 mmol) in water (30 mL) and concentrated HCl (2 mL) for 10 min. The liquid was decanted, and water (15 mL), concentrated HCl (30 mL), toluene (18 mL) and (3-Oxo-indan-1-yl)-acetic acid (7.5 g, 39 mmol) were added. The mixture was refluxed for 5 days with a portion of concentrated HCl (5 mL) being added daily. After cooling, the layers were separated, and the aqueous layer was extracted with ether (2×150 mL). The combined organic layers were extracted with 3N NaOH (2×200 mL). The basic extract was acidified with concentrated HCl and extracted with ether (3×200 mL). The combined organic layers were dried over MgSO$_4$, concentrated and purified by flash column chromatography (2% CH$_3$OH in CH$_2$Cl$_2$) to afford 5.56 g of product (81%) as a white solid. $^1$H NMR (CDCl$_3$): δ 1.76–1.88 (m, 1H), 2.42–2.58 (m, 2H), 2.78–3.05 (m, 1H), 3.59–3.69 (m, 1H), 7.20–7.30 (m, 4H). IR (cm$^{-1}$) 3421,1636,1436.

Step 3: Indan-1-yl-thioacetic acid S-Phenyl ester

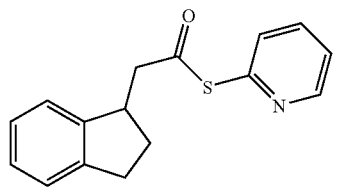

To a solution of indan-1-yl-acetic acid (5.56 g, 31.6 mmol) in CH$_2$Cl$_2$ was added Ph$_3$P (10.8 g, 41.08 mmol) and 2,2'-Dithiodipyridine (8.70 g, 39.5 mmol). The reaction mixture was stirred at room temperature for 4 h, and then partitioned between water (200 mL) and CH$_2$Cl$_2$ (2×200 mL). The combined organic layers were dried over MgSO$_4$ and concentrated. The residue was purified by flash column chromatography (20% EtOAc in hexane) to afford 6.37 g of product (79%) as yellow oil. $^1$H NMR (CDCl$_3$): δ 1.81–1.93 (m, 1H), 2.40–2.51 (m, 1H), 2.84–3.05 (m, 3H), 3.19–3.26 (m, 1H), 3.69–3.79 (m, 1H), 7.20–7.36 (m, 4H), 7.67–7.72 (m, 1H), 7.77–7.83 (m, 1H), 8.67–8.69 (m, 1H). IR (cm$^{-1}$) 3420, 1698, 1418.

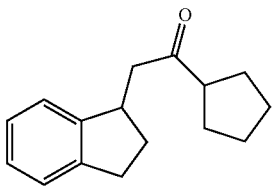

To a solution of indan-1-yl-thioacetic acid S-phenyl ester (3.26 g, 12.8 mmol) was slowly added cyclopentylmagnesium bromide (8.9 mL, 17.9 mmol) at −78° C. The reaction was stirred at −78° C. for 20 min. The reaction mixture was quenched with saturated NH₄Cl (150 mL) and extracted with diethyl ether (2×150 mL). The combined organic layers were washed with brine, dried over MgSO₄ and concentrated. The residue was purified by flash column chromatography (5% EtOAc in hexanes) to afford 2.4 g of product (82%) as pale yellow oil. ¹H NMR (CDCl₃): δ 1.58–1.89 (m, 10H), 2.37–2.48 (m, 1H), 2.63–2.74 (m, 1H), 2.86–2.99 (m, 3H), 3.64–3.74 (m, 1H), 7.16–7.32 (m, 4H). IR (cm⁻¹) 2851, 1707, 1457.

Step 5: 6-Cyclopentyl-4-hydroxy-6-indan-1-ylmethyl-5,6-dihydro-pyran-2-one

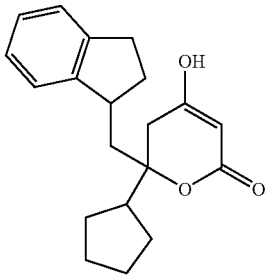

The title compound was prepared from as described in Example 1, except 1-cyclopentyl-2-(2,3-dihydro-1H-inden-1-yl)ethanone (described in step 4 above) was substituted for 3-(4-benzyloxyphenyl)-1-cyclopentylpropan-1-one in step 6 of that Example. ¹H NMR (CDCl₃): (mixture of diastereomers and enantiomers) δ 1.55–1.92 (m), 2.28–2.62 (m), 2.81–3.03 (m), 3.21–3.28 (m), 3.30–3.42 (m), 3.46 (s), 7.14–7.26 (m); Anal. Calcd. For C₂₀H₂₄O₃.0.25 H₂O: C, 75.80; H, 7.79. Found: C, 75.75; H, 7.72. IR (cm⁻¹) 2953, 1660, 1219.

Example 16

6-Cyclopentyl-4-hydroxy-6-[2-(3-methoxy-phenyl)-ethyl]-5,6-dihydropyran-2-one

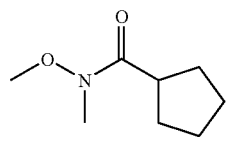

To a solution of cycopentylcarboxylic acid (15 mL, 138.4 mmol) and NMM (30.4 mL. 276.8 mmol) cooled at −10° C. were added isobutyl chloroformate (18 mL, 138.4 mmol). The reaction mixture was stirred at −10° C. for 30 min and N,O-dimethylhydroxylamine hydrochloride (13.8 g, 138.4 mmol) was added. The reaction was stirred and warmed to room temperature for 3 h, and then poured into water (200 mL), extracted with EtOAc (2×200 mL), dried over Mg SO₄ and concentrated. The residue was purified by flash column chromatography (30% EtOAc in hexane) to afford 19.11 g of product (88%) as colorless oil. ¹H NMR (CDCl₃): δ 1.56–1.68 (m, 3H), 1.71–1.90 (m, 5H), 3.12 (m, 1H), 3.22 (s, 3H), 3.73 (s, 3H). IR (cm⁻¹) 1637.

Step 2: (3-Methoxy-phenylethynyl)-trimethyl-silane

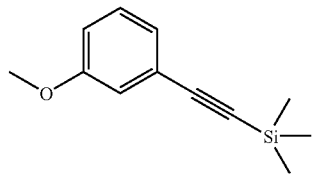

To a flask containing Pd(PhCN)₂Cl₂ (0.272 g, 0.708 mmol, 0.06) and CuI (0.090 g, 0.472 mmol) in dioxane was purged with argon for 30 minutes P(tBu)₃ (2.87 mL of 0.494 M solution in dioxane, 1.42 mmol), HN(i-Pr)₂ (1.99 mL, 14.2 mmol), 3-bromoanisole (1.5 mL, 11.8 mmol), and trimethylsilylacetylene (2.0 mL, 14.2 mmol) was added via syringe to the stirred reaction mixture. The reaction mixture was stirred at room temperature for 2 days, and then quenched with saturated NH₄Cl (100 mL) and extracted with EtOAc (2×100 mL). The combined organic layers were dried over MgSO₄ and concentrated. The residue was purified by flash column chromatography (hexane) to give an orange color oil which was used without further purification. ¹H NMR (CDCl₃): δ 0.28 (s, 9H), 3.83 (s, 3H), 6.89–6.92 (m, 1H), 7.01–7.03 (m, 1H), 7.08–7.11 (m, 1H), 7.21–7.26 (m, 1H). IR (cm⁻¹).

Step 3: 1-Ethynyl-3-methoxy-benzene

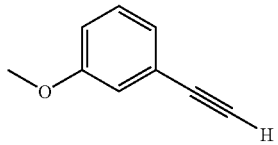

In this step, (3-Methoxy-phenylethynyl)-trimethyl-silane was dissolved in MeOH (100 mL) and added to K₂CO₃ (2.45 g, 17.7 mmol). The reaction mixture was stirred at room temperature for 1 h and then filtrated. The filtrate was concentrated under reduced pressure. The residue was dissolved in Et₂O (100 mL) and washed with citric acid (20%, 100 mL), saturated NHCO₃ (100 mL), H₂O and then concentrated under reduced pressure. The combined organic layers were washed with brine, dried over MgSO₄ and then concentrated. The residue was purified by flash column chromatography (1% EtOAc in hexane) to afford 685 mg of product (43%) as a pale yellow oil. ¹H NMR (CDCl₃): δ 3.83 (s, 3H), 6.92–6.96 (m, 1H), 7.05–7.06 (m, 1H), 7.11–7.14 (m, 1H), 7.24–7.29 (m, 1H).

Step 4: 1-Cyclopentyl-3-(3-methoxy-phenyl)-propynone

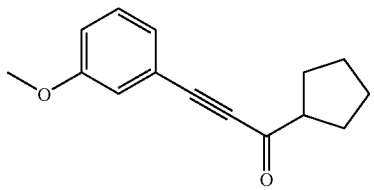

To a solution of 1-ethynyl-3-methoxy-benzene (0.669 g, 5.06 mmol) cooled at −78° C. was added nBuLi (3.16 mL, 5.06 mmol). The reaction mixture was stirred and warmed to 0° C. in 1 h, and then cooled to −78° C., and then cyclopentanecarboxylic acid methoxy-methyl-amide (0.795 g, 5.06 mmol) in THF (5 mL) was added. The reaction mixture was stirred and warmed to −10° C. in 2 h, and then quenched with H$_2$O (100 mL), extracted with EtOAc (2×80 mL), dried over MgSO$_4$ and concentrated. The residue was purified by flash column chromatography (2% EtOAc in hexane) to yield 535 mg of product (42%) as colorless oil. $^1$H NMR (CDCl$_3$): δ 1.62–1.80 (m, 4H), 1.93–2.08 (m, 4H), 3.01–3.12 (m, 1H), 3.84 (s, 3H), 7.01–7.05 (m, 1H), 7.10–7.11 (m, 1H), 7.18–7.21 (m, 1H), 7.29–7.34 (m, 1H). IR (cm$^{-1}$) 2959, 1664, 1448, 1288.

Step 5: 1-Cyclopentyl-3-(3-methoxy-phenyl)-propan-1-one

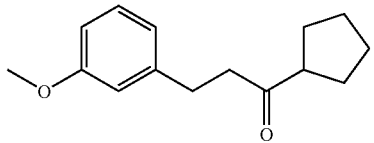

To a solution of 1-cyclopentyl-3-(3-methoxy-phenyl)-propynone (0.457 g, 2.00 mmol) in EtOAc (15 mL) was added Pd on carbon (0.060 g). The reaction mixture was stirred under H$_2$ balloon overnight, and then filtered through a pad of Celite. The filtrate was concentrated under reduced pressure and purified by flash column chromatography (3% EtOAc in hexane) to afford 387 mg of product (83%) as colorless oil. $^1$H NMR (CDCl$_3$): δ 1.55–1.87 (m, 8H), 2.77–2.94 (m, 5H), 3.82 (s, 3H), 6.76–6.82 (m, 3H), 7.20–7.25 (m, 1H). IR (cm$^{-1}$) 2953, 1707, 1601, 1260.

Step 6: 6-Cyclopentyl-4-hydroxy-6-[2-(3-methoxy-phenyl)-ethyl]-5,6-dihydropyran-2-one

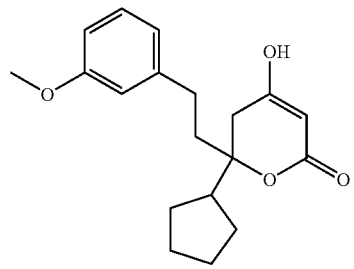

The title compound was prepared as described in Example 1, where 1-Cyclopentyl-3-(3-methoxy-phenyl)-propan-1-one (described above) was used for 3-(4-benzyloxyphenyl)-1-cyclopentylpropan-1-one in step 6 of that Example. $^1$H NMR (CDCl$_3$): δ 1.37–1.82 (m, 8H), 1.96–2.04 (m, 2H), 2.26–2.34 (m, 1H), 2.64–2.74 (m, 2H), 2.80 (s, 2H), 3.45 (s, 2H), 3.83 (s, 3H), 6.72–6.80 (m 3H), 7.24 (t, J=7.5 Hz, 1H); Anal. Calcd. For C$_{19}$H$_{24}$O$_4$.0.25 H$_2$O: C, 71.11; H, 7.70. Found: C, 71.06; H, 7.75. IR (cm$^{-1}$) 2955, 1851, 1605, 1260.

Example 17

6-[2-(4-Acetyl-3-methyl-phenyl)-ethyl]-6cyclopentyl-4-hydroxy-5,6-dihydro-pyran-2-one

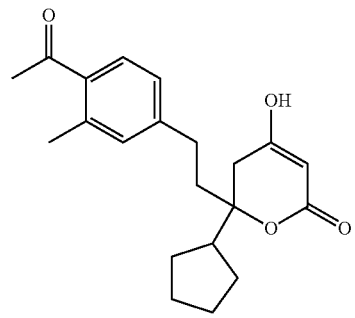

To a solution of 6-cyclopentyl-4-hydroxy-6-{2-[3-methyl-4-(2-methyl-1,3-dioxolan-2-yl)-phenyl]-ethyl}-5,6-dihydro-pyran-2-one (0.173 g) in acetone (10 mL) was added Amberlyst 15 resin. The reaction mixture was stirred at room temperature overnight, and then filtrated. The solvent was removed under reduced pressure. The residue was purified by Prep. HPLC (10–95% acentonitrile in H$_2$O) to afford 201 mg of product as pale yellow oil. $^1$H NMR (CDCl$_3$): δ 1.61–1.84 (m, 8H), 1.95–2.03 (m, 2H), 2.29–2.35 (m, 1H), 2.55 (s, 3H), 2.59 (s, 3H), 2.66–2.78 (m, 2H), 2.81 (s, 2H), 3.47 (s, 2H), 7.05–7.09 (m 2H), 7.68 (d, J=8.1 Hz, 1H). Anal. Calcd. For (C$_{21}$H$_{26}$O$_4$).0.2 H$_2$O: C, 72.89; H, 7.69. Found: 72.88; H, 7.83. HRMS (ESI) (M+Na$^+$): Calc. 365.1729. Found 365.1743. IR (cm$^{-1}$) 2956, 1678, 1254.

Step 1: 1-(4-bromo-2-methyl-phenyl)-ethanone

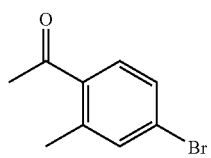

Methyl lithium (80.9 mL of 1.4 M in diethyl ether, 113.2 mmol) was added to a solution of 4-bromo-2-methylbenzoic acid (9.74 g, 45.3 mmol) in Et$_2$O (200 mL). The reaction mixture was stirred at room temperature for 1.5 h, and then quenched with saturated NH$_4$Cl (150 mL), extracted with Et$_2$O (2×100 mL), dried over MgSO$_4$ and concentrated. The residue was purified by flash column chromatography (10% EtOAc in hexane) to afford 8.29 g of product (86%) as colorless oil. $^1$H NMR (CDCl$_3$): δ 2.54 (s, 3H), 2.59 (s, 3H), 7.42–7.45 (m, 2H), 7.58–7.61 (m, 1H). IR (cm$^{-1}$) 2959, 1665, 1599, 1288.

Step 2: 1-(2-methyl-4-trimethylsilanylethynyl-phenyl)-ethanone

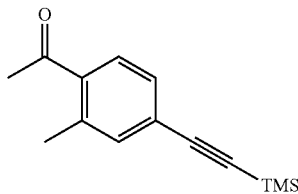

The title compound was prepared as described in Example 16, except 1-(4-bromo-2-methyl-phenyl)-ethanone was substituted for 3-bromoanisole in step 2 of that Example. $^1$H NMR (CDCl$_3$); δ 2.54 (s, 3H), 2.59 (s, 3H), 7.42–7.45 (m, 2H), 7.58–7.61 (m, 1H). IR (cm$^{-1}$) 2959, 1665, 1599, 1288.

Step 3: Trimethyl-[3-methyl-4-(2-methyl-[1,3]dioxolan-2-yl)-phenylethynyl]-silane

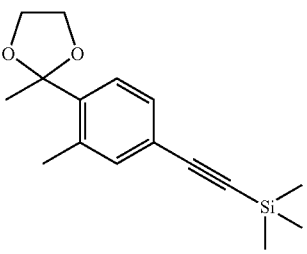

Ethylene glycol (2.05 mL, 36.8 mmol) and TsOH.H$_2$O (0.234 g, 1.23 mmol) were added to a solution of 1-(2-methyl-4-trimethylsilanylethynyl-phenyl)-ethanone (2.82 g, 12.3 mmol) in benzene (70 mL). The reaction mixture was heated to reflux with Dean-Stark trap on top. After 6 h, the reaction mixture was cooled to room temperature, poured into half-saturated NaHCO$_3$ (100 mL), and then extracted with EtOAc (2×100 mL). The combined organic layers dried over MgSO$_4$ and concentrated. The residue was purified by flash column chromatography (5% EtOAc in hexane) to afford 3.70 g of product as pale yellow oil. $^1$H NMR (CDCl$_3$): δ 0.26 (s, 9H), 1.69 (s, 3H), 2.48 (s, 3H), 3.70–3.75 (m, 2H), 4.02–4.07 (m, 2H), 7.27–7.32 (m, 2H), 7.45–7.52 (m, 1H). IR (cm$^{-1}$) 2959, 1248, 1039, 844.

Step 4: 2-(4-Ethynyl-2-methyl-phenyl)-2-methyl-1,3-dioxolane

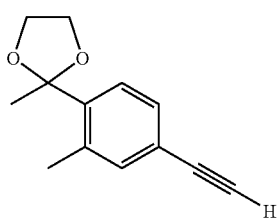

The title compound was prepared as described in Example 16, except trimethyl{[3-methyl-4-(2-methyl-1,3-dioxolan-2-yl)phenyl]ethynyl)-silane was substituted for (3-methoxyphenylethynyl)-trimethyl-silane in step 3 of that Example. $^1$H NMR (CDCl$_3$): δ 1.69 (s, 3H), 2.50 (s, 3H), 3.07 (s, 1H), 3.72–3.77 (m, 2H), 4.04–4.08 (m, 2H), 7.30–7.33 (m, 2H), 7.51–7.55 (m, 1H). IR (cm$^{-1}$) 3288, 2987, 1194, 1036.

Step 5: 1-Cyclopentyl-3-[3-methyl-4-(2-methyl-1,3-dioxolan-2-yl)-phenyl]propynone

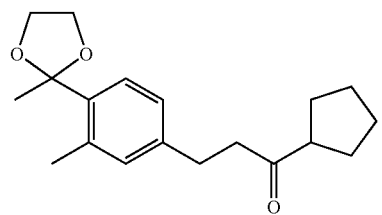

The title compound was prepared as described in Example 16, where 2-(4-ethynyl-2-methyl-phenyl)-2-methyl-1,3-dioxolane was substituted for 1-ethynyl-3-methoxy-benzene in step 4 of that Example. $^1$H NMR (CDCl$_3$): δ 1.63–1.79 (m, 7H), 1.95–2.08 (m, 4H), 2.53 (s, 3H), 3.00–3.11 (m, 1H), 3.73–3.77 (m, 2H), 4.05–4.09 (m, 2H), 7.39–7.41 (m, 2H), 7.59–7.61 (m, 1H). Anal. Calcd. For C$_{19}$H$_{22}$O$_3$: C, 76.48; H, 7.43. Found: C, 23; H, 7.33. IR (cm$^{-1}$) 3422, 2958, 1665, 1245.

Step 6: 1-Cyclopentyl-3-[3-methyl-4-(2-methyl-1,3-dioxolan-2-yl)phenyl]-propan-1-one The title compound was prepared as described in Example 16, except 1-cyclopentyl-3-[3-methyl-4-(2-methyl-1,3-dioxolan-2-yl)-phenyl]propynone was substituted for 1-cyclopentyl-3-(3-methoxy-phenyl)-propynone in step 5 of that Example. $^1$H NMR (CDCl$_3$): δ 1.63–1.79 (m, 7H), 1.95–2.08 (m, 4H), 2.53 (s, 3H), 3.00–3.11 (m, 1H), 3.73–3.77 (m, 2H), 4.05–4.09 (m, 2H), 7.39–7.41 (m, 2H), 7.59–7.61 (m, 1H). IR (cm$^{-1}$) 3422, 2958, 1665, 1245.

Step 7: 6-Cyclopentyl-4-hydroxy-6-{2-[3-methyl-4-(2-methyl-1,3-dioxolan-2-yl)-phenyl]-ethyl}-5,6-dihydro-pyran-2-one

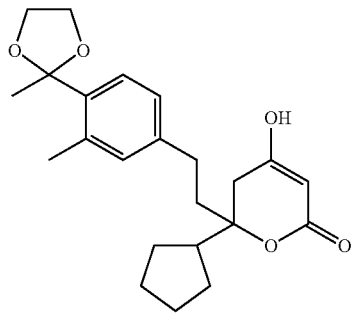

The title compound was prepared from as described in Example 1, except 1-Cyclopentyl-3-[3-methyl-4-(2-methyl-1,3-dioxolan-2-yl)-phenyl]-propan-1-one (described above) was substituted for 3-(4-benzyloxyphenyl)-1-cyclopentyl-propan-1-one in step 6 of that Example. $^1$H NMR (CDCl$_3$): δ 1.61–1.84 (m, 8H), 1.95–2.03 (m, 2H), 2.29–2.35 (m, 1H), 2.55 (s, 3H), 2.59 (s, 3H), 2.66–2.78 (m, 2H), 2.81 (s, 2H), 3.47 (s, 2H), 7.05–7.09 (m 2H), 7.68 (d, J=8.1 Hz, 1H); ESIMS (M+Na$^+$): 393.5. IR (cm$^{-1}$) 2956, 1678, 1254.

Example 18

6-Cyclopentyl-4-hydroxy-6-{2-[3-methyl-4-(2-methyl-1,3-dioxolan-2-yl)-phenyl]-ethyl}-5,6-dihydro-pyran-2-one Step 1: 1-(4-bromo-2-methyl-phenyl)-ethanone

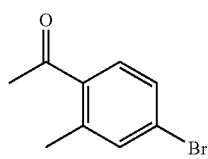

Methyl lithium (80.9 mL of 1.4 M in diethyl ether, 113.2 mmol) was added to a solution of 4-bromo-2-methylbenzoic acid (9.74 g, 45.3 mmol) in Et$_2$O (200 mL). The reaction mixture was stirred at room temperature for 1.5 h, and then quenched with saturated NH$_4$Cl (150 mL), extracted with Et$_2$O (2×100 mL), dried over MgSO$_4$ and concentrated. The residue was purified by flash column chromatography (10% EtOAc in hexane) to afford 8.29 g of product (86%) as colorless oil. $^1$H NMR (CDCl$_3$): δ 2.54 (s, 3H), 2.59 (s, 3H), 7.42–7.45 (m, 2H), 7.58–7.61 (m, 1H). IR (cm$^{-1}$) 2959, 1665, 1599, 1288.

Step 2: 1-(2-methyl-4-trimethylsilanylethynyl-phenyl)-ethanone

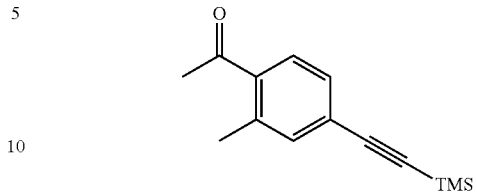

The title compound was prepared analogously to Example 16, where 1-(4-bromo-2-methyl-phenyl)-ethanone was substituted in place of 3-bromoanisole in step 2 of that example. $^1$H NMR (CDCl$_3$): δ 2.54 (s, 3H), 2.59 (s, 3H), 7.42–7.45 (m, 2H), 7.58–7.61 (m, 1H). IR (cm$^{-1}$) 2959, 1665, 1599, 1288.

Step 3: Trimethyl-[3-methyl-4-(2-methyl-[1,3]dioxolan-2-yl)-phenylethynyl]-silane:

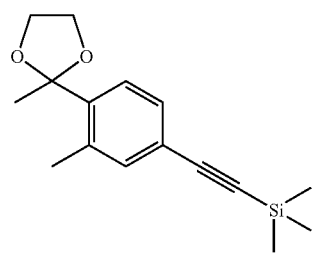

Ethylene glycol (2.05 mL, 36.8 mmol) and TsOH.H$_2$O (0.234 g, 1.23 mmol) were added to a solution of 1-(2-methyl-4-trimethylsilanylethynyl-phenyl)-ethanone (2.82 g, 12.3 mmol) in benzene (70 mL). The reaction mixture was heat to reflux with Dean-Stark trap on top. After 6 h, the reaction mixture was cooled to room temperature, poured into half saturated NaHCO$_3$ (100 mL), and then extracted with EtOAc (2×100 mL). The combined organic layers dried over MgSO$_4$ and concentrated. The residue was purified by flash column chromatography (5% EtOAc in hexane) to afford 3.70 g of product as pale yellow oil. $^1$H NMR (CDCl$_3$): δ 0.26 (s, 9H), 1.69 (s, 3H), 2.48 (s, 3H), 3.70–3.75 (m, 2H), 4.02–4.07 (m, 2H), 7.27–7.32 (m, 2H), 7.45–7.52 (m, 1H). IR (cm$^{-1}$) 2959, 1248, 1039, 844.

Step 4: 2-(4-Ethynyl-2-methyl-phenyl)-2-methyl-1,3-dioxolane

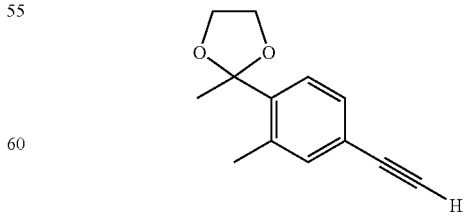

The title compound was prepared analogously to Example 16, where trimethyl{[3-methyl-4-(2-methyl-1,3-dioxolan-2-yl)phenyl]ethynyl)-silane was substituted in place of (3-methoxy-phenylethynyl)-trimethyl-silane in step 3 of that example. $^1$H NMR (CDCl$_3$): δ 1.69 (s, 3H), 2.50 (s, 3H), 3.07 (s, 1H), 3.72–3.77 (m, 2H), 4.04–4.08 (m, 2H), 7.30–7.33 (m, 2H), 7.51–7.55 (m, 1H). IR (cm$^{-1}$) 3288, 2987, 1194, 1036.

Step 5: 1-Cyclopentyl-3-[3-methyl-4-(2-methyl-1,3-dioxolan-2-yl)-phenyl]propynone

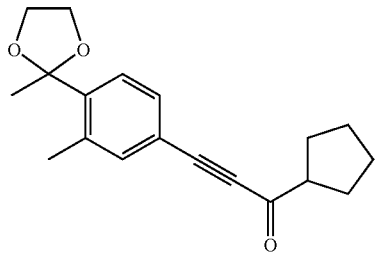

The title compound was prepared analogously to Example 16, where 2-(4-ethynyl-2-methyl-phenyl)-2-methyl-1,3-dioxolane was substituted in place of 1-ethynyl-3-methoxy-benzene in step 4 of that example. $^1$H NMR (CDCl$_3$): δ 1.63–1.79 (m, 7H), 1.95–2.08 (m, 4H), 2.53 (s, 3H), 3.00–3.11 (m, 1H), 3.73–3.77 (m, 2H), 4.05–4.09 (m, 2H), 7.39–7.41 (m, 2H), 7.59–7.61 (m, 1H). Anal. Calcd. For C$_{19}$H$_{22}$O$_3$: C, 76.48; H, 7.43. Found: C, 23; H, 7.33. IR (cm$^{-1}$) 3422, 2958, 1665, 1245.

Step 6: 1-Cyclopentyl-3-[3-methyl-4-(2-methyl-1,3-dioxolan-2-yl)-phenyl]-propan-1-one

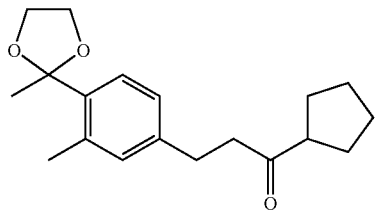

The title compound was prepared analogously to Example 16, where 1-cyclopentyl-3-[3-methyl-4-(2-methyl-1,3-dioxolan-2-yl)-phenyl]propynone was substituted in place of 1-cyclopentyl-3-(3-methoxy-phenyl)-propynone in step 5 of that example. $^1$H NMR (CDCl$_3$): δ 1.63–1.79(m, 7H), 1.95–2.08 (m, 4H), 2.53 (s, 3H), 3.00–3.11 (m, 1H), 3.73–3.77 (m, 2H), 4.05–4.09 (m, 2H), 7.39–7.41 (m, 2H), 7.59–7.61 (m, 1H). IR (cm$^{-1}$) 3422, 2958, 1665, 1245.

Step 7: 6-Cyclopentyl-4-hydroxy-6-{2-[3-methyl-4-(2-methyl-1,3-dioxolan-2-yl)-phenyl]-ethyl}-5,6-dihydro-pyran-2-one

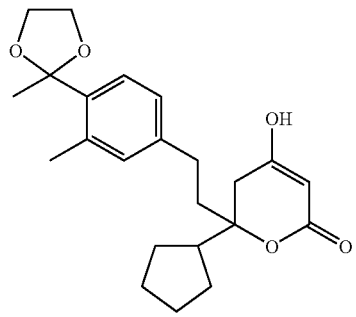

The title compound was prepared from analogously to Example 1, where 1-Cyclopentyl-3-[3-methyl-4-(2-methyl-1,3-dioxolan-2-yl)-phenyl]-propan-1-one (described below) used in place of 3-(4-benzyloxyphenyl)-1-cyclopentylpropan-1-one in step 6 of that example. $^1$H NMR (CDCl$_3$): δ 1.61–1.84 (m, 8H), 1.95–2.03 (m, 2H), 2.29–2.35 (m, 1H), 2.55 (s, 3H), 2.59 (s, 3H), 2.66–2.78 (m, 2H), 2.81 (s, 2H), 3.47 (s, 2H), 7.05–7.09 (m 2H), 7.68 (d, J=8.1 Hz, 1H); ESIMS (M+Na$^+$): 393.5. Ir (cm$^{-1}$) 2956, 1678, 1254.

Example 19

6-Cyclopentyl-4-hydroxy-6-[2-(4-hydroxy-3-methoxy-phenyl)-ethyl]-5,6-dihydro-pyran-2-one

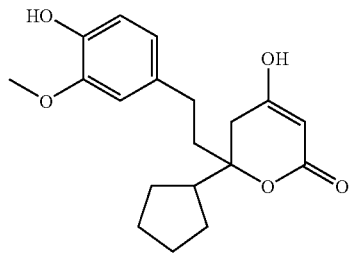

To a solution of 6-[2-(4-Benzyloxy-3-methoxy-phenyl)-ethyl]-6-cyclopentyl-4-hydroxy-5,6-dihydro-pyran-2-one (0.196 g, 0.46 mmol) in EtOAc (5 mL) was added Pd on carbon (0.035 g). The reaction mixture was stirred under H$_2$ balloon overnight, and then filtrated though a pad of Celite and concentrated. The residue was purified by flash column chromatography (1% CH$_3$OH in CH$_2$Cl$_2$) to afford 135 mg of product (88%) as colorless foam. $^1$H NMR (CDCl$_3$): δ 1.54–1.85 (m, 8H), 192–2.04 (m, 2H), 2.25–2.36 (m, 1H), 2.64 (t, J=8.4 Hz, 2H), 2.80 (s, 2H), 3.45 (s, 2H), 3.91 (s, 3H), 5.54 (s, 1H), 6.66–6.68 (m, 2H), 6.85–6.88 (m, 1H). Anal. Calcd For C$_{19}$H$_{24}$O$_5$.0.25 H$_2$O: C, 67.92; H, 7.32. ESIMS (M$^+$): 332.3. IR (cm$^{-1}$) 2955, 1651, 1515, 1269.

Example 20

6-[2-(4-Benzyloxy-3-methoxy-phenyl)-ethyl]-6-cyclopentyl-4-hydroxy-5,6-dihydro-pyran-2-one Step 1: 3-(4-Benzyloxy-3-methoxy-phenyl)-proplonic acid Ethyl ester

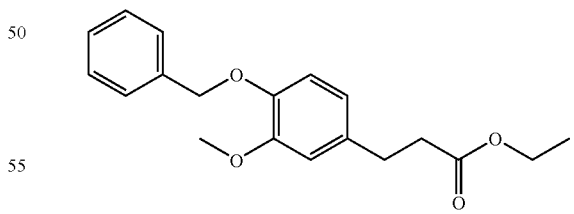

K$_2$CO$_3$ (7.59 g, 54.9 mmol) and benzyl bromide were added to ethyl 3-(4-hydroxy-3-methoxyphenyl)propionate (10.26 g, 45.75 mmol) in acetone (250 mL). The reaction mixture was heated to reflux for 40 h, and then filtrated and concentrated under reduced pressure. The residue was purified by flash column chromatography (10% EtOAc in hexanes) to afford 14.0 g of product (100%) as colorless oil. $^1$H NMR (CDCl$_3$): δ 1.27 (t, J=7.2 Hz, 3H), 2.62 (t, J=7.8 Hz, 2H), 2.92 (t, J=7.5 Hz, 2H), 3.09 (s, 3H), 4.16 (q, J=7.2 Hz, 2H), 5.16 (s, 2H), 6.68–6.72 (m, 1H), 6.78–6.84 (m, 2H), 7.35–7.48 (m, 5H). IR (cm$^{-1}$) 1730, 1514, 1265.

Step 2: 3-(4-Benzyloxy-3-methoxy-phenyl)-propionic acid

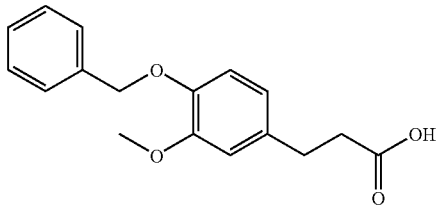

To a solution of 3-(4-Benzyloxy-3-methoxy-phenyl)-propionic acid ethyl ester (14.0 g, 45.75 mmol) was added 2N NaOH (45.75 mL, 91.5 mmol). The reaction mixture was stirred at room temperature for 2 h, and then poured into 1N HCl (150 mL) and extracted with EtOAc. The combined organic layers were dried over MgSO$_4$ and concentrated under reduced pressure to give 12.21 g of product (93%) as a white solid. $^1$H NMR (CDCl$_3$): δ 2.69 (t, J=7.8 Hz, 2H), 2.93 (t, J=7.5 Hz, 2H), 3.91 (s, 3H), 5.16 (s, 2H), 6.69–6.73 (m, 2H), 6.79–6.85 (m, 3H), 7.29–7.45 (m, 5H).

Step 3: 3-(4-Benzyloxy-3-methoxy-phenyl)-thiopropionic acid-pyridin-2-yl ester

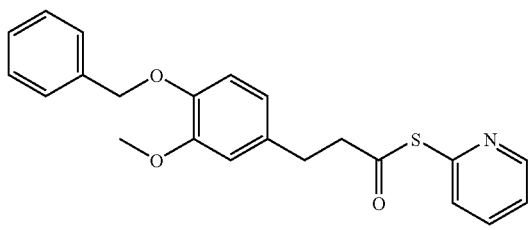

The title compound was prepared as described in Example 15, except 3-(4-Benzyloxy-3-methoxy-phenyl)-propionic acid was substituted for indan-1-yl-acetic acid in step 3 of that Example. $^1$H NMR (CDCl$_3$): δ 2.90–2.96 (m, 4H), 3.91 (s, 3H), 6.69–6.73 (m, 2H), 6.79–6.85 (m, 3H), 7.29–7.80 (m, 8H), 8.42 (m, 1H). IR (cm$^{-1}$) 2934, 1708, 1265, 787.

Step 4: 3-(4-Benzyloxy-3-methoxy-phenyl)-1-cyclopentyl-propan-1-one

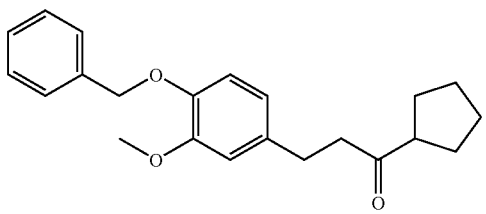

The title compound was prepared as described in Example 15, except 3-(4-benzyloxy-3-methoxy-phenyl)-thiopropionic acid-pyridin-2-yl ester was substituted for indan-1-yl-thioacetic acid S-phenyl ester in step 4 of that Example. $^1$H NMR (CDCl$_3$): δ 1.54–1.86 (m, 8H), 2.74–2.91 (m, 5H), 3.90 (s, 3H), 5.15 (s, 2H), 6.66–6.69 (m, 1H), 6.76–6.83 (m, 2H), 7.32–7.48 (m, 5H). IR (cm$^{-1}$) 3053, 1514, 1265, 727.

Step 5: 6-[2-(4-Benzyloxy-3-methoxy-phenyl)-ethyl]-6-cyclopentyl-4-hydroxy-5,6-dihydro-pyran-2-one

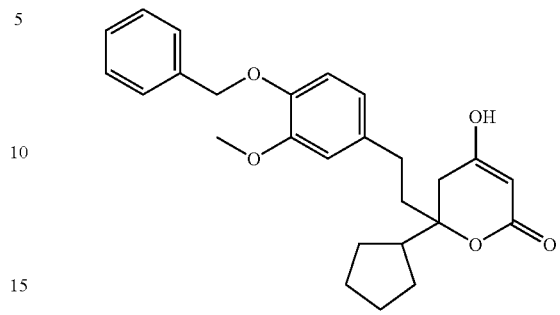

The title compound was prepared from as described in Example 1, except 3-(4-Benzyloxy-3-methoxy-phenyl)-1-cyclopentyl-propan-1-one (described above) was substituted for 3-(4-benzyloxyphenyl)-1-cyclopentylpropan-1-one in step 6 of that Example. $^1$H NMR (CDCl$_3$): δ 1.54–1.86 (m, 8H), 2.74–2.91 (m, 5H), 3.90 (s, 3H), 5.15 (s, 2H), 6.66–6.69 (m, 1H), 6.76–6.83 (m, 2H), 7.32–7.48 (m, 5H). Anal. Calcd. For C$_{26}$H$_{30}$O$_5$: C, 73.91; H, 7.16. Found: C, 73.97; H, 7.31. IR (cm$^-$) 3053, 1514, 1265, 727.

Example 21

6-Cyclopentyl-4-hydroxy-6-(3-phenyl-propyl)-5,6-dihydro-pyran-2 one

Step 1: S-pyridin-2-yl-4-phenylbutanethioate

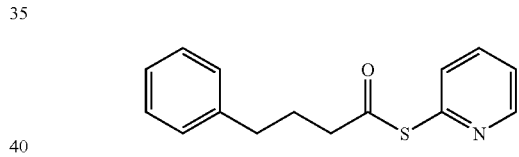

To a stirred solution of 4-phenylbutanoic acid (1a, 2.0 g, 12.2 mmol) in anhydrous CH$_2$Cl$_2$ under argon was added Aldrithiol (4.03 g, 18.3 mmol) and Ph$_3$P (4.79 g, 18.3 mmol). resulting bright yellow solution was stirred at 25° C. for 3 hrs. The reaction was stopped by addition of H$_2$O and the organic layer was washed with H$_2$O$_2$ and brine and dried over Na$_2$SO$_4$. The solvent was removed in vacuo and the residue was purified by flash column chromatography (0–15% EtOAc in hexanes) to provide the desired product (2.88 g, 92% yield). $^1$H NMR (CDCl$_3$, 300 MHz): δ 2.15–2.06 (m, 2 H), 2.84–2.72 (m, 4 H), 7.36–6.95 (m, 6 H, ArH), 7.66–7.63 (m, 1 H, ArH), 7.81–7.75 (m, 1 H, ArH), 8.68–8.65 (m, 1 H, ArH).

Step 2: 1-cyclopentyl-4-phenylbutan-1-one

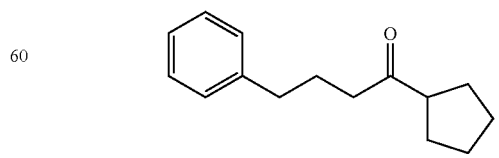

To a stirred solution of S-pyridin-2-yl-4-phenylbutanethioate (1.55 g, 6.0 mmol) in anhydrous THF at −78° C. was added cyclopentylmaganesium bromide (2.0 M, 4.5 mL). The bright yellow solution became a grey slurry after 5 minutes and stirring was continued for 2 hrs before the reaction was quenched by the addition of H$_2$O. The mixture was extracted with EtOAc (50 mL) and the combined organic extracts were washed with saturated aq. NH$_4$Cl, brine and dried over Na$_2$SO$_4$. The solvent was removed in vacuo and the residue was purified by flash column chromatography (0–10% EtOAc in hexanes) to give the desired product (1.04g, 80% yield). $^1$H NMR (CDCl$_3$, 300 MHz) δ: 1.85–1.58 (m, 8 H), 2.08–1.90 (m, 2H), 2.53–2.45 (m, 2 H), 2.68–2.63 (m, 2H), 2.92–2.82 (m, 1 H), 7.24–7.20 (m, 3 H, ArH), 7.35–7.30 (m, 2 H, ArH).

To a solution of methyl acetoacetate (0.73 mL, 6.94mmol) in anhydrous THF at 0° C. was added NaH (60%, 278 mg, 6.94 mmol). The resulting white slurry was stirred for 10 minutes before n-BuLi (1.6 M, 4.34 mL) was added dropwise over 20 min. After 15 min, a solution of 1-cyclopentyl-4-phenylbutan-1-one (500 mg, 2.31 mmol) in anhydrous THF was transferred to the reaction via cannula and the resulting solution was stirred at 0° C. for an additional 2 hrs. The reaction was quenched by the addition of saturated aq. NH$_4$Cl and extracted with EtOAc (3×20 mL). The combined organic extracts were washed with brine and dried over Na$_2$SO$_4$. The solvent was removed in vacuo and the residue was taken directly into the next step without further purification.

The crude product was dissolved in THF (4 mL) and the resulting solution was treated with 0.2 N NaOH (40 mL). The slurry was stirred at 25° C. for 3 hrs before it was acidified to pH 7 by the addition of aq. KHSO$_4$. The mixture was extracted with EtOAc (4×15 mL) and the combined organic extracts were washed sequentially with aq. NH$_4$Cl$_2$, brine, and dried over Na$_2$SO$_4$. The solvent was removed in vacuo and the residue was purified by flash column chromatography (0–25% EtOAc in hexanes) to give the desired product (250 mg, 31% yield for two steps). $^1$H NMR (CDCl$_3$, 300 MHz): δ: 1.80–1.32 (m, 12 H), 2.28–2.22 (m, 1 H), 2.76–2.59 (m, 4 H), 3.44–3.30 (m, 2 H), 7.35–7.17 (m, 5 H). Anal. calcd: (C$_{19}$H$_{24}$O$_3$) C, 75.97%; H, 8.05%; O, 15.98%. Found: C, 75.65%; H, 8.06%; O, 16.05%.

Example 22

6-(3-Cyclohexyl-propyl)-6-cyclopentyl-4-hydroxy-5,6-dihydro-pyran-2-one

Step 1: S-pyridin-2-yl-4-cyclohexylbutanethioate

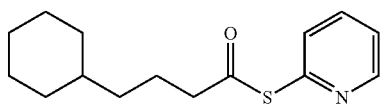

The title compound was prepared as described in step 1 of Example 21, except 4-cyclohexylbutanoic acid was substituted for 4-phenylbutanoic (yield 90%). $^1$H NMR (CDCl$_3$, 300 MHz) δ: 0.91–0.82 (m, 2 H), 1.21–1.08 (m, 5 H), 1.72–1.52 (m, 8 H), 2.61 (t, J=7.5 Hz, 2 H), 7.26–7.21 (m, 1 H, ArH), 7.56–7.53 (m, 1 H, ArH), 7.70–7.65 (m, 1 H, ArH), 8.56–8.54 (m, 1 H, ArH).

Step 2: 4-cyclohexyl-1-cyclopentylbutan-1-one

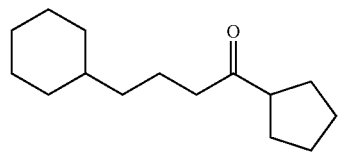

The title compound was prepared as described in step 2 of Example 21, except S-pyridin-2-yl-4-cyclohexylbutanethioate (described above) was substituted for S-pyridin-2-yl-4-phenylbutanethioate. Yield 84%. $^1$H NMR (CDCl$_3$, 300 MHz): δ 0.92–0.71 (m, 2 H), 1.18–1.04 (m, 6 H), 1.79–1.46 (m, 15 H), 2.34 (t, J=7.5 Hz, 2 H), 2.84–2.74 (m, 1 H).

Step 3: 6-(3-Cyclohexyl-propyl)-6-cyclopentyl-4-hydroxy-5,6-dihydro-pyran-2-one

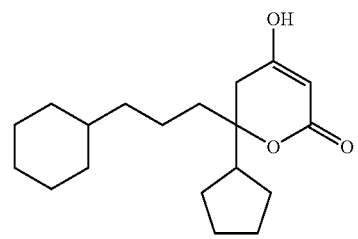

The title compound was prepared as described in Example 21, except 4-Cyclohexyl-1-cyclopentyl-butan-1-one was substituted for 1-cyclopentyl-4-phenylbutan-1-one in the final step of that Example. Yield 48% $^1$H NMR (CDCl$_3$, 300 MHz) δ 0.98–0.82 (m, 2 H), 1.30–1.16 (m, 6 H) 1.56–1.33 (m, 4 H), 1.85–1.58 (m, 13 H), 2.31–2.25 (m, 1 H), 2.75 (s, 2 H), 3.45 (s, 2 H). Anal. Calcd (C$_{19}$H$_{30}$O$_3$): C, 74.47%; H, 9.87%; O, 15.66%. Found: C, 74.22%; H, 9.88%; O, 15.65%.

Example 23

6-(2-Benzo[1,3]dioxol-5-yl-ethyl)-6-cyclopentyl-dihydro-pyran-2,4-dione

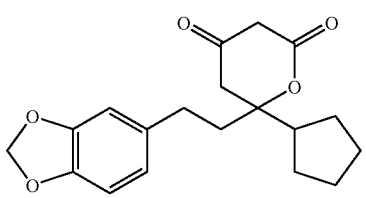

The title compound was prepared as described in Example 26, except 4-Bromo-1,2-(methylene-dioxy)benzene was substituted for 3-Bromochlorobenzene in step 1 of that Example. $^1$H NMR (CDCl$_3$-d$_6$): δ 1.4–1.85 (m, 8H), 1.93 (m, 2H), 2.23 (m, 1H), 2.60 (t, J=8.4 Hz, 2H), 2.76 (s, 2H), 3.42 (s, 2H), 5.93 (s, 2H), 6.60 (m, 1H), 6.72 (m, 1H), 7.26 (s, 1H). Anal. Calcd. For C$_{19}$H$_{22}$O$_5$.0.1 H$_2$O: C, 68.70; H, 6.74. Found: C, 68.57; H, 6.68. ESIMS (MH+): 331.

Example 24

6-Cyclopentyl-6-[2-(3-ethoxy-phenyl)-ethyl]-dihydro-pyran-2,4-dione

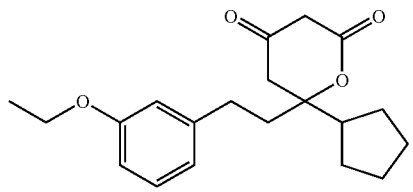

The title compound was prepared as described in Example 26, except 3-Bromophenol was substituted for 3-Bromochlorobenzene in step 1 of that Example. $^1$H NMR (CDCl$_3$-d$_6$): δ 1.41 (t, J=6.9 Hz, 3H), 1.57–1.89 (m, 8H), 1.95 (m, 2H), 2.22 (m, 1H), 2.65 (t, J=8.6 Hz, 2H), 2.76 (s, 2H), 3.41 (d, J=6.2 Hz, 2H), 4.0 (q, J=14.3, 6.9 Hz, 2H), 6.72 (m, 3H), 7.20 (m, 1H). Anal. Calcd. For C$_{20}$H$_{26}$O$_4$·0.5 H$_2$O: C, 70.77; H, 8.02. Found: C, 70.65; H, 7.98. ESIMS (MH+): 331.

Example 25

6-Cyclopentyl-6-[2-(4-ethoxy-phenyl)-ethyl]-dihydro-pyran-2,4-dione

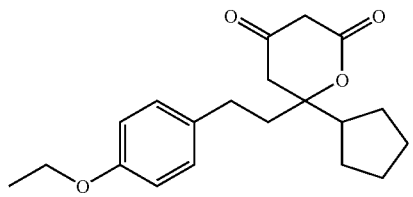

The title compound was prepared as described in Example 26, except 4-Bromophenetole was substituted for 3-Bromochlorobenzene in step 1 of that Example. $^1$H NMR (CDCl$_3$-d$_6$): δ 1.4 (t, J=6 Hz, 3H), 1.57–1.89 (m, 8H), 1.92 (m, 2H), 2.28 (t, J=7.7 Hz, 1H), 2.62 (t, J=8.5 Hz, 2H), 2.76 (s, 2H), 3.42 (s, 2H), 4.0 (q, J=13.9, 6.9 Hz, 2H), 6.81 (d, J=8.5 Hz, 2H), 7.04 (d, J=8.5 Hz, 2H). Anal. Calcd. For C$_{20}$H$_{26}$O$_4$·0.75 H$_2$O: C, 69.84; H, 8.06. Found: C, 69.60; H, 7.90. ESIMS (MH+): 331.

Example 26

6-[2-(3-Chloro-phenyl)-ethyl]-6-cyclopentyl-dihydro-pyran-2,4-dione

Step 1: 3-(3-Chloro-phenyl)-1-cyclopentyl-propan-1-one

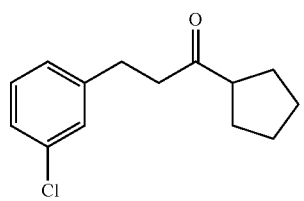

To stirred solution of 3-Bromochlorobenzene (0.50g, 2.61 mmol) and 1-Cyclopentyl-2-propen-1-ol (1.5 eq, 0.49 g, 3.88 mmol) in anhydrous N-methylpyrrolidinone (3.0 mL), under argon at room temperature, was added sodium bicarbonate (1.2 eq, 0.26 g, 3.10 mmol) followed by dichlorobis(triphenylphosphine) palladium (II) (0.02 eq, 36.7 mg, 0.05 mmol). The resulting mixture was heated to 140° C. in an oil bath and maintained for 4 hours. The resulting reaction mixture was cooled to room temperature and poured into water (50 mL), and extracted with EtOAc (2×25 mL). The organics were washed with water (50 mL) and brine (50 mL) then dried over Na$_2$SO$_4$, filtered and concentrated. The crude residue was purified by flash chromatography (1% through 10% EtOAc in Hexanes) to yield the intermediate ketone as a slightly yellow oil (0.49 g, 79%). $^1$H NMR (CDCl$_3$): δ 1.45–1.87 (m, 8H), 2.70–2.95 (m, 5H), 7.07 (d, J=7.0 Hz, 1 H), 7.10–7.25 (m, 3H).

Step 2: 6-[2-(3-Chloro-phenyl)-ethyl]-6-cyclopentyl-dihydro-pyran-2,4-dione

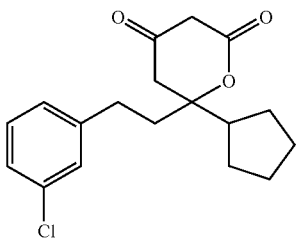

The title compound was prepared as described in Example 1, except 3-(3-Chloro-phenyl)-1-cyclopentyl-propan-1-one (described in step 1 above) was substituted for 3-(4-Benzyloxyphenyl)-1-cyclopentylpropan-1-one in step 6 of that Example. The product was purified by flash column chromatography (10% through 40% EtOAc in Hexanes). The result was a clear gum, which was crystallized by trituration with Hexanes. (0.26 g, 64%). $^1$H NMR (CDCl$_3$): δ 1.41–1.85 (brm, 8H), 1.95 (m, 2H), 2.29 (t, J=7.6 Hz, 1H), 2.65 (t, J=8.6 Hz, 2H), 2.80 (s, 2H), 3.40 (s, 2H), 7.03 (d, J=6.6 Hz, 1H), 7.14 (brs, 1H), 7.20 (m, 2H). ESIMS (MH+): 321.8.

Example 27

6-[2-(3-Chloro-4-methoxy-phenyl)-ethyl]-6-cyclopentyl-dihydro-pyran-2,4-dione

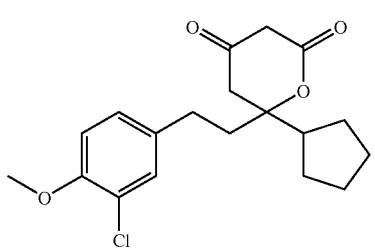

The title compound was prepared as described in Example 26, except 4-Bromo-2-chloroanisole was substituted for 3-Bromochlorobenzene in step 1 of that Example. $^1$H NMR (CDCl$_3$): δ 1.41–1.86 (brm, 8H), 1.96 (m, 2H), 2.29 (t, J=7.6 Hz, 1H), 2.61 (t, J=8.6 Hz, 2H), 2.81 (s, 2H), 3.40 (s, 2H), 3.89, (s, 3H), 6.45 (d, J=8.5 Hz, 1H), 7.0 (d, J=8.5 Hz, 1H), 7.15 (brs, 1H). ESIMS (MH+): 351.8.

Example 28

6-Cyclopentyl-6-[2-(4-methanesulfonyl-phenyl)-ethyl]-dihydro-pyran-2,4-dione

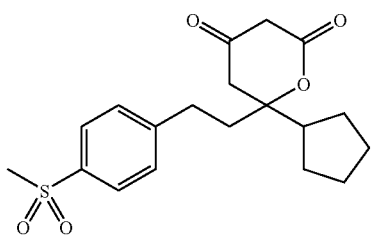

The title compound was prepared as described in Example 26, except 4-Bromophenyl methyl sulfone was substituted for 3-Bromochlorobenzene in step 1 of that Example. $^1$H NMR (CDCl$_3$): δ 1.42–1.85 (brm, 8H), 1.97 (m, 2H), 2.29 (t, J=7.6 Hz, 1H), 2.79 (m, 4H), 3.04 (s, 3H), 3.45 (s, 2H), 7.36 (d, J=8.3 Hz, 2H), 7.88 (d, J=8.3 Hz, 2H). Anal. Calcd. For C$_{19}$H$_{24}$O$_5$S: C, 62.61; H, 6.64. Found: C, 62.51; H, 6.94.

Example 29

6-Cyclopentyl-6-[2-(4-methoxy-3-methyl-phenyl)-ethyl]-dihydro-pyran-2,4-dione

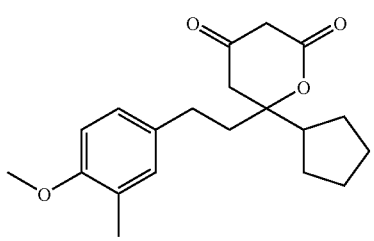

The title compound was prepared as described in Example 2, except 4-Bromo-2-methylanisole was substituted for 3-Bromochlorobenzene in step 1 of that Example. $^1$H NMR (CDCl$_3$): δ 1.41–1.80 (brm, 8H), 1.94 (m, 2H), 2.19 (s, 3H), 2.28 (m, 1H), 2.58 (t, J=8.4 Hz, 2H), 2.76 (s, 2H), 3.42 (s, 2H), 3.85 (s, 3H), 6.73 (d, J=7.9 Hz, 1H), 6.92 (m, 2H). Anal. Calcd. For C$_{20}$H$_{26}$O$_4$: C, 72.70; H, 7.93. Found: C, 72.45; H, 7.74.

Example 30

6-Cyclopentyl-6-[2-(3-fluoro-4-methoxy-phenyl)-ethyl]-dihydro-pyran-2,4-dione

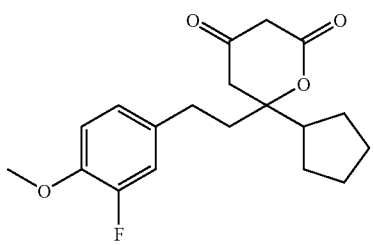

The title compound was prepared as described in Example 26, except 4-Bromo-2-fluoroanisole was substituted for 3-Bromochlorobenzene in step 1 of that Example. $^1$H NMR (CDCl$_3$): δ 1.43–1.82 (brm, 8H), 1.92 (m, 2H), 2.27 (m, 1H), 2.62 (t, J=8.5 Hz, 2H), 2.76 (s, 2H), 3.86 (s, 3H), 6.85 (m, 3H). Anal. Calcd. For C$_{19}$H$_{23}$FO$_4$: C, 68.24; H, 6.93. Found: C, 68.46; H, 6.84.

Example 31

6-[2-(3-Chloro-4-fluoro-phenyl)-ethyl]-6-cyclopentyl-dihydro-pyran-2,4-dione

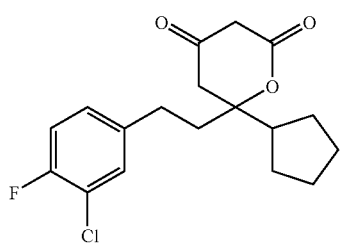

The title compound was prepared as described in Example 26, except 4-Bromo-2-chloro-1-fluorobenzene was substituted for 3-Bromochlorobenzene in step 1 of that Example. $^1$H NMR (CDCl$_3$): δ 1.42–1.82 (brm, 8H), 1.92 (m, 2H), 2.27 (m, 1H), 2.65 (t, J=8.1 Hz, 2H), 2.77 (s, 2H), 3.44 (s, 2H), 7.06 (m, 3H). Anal. Calcd. For C$_{18}$H$_{20}$ClFO$_3$: C, 63.81; H, 5.95. Found: C, 63.57; H, 6.05.

Example 32

6-Cyclopentyl-6-[2-(2,3-dihydro-benzo[1,4]dioxin-6-yl)-ethyl]-dihydro-pyran-2,4-dione

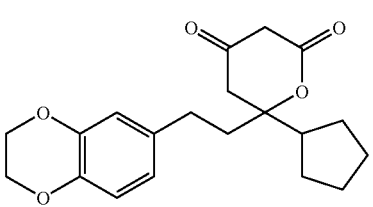

The title compound was prepared as described in Example 26, except 1-Bromo-1,2-(ethylene-dioxy)benzene was substituted for 3-Bromochlorobenzene in step 1 of that Example. $^1$H NMR (CDCl$_3$-d$_6$): δ 1.5–1.6 (m, 8H), 1.71–1.97 (m, 2H), 2.2–2.3 (m, 1H), 2.57 (t, J=8.5 Hz, 2H), 2.76 (s, 2H), 3.42 (s, 2H), 4.24 (s, 4H), 6.59–6.85 (m, 2H), 6.78 (d, J=8.3 Hz, 1H). Anal. Calcd. For C$_{20}$H$_{24}$O$_5$: C, 69.75; H, 7.02. Found: C, 69.83; H, 7.31. ESIMS (MH+): 345.2.

Example 33

6-Cyclopentyl-6-[2-(3-isopropoxy-phenyl)-ethyl]-dihydro-pyran-2,4-dione

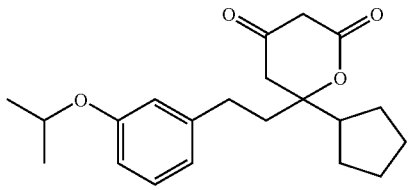

The title compound was prepared as described in Example 26, except 1-Bromo-3-isopropoxybenzene was substituted for 3-Bromochlorobenzene in step 1 of that Example. $^1$H NMR (CDCl$_3$-d$_6$): δ 1.33 (d, J=6.03 Hz, 6H), 1.50–1.8 (m, 8H), 1.92–2 (m, 2H), 2.28 (m, 1H), 2.64 (t, J=8.6 Hz, 2H), 2.76 (s, 2H), 3.42 (s, 2H), 4.54 (m, 1H), 6.67–6.74 (m, 3H), 7.19 (t, J=7.7 Hz, 1H). Anal. Calcd. For C$_{21}$H$_{28}$O$_4$·0.25 H$_2$O: C, 72.28; H, 8.23. Found: C, 72.34; H, 8.35 ESIMS (MH+): 345.2.

Example 34

6-Cyclopentyl-6-[2-(3-isopropyl)-ethyl]-4-methyoxy-5,6-dihydro-pyran-2-one

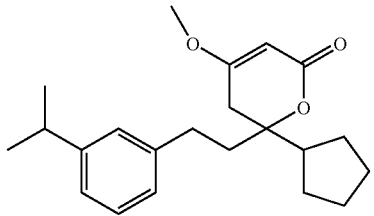

To a solution of 6-Cyclopentyl-4-hydroxy-6-[2-(3-isopropyl-phenyl)-ethyl]-5,6-dihydro-pyran-2-one (75 mg, 0.23 mmol, preparation as described in Example 9 in THF was added 1,8-diazabicyclo[5.4.0]undec-7-ene (105 mg, 0.69 mmol) and Iodomethane (98 mg, 0.69 mmol). The reaction mixture was stirred at room temperature for 3 hours. Solvent was evaporated under reduced pressure, and a solution of the resulting residue in ethyl acetate was extracted with water (5 ml×3), brine, dried with MgSO$_4$, filtered and concentrated to give crude product, which was purified by flash chromatography (eluting with 10% EtOAc/90% CH$_2$Cl$_2$), giving 22 mg of the product (29% yield). $^1$H NMR (CDCl$_3$): δ 1.24 (d, 2H, J=7.0 Hz), 1.35–1.46 (m, 1H), 1.59–1.70 (m, 8H), 2.02–2.21 (m, 2H), 2.37–2.43 (m, 2H), 2.63–2.69 (m, 2H), 2.83–2.90 (m, 1H), 3.74 (s, 3H), 5.17 (s, 1H), 6.95–7.01 (m, 3H), 7.21 (t, 1H, J=7.45 Hz); ESIMS: (M+H): 343.

Example 35

6-Cyclopentyl-6-phenethyl-dihydro-pyran-2,4-dione

Step 1: 1-Cyclopentyl-3-phenyl-propan-1-ol

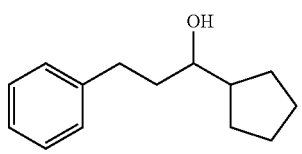

Cyclopentylmagnesium bromide (50 mL of a 2.0 M solution in Et$_2$O, 100 mmol, 1.0 equiv) was added to a solution of hydrocinamaldehyde (13.4 g, 100 mmol, 1 equiv) in THF (150 mL) at −78° C. The resulting gray suspension was stirred for 15 min at −78° C., then warmed to 0° C. for an additional 15 min. The reaction mixture was partitioned between 0.5 M HCl (150 mL) and a 1:1 mixture of EtOAc and hexanes (2×100 mL) and the combined organic layers were dried over Na$_2$SO$_4$ and concentrated. Purification of the residue by flash column chromatography (gradient elution, 20→30% EtOAc in hexanes) yielded the title compound (7.33 g, 36% yield) as a pale yellow liquid.

Step 2: 1-Cyclopentyl-3-phenyl-propan-1-one

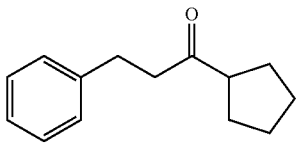

Dimethyl sulfoxide (5.57 mL, 78.5 mmol, 2.2 equiv) was added to a solution of oxalyl chloride (3.43 mL, 39.3 mmol, 1.1 equiv) in CH$_2$Cl$_2$ (150 mL) at −78° C. The mixture was stirred for 10 min at −78° C., then a solution of 1-Cyclopentyl-3-phenyl-propan-1-ol (7.30 g, 35.7 mmol, 1.0 equiv, form step 1 above) in CH$_2$Cl$_2$ (50 mL) was added via cannula over 10 minutes. After stirring for 25 min at −78° C., Et$_3$N (24.9 mmol, 179 mmol, 5.0 equiv) was added and the reaction mixture was maintained at 23° C. for 20 minutes. The mixture was then poured into 0.5 M HCl (150 mL) and extracted with CH$_2$Cl$_2$ (100 mL) and a 1:1 mixture of EtOAc and hexanes (150 mL). The combined organic layers were dried over Na$_2$SO$_4$, concentrated, and the residue was purified by flash column chromatography (5% EtOAc in hexanes) to yield the title compound (3.89 g, 54% yield) as a pale yellow liquid IR (cm$^{-1}$) 2953, 1708; $^1$H NMR (CDCl$_3$): δ 1.26–1.81 (m, 8H), 2.75–2.93 (m, 5H), 7.16–7.30 (m, 5H); Anal. (C$_{14}$H$_{18}$O) C, H, N.

Step 3: 6-Cyclopentyl-6-phenethyl-dihydro-pyran-2,4-dione

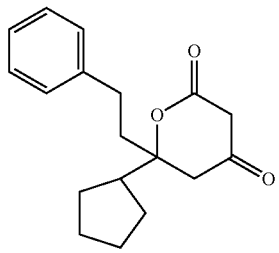

Methyl acetoacetate (0.318 mL, 2.95 mmol, 1.0 equiv) was added dropwise to a suspension of sodium hydride (0.130 g, 60% dispersion in paraffin, 3.25 mmol, 1.1 equiv) in THF (30 mL) at 0° C. After stirring 10 min at 0° C., n-butyllithium (1.84 mL of a 1.6 M solution in hexanes, 2.94 mmol, 1.0 equiv) was added and the resulting yellow solution was stirred an additional 10 min at 0° C. A solution of 1-Cyclopentyl-3-phenyl-propan-1-one (0.597 g, 2.95 mmol, 1.0 equiv; from step 2 above) in THF (15 mL) was added via cannula and the reaction mixture was maintained at 0° C. for 30 min then was partitioned between 0.5 M HCl (150 mL) and a 1:1 mixture of EtOAc and hexanes (2×100 mL). The combined organic layers were dried over Na₂SO₄ and concentrated to yield a pale yellow oil.

This material was dissolved in THF (10 mL) at 23° C. and NaOH (80 mL of a 0.24 M aqueous solution) was added. After stirring for 16 h at 23° C., the reaction mixture was partitioned between 10% KHSO₄ (150 mL) and EtOAc (2×100 mL). The combined organic layers were dried over Na₂SO₄ and concentrated and the residue was purified by flash column chromatography (40% EtOAc in hexanes) to yield the title compound (0.177 g, 21% yield) as a viscous foam which slowly crystallized; mp was 96–99° C. ¹H NMR (CDCl₃) δ 1.47–1.88 (m, 7H), 1.90–2.09 (m, 3H), 2.26–2.32 (m, 1H), 2.68 (t, 2H, J=8.5 Hz), 2.77 (s, 2H); 3.42 (s, 2H), 7.13–7.32 (m, 5H); Anal. (C₁₈H₂₂O₃.0.10H₂O) C, H, N IR (cm⁻¹) 2955, 2870, 1664, 1611.

Example 36

6-Cyclopentyl-6-(2-m-tolyl-ethyl)-dihydro-pyran-2,4-dione

Step 1: Cyclopentanecarboxylic acid methoxy-methyl-amide

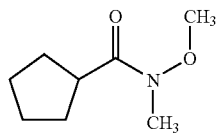

Isobutylchloroformate (11.59 mL, 89.3 mmol, 1.0 equiv) was added to a solution of cyclopentane carboxylic acid (10.2 g, 89.4 mmol, 1.0 equiv) and N-methylmorpholine (19.65 mL, 179 mmol, 2.0 equiv) in CH₂Cl₂ (150 mL) at 0° C. After stirring for 15 min at that temperature, N,O-demethylhydroxylamine hydrochloride (8.75 g, 89.3 mmol, 1.0 equiv) was added. The reaction mixture was warmed to 23° C., maintained for 16 h at that temperature, then poured into half-saturated NaHCO₃ (150 mL) and extracted with CH₂Cl₂ (100 mL) and a 1:1 mixture of EtOAc and hexanes (100 mL). The combined organic layers were dried over Na₂SO₄ and concentrated and the residue was purified by flash column chromatography (20% EtOAc in hexanes) to afford the title compound (11.3 g, 80% yield) as a clear oil.

Step 2: 1-Cyclopentyl-3-trimethylsilanyl-propynone

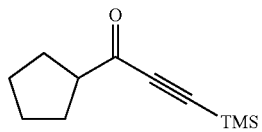

n-Butyllithium (16.65 mL of a 1.6 M solution in hexanes, 26.64 mmol, 1.0 equiv) was added to a solution of (trimethylsilyl)acetylene (3.77 mL, 26.68 mmol, 1.0 equiv) in THF (100 mL) at −78° C. After stirring for 15 min at −78° C., a solution of cyclopentanecarboxylic acid methoxy-methyl-amide (4.19 g, 26.65 mmol, 1.0 equiv: from step 1 above) in THF (30 mL) was added via cannula. The reaction mixture was stirred an additional 3 h at −78° C., then was partitioned, between 0.5 M HCl (150 mL) and a 1:1 mixture of EtOAc and hexanes (2×100 mL). The combined organic layers were dried over Na₂SO₄ and concentrated, and the residue was purified by flash column chromatography (5% EtOAc in hexanes) to afford the title compound (1.44 g, 28% yield) as a somewhat volatile and unstable liquid: ¹H NMR (CDCl₃) δ 0.24 (s, 9H), 1.55–1.73 (m, 4H), 1.81–1.97 (m, 4H), 2.87–2.97 (m, 1H).

Step 3: 6-Cyclopentyl-6-ethynyl-dihydro-pyran-2,4-dione

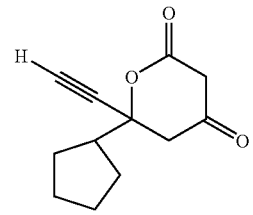

Methyl acetoacetate (0.0.957 mL, 8.87 mmol, 1.2 equiv) was added dropwise to a suspension of sodium hydride (0.356 g, 60% dispersion in paraffin, 8.90 mmol, 1.2 equiv) in THF (50 mL) at 0° C. After stirring 10 min at 0° C., n-butyllithium (5.56 mL of a 1.6 M solution in hexanes, 8.90 mmol, 1.2 equiv) was added, and the resulting yellow solution was stirred an additional 10 min at 0° C. A solution of 1-Cyclopentyl-3-trimethylsilanyl-propynone (1.44 g, 7.41 mmol, 1.0 equiv: from step 2 above) in THF (20 mL) was added via cannula, and the reaction mixture was maintained at 0° C. for 2 h then was partitioned between 0.5 M HCl (150 mL) and a 1:1 mixture of EtOAc and hexanes (2×100 mL). The combined organic layers were dried over Na₂SO₄ and concentrated to yield a pale yellow oil.

This material was dissolved in THF (25 mL) at 23° C. and NaOH (100 mL of a 0.30 M aqueous solution) was added. After stirring for 16 h at 23° C., 10% KHSO₄ (50 mL) was added to the reaction mixture, and stirring was continued for an additional 2 h. The phases were separated, and the aqueous phase was extracted sequentially with a 1:1 mixture of EtOAc and hexane (100 mL) and EtOAc (150 mL). The combined organic layers were dried over Na₂SO₄ and concentrated and the residue was purified by flash column chromatography (50% EtOAc in hexanes) to afford the title compound (0.494 g, 32% yield) as an orange oil: IR (cm⁻¹) 3288, 2959, 1666; ¹H NMR (CDCl₃, mixture of tautomers) δ 1.51–1.98 (m), 2.31–2.39 (m), 2.67 (d, J=16.4 Hz), 2.70 (s), 2.91 (d, J=16.4 Hz); 3.41–3.52 (m), 3.92 (d, J=20.0 Hz).

Step 4: 6-Cyclopentyl-6-m-tolylethynyl-dihydro-pyran-2,4-dione

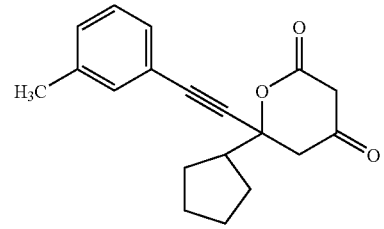

Triethylamine (0.333 mL, 2.39 mmol, 2.0 equiv), copper (I)iodide (0.034 g, 0.179 mmol, 0.15 equiv), and dichlorobis (triphenylphosphine)-palladium (II) (0.042 g, 0.06 mmol, 0.05 equiv) were added sequentially to a solution of 6-Cyclopentyl-6-ethynyl-dihydro-pyran-2,4-dione (0.247 g, 1.20 mmol, 1.0 equiv; from step 3 above) and 3-iodotoluene (0.192 mL, 1.50 mmol, 1.25 equiv) in THF (10 mL) at 23° C. The reaction vessel was then sequentially evacuated and filled with argon (10 cycles). After stirring at 23° C. for 12 h, the reaction mixture was partitioned between half-saturated NH₄Cl (100 mL) and a 1:1 mixture of EtOAc and hexanes (2×100 mL). The combined organic layers were dried over Na₂SO₄ and concentrated, and the residue was purified by flash column chromatography (40% EtOAc in hexanes) yield the title compound (0.044 g, 12% yield) as a clear oil.

Step 5: 6-Cyclopentyl-6-(2-m-tolyl-ethyl)-dihydro-pyran-2,4-dione

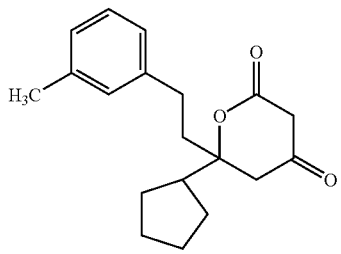

Palladium on carbon (10%, 0.100 g) was added to a solution of 6-Cyclopentyl-6-m-tolylethynyl-dihydro-pyran-2,4-dione (0.040 g, 0.135 mmol; from step 4 above) in EtOAc (10 mL) at 23° C. The reaction mixture was stirred at 23° C. under an H₂ atmosphere (balloon) for 24 h, then filtered through Celite. The Celite was washed with EtOAc (2×10 mL) and the combined filtrate and washings were concentrated. Purification of the residue by flash column chromatography (40% EtOAc in hexanes) yielded the title compound (0.022 g, 53% yield) as a pale yellow oil. ¹H NMR (CDCl₃) δ 1.26–2.13 (m, 7H), 2.23–2.29 (m, 4H), 2.33 (s, 3H), 2.42–2.69 (m, 2H), 2.77 (s, 2H); 3.42 (s, 2H), 6.93–7.28 (m, 4H). IR (cm⁻¹) 2954, 2869, 1662.

Example 37

6-Cyclopentyl-6-[2-(1-methyl-2-oxo-1,2-dihydro-pyridin-3-yl)-ethyl]-dihydro-pyran-2,4-dione

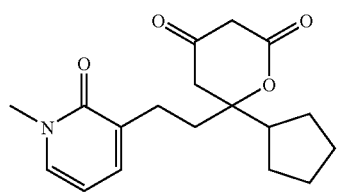

The title compound was prepared as described in Example 26, except 3-Bromo-1-methyl-1H-pyridin-2-one (prepared as described in *JACS*, 4142–4246 (1982)) was substituted for 3-Bromochlorobenzene in step 1 of that Example. ¹H NMR (CDCl₃); δ 1.41–1.96 (brm, 9H), 2.08 (m, 1H), 2.32 (m, 1H), 2.54–2.66 (m, 2H), 2.74 (d, J=16.1 Hz, 1H), 2.85 (d, J=16.1 Hz, 1H), 3.40 (d, J=21.0 Hz, 1H), 3.54 (s, 3H), 3.55 (d, J=21.0 Hz, 1H), 6.11 (t, J=6.8 Hz, 1H), 7.19 (m, 2H). Exact mass calculated for C₁₈H₂₄NO₄ (M+H)⁺ 318.1705. found 318.1721.

Step 1: 3-[2-(2,4-dimethoxyphenyl)ethyl]-1-cyclopentyl-propan-1-one

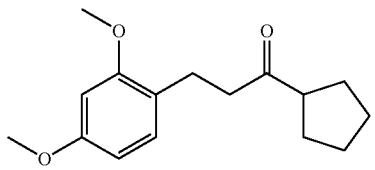

The title compound was prepared using the conditions in step 1 of Example 45, and substituting 2,4-dimethoxybenzaldehyde for 3-(4-methoxyphenoxy)benzaldehyde. ¹H NMR (CDCl₃): δ1.48–1.81 (m, 8H), 2.67 (m, 2H), 2.80 (m, 3H), 3.76 (s, 3H), 3.75 (s, 3H), 6.37 (dd, 1H, J=8.1, 2.1 Hz), 6.41 (d, 1H, J=2.1 Hz), 7.00 (d, 1H, J=8.1 Hz). MS(APCI) calcd for C₁₆H₂₂O₃: 262.2. found (M+H⁺): 263.1.

Step 2: 6-Cyclopentyl-6-[2-(2,4-dimethoxy-phenyl)-ethyl]-dihydro-pyran-2,4-dione

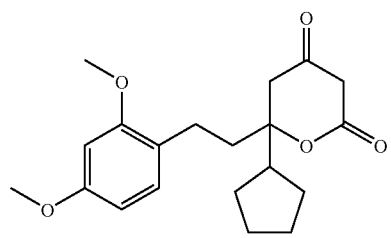

The title compound was prepared as described in step 6 of Example 1, except substituting 3-(2,4-dimethoxyphenyl)-1-cyclopentylpropan-1-one for 3-(4-benzyloxyphenyl)-1-cyclopentylpropan-1-one. ¹H NMR (CDCl₃)δ 1.43 (m, 2 H), 1.78 (m, 8 H), 2.33 (m, 1H), 2.58 (m, 2H), 2.78 (s, 2H), 3.43 (s, 2H), 3.78 (s, 6H), 6.37 (s, 1H), 6.47 (s, 1H), 6.93 (d, 1H, J=7.93 Hz). MS (APCI) calcd for C₂₀H₂₆O₅: 346.2. found (M+1): 347.0.

Example 38

6-Cyclopentyl-6-[2-(2,4-dimethoxy-phenyl)-ethyl]-dihydro-pyran-2,4-dione

Step 1: 3-[2-(2,4-dimethoxyphenyl)ethyl]-1-cyclopentyl-propan-1-one

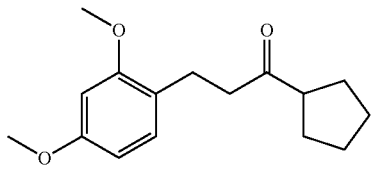

The title compound was prepared using the conditions in step 1 of Example 45, employing 2,4-dimethoxybenzaldehyde in place of 3-(4-methoxyphenoxy)benzaldehyde. ¹H NMR (CDCl₃): δ 1.48–1.81 (m, 8H), 2.67 (m, 2H), 2.80 (m, 3H), 3.76 (s, 3H), 3.75 (s, 3H), 6.37 (dd, J=8.1, 2.1 Hz), 6.41 (d, 1H, J=2.1 Hz), 7.00 (d, 1H, J=8.1 Hz). MS(APCI) calcd for C₁₆H₂₂O₃: 262.2. found (M+H⁺): 263.1.

Step 2: 6-Cyclopentyl-6-[2-(2,4-dimethoxy-phenyl)-ethyl]-dihydro-pyran-2,4-dione

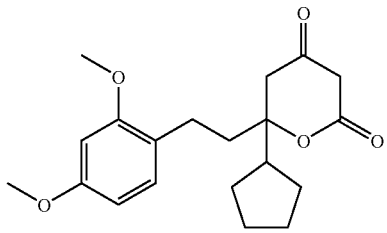

The title compound was prepared employing step 6 of example 1 using 3-(2,4-dimethoxyphenyl)-1-cyclopentyl-propan-1-one in place of 3-(4-benzyloxyphenyl)-1-cyclopentylpropan-1-one. $^1$H NMR (CDCl$_3$) δ 1.43 (m, 2 H), 1.78 ((m, 8 H), 2.33 (m, 1H), 2.58 (m, 2H), 2.78 (s, 2H), 3.43 (s, 2H), 3.78 (s, 6H), 6.37 (s, 1H), 6.47 (s, 1H), 6.93 (d, 1H, J=7.93 Hz). MS (APCI) calcd for C$_{20}$H$_{26}$O$_5$: 346.2. found (M+1): 347.0.

Example 39

6-[2-(5-chloro-2,4-dimethoxyphenyl)ethyl]-6-cyclopentyldihydro-2H-pyran-2,4(3H)-dione

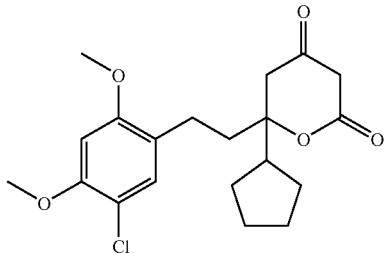

A solution of 6-[2-(2,4-dimethoxyphenyl)ethyl]-6-cyclopentyldihydro-2H-pyran-2,4(3H)-dione (from Example 39; 4.50 g, 13 mmol) in CH$_2$Cl$_2$ (20 mL) was cooled to −5° C. and treated with a solution of SO$_2$Cl$_2$ (1.94 g, 14.3 mmol) in CH$_2$Cl$_2$ (10 mL) dropwise under nitrogen. The reaction mixture was stirred for an additional 15 minutes at −5° C., then allowed to warm gradually to room temperature. After a total reaction time of 2 h, an aqueous solution of NaHCO$_3$ (5 wt %) was added to achieve a pH of 8 in the aqueous phase. The volatiles were removed in vacuo. The residue was treated with water and extracted with ethyl acetate (3×25 mL). The combined ethyl acetate extract was acidified to a pH 2 using 2 N HCl, then washed with water. The organic phase was dried over Na$_2$SO$_4$, filtered, and concentrated to a yellowish solid. Recrystallization from ether yielded the title product as a white solid (2.18 g, 44%). $^1$H NMR (CDCl$_3$) δ 1.74 (m, 8H), 2.32 (m, 1H), 2.58 (m, 2H), 2.78 (s, 2H), 3.43 (s, 2H), 3.82 (s, 3H), 3.92 (s, 3H), 6.44 (s, 1H), 7.07 (s, 1H). HRMS calcd for C$_{20}$H$_{25}$O$_5$Cl (M+H$^+$): 381.1469. found 381.1475.

Example 40

6-Cyclopentyl-6-[2-(4-isopropyl-phenyl)-ethyl]-dihydro-pyran-2,4-dione

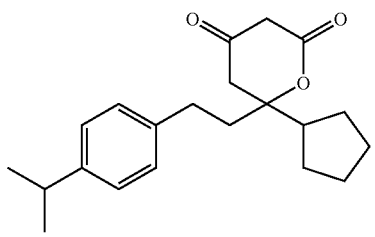

The title compound was prepared as described in Example 26, except 4-Bromoisopropylbenzene was substituted for 3-Bromochlorobenzene in step 1 of that Example. $^1$H NMR (CDCl$_3$-d$_6$): δ 1.93 (d, J=6.9 Hz, 6H), 1.58–1.78 (m, 8H), 1.93–2.05 (m, 2H), 2.2–2.31 (m, 1H), 2.65 (t, J=8.6 Hz, 2H), 2.77 (s, 2H), 2.81–2.92 (m, 1H), 3.42 (s, 2H), 7.07 (d, J=7.9 Hz, 2H), 7.15 (d, J=7.9 Hz, 2H). Anal. Calcd. For C$_{21}$H$_{28}$O$_3$.0.1 H$_2$O: C, 76.38; H, 8.61. Found: C, 76.26; H, 8.83. ESIMS (MH+): 351.2.

Example 41

6-Cyclopentyl-6-[2-(4-isopropoxy-phenyl)-ethyl]-dihydro-pyran-2,4-dione

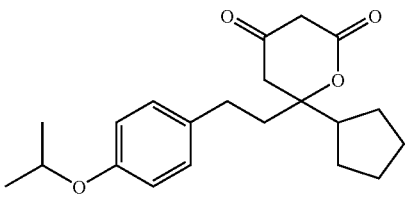

The title compound was prepared as described in Example 26, except 4-Bromo4-isopropoxylbenzene was substituted for 3-Bromochlorobenzene in step 1 of that Example. $^1$H NMR (CDCl$_3$-d$_6$): δ 1.32 (d, J=6.2 Hz, 6H), 1.58–1.7 (m, 8H), 1.89–1.99 (m, 1H), 2.2–2.31 (m, 2H), 2.61 (t, J=8.6 Hz, 2H), 2.77 (s, 2H), 3.43 (s, 2H), 4.52 (septet, J=12, 6 Hz, 1H), 6.82 (d, J=8.5 Hz, 2H) 7.03 (d, J=8.5 Hz, 2H). Anal. Calcd. For C$_{21}$H$_{28}$O$_4$: C, 73.23; H, 8.19. Found: C, 73.43; H, 8.44. ESIMS (MH+): 345.2.

Example 42

6-Cyclopentyl-6-[2-(3-ethoxy-phenyl)-ethyl]-dihydro-pyran-2,4-dione 6-Cyclopentyl-6-[2-(4-ethoxy-phenyl)-ethyl]-dihydro-pyran-2,4-dione

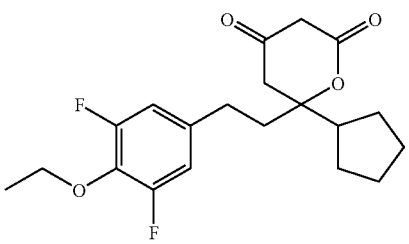

The title compound was prepared as described in Example 26, except 5-Bromo-2-ethoxy-1,3-difluoro-benzene was substituted for 3-Bromochlorobenzene in step 1 of that Example. $^1$H NMR (CDCl$_3$-d$_6$): δ 1.37 (t, J=6.9 Hz, 3H), 1.61–1.73 (m, 8H), 1.89–1.96 (m, 2H), 2.22–2.28 (m, 1H), 2.61 (t, J=7.4 Hz, 2H), 2.76 (d, J=5.6, 2H), 3.4 (s, 2H), 4.16 (q, J=14.2, 6.9 Hz, 2H), 6.68 (d, J=8.6 Hz, 2H). Anal. Calcd. For C$_{20}$H$_{24}$F$_2$O$_4$: C, 65.56; H, 6.60. Found: C, 65.66; H, 6.68. ESIMS (MNa+): 389.1.

Example 43

6-Cyclopentyl-6-[2-(3,5-difluoro-4-methoxy-phenyl)-ethyl]-dihydro-pyran-2,4-dione

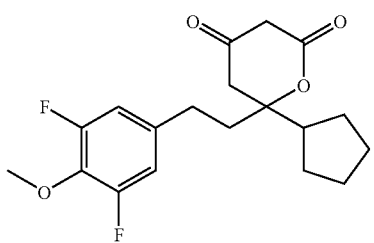

The title compound was prepared as described in Example 26, except 5-Bromo-2-methoxy-1,3-difluoro-benzene was substituted for 3-Bromochlorobenzene in step 1 of that Example. $^1$H NMR (CDCl$_3$-d$_6$): δ 1.50–1.73 (m, 8H), 1.89–2.01 (m, 2H), 2.22–2.28 (m, 1H), 2.64 (t, J=6.7 Hz, 2H), 2.76 (d, J=5.6, 2H), 3.44 (s, 2H), 3.96 (s, 3H), 6.68 (d, J=8.9 Hz, 2H). Anal. Calcd. For C$_{19}$H$_{22}$F$_2$O$_4$·0.1 H$_2$O: C, 64.43; H, 6.32. Found: C, 64.27; H, 6.38. ESIMS (MNa+): 375.1F.

Example 44

AG-021565, {MAR3647.138}6-Cyclopentyl-6-[2-(3-ethoxy-phenyl)-ethyl]-dihydro-pyran-2,4-dione 6-Cyclopentyl-6-[2-(4-ethoxy-phenyl)-ethyl]-dihydro-pyran-2,4-dione

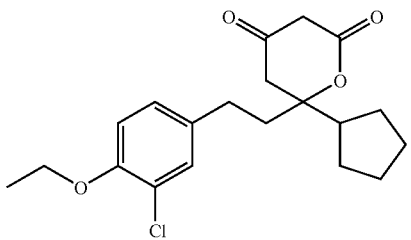

The title compound was prepared as described in Example 26 except 4-Bromo-2-chloro-1-ethoxy-benzene was substituted for 3-Bromochlorobenzene in step 1 of that Example. $^1$H NMR (CDCl$_3$-d$_6$): δ 1.45 (t, J=6.9 Hz, 3H), 1.59–1.70 (m, 8H), 1.91–1.94 (m, 2H), 2.22–2.27 (m, 1H), 2.60 (t, J=8.6 Hz, 2H), 2.76 (s, 2H), 3.43 (s, 2H), 4.08 (q, J=14, 6.9 Hz, 2H), 6.84 (d, J=8.3 Hz, 1H), 6.97 (dd, J=8.3, 2.3 Hz, 1H), 7.14 (d, J=2.3 Hz, 1H). Anal. Calcd. For C$_{20}$H$_{25}$ClO$_4$·0.5H$_2$O: C, 64.25; H, 7.01. Found: C, 64.29; H, 6.77. ESIMS (MH+): 365.1.

Example 45

6-cyclopentyl-6-{2-[3-(4-methoxyphenoxy)phenyl]ethyl}-4-hydroxy-5,6-dihydro-2H-pyran-2-one Step 1: 1-Cyclopentyl-3-[3-(4-methoxyphenoxy)phenyl]propan-1-one

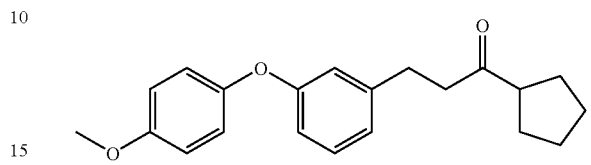

A solution of 3-(4-methoxyphenoxy)benzaldehyde (10.27 g, 45 mmol) and methyl cyclopentyl-ketone (6.06 g, 54 mmol) in anhydrous ethanol (81 mL) was treated with 5 M NaOH (aq) (18 mL, 90 mmol), and the mixture stirred at room temperature for 18 h. The volatiles were removed in vacuo. The residue was extracted with ether (100 mL) and the extract washed with water (3×60 mL), then with brine. The ethereal solution was dried over MgSO$_4$, filtered, and concentrated in vacuo, yielding the intermediate chalcone in a crude yield of 14.63 g. The crude intermediate (14.52 g) was dissolved in 110 mL ethyl acetate, treated with platinum oxide (5 mole %) and stirred over 1 atm of H$_2$ at room temperature overnight. The precipitate was filtered through a fine fritted funnel and the black residue washed with ethyl acetate. The filtrate was concentrated in vacuo to give a yellowish resin. The resin was chromatographed using silica gel and 6:1 hexanes/ethyl acetate, yielding 6.02 g (41%) of the ketone as a colorless oil. $^1$H NMR (CDCl$_3$); δ 1.45–1.85 (m, 8H), 2.76 (m, 2H), 2.85 (m, 3H), 3.81 (s, 3H), 6.77 (m, 2H), 6.90 (m, 3H), 6.97 (d, 2H, J=9 Hz), 7.20 (t, 1H, J=8 Hz). MS calcd for C$_{21}$H$_{24}$O$_3$: 324.2. found (M+H$^+$) 325.2.

Step 2: 6-cyclopentyl-6-{2-[3-(4-methoxyphenoxy)phenyl]ethyl}-4-hydroxy-5,6-dihydro-2H-pyran-2-one

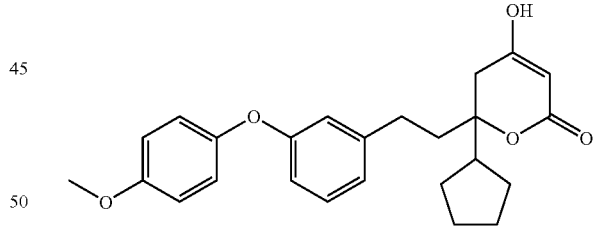

A solution of methyl acetoacetate (11 mg, 0.096 mmol, 1.2 equiv) in 3:1 DME/THF (0.15 mL) was cooled to −40° C. and treated with dry sodium hydride (2.4 mg, 0.10 mmol). After stirring for 30 min, the mixture was cooled to −70° C. and treated with a solution of n-butyllithium in hexanes (0.042 mL of a 2.4 M solution, 0.10 mmol).

The resulting mixture was stirred for another 45 min at −70° C., then added to a cold (−70° C.) solution of 1-cyclopentyl-3-[3-(4-methoxyphenoxy)phenyl]propan-1-one (26 mg, 0.080 mmol) in 3:1 DME/THF (0.18 mL). The reaction mixture was stirred for 30 min at −70° C., then allowed to warm to 20° C. over the course of 3.5 h. The mixture was treated with water (0.070 mL) then heated at 80° C. for 18 h. The reaction mixture was cooled to room temperature and treated with 1 N HCl (0.183 mL, 0.183 mmol), stirred for 15 min, then the volatiles removed in vacuo. The resulting mixture was purified by preparative supercritical fluid chromatography (SFC), yielding the title product in 30% yield. $^1$H NMR (DMSO): δ 1.35–1.60 (m, 8H), 1.85 (m, 2H), 2.24–2.4 (m, 5H, overlap with DMSO peak), 3.70 (s, 3H), 4.92 (s, 1H), 6.63 (d, 1H, J=8 Hz), 6.71 (s, 1H), 6.83 (d, 1H, J=8 Hz), 6.90 (m, 4H), 7.17 (t, 1H, J=8 Hz). MS (APCI) calcd for $C_{25}H_{28}O_5$: 408.2. found (M-17 fragment) 391.1.

Example 46

6-[2-(1-benzofuran-2-yl)ethyl]-6-cyclopentyl-4-hydroxy-5,6-dihydro-2H-pyran-2-one Step 1: 3-(1-Benzofuran-2-yl)-1-cyclopentylpropan-1-one

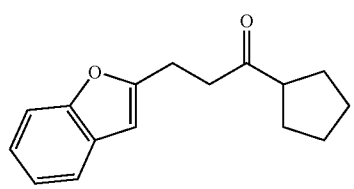

The title compound was prepared using the conditions in step 1 of Example 45, except substituting benzofuran-1-carboxaldehyde for 3-(4-methoxyphenoxy)benzaldehyde. $^1$H NMR (CDCl$_3$) δ 1.5–1.78 (m, 8H), 2.92 (m, 5H), 6.56 (s, 1H), 7.18 (m, 2H), 7.51 (m, 2H). MS(APCI) calcd for $C_{16}H_{18}O_2$, 242.1. found (M+H$^+$) 243.1.

Step 2: 6-[2-(1-benzofuran-2-yl)ethyl]-6-cyclopentyl-4-hydroxy-5,6-dihydro-2H-pyran-2-one

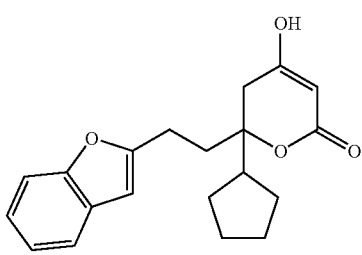

The title compound was prepared as described in Example 45, except substituting 3-(2-benzofuranyl)-1-cyclopentylpropan-1-one for 1-cyclopentyl-3-[3-(4-methoxyphenoxy)phenyl]propan-1-one in the final step of that Example. $^1$H NMR (DMSO): δ 1.3–1.6 (m, 8H), 2.06 (m, 2H), 2.32 (m, 1H, overlap with DMSO peak), 2.75 (m, 2H), 3.20 (m, 2H, overlap with H$_2$O peak), 4.95 (s, 1H), 6.57 (s, 1H), 7.13 (m, 2H), 7.42 (d, 1H, J=8 Hz), 7.47 (d, 1H, J=9.3 Hz). MS (APCI) calcd for $C_{20}H_{22}O_4$: 326.15. found (M+H$^+$) 327.1.

Example 47

6-cyclopentyl-6-[2-(4-phenoxyphenyl)ethyl]-4-hydroxy-5,6-dihydro-2H-pyran-2-one

Step 1: 3-(4-phenoxyphenyl)-1-cyclopentylpropan-1-one

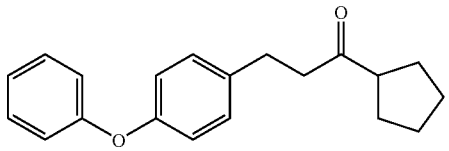

The title compound was prepared using the conditions in step 1 of Example 45, except substituting 4-phenoxybenzaldehyde for 3-(4-methoxyphenoxy) benzaldehyde. $^1$H NMR (DMSO-d$_6$) δ 1.47–1.69 (m, 8H), 2.76 (s, 4H), 2.89 (m, 1H), 6.90 (m, 4H), 7.05 t, 1H, J=8 Hz), 7.18 (d, 2H, J=8.3 Hz), 7.32 (t, 2H, J=8.3 Hz). MS calcd for $C_{20}H_{22}O_2$, 294.2. found (M) 294.0.

Step 2: 6-cyclopentyl-6-[2-(4-phenoxyphenyl)ethyl]-4-hydroxy-5,6-dihydro-2H-pyran-2-one

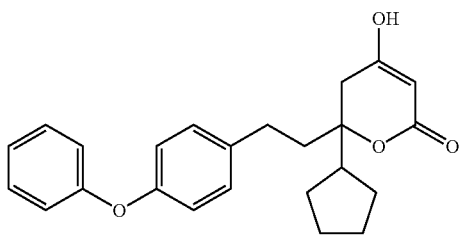

The title compound was prepared as described in Example 45 except substituting 3-(4-phenoxyphenyl)-1-cyclopentylpropan-1-one for 1-cyclopentyl-3-[3-(4-methoxyphenoxy)phenyl]propan-1-one in the final step of that Example. $^1$H NMR (DMSO): δ 1.4–1.65 (m, 8H), 1.88 (m, 2H), 2.28 (m, 1H), 2.7 (m, 2H, overlap with DMSO peak), 3.19 (m, 2H, overlap with H$_2$O peak), 4.93 (s, 1H), 6.87 (d, 2H, J=8.5 Hz), 6.92 (d, 2H, J=7.5 Hz), 7.04 (t, 1H, J=7.5 Hz), 7.15 (d, 2H, J=8.5 Hz), 7.30 (t, 2H, J=7.5 Hz). MS calcd for $C_{24}H_{26}O_4$: 378.2. found (M+H$^+$) 379.1.

Example 48

6-Cyclopentyl-6-(2-{4-[(3-methyl-1,2,4-oxadiazol-5-yl)methoxy]phenyl}ethyl)4-hydroxy-5,6-dihydro-2H-pyran-2-one Step 1: 3-(4-Hydroxyphenyl)-1-cyclopentylpropan-1-one

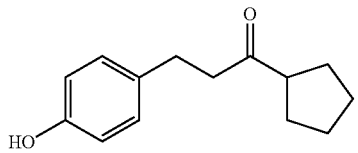

A mixture of 3-(4-benzyloxyphenyl)-1-cyclopentylpropan-1-one, as described in Example 1, step 5 (81.5 g, 0.262 mol), ammonium formate (83 g, 1.315 mole, 5 equiv), 10% Pd/C (6.6 g, 0.0062 mol, 2.35 mole %) and methanol (330 mL) was stirred under nitrogen at 40° C. for 3 h. The reaction mixture was then cooled to room temperature and filtered through celite. Water (200 mL) was added to the filtrate and the resulting mixture extracted with ethyl acetate (3×300 mL). The combined organic phases were dried over MgSO$_4$, filtered and concentrated in vacuo. The resulting resin was chromatographed on silica gel using 7:1 hexanes/ethyl acetate, yielding the title product as an oil (36.13 g, 63%). $^1$H NMR (DMSO-d$_6$) δ 1.45–1.73 (m, 8H), 2.64 (m, 4H), 2,85 (m, 1H), 6.60 (d, 2H, J=8.5 Hz), 6.98 (d, 2H, J=8.5 Hz), 9.11 (s, 1H). MS calcd for C$_{14}$H$_{18}$O$_2$: 218; found (M–H$^+$): 217.

Step 2: 1-cyclopentyl-3-{4-[(3-methyl-1,2,4-oxadiazol-5-yl)methoxy]phenyl}propan-1-one

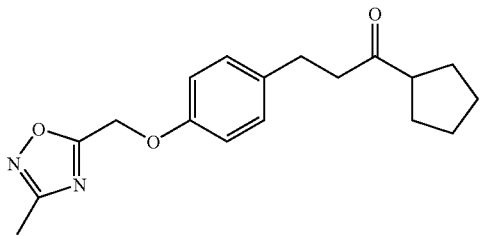

A mixture of 3-(4-hydroxyphenyl)-1-cyclopentylpropan-1-one (4.36 g, 20 mmol), 5-(chloromethyl)-3-methyl-1,2,4-oxadiazole (2.65 g, 20 mmol; prepared according to a reported procedure: Durden, et al. *J. Org. Chem.*, 36: 1306 (1971)), K$_2$CO$_3$ (2.76 g, 20 mmol), and CH$_3$CN (28 mL) was stirred and refluxed overnight under a blanket of N$_2$. The reaction was allowed to cool to room temperature, filtered, and the solvent removed in vacuo. The light orange-colored solid was recrystallized from warm ether, and the resulting white solid dried in vacuo, yielding 3.83 g (61%) of the title product. $^1$H NMR (CDCl$_3$) δ 1.5–1.8 (m, 8H), 2.43 (s, 3H), 2.70 (m, 2H), 2.88 (m, 3H), 5.24 (s, 2H), 6.85 (d, 2H, J=8.69 Hz), 7.11 (d, 2H, J=8.69 Hz). MS (APCI) calcd for C$_{18}$H$_{22}$N$_2$O$_3$: 314.2. found (M+H$^+$): 315.1.

Step 3: 6-Cyclopentyl-6-(2-{4-[(3-methyl-1,2,4-oxadiazol-5-yl)methoxy]phenyl}ethyl)-4-hydroxy-5,6-dihydro-2H-pyran-2-one

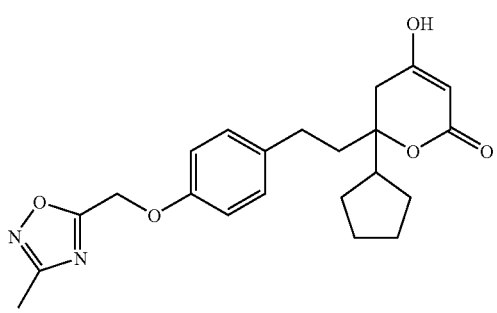

The title compound was prepared as described in Example 45 using 1-cyclopentyl-3-{4-[(3-methyl-1,2,4-oxadiazol-5-yl)methoxy]phenyl}propan-1-one for 1-cyclopentyl-3-[methoxyphenoxy)phenyl]propan-1-one in the final step of that Example. $^1$H NMR (DMSO): δ 1.4–1.65 (m, 8H), 1.83 (m, 2H), 2.26 (m, 1H), 2.30 (s, 3H), 2.7 (m, 2H, overlap with DMSO peak), 3.18 (m, 2H, overlap with H$_2$O peak), 4.52 (s, 1H), 5.34 (s, 2H), 6.88 (d, 2H, J=8.2 Hz), 7.07 (d, 2H, J=8.2 Hz). MS (APCI) calcd for C$_{22}$H$_{26}$N$_2$O$_5$: 398.2. found (M-17 fragment): 381.2.

Example 49

6-Cyclopentyl-6-(2-{4-[(3,5-dimethylisoxazol-4-yl)methoxy]phenyl}ethyl)-4-hydroxy-5,6-dihydro-2H-pyran-2-one Step 1: 1-Cyclopentyl-3-{4-[(3,5-dimethylisoxazol-4-yl)methoxy]phenyl}propan-1-one

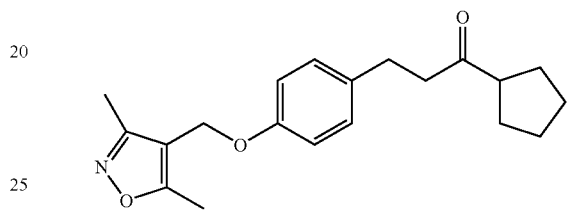

The title compound was prepared as described in step 2, except substituting 4-chloromethyl-3,5-dimethylisoxazole for 5-chloromethyl-3-methyl-1,2,4-oxadiazole. $^1$H NMR (CDCl$_3$): δ 1.5–1.85 (m, 8H), 2.28 (s, 3H), 2.39 (s, 3H), 2.74 (m, 2H), 2.84 (m, 3H), 4.76 (s, 2H), 6.85 (d, 2H, J=8.31 Hz), 7.17 (d, 2H, J=8.31 Hz). MS (APCI) calcd for C$_{20}$H$_{25}$NO$_3$, 327.2. found (M+H$^+$): 328.2.

Step 2: 6-Cyclopentyl-6-(2-{4-[(3,5-dimethylisoxazol-4-yl)methoxy]phenyl}ethyl)-4-hydroxy-5,6-dihydro-2H-pyran-2-one

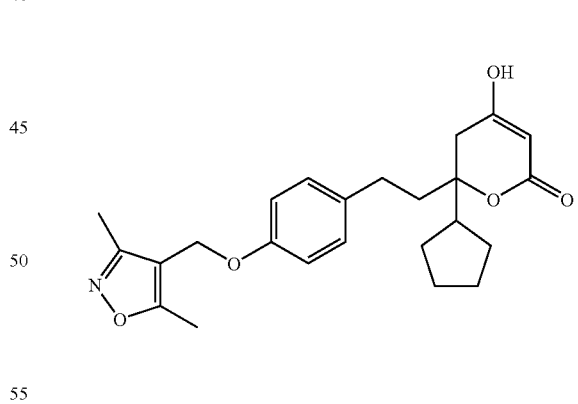

The title compound was prepared as described in Example 45, except substituting 1-cyclopentyl-3-{4-[(3,5-dimethylisoxazol-4-yl)methoxy]phenyl}propan-1-one for 1-cyclopentyl-3-[3-(4-methoxyphenoxy)phenyl]propan-1-one in the final step of that Example. $^1$H NMR (DMSO): δ 1.4–1.65 (m, 8H), 1.81 (m, 2H), 2.07 (m, 1H), 2.13 (s, 3H), 2.33 (s, 3H), 2.65 (m, 2H, overlap with DMSO peak), 3.11 (m, 2H, overlap with H$_2$O peak), 4.81 (s, 2H), 4.93 (s, 1H), 6.84 (d, 2H, J=8.52 Hz), 7.05 (d, 2H, J=8.52 Hz). MS (APCI) calcd for C$_{24}$H$_{29}$NO$_5$: 411.2. found (M+H$^+$): 412.1.

Example 50

6-Cyclopentyl-6-(2-{4-[(1-methyl-1H-benzimidazol-2-yl)methoxy]phenyl}ethyl)-4-hydroxy-5,6-dihydro-2H-pyran-2-one Step 1: 1-Cyclopentyl-3-{4-[(1-methyl-1H-benzimidazol-2-yl)methoxy]phenyl}propan-1-one

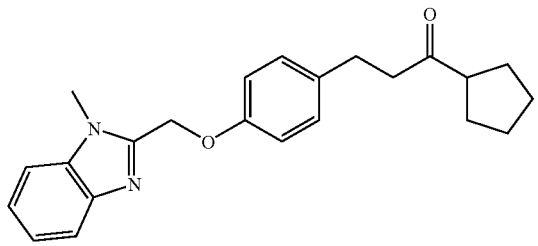

The title compound was prepared as described in Example 48, step 2 using 2-chloromethyl-1-methyl-1H-benzimidazole (prepared according to the procedure of Skolnick, et al. *J. Am. Chem. Soc.* 65, 1854 (1943)) for 5-chloromethyl-3-methyl-1,2,4-oxadiazole. $^1$H NMR (CDCl$_3$): δ 1.47–1.86 (m, 8H), 2.70 (m, 2H), 2.83 (m, 3H), 3.86 (s, 3H), 5.37 (s, 2H), 6.98 (d, 2H, J=9 Hz), 7.10 (d, 2H, J=9 Hz), 7.25–7.4 (m, 3H), 7.83 (m, 1H). MS (APCI) calcd for C$_{23}$H$_{26}$N$_2$O$_2$: 362.2. found (M+H$^+$): 363.3.

Step 2: 6-Cyclopentyl-6-(2-{4-[(1-methyl-1H-benzimidazol-2-yl)methoxy]phenyl}ethyl)-4-hydroxy-5,6-dihydro-2H-pyran-2-one

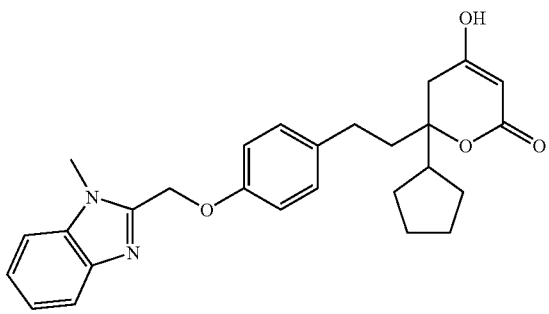

The title compound was prepared as described in Example 45 using 1-cyclopentyl-3-{4-[(1-methyl-1H-benzimidazol-2-yl)methoxy]phenyl}propan-1-one for 1-cyclopentyl-3-[3-(4-methoxyphenoxy)phenyl]propan-1-one in the final step of that Example. $^1$H NMR (DMSO): δ 1.25–1.60 (m, 8H), 1.82 (m, 2H), 2.23 (m, 1H), 2.64 (m, 2H, overlap with DMSO peak), 3.14 (m, 2H, overlap with H$_2$O peak), 3.79 (s, 3H), 4.94 (s, 1H), 5.30 (s, 2H), 6.97 (d, 2H), 7.07 (d, 2H), 7.15 (d, 1H), 7.25 (t, 1H), 7.49 (d, 1H), 7.58 (d, 1H). MS (APCI) calcd for C$_{27}$H$_{30}$N$_2$O$_4$: 446.2. found (M+H$^+$) 447.2.

Example 51

6-Cyclopentyl-6-(2-{4-[(3,4-dichlorobenzyl)oxy]phenyl}ethyl)-4-hydroxy-5,6-dihydro-2H-pyran-2-one Step 1: 1-Cyclopentyl-3-{4-[(3,4-dichlorobenzyl)oxy]phenyl}propan-1-one

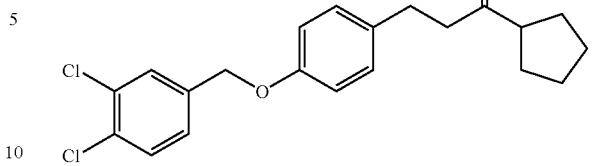

The title compound was prepared as described in Example 48, step 2 using 3,4-dichlorobenzyl bromide for 5-chloromethyl-3-methyl-1,2,4-oxadiazole. $^1$H NMR (CDCl$_3$): δ 1.5–1.8 (m, 8H), 2.74 (m, 2H), 2.87 (m, 3H), 5.00 (s, 2H), 6.88 (d, 1H, J=8.31 Hz), 7.13 (d, 2H, J=8.31 Hz), 7.28 (d, 1H, J=8.3 Hz), 7.44 (d, 1H, J=8.3 Hz), 7.55 (s, 1H). MS calcd for C$_{21}$H$_{22}$Cl$_2$O$_2$: 377.0.

Step 2: 6-Cyclopentyl-6-(2-{4-[(3,4-dichlorobenzyl)oxy]phenyl}ethyl)-4-hydroxy-5,6-dihydro-2H-pyran-2-one

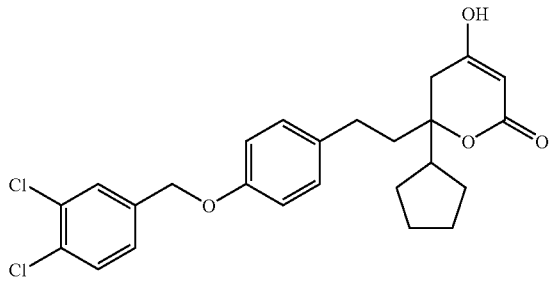

The title compound was prepared as described in Example 45 using 1-cyclopentyl-3-{4-[(3,4-dichlorobenzyl)oxy]phenyl}propan-1-one for 1-cyclopentyl-3-[3-(4-methoxyphenoxy)phenyl]propan-1-one in the final step of that Example. $^1$H NMR (DMSO): δ 1.27–1.58 (m, 8H), 1.81 (m, 2H), 2.11 (m, 1H), 2.69 (m, 2H, overlap with DMSO peak), 3.16 (m, 2H, overlap with H$_2$O peak), 4.92 (s, 1H), 5.05 (s, 2H), 6.87 (d, 2H, J=8 Hz), 7.05 (d, 2H, J=8 Hz), 7.36 (d, 1H, J=8 Hz), 7.58 (d, 1H, J=8.0 Hz), 7.66 (s, 1H). MS (APCI) calcd for C$_{25}$H$_{26}$Cl$_2$O$_4$: 460.1. found (M+H$^+$): 461.0.

Example 52

6-Cyclopentyl-6-[2-(4-{[6-(trifluoromethyl)pyridin-3-yl]methoxy}phenyl)ethyl]4-hydroxy-5,6-dihydro-2H-pyran-2-one Step 1: 1-Cyclopentyl-3-{4-[(6-(trifluoromethyl)pyridin-3-yl)methoxy]phenyl}propan-1-one

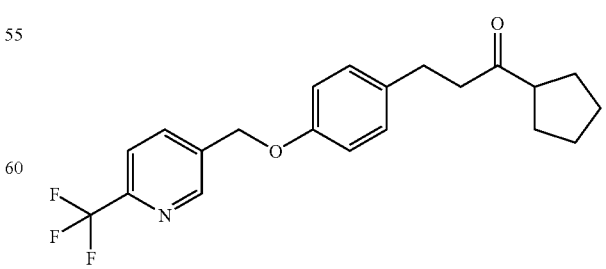

The title compound was prepared as described in Example 48, step 2 using 3-chloromethyl-6-(trifluoromethyl)pyridine for 5-chloromethyl-3-methyl-1,2,4-oxadiazole. $^1$H NMR (CDCl$_3$): δ 1.5–1.85 (m, 8H), 2.69 (m, 2H), 2.86 (m, 3H), 5.14 (s, 2H), 6.87 (d, 2H, J=8.5 Hz), 7.13 (d, 2H, J=8.5 Hz), 7.69 (d, 1H, J=8 Hz), 8.01 (d, 1H, J=8 Hz), 8.79 (s, 1H). MS (APCI) calcd for C$_{21}$H$_{22}$F$_3$NO$_2$: 377.2; found (M+H$^+$): 378.3.

Step 2: 6-Cyclopentyl-6-[2-(4-{[6-(trifluoromethyl)pyridin-3-yl]methoxy}phenyl)ethyl]-4-hydroxy-5,6-dihydro-2H-pyran-2-one

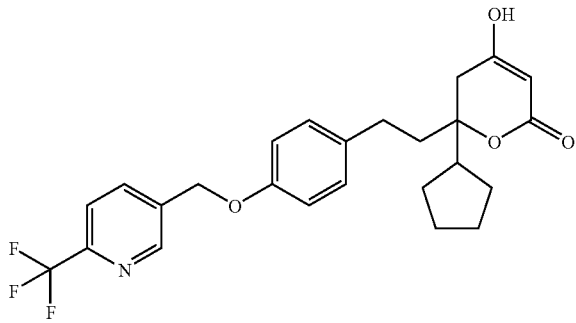

The title compound was prepared as described in Example 45 using 1-cyclopentyl-3-{4-[(3,4-dichlorobenzyl)oxy]phenyl}propan-1-one for 1-cyclopentyl-3-[3-(4-methoxyphenoxy)phenyl]propan-1-one in the final step of that Example. $^1$H NMR (DMSO): δ 1.2–1.65 (m, 8H), 1.84 (m, 2H), 2.25 (m, 1H), 2.64 (m, 2H, overlap with DMSO peak), 3.12 (m, 2H, overlap with H$_2$O peak), 4.91 (s, 1H), 5.19 (s, 2H), 6.89 (d, 2H, J=8.52 Hz), 7.08 (d, 2H, J=8.52 Hz), 7.87 (d, 1H, J=8.5 Hz), 8.07 (d, 1H, J=8.5 Hz), 8.76 (s, 1H). MS (APCI) calcd for C$_{25}$H$_{26}$F$_3$NO$_4$: 461.2. found (M+H$^+$): 462.2.

Example 53

6-Cyclopentyl-6-[2-(3,4-dichloro-phenyl)-ethyl]-dihydro-pyran-2,4-dione

Step 1: 1-Cyclopentyl-3-(3,4-dichloro-phenyl)-propan-1-one

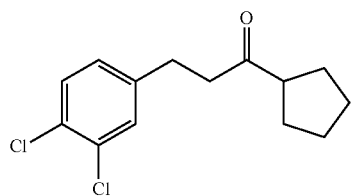

The title compound was prepared employing steps 4 and 5 of Example 1 using 3-(3,4-Dichloro-phenyl)-propionic acid for 3-(4-Benzyloxyphenyl)propionic acid in step 4 of that Example. $^1$H NMR (CDCl$_3$):: 1.55–1.85 (m, 9H), 2.72–2.88 (m, 4H), 7.02 (dd, J=8.1, 2.0 Hz, 1H), 7.27 (t, J=2.0 Hz, 1H), 7.82 (d, J=8.1 Hz, 1H). ESIMS (MH+): 374.1.

Step 2: 6-Cyclopentyl-6-[2-(3,4-dichloro-phenyl)-ethyl]-dihydro-pyran-2,4-dione

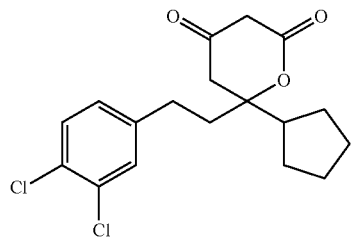

The title compound was obtained as described in Example 1, except 1-Cyclopentyl-3-(3,4-dichloro-phenyl)-propan-1-one from step 1 above was substituted for 3-(4-benzyloxyphenyl)-1-cyclopentylpropan-1-one in step 6 of that Example. $^1$H NMR (CDCl$_3$-d$_6$): δ 1.24–1.73 (m, 8H), 1.93 (t, J=9.6 Hz, 2H), 2.24–2.28 (m, 1H), 2.65 (t, J=9.6 Hz, 2H), 2.77 (d, J=7.6 Hz, 2H), 3.43 (d, J=3.0 Hz, 2H), 6.99 (dd, J=8.3, 2.3 Hz, 1H), 7.24 (d, J=2.3 Hz, 1H), 7.86 (d, J=8.3 Hz, 1H). Anal. Calcd. For C$_{18}$H$_{20}$Cl$_2$O$_3$: C, 60.86; H, 5.67. Found: C, 61.11; H, 5.87. ESIMS (MH+): 356.

Example 54

6-Cyclopentyl-6-[2-(3,4-difluoro-phenyl)-ethyl]-dihydro-pyran-2,4-dione

Step 1: 1-Cyclopentyl-3-(3,4-difluoro-phenyl)-propan-1-one

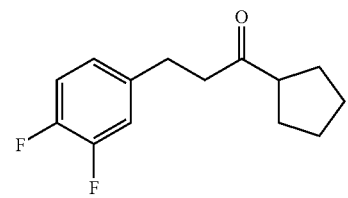

The title compound was prepared employing steps 4 and 5 of Example 1 using 3-(3,4-Difluoro-phenyl)-propionic acid for 3-(4-Benzyloxyphenyl)propionic acid in step 4 of that Example. $^1$H NMR (CDCl$_3$): δ 1.52–1.83 (m, 9H), 2.72–2.88 (m, 4H), 6.86–7.09 (m, 3H).

Step 2: 6-Cyclopentyl-6-[2-(3,4-difluoro-phenyl)-ethyl]-dihydro-pyran-2,4-dione

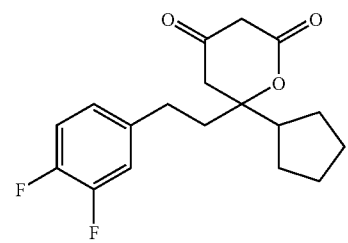

The title compound was obtained as described in Example 1, except -Cyclopentyl-3-(3,4-difluoro-phenyl)-propan-1-one from step 1 above was substituted for 3-(4-benzylox yphenyl)-1-cyclopentylpropan-1-one in step 6 of that Example. $^1$H NMR (CDCl$_3$-d$_6$): δ 1.44–1.8 (m, 8H), 1.90–1.96 (m, 2H), 2.24–2.28 (m, 1H), 2.62–2.68 (m, 2H), 2.77 (d, J=7.1 Hz, 2H), 3.43 (d, J=3.5 Hz, 2H), 6.85–6.87 (m, 1H), 6.94–6.96 (m, 1H), 7.04–7.09 (m, 1H). Anal. Calcd. For C$_{18}$H$_{20}$F$_2$O$_3$: C, 67.07; H, 6.25. Found: C, 67.28; H, 6.24. ESIMS (MH+): 323.

Example 55

6-Cyclopentyl-6-[2-(3,4-difluoro-phenyl)-ethyl]-dihydro-pyran-2,4-dione

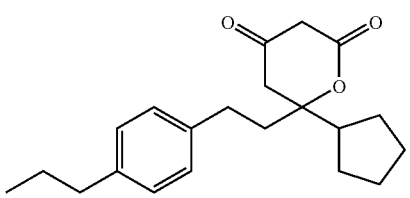

The title compound was prepared as described in Example 26, except 1-Bromo-4-propyl-benzene was substituted for 3-Bromochlorobenzene in step 1 of that Example. $^1$H NMR (CDCl$_3$-d$_6$): δ 0.93 (t, J=7.3 Hz, 3H), 1.46–1.82 (m, 10H), 1.92–2.02 (m, 2H), 2.26–2.31 (m, 1H), 2.53 (t, J=7.3 Hz, 2H), 2.64 (t, J=8.5 Hz, 2H), 2.77 (s, 2H), 3.42 (s, 2H), 7.05 (d, J=8.0 Hz, 2), 7.10 (d, J=8.0 Hz, 2H). Anal. Calcd. For C$_{21}$H$_{28}$O$_3$: C, 76.79; H, 8.59. Found: C, 76.65; H, 8.65. ESIMS (MH+): 329.

Example 56

6-[2-(4-Cyclobutoxy-3-fluoro-phenyl)-ethyl]-6-cyclopentyl-dihydro-pyran-2,4-dione Step 1: 4-Bromo-1-cyclobutoxy-2-fluoro-benzene

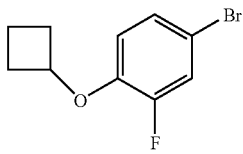

4-bromo-2-fluorophenol (1.09 g, 5.69 mmol), cyclobutyl bromide (1.0 g, 7.40 mmol), K$_2$CO$_3$ (2.36 g, 17.07 mmol) and KI (1.89 g, 11.38 mmol) were combined in anhydrous DMF (3.0 mL), under argon and heated at 55° C. in an oil bath for 24 hours. The resulting reaction mixture was cooled to room temperature and poured into water (50 mL) and extracted with Et$_2$O (2×25 mL). The organics were washed with water (50 mL) and brine (50 mL) then dried over Na$_2$SO$_4$, filtered and concentrated. The crude residue was purified by flash chromatography (10% EtOAc in Hexanes) to yield the intermediate ether as a colorless oil (0.81 g, 58%). $^1$H NMR (CDCl$_3$): δ 1.59–1.75 (m, 1H), 1.82–1.93 (m, 1H), 2.15–2.28 (m, 2H), 2.39–2.49 (m, 2H), 4.63 (pentet, J=14.1, 7.2 Hz, 1H), 6.70 (t, J=8.7 Hz, 1H), 7.12–7.16 (m, 1H), 7.23 (dd, J=10.5, 2.5 Hz, 1H). ESIMS (MH+): 246.1.

Step 2: 6-[2-(4-Cyclobutoxy-3-fluoro-phenyl)-ethyl]-6-cyclopentyl-dihydro-pyran-2,4-dione

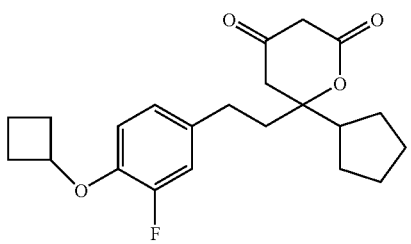

The title compound was prepared as described in Example 26, except 4-Bromo-1-cyclobutoxy-2-fluoro-benzene from step 1 above was substituted for 3-Bromochlorobenzene in step 1 of that Example. $^1$H NMR (CDCl$_3$-d$_6$): δ 1.57–1.99 (m, 12H), 2.17–2.29 (m, 3H), 2.38–2.45 (m, 2H), 2.60 (t, J=7.8 Hz, 2H), 2.75 (s, 2H), 3.42 (s, 2H), 4.63 (pentet, J=14.3, 7.2 Hz, 1H), 6.74 (s, 1H), 6.76–6.78 (m, 1H), 6.84–6.88 (m, 1H). Anal. Calcd. For C$_{22}$H$_{27}$FO$_4$: C, 70.57; H, 7.27. Found: C, 70.64; H, 7.38. ESIMS (MNa+): 397.1

Example 57

6-Cyclopentyl-6-[2-(4-cyclopropylmethoxy-3-fluoro-phenyl)-ethyl]-dihydro-pyran-2,4-dione Step 1: 4-Bromo-1-cyclopropylmethoxy-2-fluoro-benzene

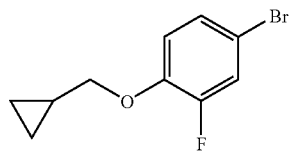

The title compound was prepared as described in Example 56 except (bromomethyl)-cyclopropane was substituted for cyclobutyl bromide in step 1 of that Example. $^1$H NMR (CDCl$_3$): δ 0.32–0.42 (m, 2H), 0.62–0.68 (m, 2H), 1.23–1.33 (m, 1H), 3.85 (d, J=6.9 Hz, 2H) 6.82 (t, J=8.8 Hz, 1H), 7.14–7.18 (m, 1H), 7.23 (dd, J=10.5, 2.3 Hz, 1H). ESIMS (MH+): 246.1.

Step 2: 6-Cyclopentyl-6-[2-(4-cyclopropylmethoxy-3-fluoro-phenyl)-ethyl]-dihydro-pyran-2,4-dione

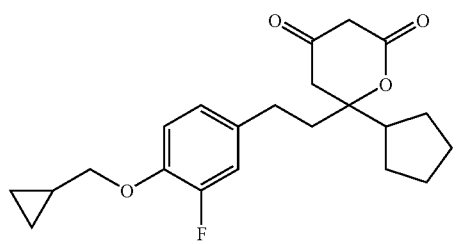

The title compound was prepared as described in Example 26, except 4-Bromo-1-cyclopropylmethoxy-2-fluoro-benzene from step 1 above was substituted for 3-Bromochlorobenzene in step 1 of that Example. $^1$H NMR (CDCl$_3$-d$_6$): δ 0.32–0.37 (m, 2H), 0.61–0.67 (m, 2H), 1.26–1.30 (m, 1H), 1.57–1.84 (m, 8H), 1.89–1.96 (m, 2H), 2.26 (t, J=8.4 Hz, 1H), 2.61 (t, J=8.4 Hz, 2H), 2.75 (s, 2H), 3.42 (s, 2H), 3.84

(d, J=6.9 Hz, 2H), 6.78–6.89 (m, 3H). Anal. Calcd. For C$_{22}$H$_{27}$FO$_4$: C, 70.57; H, 7.27. Found: C, 70.63; H, 7.40. ESIMS (MNa+): 397.1.

Example 58

6-Cyclopentyl-6-(4-methoxy-phenoxymethyl)-dihydro-pyran-2,4-dione

Step1: 1-Cyclopentyl-2-(4-methoxy-phenoxy)-ethanone

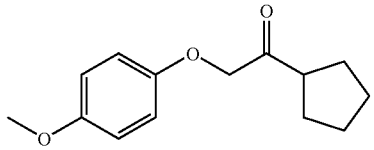

The title compound was prepared employing steps 4 and 5 of Example 1: using 4-methoxyphenoxy acetic acid for 3-(4-Benzyloxyphenyl)propionic acid in step 4 of that Example. $^1$H NMR (CDCl$_3$): δ 1.55–1.91 (m, 8H), 3.15 (pentet, J=16, 7.5 Hz, 1H), 3.77 (s, 3H), 4.57 (s, 2H), 6.84 (s, 4H). ESIMS (MH+): 235.1.

Step 2: 6-Cyclopentyl-6-(4-methoxy-phenoxymethyl)-dihydro-pyran-2,4-dione

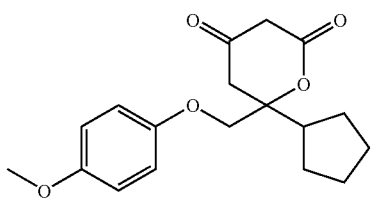

The title compound was obtained as described in Example 1, except 1-cyclopentyl-2-(4-methoxy-phenoxy)-ethanone from step 1 above, was substituted for 3-(4-benzyloxyphenyl)-1-cyclopentylpropan-1-one in step 5 of that Example. $^1$H NMR (CDCl$_3$-d$_6$): δ 1.50–1.83 (m, 8H), 2.17–2.25 (m, 1H), 2.74 (s, 2H), 3.34 (d, J=20.9 Hz, 1H), 3.63 (d, J=20.9 Hz, 1H), 3.75 (s, 3H), 3.89 (d, J=9.9 Hz, 1H), 4.21 (d, J=9.9 Hz, 1H), 6.72 (d, J=9.1 Hz, 2H), 6.80 (d, J=9.1 Hz, 2H). Anal. Calcd. For C$_{18}$H$_{22}$O$_5$·0.1H$_2$O: C, 67.53; H, 6.99. Found: C, 67.46; H, 6.90. ESIMS (MH+): 319.1.

Example 59

6-[2-(4-Acetyl-3-fluoro-phenyl)-ethyl]-6-cyclopentyl-dihydro-pyran-2,4-dione

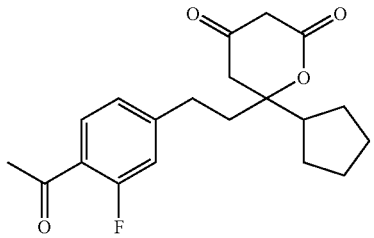

The title compound was prepared as described in Example 17, except 6-Cyclopentyl-6-{2-[3-fluoro-4-(2-methyl-[1,3] dioxolan-2-yl)-phenyl]-ethyl}-dihydro-pyran-2,4-dione prepared above (Example 60, step 2) was substituted for 6-cyclopentyl-4-hydroxy-6-{2-[3-methyl-4-(2-methyl-1,3-dioxolan-2-yl)-phenyl]-ethyl}-5,6-dihydro-pyran-2-one in that Example. $^1$H NMR (CDCl$_3$-d$_6$): δ 1.50–1.82 (m, 8H), 1.96 (t, J=8.7 Hz, 2H), 2.25–2.30 (m, 1H), 2.63 (d, J=4.9 Hz, 3H), 2.70–2.75 (m, 2H), 2.78 (d, J=5.5 Hz, 2H), 3.45 (d, J=2.5 Hz, 2H), 6.93 (dd, J=11.7, 1.5 Hz, 1H), 7.02 (dd, J=8.1, 1.5 Hz, 1H), 7.82 (t, J=8.1 Hz, 1H). Anal. Calcd. For C$_{20}$H$_{23}$FO$_4$: C, 69.35; H, 6.69. Found: C, 69.27; H, 6.83. ESIMS (MH+): 347.1.

Example 60

6-Cyclopentyl-6-{2-[3-fluoro-4-(2-methyl-[1,3]dioxolan-2-yl)-phenyl]-ethyl}-dihydro-pyran-2,4-dione Step 1: 4-Bromo-2-fluoro-thiobenzoic acid S-pyridin-2-yl ester

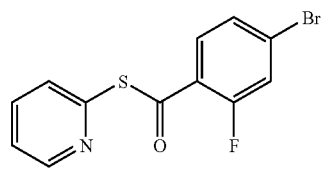

The title compound was prepared as described in Example 1 3-(4-Benzyloxyphenyl)thiopropionic acid S-pyridin-2-yl ester, where 4-bromo-2-fluorobenzoic acid was substituted for 3-(4-Benzyloxyphenyl)propionic acid in step 4 of that Example. $^1$H NMR (CDCl$_3$): δ 7.33–7.44 (m, 3H), 7.71–7.83 (m, 3H), 8.67–8.71 (m, 1H). ESIMS (MH+): 313.1.

Step 2: 1-(4-Bromo-2-fluoro-phenyl)-ethanone

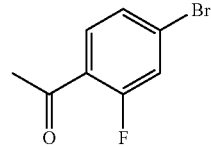

The title compound was prepared as described in Example 1, except 4-Bromo-2-fluoro-thiobenzoic acid S-pyridin-2-yl ester from step 1 above was substituted for 3-(4-Benzyloxyphenyl)thiopropionic acid S-pyridin-2-yl ester and methyl magnesium bromide 1.4M in toluene was substituted for cyclopentylmagnesium bromide in Et$_2$O in step 5 of that Example. $^1$H NMR (CDCl$_3$):: δ 2.63 (d, 3H, J=5.1 Hz, 3H), 7.37 (dd, J=8.8, 1.9 Hz, 1H), 7.37 (s, 1H), 7.77 (7, J=8.8 Hz, 1H). ESIMS (MH+): 218.2.

Step 3: 2-(4-Bromo-2-fluoro-phenyl)-2-methyl-[1,3]dioxolane

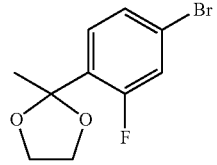

The title compound was prepared as described in Example 22, except 1-(4-Bromo-2-fluoro-phenyl)-ethanone from step 2 above was substituted for 1-(2-methyl-4-trimethyl silanyl-ethynyl-phenyl)-ethanone in step 3 of that Example. $^1$H NMR (CDCl$_3$): δ 1.73 (s, 3H), 3.81–3.85 (m, 2H), 4.05–4.10 (m, 2H), 7.23–7.27 (m, 2H), 7.35–7.41 (m, 1H). ESIMS (MH+): 262.2.

Step 4: 6-Cyclopentyl-6-{2-[3-fluoro-4-(2-methyl-[1,3]dioxolan-2-yl)-phenyl]-ethyl}-dihydro-pyran-2,4-dione

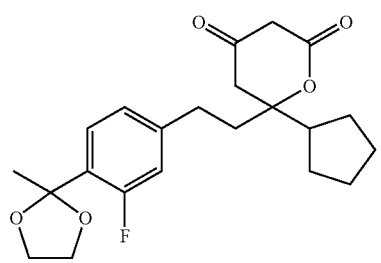

The title compound was prepared as described in Example 26, except 2-(4-Bromo-2-fluoro-phenyl)-2-methyl-[1,3]dioxolane from step 3 above, was substituted for 3-Bromo-chlorobenzene in step 1 of that Example. $^1$H NMR (CDCl$_3$-d$_6$): δ 1.5–1.7 (m, 8H), 1.73 (s, 3H), 1.91–1.98 (m, 2H), 2.28 (t, J=8.5 Hz, 1H), 2.62–2.67 (m, 2H), 2.77 (d, J=1.7 Hz, 2H), 3.43 (s, 2H), 3.81–3.86 (m, 2H), 4.05–4.09 (m, 2H), 6.83–6.91 (m, 2H), 7.41 (t, J=8.0 Hz, 1H). ESIMS (MH+): 391.1.

Example 61

6-[2-(4-Acetyl-3-chloro-phenyl)-ethyl]-6-cyclopentyl-dihydro-pyran-2,4-dione

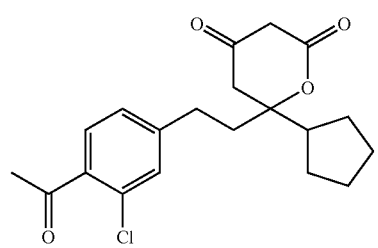

The title compound was prepared as described in Example 17, except 6-{2-[3-Chloro-4-(2-methyl-[1,3]dioxolan-2-yl)-phenyl]-ethyl}-6-cyclopentyl-dihydro-pyran-2,4-dione from step above was substituted for 6-cyclopentyl-4-hydroxy-6-{2-[3-methyl-4-(2-methyl-1,3-dioxolan-2-yl)-phenyl]-ethyl}-5,6-dihydro-pyran-2-one in that Example. $^1$H NMR (CDCl$_3$-d$_6$): δ 1.51–1.82 (m, 8H), 1.95 (t, J=8.5 Hz, 2H), 2.24–72.30 (m, 1H), 2.64 (s, 3H), 2.70–2.72 (m, 2H), 2.78 (d, J=4.9 Hz, 2H), 3.45 (d, J=2.1 Hz, 2H), 7.11 (dd, J=7.9, 1.7 Hz, 1H), 7.22 (d, J=1.7 Hz, 1H), 7.63 (d, J=7.9 Hz, 1H). Anal. Calcd. For C$_{20}$H$_{23}$ClO$_4$: C, 66.20; H, 6.39. Found: C, 66.71; H, 6.52. ESIMS (MH+): 363.2.

Example 62

6-{2-[3-Chloro-4-(2-methyl-[1,3]dioxolan-2-yl)-phenyl]-ethyl}-6-cyclopentyl-dihydro-pyran-2,4-dione Step 1: 4-Bromo-2-chloro-thiobenzoic acid S-pyridin-2-yl ester

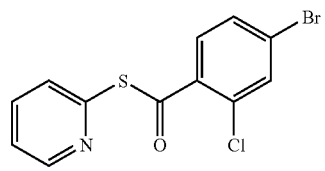

The title compound was prepared as described in Example 1, except 4-bromo-2-chlorobenzoic acid was substituted for 3-(4-Benzyloxyphenyl)propionic acid in step 4 of that Example. $^1$H NMR (CDCl$_3$): δ 7.34–7.38 (m, 1H), 7.53 (dd, J=8.3, 1.7 Hz, 1H), 7.67–7.85 (m, 4H), 8.68 (d, J=5.6 Hz, 1H). ESIMS (MH+): 329.1.

Step 2: 1-(4-Bromo-2-chloro-phenyl)-ethanone

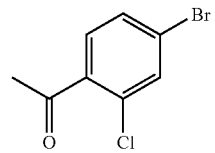

The title compound was prepared as described in Example 1, except 4-Bromo-2-chloro-thiobenzoic acid S-pyridin-2-yl ester from step 1 above was substituted for 3-(4-Benzyloxyphenyl)thiopropionic acid S-pyridin-2-yl ester and methyl magnesium bromide 1.4M in toluene was substituted for cyclopentylmagnesium bromide in Et$_2$O in step 5 of that example. $^1$H NMR (CDCl$_3$): δ 2.64 (s, 3H), 7.46–7.48 (m, 2H), 7.61 (s, 1H). ESIMS (MH+): 234.1.

Step 3: 2-(4-Bromo-2-chloro-phenyl)-2-methyl-[1,3]dioxolane

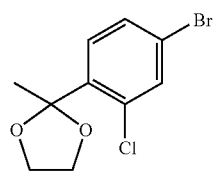

The title compound was prepared as described in Example 22, except 1-(4-Bromo-2-chloro-phenyl)-ethanone from step 2 above was substituted for 1-(2-methyl-4-trimethylsilanylethynyl-phenyl)-ethanone in step 3 of that example. $^1$H NMR (CDCl$_3$): δ 1.77 (s, 3H), 3.74–3.79 (m, 2H), 4.04–4.09 (m, 2H), 7.37 (dd, J=8.5, 1.9 Hz, 1H), 7.52 (d, J=8.5 Hz, 1H), 7.55 (d, J=1.9 Hz, 1H). ESIMS (MH+): 278.2.

Step 4: 6-{2-[3-Chloro-4-(2-methyl-[1,3]dioxolan-2-yl)-phenyl]-ethyl}-6-cyclopentyl-dihydro-pyran-2,4-dione

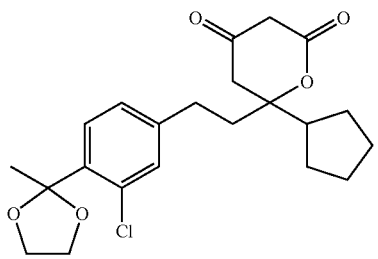

The title compound was prepared as described in Example 26, except 2-(4-Bromo-2-chloro-phenyl)-2-methyl-[1,3]dioxolane from step 3 above was substituted for 3-Bromochlorobenzene in step 1 of that Example. $^1$H NMR (CDCl$_3$-d$_6$): δ 1.57–1.73 (m, 8H), 1.78 (s, 3H), 1.91–1.98 (m, 2H), 2.2–2.3 (m, 1H), 2.62–2.68 (m, 2H), 2.77 (d, J=2.2 Hz, 2H), 3.43 (s, 2H), 3.75–3.79 (m, 2H), 4.04–4.09 (m, 2H), 7.01 (dd, J=7.9, 1.8 Hz, 1H), 7.17 (d, J=1.8 Hz, 1H), 7.55 (d, J=7.9 Hz, 1H). ESIMS (MNa+): 429.1.

Example 63

6-[2-(4-Acetyl-phenyl)-ethyl]-6-cyclopentyl-dihydro-pyran-2,4-dione

Step 1: 2-(4-Bromo-phenyl)-2-methyl-[1,3]dioxolane

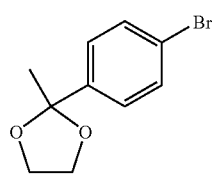

The title compound was prepared as described in Example 22, except 4-bromoacetophenone was substituted for 1-(2-methyl-4-trimethylsilanylethynyl-phenyl)-ethanone in step 3 of that Example. $^1$H NMR (CDCl$_3$-d$_6$): δ 1.63 (s, 3H), 3.74–3.76 (m, 2H), 4.02–4.05 (m, 2H), 7.36 (d, J=8.5 Hz, 1H), 7.47 (d, J=8.5 Hz, 1H). ESIMS (Na+): 244.1.

Step 2: 6-[2-(4-Acetyl-phenyl)-ethyl]-6-cyclopentyl-dihydro-pyran-2,4-dione

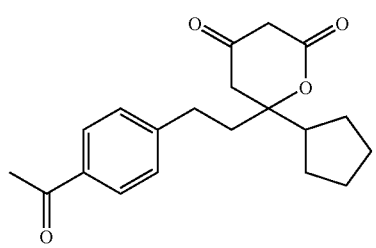

The title compound was prepared as described in Example 26, except 2-(4-Bromo-phenyl)-2-methyl-[1,3]dioxolane from step 1 above, was substituted for 3-Bromochlorobenzene in step 1 of that Example. The acetal moiety cleaved of during work up. $^1$H NMR (CDCl$_3$-d$_6$): δ 1.4–1.6 (m, 8H), 1.95–2.0 (m, 2H), 2.25–2.29 (m, 1H), 2.59 (s, 3H), 2.75 (t, J=7.2 Hz, 2H), 2.78 (d, J=3.0 Hz, 2H), 3.43 (d, J=3.0 Hz, 2H), 7.25 (d, J=8.3 Hz, 2H), 7.89 (d, J=8.3 Hz, 2H). Anal. Calcd. For C$_{20}$H$_{24}$O$_4$: C, 73.15; H, 7.37. Found: C, 72.90; H, 7.40. ESIMS (Na+): 351.1.

Example 64

6-[2-(3-Acetyl-phenyl)-ethyl]-6-cyclopentyl-dihydro-pyran-2,4-dione

Step 1: 2-(3-Bromo-phenyl)-2-methyl-[1,3]dioxolane

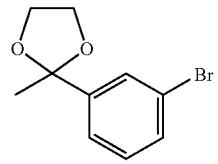

The title compound was prepared as described in Example 22, except 3-bromoacetophenone was substituted for 1-(2-methyl-4-trimethylsilanylethynyl-phenyl)-ethanone in step 3 of that Example. $^1$H NMR (CDCl$_3$-d$_6$): δ 1.63 (s, 3H), 3.75–3.79 (m, 2H), 4.02–4.06 (m, 2H), 7.21 (t, J=7.8 Hz, 1H), 7.40–7.43 (m, 2H), 7.64 (t, J=1.8 Hz, 1H). ESIMS (Na+): 244.1.

Step 2: 6-[2-(3-Acetyl-phenyl)-ethyl]-6-cyclopentyl-dihydro-pyran-2,4-dione

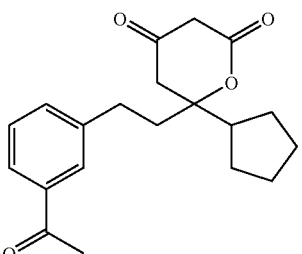

The title compound was prepared as described in Example 26, except 2-(3-Bromo-phenyl)-2-methyl-[1,3]dioxolane was substituted for 3-Bromochlorobenzene in step 1 of that Example. The acetal fell of during work up. $^1$H NMR (CDCl$_3$-d$_6$): δ 1.4–1.8 (m, 8H), 1.97–2.0 (m, 2H), 2.27–2.31 (m, 1H), 2.61 (s, 3H), 2.74–2.77 (m, 2H), 2.79 (s, 2H), 3.44 (s, 2H), 7.35–7.42 ((m, 2H), 7.75 (s, 1H), 7.80 (d, J=7.3 Hz, 1H). Anal. Calcd. For C$_{20}$H$_{24}$O$_4$: C, 73.15; H, 7.37. Found: C, 73.4; H, 7.45. ESIMS (Na+): 351.1.

Example 65

4-[2-(2-Cyclopentyl-4,6-dioxo-tetrahydro-pyran-2-yl)-ethyl]-benzoic acid methyl ester

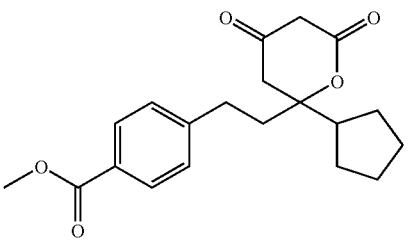

The title compound was prepared as described in Example 26, except 4-Bromo-benzoic acid methyl ester was substituted for 3-Bromochlorobenzene in step 1 of that Example. $^1$H NMR (CDCl$_3$-d$_6$): δ 1.58–1.76 (m, 8H), 1.95–2.01 (m, 2H), 2.27–2.31 (m, 1H), 2.74 (t, J=7.5 Hz, 2H), 2.78 (d, J=2.5 Hz, 2H), 3.43 (d, J=2.3 Hz, 2H), 3.91 (s, 3H), 7.22 (d, J=8.5 Hz, 2H), 7.97 (d, J=8.4 Hz, 2H), Anal. Calcd. For C$_{20}$H$_{24}$O$_5$: C, 69.75; H, 7.02. Found: C, 69.90; H, 7.25. ESIMS (Na+): 367.1.

Example 66

6-[2-(6-methyl-dihydro-pyran-2,4-dione)-ethyl]-6-cyclopentyl-dihydro-pyran-2,4-dione

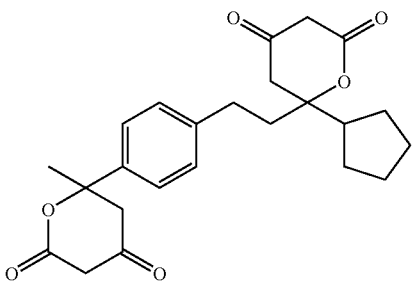

The title compound was prepared as described in Example 26, except 1-(4-Bromo-phenyl)-ethanone was substituted for 3-Bromochlorobenzene in step 1 of that Example, and where twice the amount of the acetoacetate dianion was added in the final step of that Example. $^1$H NMR (CDCl$_3$-d$_6$): δ 1.54–2.02 (m, 10H), 2.18 (s, 3H), 2.25–2.82 (m, 1H), 2.68 (t, J=8.6 Hz, 2H), 2.76 (d, J=2.5 Hz, 2H), 2.89 (d, J=17.5 Hz, 1H), 2.97 (dd, J=20.3, 1.7 Hz, 1H), 3.24–3.86 (m, 2H), 3.42 (s, 2H), 7.18 (d, J=8.3 Hz, 2H), 7.28 (d, J=8.3 Hz, 2H). Anal. Calcd. For C$_{24}$H$_{28}$O$_6$·1.0H$_2$O: C, 66.96; H, 7.02. Found: C, 67.20; H, 6.78. ESIMS (MH+): 413.1.

Example 67

6-Cyclopentyl-6-(2-[4-(4-hydroxy-piperidine-1-carbonyl)-phenyl]-ethyl}-dihydro-pyran-2,4-dione Step 1: (4-Bromo-phenyl)-(4-hydroxy-piperidin-1-yl)-methanone

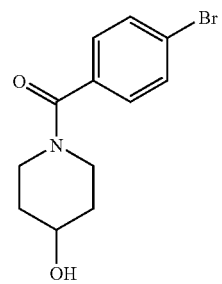

To a stirred solution of 4-Bromobenzoyl chloride (1.0 g, 4.56 mmol) in anhydrous CH$_2$Cl$_2$ under argon were added 4-hydroxypiperidine (0.51 g, 5.01 mmol) and TEA (0.70 ml, 5.01 mmol). The resulting solution was stirred at 25° C. overnight. CH$_2$Cl$_2$ was evaporate and residue partitioned between ETOAC and 1N HCl. The organic layer was washed with H$_2$O, brine and dried over Na$_2$SO$_4$. The solvent was removed in vacuo and the residue was purified by flash column chromatography (40% EtOAc in hexanes) to provide the desired product (1.12 g, 91%) as a white solid. $^1$H NNR (CDCl$_3$): δ 1.49–2.08 (m, 5H), 3.15–4.22 (m, 5H), 7.28 (d, J=8.3 Hz, 2H), 7.65 (d, J=8.3 Hz, 2H). ESIMS (MH+): 285.1.

Step 2: 6-Cyclopentyl-6-{2-[4-(4-hydroxy-piperidine-1-carbonyl)-phenyl]-ethyl}-dihydro-pyran-2,4-dione The title compound was prepared as described in Example 26, except (4-Bromo-phenyl)-(4-hydroxy-piperidin-1-yl)-methanone from step 1 above, was substituted for 3-Bromochlorobenzene in step 1 of that Example. $^1$H (CDCl$_3$-d$_6$): δ 1.45–1.92 (m, 12H), 1.94–1.97 (m, 2H), 2.26–2.32 (m, 1H), 2.71 (t, J=8.5 Hz, 2H), 2.78 (s, 2H), 3.2–3.3 (m, 2H), 3.43 (s, 2H), 3.7–3.8 (m, 2H), 3.9–3.99 (m, 1H), 7.18 (d, J=8.3 Hz, 2H), 7.33 (d, J=8.3 Hz, 2H). ESIMS (MH+): 414.2.

Example 68

6-Cyclopentyl-6-{2-[4-(morpholine-4-carbonyl)-phenyl]-ethyl}-dihydro-pyran-2,4-dione Step 1: (4-Bromo-phenyl)-morpholin-4-yl-methanone

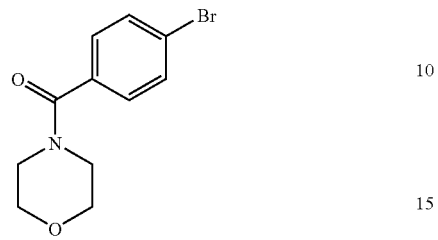

The title compound was prepared as described in Example 67, except morpholine was substituted for 4-hydroxypiperidine in step 1 of that Example. $^1$H NMR (CDCl$_3$): δ 3.39–3.82 (m, 8H), 7.29 (d, J=8.3 Hz, 2H), 7.56 (d, J=8.3 Hz, 2H). ESIMS (MH+): 270.1.

Step 2: 6-Cyclopentyl-6-{2-[4-(morpholine-4-carbonyl)-phenyl]-ethyl}-dihydro-pyran-2,4-dione

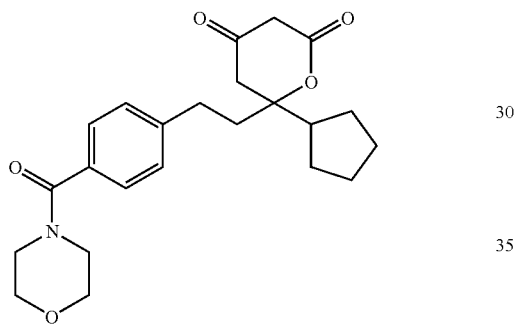

The title compound was prepared as described in Example 26, except (4-Bromo-phenyl)-morpholin-4-yl-methanone from step 1 above, was substituted for 3-Bromochlorobenzene in step of that Example. $^1$H NMR (CDCl$_3$-d$_6$): δ 1.60–1.63 (m, 8H), 1.94 (t, J=8.5 Hz, 2H), 2.25–230 (m, 1H), 2.71 (t, J=8.5 Hz, 2H), 2.77 (d, J=3.3 Hz, 2H), 3.43 (d, J=3.3 Hz, 2H), 3.54–4 (m, 8H), 7.19 (d, J=8.3 Hz, 2H), 7.34 (d, J=8.3 Hz, 2H). ESIMS (MH+): 400.2.

Example 69

6-Cyclopentyl-6-{2-[4-(3-hydroxy-pyrrolidine-1-carbonyl)-phenyl]-ethyl}-dihydro-pyran-2,4-dione Step 1: (4-Bromo-phenyl)-(3-hydroxy-pyrrolidine-1-yl)-methanone

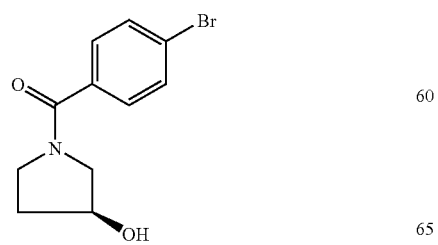

The title compound was prepared as described in Example 67, except (R)-(+)-3-pyrrolidinol was substituted for 4-hydroxypiperidine in step 1 of that Example. $^1$H NMR (CDCl$_3$): δ 1.73–2.14 (m, 3H), 3.4–3.85 (m, 4H), 4.60 (s, 1H), 7.38–7.46 (m, 2H), 7.54–7.68 (m, 2H). ESIMS (MH+): 271.2.

Step 2: 6-Cyclopentyl-6-{2-[4-(3-hydroxy-pyrrolidine-1-carbonyl)-phenyl]-ethyl}-dihydro-pyran-2,4-dione

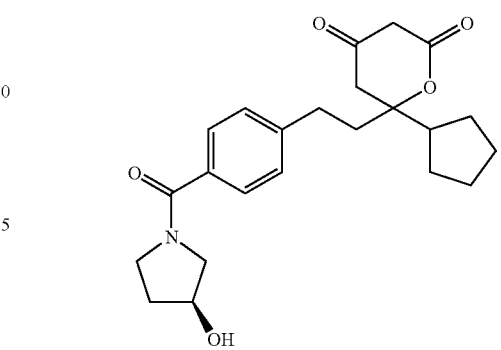

The title compound was prepared as described in Example 26, except (4-Bromo-phenyl)-(3-hydroxy-pyrrolidin-1-yl)-methanone from step 1 above was substituted for 3-Bromochlorobenzene in step 1 of that Example. $^1$H NMR (CDCl$_3$-d$_6$): δ 1.57–1.99 (m, 10H), 2.27–2.31 (m, 1H), 2.71 (t, J=9.0 Hz, 2H), 2.78 (s, 2H), 2.85–2.88 (m, 1H), 3.38–3.40 (m, 1H), 3.43 (d, J=1.8 Hz, 2H) 3.49–3.79 (m, 4H), 4.40 (s, 1H), 4.60 (s, 1H), 7.18 (d, J=8.0 Hz, 2H), 7.48 (dd, J=14.4, 8.0 Hz, 2H). Anal. Calcd. For C$_{23}$H$_{29}$NO$_5$.0.75H$_2$O: C, 66.89; H, 7.44; N, 3.39. Found: C, 66.97; H, 7.30; N, 3.63. ESIMS (MH+): 400.2.

Example 70

6-Cyclopentyl-6-[2-(3-fluoro-4-isobutoxy-phenyl)-ethyl]-dihydro-pyran-2,4-dione

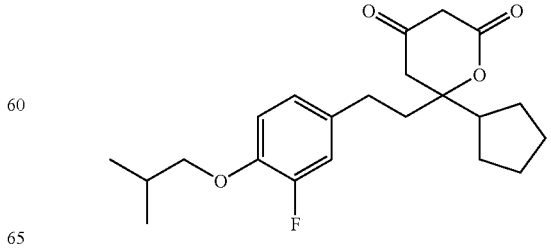

The title compound was prepared as described in Example 26, except 4-Bromo-2-chloro-1-isobutoxy-benzene was substituted for 3-Bromochlorobenzene in step 1 of that Example. $^1$H NMR (CDCl$_3$): δ 2.85 (d, 6H, J=6.6 Hz) 1.46–1.96 (br m, 8H), 1.93 (m, 2H), 2.11 (m, 1H), 2.26 (m, 1H), 2.61 (m, 2H), 2.76 (s, 2H), 3.42 (s, 2H), 3.75 (d, 2H, J=6.6 Hz), 6.84 (m, 3H). Anal. Calcd. For C$_{22}$H$_{29}$O$_4$F: C, 70.19; H, 7.77. Found: C, 70.00; H, 7.76.

Example 71

6-Cyclopentyl-6-[2-(4-ethoxy-3-fluoro-phenyl)-ethyl]-dihydro-pyran-2,4-dione

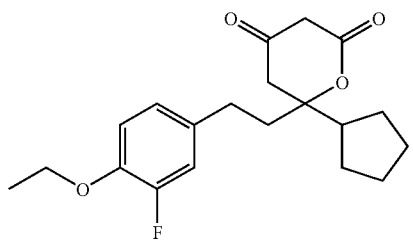

The title compound was prepared as described in Example 26, except 4-Bromo-1-ethoxy-2-fluoro-benzene was substituted for 3-Bromochlorobenzene in step 1 of that Example. $^1$H NMR (CDCl$_3$): δ 1.43 (t, J=7.0 Hz, 3H), 1.54–1.82 (brm, 8H), 1.91 (m, 2H), 2.27 (m, 1H), 2.61 (t, J=8.1 Hz, 2H), 2.76 (s, 2H), 3.43 (s, 2H), 4.08 (q, J=7.0 Hz, 2H), 6.80–6.91 (m, 3H). Anal. Calcd. For C$_{20}$H$_{25}$FO$_4$: C, 68.94; H, 7.23. Found: C, 68.57; H, 7.45.

Example 72

6-Cyclopentyl-6-[2-(3-fluoro-4-propoxy-phenyl)-ethyl]-dihydro-pyran-2,4-dione

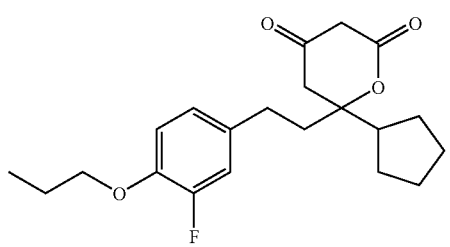

The title compound was prepared as described in Example 26, except 4-Bromo-2-fluoro-1-propoxy-benzene was substituted for 3-Bromochlorobenzene in step 1 of that Example. $^1$H NMR (CDCl$_3$): δ 1.04 (t, J=7.5 Hz, 3H), 1.44–1.84 (brm, 12H), 1.92 (m, 2H), 2.26 (m, 1H), 2.61 (t, J=7.9 Hz, 2H), 2.76 (s, 2H), 3.43 (s, 2H), 3.96 (t, J=6.6 Hz, 2H), 6.82–6.90 (m, 3H). Anal. Calcd. For C$_{21}$H$_{27}$FO$_4$: C, 69.59; H, 7.51. Found: C, 69.33; H, 7.43.

Example 73

6-Cyclopentyl-6-[2-(3-fluoro-4-isopropoxy-phenyl)-ethyl]-dihydro-pyran-2,4-dione

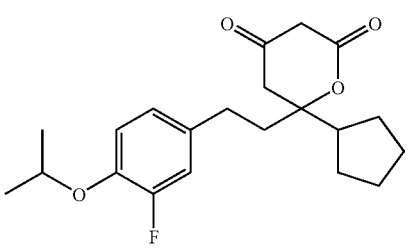

The title compound was prepared as described in Example 26, except 4-Bromo-2-fluoro-1-isopropoxy-benzene was substituted for 3-Bromochlorobenzene in step 1 of that Example. $^1$H NMR (CDCl$_3$): δ 1.34 (d, J=6 Hz, 6H), 1.52–1.86 (brm, 8H), 1.92 (m, 2H), 2.27 (m, 1H), 2.65 (t, J=7.9 Hz, 2H), 2.76 (s, 2H), 3.43 (s, 2H), 4.48 (m, 1H), 6.81–6.92 (m, 3H). Anal. Calcd. For C$_{21}$H$_{27}$FO$_4$: C, 69.59; H, 7.51. Found: C, 69.63; H, 7.23.

Example 74

6-Cyclopentyl-6-[2-(2,5-difluoro-4-methoxy-phenyl)-ethyl]-dihydro-pyran-2,4-dione

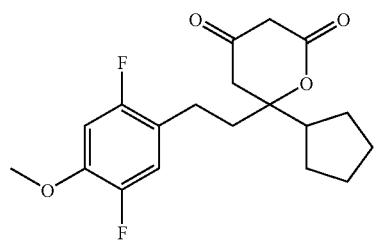

The title compound was prepared as described in Example 26, except 1-Bromo-2,5-difluoro-4-methoxy-benzene was substituted for 3-Bromochlorobenzene in step 1 of that Example. $^1$H NMR (CDCl$_3$): δ 1.51–1.82 (brm, 8H), 1.92 (m, 2H), 2.28 (m, 1H), 2.64 (t, J=7.9 Hz, 2H), 2.77 (s, 2H), 3.43 (s, 2H), 3.85 (s, 3H), 6.68 (d, J=7.2 Hz, 2H), 6.87 (d, J=7.2 Hz, 2H). Anal. Calcd. For C$_{19}$H$_{22}$F$_2$O$_4$: C, 64.76; H, 6.29. Found: C, 64.55; H, 6.13.

Example 75

6-Cyclopentyl-6-[2-(4-ethylsulfanyl-phenyl)-ethyl]-dihydro-pyran-2,4-dione

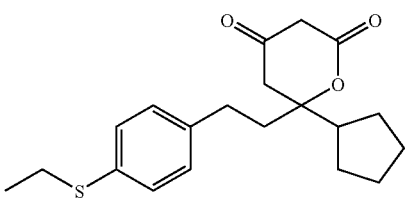

The title compound was prepared as described in Example 26, except 1-Bromo-4-ethylsulfanyl-benzene was substituted for 3-Bromochlorobenzene in step 1 of that Example. $^1$H NMR (CDCl$_3$): δ 1.29 (t, J=7.3 Hz, 3H) 1.52–1.82 (brm, 8H), 1.95 (m, 2H), 2.27 (m, 1H), 2.65 (t, J=7.9 Hz, 2H), 2.77 (s, 2H), 2.90 (q, J=7.3 Hz, 2H) 3.42 (s, 2H), 7.06 (d, J=8.1 Hz, 2H), 7.26 (d, J=8.1 Hz, 2H). Anal. Calcd. For C$_{20}$H$_{26}$O$_2$S: C, 69.33; H, 7.56. Found: C, 69.47; H, 7.37.

Example 76

4-[2-(2-Cyclopentyl-4,6-dioxo-tetrahydro-pyran-2-yl)-ethyl]-dimethyl-benzenesulfonamide

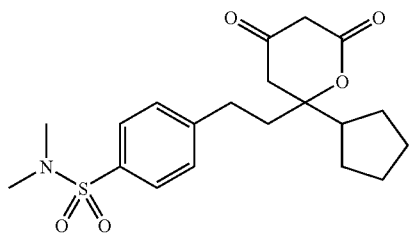

The title compound was prepared as described in Example 26, except 4-Bromo-dimethyl-benzenesulfonamide was substituted for 3-Bromochlorobenzene in step 1 of that Example. $^1$H NMR (CDCl$_3$): δ 1.52–1.82 (brm, 8H), 1.92 (m, 2H), 2.27 (m, 1H), 2.70 (s, 6H), 2.79 (m, 4H), 3.44 (s, 2H), 7.32 (d, J=8.2 Hz, 2H), 7.70 (d, J=8.2 Hz, 2H). Anal. Calcd. For C$_{20}$H$_{27}$NO$_5$S: C, 61.04; H, 6.92; N, 3.56. Found: C, 61.14; H, 6.86; N, 3.25.

Example 77

6-Cyclopentyl-6-[2-(4-cyclopentyloxy-3-fluoro-phenyl)-ethyl]-dihydro-pyran-2,4-dione

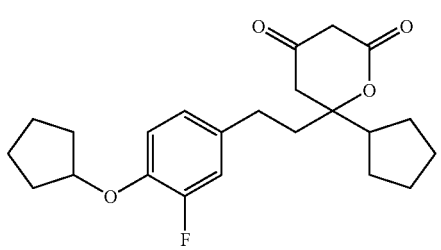

The title compound was prepared as described in Example 26, except 4-Bromo-1-cyclopentyloxy-2-fluoro-benzene was substituted for 3-Bromochlorobenzene in step 1 of that Example. $^1$H NMR (CDCl$_3$): δ 1.54–1.97 (brm, 18H), 2.27 (m, 1H), 2.60 (t, J=7.9 Hz, 2H), 2.76 (s, 2H), 3.43 (s, 2H), 4.76 (m, 1H), 6.77–6.89 (m, 3H). Anal. Calcd. For C$_{23}$H$_{29}$FO$_4$: C, 71.11; H, 7.53. Found: C, 70.87; H, 7.27.

Example 78

6-Cyclopentyl-6-[2-(4-[1,3]dioxolan-2-yl-3-fluoro-phenyl)-ethyl]-dihydro-pyran-2,4-dione

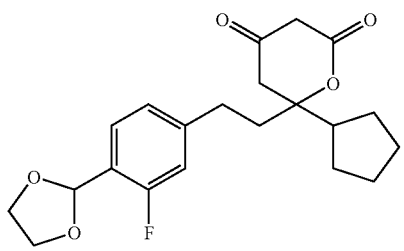

The title compound was prepared as described in Example 26, except 2-(4-Bromo-2-fluoro-phenyl)-[1,3]dioxolane was substituted for 3-Bromochlorobenzene in step 1 of that Example. $^1$H NMR (CDCl$_3$): δ 1.52–1.82 (brm, 8H), 1.94 (m, 2H), 2.27 (m, 1H), 2.68 (t, J=7.9 Hz, 2H), 2.77 (s, 2H), 3.43 (s, 2H), 4.01–4.17 (m, 4H), 6.05 (s, 1H), 6.87 (d, J=7.9 Hz, 1H), 6.94 (d, J=7.9 Hz, 1H), 7.45 (t, J=7.8 Hz, 1H). Anal. Calcd. For C$_{21}$H$_{25}$FO$_5$: C, 67.00; H, 6.69. Found: C, 66.87; H, 6.35.

Example 79

6-Cyclopentyl-6-{2-[4-(2-oxo-pyrrolidin-1-yl)-phenyl]-ethyl}-dihydro-pyran-2,4-dione

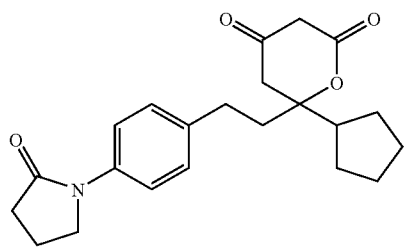

The title compound was prepared as described in Example 26, except 1-(4-Bromo-phenyl)-pyrrolidin-2-one was substituted for 3-Bromochlorobenzene in step 1 of that Example. $^1$H NMR (CDCl$_3$): δ 1.48–1.82 (brm, 8H), 1.92 (m, 2H), 2.11–2.31 (m, 3H), 2.65 (m, 4H), 2.77 (s, 2H), 3.42 (s, 2H), 3.85 (t, J=7.2 Hz, 2H), 7.14 (d, J=8.5 Hz, 2H) 7.52 (d, J=8.5 Hz, 2H). Anal. Calcd. For C$_{22}$H$_{27}$NO$_4$; C, 71.52; H, 7.37; N, 3.79. Found: C, 71.27; H, 7.52; N, 3.83.

Example 80

6-Cyclopentyl-6-{2-[3-fluoro-4-(2-oxo-pyrrolidin-1-yl)-phenyl]-ethyl}-dihydro-pyran-2,4-dione

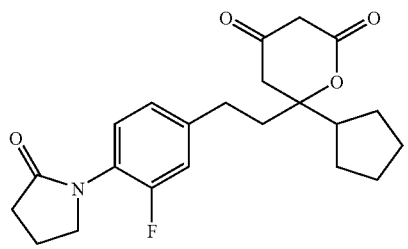

The title compound was prepared as described in Example 26, except 1-(4-Bromo-2-fluoro-phenyl)-pyrrolidin-2-one was substituted for 3-Bromochlorobenzene in step 1 of that Example. $^1$H NMR (CDCl$_3$): δ 1.54–1.82 (brm, 8H), 1.94 (m, 2H), 2.23 (m, 3H), 2.57 (t, J=7.9 Hz, 2H), 2.67 (m, 2H), 2.77 (s, 2H), 3.44 (s, 2H), 3.81 (t, J=7.2 Hz, 2H), 6.92–6.98 (m, 2H), 7.32 (t, J=7.9 Hz, 1H). Anal. Calcd. For C$_{22}$H$_{26}$FNO$_4$: C, 68.20; H, 6.76; N, 3.62. Found: C, 68.46; H, 6.44; N, 3.44.

Example 81

6-[2-(3-Chloro-4-isopropoxy-phenyl)-ethyl]-6-cyclopentyl-dihydro-pyran-2,4-dione

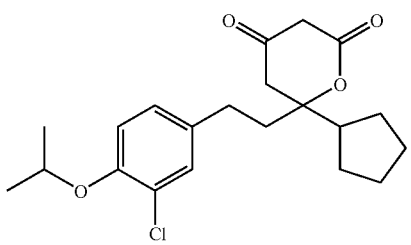

The title compound was prepared as described in Example 26, except 4-Bromo-2-chloro-1-isopropoxy-benzene was substituted for 3-Bromochlorobenzene in step 1 of that Example. $^1$H NMR (CDCl$_3$): δ 1.36 (d, J=6.0 Hz, 6H), 1.52–1.82 (brm, 8H), 1.94 (m, 2H), 2.27 (m, 1H), 2.60 (t, J=7.9 Hz, 2H), 2.76 (s, 2H), 3.43 (s, 2H), 4.50 (m, 1H), 6.86 (d, J=8.5 Hz, 1H), 6.94 (d, J=8.5 Hz, 1H), 7.14 (s, 1H) (m, 3H). Anal. Calcd. For C$_{21}$H$_{27}$ClO$_4$: C, 66.57; H, 7.18. Found: C, 66.33; H, 6.96.

Example 82

6-Cyclopentyl-[6-(2-Chloro-phenyl)-6-methyl-dihydro-pyran-2,4-dione]-dihydro-pyran-2,4-dione

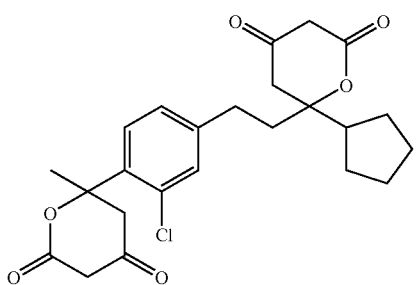

The title compound was prepared as described in Example 26, except 1-(4-Bromo-2-chloro-phenyl)-ethanone, prepared as described in step 2 of Example 62, was substituted for 3-Bromochlorobenzene in step 1 of that Example. $^1$H NMR (CDCl$_3$-d$_6$): δ 1.44–1.69 (m, 8H), 1.85 (s, 3H), 1.86–1.90 (m, 2H), 2.17–2.22 (m, 1H), 2.57–2.63 (m, 2H), 2.69 (d, J=8.1 Hz, 2H), 2.88 (d, J=17.3 Hz, 1H), 3.06 (dd, J=20.5, 3.4 Hz, 1H), 3.29 (d, J=20.5 Hz, 1H), 3.36 (s, 2H), 3.86 (dd, J=17.3, 1.7 Hz, 1H), 7.02 (dd, J=8.3, 1.7 Hz, 1H), 7.15 (d, J=1.7 Hz, 1H), 7.86 (d, J=8.1 Hz, 1H). Anal. Calcd. For C$_{24}$H$_{27}$ClO$_6$.0.5H$_2$O: C, 63.22; H, 6.19. Found: C, 63.45; H, 6.3. ESIMS (MH+): 447.1.

Example 83

6-Cyclopentyl-4-hydroxy-6-[2-(4-hydroxyphenyl)ethyl-3-(naphthalen-2-ylsulfanyl)-5,6-dihydropyran-2-one Step 1: 3-Bromo-6-cyclopentyl-4-hydroxy-6-[2-(4-methoxyphenyl)ethyl]-5,6-dihydropyran-2-one

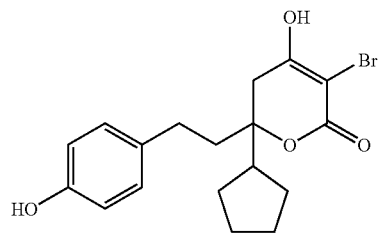

6-Cyclopentyl-6-[2-(4-hydroxyphenyl)ethyl]dihydropyran-2,4-dione (0.087 g, 0.29 mmol) prepared as described in the final step of Example 1, and NBS (0.051 g, 0.29 mmol) were combined in tert-butyl alcohol (4 mL) and stirred 16 h in darkness. The reaction mixture was then partitioned between H$_2$O (50 mL) and CH$_2$Cl$_2$ (3×50 mL). The organic phases were dried over MgSO$_4$ and evaporated to provide the product, which was used without further purification.

Step 2: 6-Cyclopentyl-4-hydroxy-6-[2-(4-hydroxyphenyl)ethyl-3-(naphthalen-2-ylsulfanyl)-5,6-dihydropyran-2-one

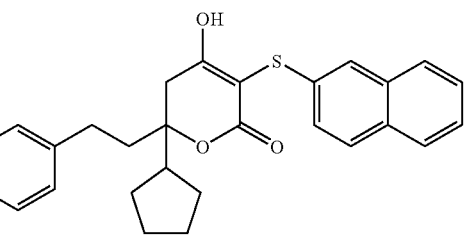

The 3-bromo-6-cyclopentyl-6-[2-(4-hydroxyphenyl)ethyl]dihydropyran-2,4-dione (0.29 mmol theoretical yield) from step 1 above was dissolved in CH$_3$CN and cooled to 0° C. 2-Naphthalenethiol (0.049 g, 0.31 mmol) and morpholine (0.027 mL, 0.31 mmol) were added successively, then the reaction mixture was allowed to warm to ambient temperature overnight. It was then partitioned between 3% aq KHSO$_4$ (35 mL) and CH$_2$Cl$_2$ (3×25 mL). The organic phases were dried over MgSO$_4$ and evaporated. The residue was purified by preparative TLC (10% MeOH in CHCl$_3$) to provide a material which was stirred in acetone and filtered (3×1 mL). The combined filtrates were evaporated to give the title compound (0.030 g, 23%) as a film. $^1$H NMR (acetone-d$_6$) δ 1.38–1.81 (br m, 8H), 2.09–2.17 (br m, 2H), 2.35–2.49 (br m, 1H), 2.56–2.69 (br m, 2H), 2.77–3.10 (br m, 2H), 6.70–6.80 (m, 2H), 6.95–7.04 (m, 2H), 7.30–7.48 (m, 3H), 7.51–7.84 (m, 4H); HRMS calcd for C$_{28}$H$_{28}$O$_4$S (M+H$^+$) 461.1787. found 461.1797.

Example 84

3-Benzylsulfanyl-6-cyclopentyl-4-hydroxy-6-[2-(4-hydroxyphenyl)ethyl]-5,6-dihydropyran-2-one

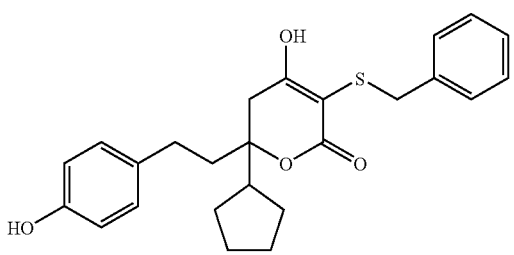

The title compound was prepared as described in Example 83, except benzyl mercaptan was used for naphthalene thiol in the final step of that Example. $^1$H NMR (CDCl$_3$): δ 1.32–1.74 (m, 8H), 1.83–1.94 (m, 2H), 2.23–2.38 (m, 1H), 2.43 (d, 1H, J=17.9), 2.50–2.58 (m, 2H), 2.59 (d, 1H, J=17.9), 3.81 (d, 1H, J=12.8), 3.87 (d, 1H, J=12.8), 6.00 (br s, 1H), 6.76–6.82 (m, 2H), 6.93–6.99 (m, 2H), 7.12–7.22 (m, 5H), 7.31 (br s, 1H); HRMS calcd for C$_{25}$H$_{28}$O$_4$S (M+H$^+$) 425.1787. found 425.1785.

Example 85

6-Cyclopentyl-4-hydroxy-6-[2-(4-hydroxyphenyl)ethyl]-3-(naphthalen-1-ylsulfanyl)-5,6-dihydropyran-2-one

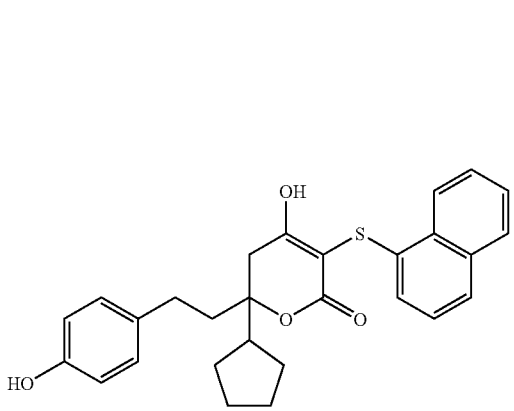

The title compound was prepared as described in Example 83 except 1-napthalenethiol was used for 2-naphthalenethiol in the final step of that Example. $^1$H NMR (methanol-d$_4$) δ 1.35–1.79 (m, 8H), 1.89–2.06 (m, 2H), 2.34–2.60 (m, 3H), 2.66–2.80 (br m, 1H), 2.93–3.06 (br m, 1H), 6.65–6.71 (m, 2H), 6.81–6.86 (m, 2H), 7.24–7.53 (m, 4H), 7.64–7.70 (m, 1H), 7.81–7.85 (m, 1H), 8.39–8.45 (m, 1H); HRMS calcd for C$_{28}$H$_{28}$O$_4$S (M+H$^+$) 461.1787. found 461.1774.

Example 86

6-[2-(4-Benzyloxyphenyl)ethyl]-6-cyclopentyl-4-hydroxy-3-(napthalen-1-ylsulfanyl)-5,6-dihydropyran-2-one

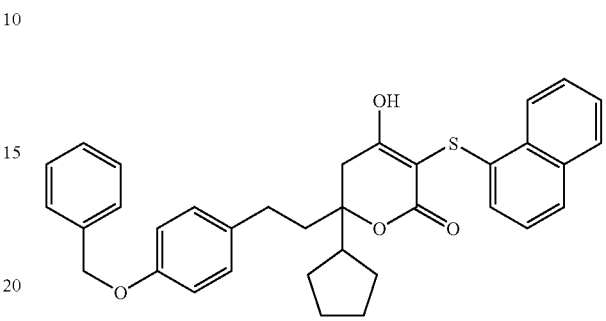

The title compound was prepared as described in Example 83, except 6-[2-(4-benzyloxyphenyl)ethyl]-6-cyclopentyldihydropyran-2,4-dione (prepared as described in step 6 of Example 1), was used for 6-cyclopentyl-6-[2-(4-hydroxyphenyl)ethyl]dihydropyran-2,4-dione in step 1, and 1-napthalenethiol was used for 2-napthalenethiol in the final step. HRMS calcd for C$_{35}$H$_{34}$O$_4$S (M+H$^+$) 551.2256. found 551.2269.

Example 87

3-Chloro-6-cyclopentyl-4-hydroxy-6-[2-(4-methoxyphenyl)ethyl]-5,6-dihydropyran-2-one

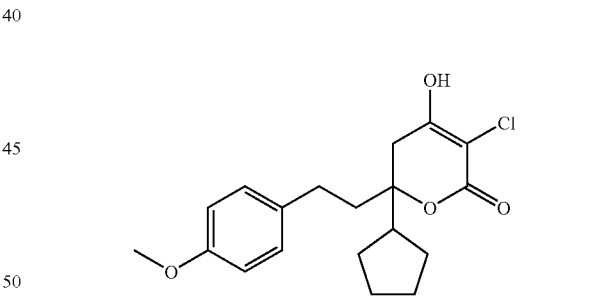

6-Cyclopentyl-6-[2-(4-hydroxyphenyl)ethyl]dihydropyran-2,4-dione (0.074 g, 0.23 mmol), prepared as described in the final step of Example 3, was slurried in dry CH$_2$Cl$_2$ (0.5 mL) and cooled to −10° C. Sulfuryl chloride (0.0207 mL, 0.258 mmol) was added and the reaction mixture was allowed to warm to 23° C. After stirring 2 h, the mixture was partitioned between 1% 1 M HCl in brine (20 mL) and CH$_2$Cl$_2$ (3×30 mL). The combined organic phases were dried over MgSO$_4$ and evaporated. The residue was purified by flash column chromatography (5% MeOH in CH$_2$Cl$_2$) to yield the title compound (0.038 g, 46%). $^1$H NMR (CDCl$_3$): δ 1.33–1.81 (m, 8H), 2.00–2.08 (m, 2H), 2.34–2.46 (m, 1H), 2.60–2.67 (m, 2H), 2.67 (d, 1H, J=17.7), 2.88 (d, 1H, J=17.7), 3.78 (s, 3H), 6.80–6.85 (m, 2H), 7.04–7.10 (m, 2H); HRMS calcd for C$_{19}$H$_{23}$ClO$_4$ (M+H$^+$) 351.1363. found 351.1383.

Example 88

3-benzyl-6-cyclopentyl-6-(2-phenylethyl)dihydro-2H-pyran-2,4(3H)-dione

Step 1: 6-Cyclopentyl-6-phenethyl-dihydro-pyran-2,4-dione

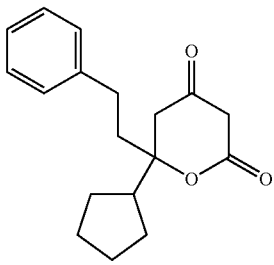

The title compound was prepared from 1-cyclopentyl-3-phenyl-propan-1-one as described in step 5 of Example 1. $^1$H NMR (CDCl$_3$): δ 1.40–1.82 (m, 8H), 2.12–2.36 (m, 2H), 2.26–2.38 (m, 1H), 2.67–2.74 (m, 2H), 2.82 (s, 2H), 3.46 (s, 2H), 7.18–7.27 (m, 5H). IR (cm$^{-1}$) 3442, 1639.

Step 2: 3-benzyl-6-cyclopentyl-6-(2-phenylethyl)dihydro-2H-pyran-2,4(3H)-dione

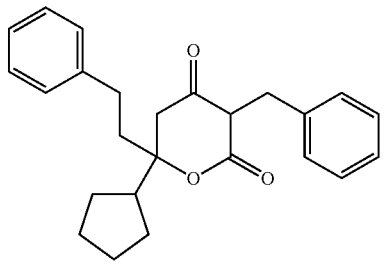

Into a dry flask containing AlCl$_3$ (0.560 mg, 4.2 mmol) at −78° C. was slowly added of THF (10 mL) via syringe under argon. The flask was warmed to room temperature with vigorously stirring, then cannulated into a solution of benzaldehyde (0.213 mL, 4.2 mmol) and 6-cyclopentyl-6-(2-phenylethyl)-dihydro-2H-pyran-2,4(3H)-dione (0.600 mg 2.1 mmol) in THF (20 mL). After 2 h the reaction mixture was treated with Na$_2$CO$_3$ (1.5 g) for 15 min. The suspension was diluted with diethyl ether (15 mL) and filtered through a pad of Celite with diethyl ether washes. The combined filtrates were concentrated under reduced pressure. The residue dissolved in EtOAc (10 mL), and was added Pd on carbon (0.080 g). The mixture was stirred under H$_2$ balloon for 2 h and then filtered through a pad of Celite and with EtOAc washes. The filtrates was concentrated under reduced pressure and purified by flash column chromatography (20% EtOAc in hexane) to afford 650 mg of product (29%) as a white foam. $^1$H NMR (CDCl$_3$): δ 1.45–1.79 (m, 8H), 1.98–2.06 (m, 2H), 2.33–2.47 (m, 2H), 2.62–2.82 (m, 3H), 3.75 (s, 2H), 6.94 (m, 1H), 7.08–7.11 (m, 2H), 7.18–7.27 (m, 8H); Anal. Calcd. For C$_{25}$H$_{28}$O$_3$·0.3H$_2$O: C, 78.62; H, 7.55. Found: C, 78.76; H, 7.68. IR (cm$^{-1}$) 3319, 1722, 1496.

Example 89

3-[(4-amino-2-tert-butyl-5-methylphenyl)thio]-4-hydroxy-6,6-dimethyl-5,6-dihydro-2H-pyran-2-one Step 1: 4-Hydroxy-6,6-dimethyl-5,6-dihydro-2H-pyran-2-one

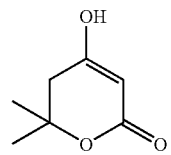

The title compound was prepared as described in Example 1, except acetone was substituted for 3-(4-benzyloxyphenyl)-1-cyclopentylpropan-1-one in step 6 of that Example. $^1$H NMR (CDCl$_3$): δ 1.48 (s, 6H), 2.56 (s, 2H), 3.33–3.36 (m, 1H), (4.92 s, br. 1H). ESIMS (MH$^+$): 143.1.

Step 2: tert-butyl-5-tert-butyl-4-mercapto-2-methylphenyl-carbamate

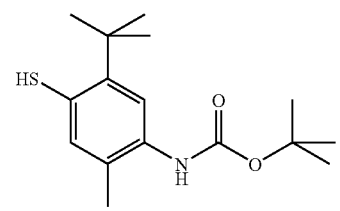

To tert-butyl 5-tert-butyl-2-methyl-4-thiocyanatophenyl-carbamate (2.08 g, 6.5 mmol) in EtOH (16 mL) was added DTT (4.0 g, 26 mmol) and 0.2 M KH$_2$PO$_4$ (4 mL). The reaction mixture was heated to 50° C. overnight and concentrated. The residue was partition between H$_2$O (100 mL) and CH$_2$Cl$_2$ (2×80 mL). The organic layer was dried over MgSO$_4$ and concentrated. The residue was purified by flash column chromatography (5% EtOAc in CHCl$_3$) to give 905 mg of product (47%) as a white solid. $^1$H NMR (CDCl$_3$): δ 1.50 (s, 9H), 1.55 (m, 9H), 2.18 (s, 3H), 4.17 (s, 1H), 6.17 (s, 1H), 7.07 (s, 1H), 7.80 (s, 1H).

Step 3: 3-Bromo-4-hydroxy-6,6-dimethyl-5,6-dihydro-2H-pyran-2-one

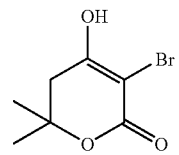

N-Bromosuccinimide (0.126 g, 0.71 mmol) was added to a solution of 4-hydroxy-6,6-dimethyl-5,6-dihydro-2H-pyran-2-one (0.101 g, 0.71 mmol) in tBuOH (8 mL). The reaction mixture was stirred at room temperature overnight, quenched with H$_2$O (50 mL) and extracted with CH$_2$Cl$_2$ (2×50 mL). The organic layers were dried over MgSO$_4$ and concentrated to give 125 mg of the title product (80%) as pale brown oil. $^1$H NMR (CDCl$_3$): δ 1.31 (s, 6H), 2.75 (s, 2H), 6.48 (s, 1H).

Step 4: tert-butyl-5-tert-butyl-4-[(4-hydroxy-6,6-dimethyl-2-oxo-5,6-dihydro-2H-pyran-3-yl)thio]-2-methylphenylcarbamate

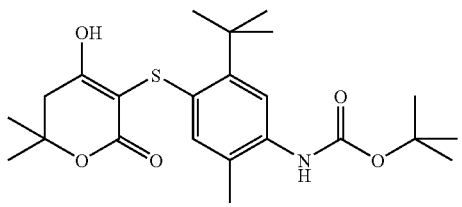

To a solution of 3-bromo-4-hydroxy-6,6-dimethyl-5,6-dihydro-2H-pyran-2-one (0.122 g, 0.55 mmol) cooled at 0° C. was added tert-butyl 5-tert-butyl-4-mercapto-2-methylphenylcarbamate (0.171 g, 0.58 mmol) and piperidine (0.057 mL, 0.58 mmol). The reaction mixture was stirred at room temperature for 3 h, poured into H$_2$O (50 mL) and extracted with CH$_2$Cl$_2$ (2×50 mL). The organic layers were dried over MgSO$_4$ and concentrated. The residue was purified by flash column chromatography (2% CH$_3$OH in CH$_2$Cl$_2$) to give 151 mg of the title product (63%) as a white solid. $^1$H NMR (CDCl$_3$): δ 1.55 (s, 9H), 1.58 (s, 6H), 1.60 (s, 9H), 2.14 (s, 3H), 2.83 (s, 2H), 5.33 (s, 1H), 6.17 (s, 1H), 6.81 (s, 1H), 7.84 (s, 1H).

Step 5: 3-[(4-amino-2-tert-butyl-5-methylphenyl)thio]-4-hydroxy-6,6-dimethyl-5,6-dihydro-2H-pyran-2-one

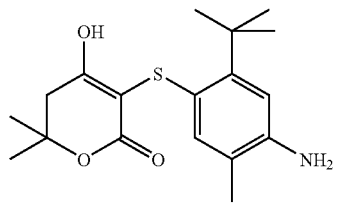

TFA (1.5 mL) was added to a solution of tert-butyl-5-tert-butyl-4-[(4-hydroxy-6,6-dimethyl-2-oxo-5,6-dihydro-2H-pyran-3-yl)thio]-2-methylphenylcarbamate (0.150 g, 0.34 mmol) in CH$_2$Cl$_2$ (3 mL). The reaction mixture was stirred at room temperature for 15 min and concentrated under reduced pressure. The solid was triturated with Et$_2$O, filtered, washed with Et$_2$O to give 103 mg of product (90%) as a white solid. $^1$H NMR (CDCl$_3$): δ 1.45 (s, 6H), 1.50 (s, 9H), 2.18 (s, 3H), 2.91 (s, 2H), 6.86 (s, 1H), 7.29 (s, 1H); Anal. Calcd. For C$_{18}$H$_{25}$NO$_3$S.0.5 H$_2$O: C, 62.76; H, 7.61; N, 4.07. Found: C, 62.35; H, 7.40; N, 3.95. ESIMS (MH$^+$): 336.1

Example 90

6-[2-(5-chloro-2,4-dimethoxyphenyl)ethyl]-6-cyclopentyl-4-hydroxy-5,6-dihydro-2H-pyran-2-one

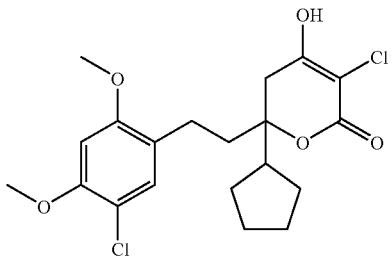

The title compound was prepared as described in Example 87, except 6-[2-(5-chloro-2,4-dimethoxyphenyl)ethyl]-6-cyclopentyldihydro-2H-pyran-2,4(3H)-dione (described in Example 40) was used for 6-[2-(4-methoxyphenyl)ethyl]-6-cyclopentyldihydro-2H-pyran-2,4(3H)-dione. $^1$H NMR (CDCl$_3$): δ 1.51 (m, 8H), 1.79 (m, 1H), 2.06, (m, 2H), 2.45 (m, 2H), 2.60 (m, 1H), 2.67 (d, 1H, J=17.75), 2.92 (d, 1H, J=17.75), 3.82 (s, 3H), 3.92 (s, 3H), 6.44 (s, 1H), 7.06 (s, 1H). HRMS calcd for C$_{20}$H$_{24}$O$_5$Cl$_2$ (M+H$^+$) 415.1079. found 415.1063.

Example 91

6-[2-(5-Chloro-2,4-dimethoxyphenyl)ethyl]-6-cyclopentyl-3-[(5,7-dimethyl[1,2,4]triazolo[1,5-a]pyrimidin-2-yl)thio]-4-hydroxy-5,6-dihydro-2H-pyran-2-one

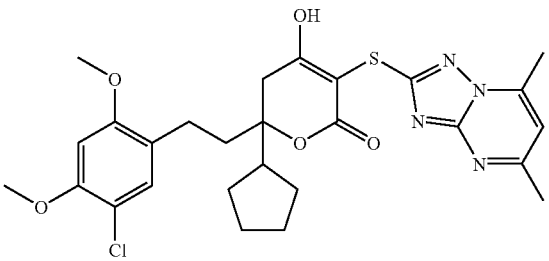

3-Chloro-6-[2-(5-chloro-2,4-dimethoxyphenyl)ethyl]-6-cyclopentyl-4-hydroxy-5,6-dihydro-2H-pyran-2-one (described in Example 90) (160 mg, 0.385 mmol) in DMF (3 mL) was treated with 5,7-dimethyl-2-mercapto-s-triazolo[1,5-a]pyrimidine (69 mg, 0.385 mmol) in DMF (3 mL) and triethylamine (385 μL of a 1 M solution in DMF, 1 equiv). The mixture was stirred at 55° C. under a blanket of N$_2$ for 6 h. The DMF was removed in vacuo to give a yellow resin. This was treated with water (20 mL) and extracted with ethyl acetate (3×20 mL). The organic layers were combined, dried over Na$_2$SO$_4$, filtered, and concentrated to a slurry. The resulting mixture was treated with ether and the beige precipitate filtered. This solid was recrystallized from hot 1:1 methylene chloride/ethyl acetate to yield 47.7 mg (22%) of the product as a fine white powder. $^1$H NMR (DMSO-d$_6$): δ 1.58 (m, 8H), 1.98 (m, 2H), 2.18 (m, 1H), 2.23 (s, 3H), 2.40 (m, 2H), 2.47 (s, 3H), 2.76 (d, 1H, J=17.37 Hz), 2.94 (d, 1H, J=17.37 Hz), 3.64 (s, 3H), 3.85 (s, 3H), 6.57 (s, 1H), 7.01 (s, 1H), 7.20 (s, 1H), 12.05 (s, 1H). HRMS calcd for C$_{27}$H$_{31}$N$_4$O$_5$ClS (M+H$^+$) 559.1782. found 559.1689. Anal. Calcd. For C$_{27}$H$_{31}$N$_4$O$_5$ClS: C, 58.00; H, 5.59; N, 10.02; S, 5.74. Found: C, 57.57; H, 5.81, N, 9.85; S, 5.64.

Example 92

6-[2-(4-methoxyphenyl)ethyl]-6-cyclopentyl-3-[(5,7-dimethyl[1,2,4]triazolo[1,5-a]pyrimidin-2-yl)thio]-4-hydroxy-5,6-dihydro-2H-pyran-2-one

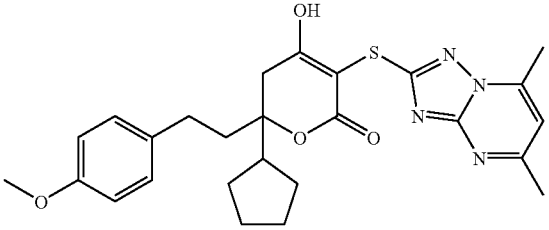

The title compound was prepared as described in Example 91, except 3-chloro-6-[2-(4-methoxyphenyl)ethyl]-6-cyclopentyl-4-hydroxy-5,6-dihydro-2H-pyran-2-one (prepared as described in Example 87), was used for 3-chloro-6-[2-(5-chloro-2,4-dimethoxyphenyl)ethyl]-6-cyclopentyl-4-hydroxy-5,6-dihydro-2H-pyran-2-one. $^1$H NMR (CDCl$_3$): δ 1.65 (m, 8H), 2.16 (m, 2H), 2.44 (m, 1H), 2.52 (s, 3H), 2.63 (s, 3H), 2.68 (m, 2H), 2.82 (d, 1H, J=17.75 Hz), 3.02 (d, 1H, J=17.75 Hz), 3.73 (s, 3H), 6.72 (s, 1H), 6.86 (d, 2H, J=8.69), 7.12 (d, 2H, J=8.31 Hz). HRMS calcd for C$_{26}$H$_{30}$N$_4$O$_4$S (M+H$^+$) 495.2066. found 495.2061. Anal. Calcd. For C$_{26}$H$_{30}$N$_4$O$_4$S: C, 63.14; H, 6.11; N, 11.33; S, 6.48. Found: C, 62.68; H, 6.01, N, 11.07; S, 6.40.

Example 93

6-[2-(5-Chloro-2,4-dimethoxyphenyl)ethyl]-6-cyclopentyl-4-hydroxy-3-(1H-1,2,4-triazol-3-ylthio)-5,6-dihydro-2H-puran-2-one

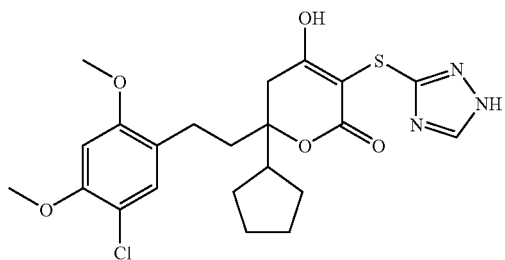

The title compound was prepared as described in Example 91, using 3-mercapto-1,2,4-triazole for 5,7-dimethyl-2-mercapto-s-triazolo[1,5-a]pyrimidine. $^1$H NMR (DMSO-d$_6$): δ 1.3–1.6 (m, 8H), 1.66 (m, 2H), 1.90 (m, 2H), 2.35 (m, 1H), 2.7–2.9 (m, 2H), 3.77 (s, 3H), 3.84 (s, 3H), 6.69 (s, 1H), 7.15 (s, 1H). MS calcd for C$_{22}$H$_{26}$ClN$_3$O$_5$S 479.12. found (M+H$^+$) 480.1.

Example 94

6-({6-[2-(5-chloro-2,4-dimethoxyphenyl)ethyl]-6-cyclopentyl-4-hydroxy-2-oxo-5,6-dihydro-2H-pyran-3-yl}thio)nicotinic acid

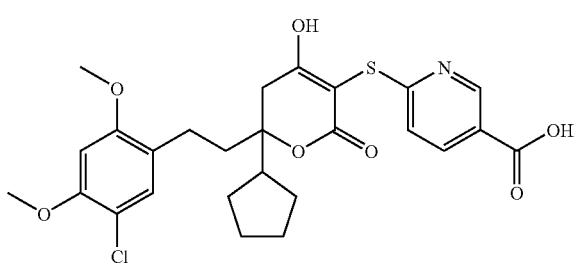

The title compound was prepared as described in Example 91, using 6-mercaptonicotinic acid for 5,7-dimethyl-2-mercapto-s-triazolo[1,5-a]pyrimidine. $^1$H NMR (DMSO-d$_6$): δ 1.4–1.6 (m, 8H), 1.73 (m, 2H), 2.02 (m, 3H), 2.79 (m, 2H) 3.73 (s, 3H), 3.87 (s, 3H), 6.74 (s, 1H), 7.08 (m, 1H), 7.17 (s, 1H), 7.93 (m, 1H), 8.69 (s, 1H). MS (APCI) calcd for C$_{26}$H$_{28}$ClNO$_7$S: 533.1; found (M+H$^+$) 534.1.

Example 95

6-[2(5-chloro-2,4-dimethoxyphenyl)ethyl]-6-cyclopentyl-4-hydroxy-3-[(5-hydroxy-4-methyl-4H-1,2,4-triazol-3-yl)thio]-5,6-dihydro-2H-pyran-2-one

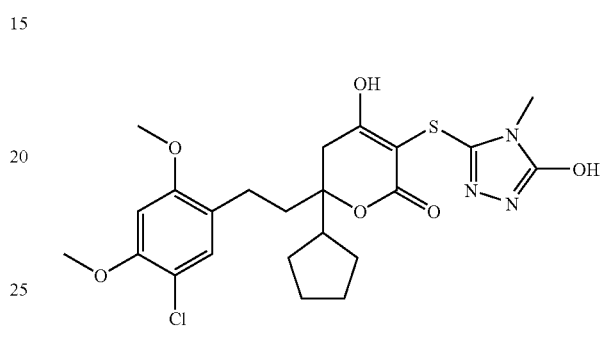

The title compound was prepared as described in Example 91, using 5-hydroxy-4-methyl-4H-1,2,4-triazole-3-thiol for 5,7-dimethyl-2-mercapto-s-triazolo[1,5-a]pyrimidine. $^1$H NMR (DMSO-d$_6$): δ 1.3–1.54 (m, 8H), 1.64 (m, 2H), 1.80 (m, 2H), 2.30 (m, 1H), 2.77 (m, 2H), 3.30 (s, 3H, overlap with H$_2$O peak), 3.77 (s, 3H), 3.84 (s, 3H), 6.70 (s, 1H), 7.12 (s, 1H), 11.62 (s, 1H). MS (APCI) calcd for C$_{23}$H$_{28}$ClN$_3$O$_6$S: 509.1. found (M+H$^+$) 510.1.

Example 96

6-[2-(5-chloro-2,4-dimethoxyphenyl)ethyl]-6-cyclopentyl-4-hydroxy-3-[(4-methyl-5-thien-2-yl 4H-1,2,4-triazol-3-yl)thio]-5,6-dihydro-2-one

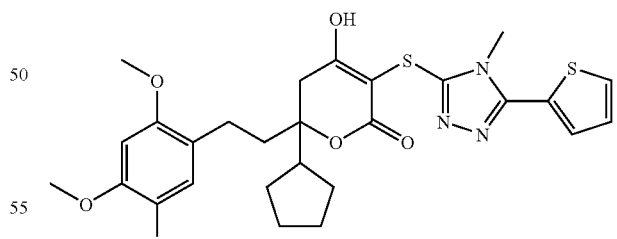

The title compound was prepared as described in Example 91, using 4-methyl-5-(thien-2-yl)-4H-1,2,4-triazole-3-thiol for. 5,7-dimethyl-2-mercapto-s-triazolo[1,5-a]pyrimidine. $^1$H NMR (DMSO-d$_6$): δ 1.3–1.55 (m, 8H), 1.67 (m, 2H), 1.89 (m, 2H), 2.30 (m, 1H), 2.70 (d, J=18 Hz, 1H), 2.86 (d, J=18 Hz, 1H), 3.76 (s, 6H), 3.84 (s, 3H), 6.70 (s, 1H) 7.18 (s, 1H), 7.24 (m, 1H), 7.54 (m, 1H), 7.75 (d, J=5 Hz, 1H). MS (APCI) calcd for C$_{27}$H$_{30}$ClN$_3$O$_5$S$_2$: 575.1. found (M+H$^+$) 576.1.

Example 97

3-[(4-amino-1H-pyrazolo[3,4-d]pyrimidin-6-yl)thio]-6-[2-(5-chloro-2,4-dimethoxyphenyl)ethyl]-6-cyclopentyl-4-hydroxy-5,6-dihydro-2H-pyran-2-one

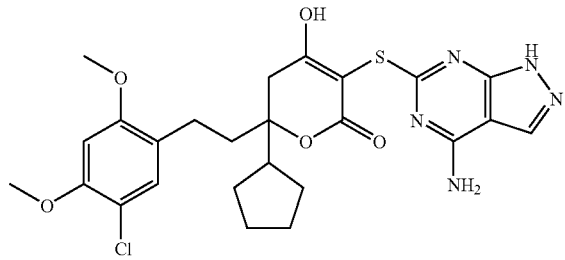

The title compound was prepared as described in Example 91, using 4-amino-6-mercaptopyrazolo[3,4-d]pyrimidine for 5,7-dimethyl-2-mercapto-s-triazolo[1,5-a]pyrimidine. $^1$H NMR (DMSO-$d_6$): δ 1.43 (m, 1H), 1.55 (m, 6H), 1.73 (m, 2H), 1.98 (m, 2H), 2.12 (m, 3H), 3.83 (s, 3H), 6.65 (s, 1H), 7.19 (s, 1H), 7.93 (s, 1H), 8.97 (m, 2H). MS (APCI) calcd for $C_{25}H_{28}ClN_5O_5S$: 545.1. found (M+H$^+$) 546.1.

Example 98

6-[2-(5-chloro-2,4-dimethoxyphenyl)ethyl]-6-cyclopentyl-4-hydroxy-3-([5-(hydroxymethyl)-1-methyl-1H-imidazol-2-yl]thio)-5,6-dihydro-2H-pyran-2-one

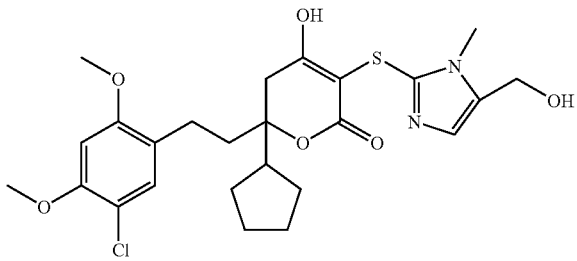

The title compound was prepared as described in Example 91, using 5-(hydroxymethyl)-2-mercapto-1-methylimidazole for 5,7-dimethyl-2-mercapto-s-triazolo[1,5-a]pyrimidine. $^1$H NMR (DMSO-$d_6$): δ 1.37 (m, 1H), 1.57 (m, 8H), 1.83 (m, 2H), 2.26 (m, 2H), 3.33 (m, 2H), 3.62 (s, 3H), 3.77 (s, 3H), 3.86 (s, 3H), 4.44 (s, 2H), 6.73 (s, 1H), 7.05 (s, 1H), 7.33 (s, 1H). MS (APCI) calcd for $C_{25}H_{31}ClN_2O_6S$: 522.15. found (M+H$^+$) 523.1.

Example 99

2-({6-[2-(5-chloro-2,4-dimethoxyphenyl)ethyl]-6-cyclopentyl-4-hydroxy-2-oxo-5,6-dihydro-2H-pyran-3-yl}thio)-1H-benzimidazole-5-carboxylic acid

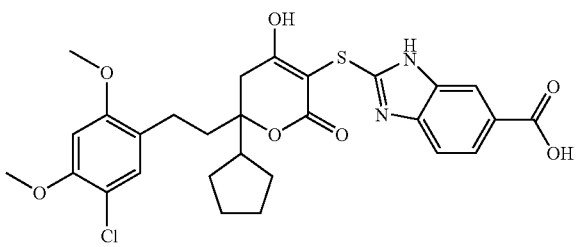

The title compound was prepared as described in Example 91, using 2-mercapto-1H-benzimidazole-5-carboxylic acid (prepared from 3,4-diaminobenzoic acid: *Arch. Pharm.* 1977, 310, 522) for 5,7-dimethyl-2-mercapto-s-triazolo[1,5-a]pyrimidine. $^1$H NMR (DMSO-$d_6$): δ 1.42 (m, 1H) 1.57 (m, 8H), 1.72 (m, 2H), 1.98 (m, 2H), 2.73 (d, J=18 Hz, 1 H), 2.93 (d, J=18 Hz, 1 H), 3.78 (s, 3H), 3.86 (s, 3H), 6.72 (s, 1H), 7.18 (s, 1H), 7.45 (d, J=8 Hz, 1H), 7.70 (d, J=8 Hz, 1H), 7.92 (s, 1H). MS (APCI) calcd for $C_{28}H_{29}ClN_2O_7S$: 572.1. found (M+H$^+$) 573.1.

Example 100

Ethyl 2-({6-[2-(5-chloro-2,4-dimethoxyphenyl)ethyl]-6-cyclopentyl-4-hydroxy-2-oxo-5,6-dihydro-2H-pyran-3-yl}thio)-1H-imidazol-4-carboxylate

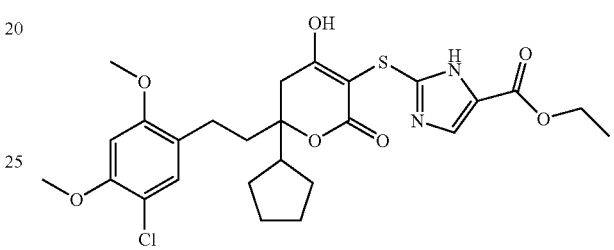

The title compound was prepared as described in Example 91, using ethyl 2-mercapto-1H-imidazole-4-carboxylate for 5,7-dimethyl-2-mercapto-s-triazolo[1,5-a]pyrimidine. $^1$H NMR (DMSO-$d_6$): δ 1.22 (t, 3H), 1.36 (m, 1H), 1.52 (m, 8H), 1.70 (m, 2H), 1.89 (m, 2H), 2.69 (d, J=17 Hz, 1H), 2.91 (d, J=17 Hz, 1H), 3.75 (s, 3H), 3.86 (s, 3H), 4.20 (q, 2H), 6.67 (s, 1H), 7.13 (s, 1H), 7.66 (s, 1H). MS (APCI) calcd for $C_{26}H_{31}ClN_2O_7S$: 550.15. found (M+H$^+$) 551.1.

Example 101

6-[2-(3-Chloro-4-methoxy-phenyl)-ethyl]-6-cyclopentyl-3-(5,7-dimethyl-[1,2,4]triazolo[1,5-a]pyrimidin-2-ylsulfanyl)-4-hydroxy-5,6-dihydro-pyran-2-one Step 1: 2-Chloro-7-(3-chloro-4-methoxy-phenyl)-5-cyclopentyl-5-hydroxy-3-oxo-heptanoic acid methyl ester

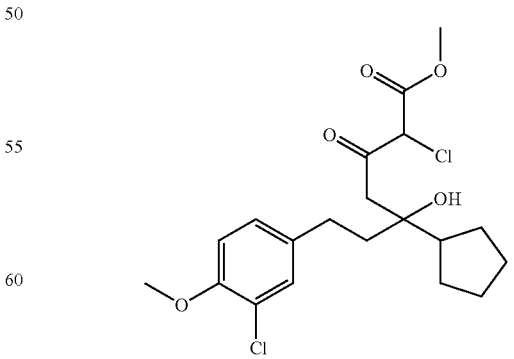

Methyl-2-chloroacetoacetate (2.5 g, 16.9 mmol) was added to a cooled 0° C. suspension of NaH (0.68 g, 16.9 mmol, 60% dispersion in mineral oil) in THF (30 ml). After 15 min the solution was cooled to −40° C. and n-BuLi (10.6 mL, 16.9 mmol, 1.6M in hexanes) was added. The resulting dianion was stirred for an additional 30 min and then treated with a solution of 3-(3-Chloro-4-methoxy-phenyl)-1-cyclopentyl-propan-1-one (1.5 g, 5.6mmol, prepared from Heck route) in THF (10 ml). After stirring for 1 h at −40° C., the reaction mixture was quenched with saturated NH$_4$Cl and extracted with EtOAc. The organic layers were washed with brine, dried with Na$_2$SO$_4$ and concentrated to an orange oil that was used without further purification.

Step 2: 3-Chloro-6-[2-(3-chloro-4-methoxy-phenyl)-ethyl]-6-cyclopentyl-4-hydroxy-5,6-dihydro-pyran-2-one

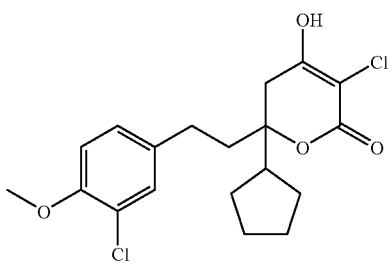

A solution of 2-Chloro-7-(3-chloro-4-methoxy-phenyl)-5-cyclopentyl-5-hydroxy-3-oxo-heptanoic acid methyl ester (2.33 g, 5.6 mmol, from step 1), and bis(dibutylchlorotin) oxide (1.38 g, 2.5 mmol), dissolved in toluene (18 mL) were heated at reflux for 30 mins. The resulting mixture was concentrated and purified by silica gel chromatography to give the title compound (1.57 g, 75% yield, two steps). $^1$H NMR (CDCl$_3$): δ 1.36–1.79 (br m, 8H), 2.02 (m, 2H), 2.41 (m, 1H), 2.65 (m, 3H), 2.89 (d 1H, J=17.7 Hz), 3.88 (s, 3H), 6.47 (br s, 1H), 6.85 (d, 1H, J=8.4 Hz), 7.01 (dd, 1H, J=8.4, 2.1 Hz), 7.16 (d, 1, J=2.1 Hz).

Step 3: 6-[2-(3-Chloro-4-methoxy-phenyl)-ethyl]-6-cyclopentyl-3-(5,7-dimethyl-[1,2,4]triazolo[1,5-a]pyrimidin-2-ylsulfanyl)-4-hydroxy-5,6-dihydro-pyran-2-one

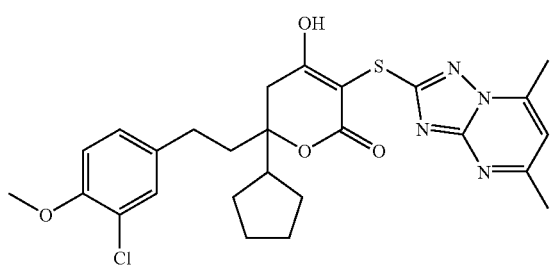

A solution of 3-Chloro-6-[2-(3-chloro-4-methoxy-phenyl)-ethyl]-6-cyclopentyl-4-hydroxy-5,6-dihydro-pyran-2-one (150 mg, 0.39 mmol, from step 2 above), 5,7-dimethyl-[1,2,4]triazolo[1,5-a]pyrimidine-2-thiol (70 mg, 0.39 mmol), and triethylamine (54 µL, 0.39 mmol dissolved in DMF (3 mL) was heated to 55° C. under N$_2$ for 4 h. The resulting mixture was concentrated and purified by Prep HPLC to give the title compound (52 mg, 30%) as a white solid. $^1$H NMR (DMSO-d$_6$): δ 1.49–1.82 (br m, 8H), 2.25 (m, 3H), 2.46 (s, 3H), 2.61 (s, 3H), 2.68 (m, 2H), 2.84 (d, 1H, J=17.6 Hz), 3.06 (d, 1H, J=17.6 Hz), 3.88 (s, 3H), 7.11 (d, 1H, J=8.3), 7.13 (s, 1H), 7.33 (d, 1H, J=8.3 ), 7.36 (s, 1H), 12.31 (s, 1H). Anal. Calcd. For C$_{26}$H$_{29}$N$_4$O$_4$ClS.0.6 TFA C, 54.68; H, 4.99; N, 9.38. Found: C, 54.83; H, 5.24, N, 9.38.

Example 102

6-[2-(3-Chloro-4-methoxy-phenyl)-ethyl]-6-cyclopentyl-4-hydroxy-3-phenylsulfanyl-5,6-dihydro-pyran-2-one

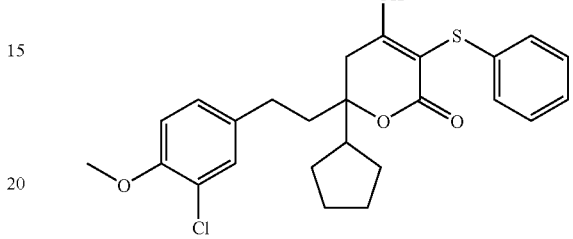

The title compound was prepared as described in Example 101 where benzenethiol was substituted for 5,7-Dimethyl-[1,2,4]triazolo[1,5-a]pyrimidine-2-thiol. $^1$H NMR (DMSO-d$_6$): δ 1.37–1.69 (br m, 8H), 1.98 (m, 2H), 2.37 (m, 1H), 2.45–2.69 (m, 4H), 3.83 (s, 3H), 7.06–7.17 (m, 4H), 7.23 (s, 1H,). Anal. Calcd. For C$_{25}$H$_{27}$O$_4$ClS.1.6 H$_2$O: C, 61.55; H, 6.24. Found: C, 61.41; H, 6.23.

Example 103

7-Cyclopentyl-7-[2-(2,4-dimethoxyphenyl)ethyl]-3,4,7,8-tetrahydro-2H,5H-pyrano[4,3-b]pyran-5-one

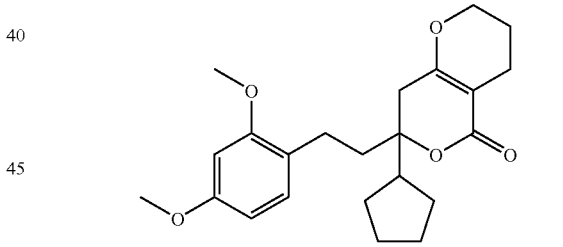

A solution of ethyl 6-methyl-3,4-dihydro-2H-pyran-5-carboxylate (511 mg, 3 mmol) in 3:1 DME/THF (2.5 mL) was cooled to −80° C. and treated with a solution of LDA (3.3 mL of 1.0 M in THF/hexanes/ethylbenzene, obtained by diluting commercial 2.0 M LDA with THF, 3.3 mmol). The mixture was stirred and allowed to stand at −80° C. for 40 min, then warmed to −60° C. over the course of another 10 min. To this was added a cold (−60° C.) solution of 3-[2-(2,4-dimethoxyphenyl)ethyl]-1-cyclopentylpropan-1-one (787 mg, 3.0 mmol; Example 39), step 1) in 3:1 DME/THF (2.5 mL). The reaction was allowed to warm gradually to room temperature over the course of 1.25 h. The reaction mixture was treated with acetic acid (2 equiv) and partitioned between brine and ethyl acetate. The organic phase was dried over Na$_2$SO$_4$, filtered and evaporated, affording 1.44 g yellowish resin. This was chromatographed on silica gel using 1:4 ethyl acetate/petroleum ether and recrystallized from this same solvent system, yielding 292 mg (25%) of the title product as a white solid. $^1$H NMR (CDCl$_3$): δ1.28–1.85 (m, 8H, overlap with H$_2$O peak), 1.96 (m, 4H), 2.25–2.42 (m, 4H), 2.62 (m, 3H), 3.80 (s, 6H), 4.15 (m, 2H), 6.44 (m, 2H), 7.0 (d, 1H). MS (APCI) calcd for C$_{23}$H$_{30}$O$_5$: 386.2. found (M+1): 387.2. Anal calcd for C$_{23}$H$_{30}$O$_5$: C, 71.48; H, 7.82. Found: C, 71.35; H, 7.84.

Example 104

6-(2-Allyloxy-ethyl)-6-cyclopentyl-3-(5,7-dimethyl-[1,2,4]triazolo[1,5-a]pyrimidin-2-ylsulfanyl)-4-hydroxy-5,6-dihydro-pyran-2-one Step 1: 3-Allyloxy-thiopropionic acid S-pyridin-2-yl ester

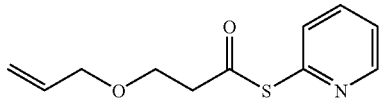

The title compound was prepared as described in Example 1 except 3-allyloxypropionic acid was substituted for 3-(4-Benzyloxyphenyl)propionic acid in step 4 of that Example. $^1$H NMR (CDCl$_3$): δ 2.99 (t, J=6.4 Hz, 2H), 3.79 (t, J=6.4 Hz, 2H), 4.00 (d, J=6.8 Hz, 2H), 5.1–5.82 (m, 2H), 5.84–5.97 (m, 1H), 7.27–7.33 (m, 1H), 7.63 (d, J=7.7 Hz, 1H), 7.74 (t, J=7.7 Hz, 1H), 8.63 (d, J=5.6 Hz, 1H). ESIMS (MH+): 224.2.

Step 2: 3-Allyloxy-1-cyclopentyl-propan-1-one

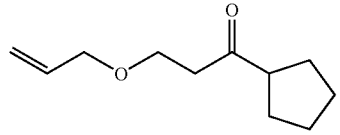

The title compound was prepared as described in Example 1 except 3-Allyloxy-thiopropionic acid S-pyridin-2-yl ester from step 1 above was substituted for 3-(4-Benzyloxyphenyl)thiopropionic acid S-pyridin-2-yl ester in step 5 of that Example. $^1$H NMR (CDCl$_3$): δ 1.51–1.88 (m, 9H), 2.73 (t, J=6.4 Hz, 2H), 3.71 (t, J=6.4 Hz, 2H), 3.96–4.01 (m, 2H), 5.15–5.31 (m, 2H), 5.82–5.97 (m, 1H). ESIMS (MH+): 183.2.

Step 3: 6-(2-Allyloxy-ethyl)-3-chloro-6-cyclopentyl-4-hydroxy-5,6-dihydro-pyran-2-one

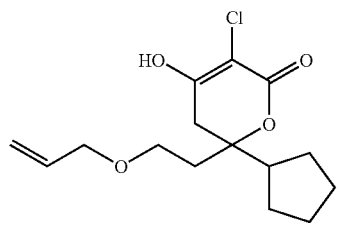

To a suspension of NaH (60%, 0.65 g, 16.47 mmol) in anhydrous THF at 0° C. was added methyl 2-chloroacetoacetate (0.69 mL, 5.65 mmol). The resulting white slurry suspension was stirred for 20 min before n-BuLi (1.6 M, 10.29 mL) was added dropwise over 20 min. After 30 min, a solution of 3-Allyloxy-1-cyclopentyl-propan-1-one from step 2 above (1 g, 5.49 mmol), in anhydro THF was transferred to the reaction via cannula and the resulting solution was stirred at 0° C. for an additional 2 hrs. The reaction was quenched by the addition of 1 N HCl and extracted with EtOAc (3×20 mL). The combined organic extracts were washed with brine and dried over Na$_2$SO$_4$. The solvent was removed in vacuo and the residue was taken directly into next step without further purification.

The crude product was dissolved in toluene (20 mL) and bis(dibutylchlorotin) oxide (1.52 g, 2.75 mmol) was added. The slurry was stirred at 100° C. for 30 minutes before it was acidified to pH 7 by the addition of 1H HCl. The mixture was extracted with EtOAc (4×15 mL), and the combined organic extracts were washed sequentially with aq. NH$_4$Cl, brine, and dried over Na$_2$SO$_4$. The solvent was removed in vacuo, and the residue was purified by flash column chromatography (30–60% EtOAc in hexanes) to give the desired product as a tan solid (1.0 g, 54% yield for two steps). $^1$H NMR (CDCl$_3$): 1.26–1.79 (m, 9H), 2.01–2.13 (m, 2H), 2.88 (d, J=7.5 Hz, 2H), 3.51–3.59 (m, 2H), 3.91 (d, J=5.3 Hz, 2H), 5.16–5.29 (m, 2H), 5.81–5.92 (m, 1H). ESIMS (MNa+): 323.1.

Step 4: 6-(2-Allyloxy-ethyl)-6-cyclopentyl-3-(5,7-dimethyl-[1,2,4]triazolo[1,5-a]pyrimidin-2-ylsulfanyl)-4-hydroxy-5,6-dihydro-pyran-2-one

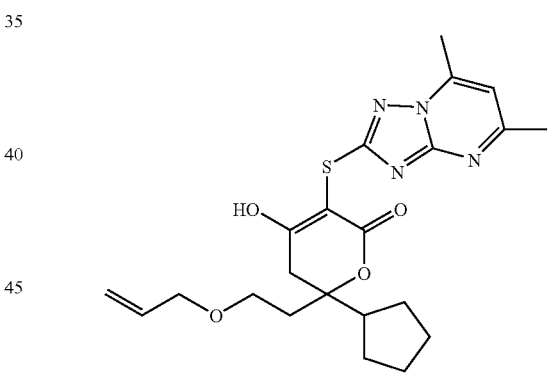

6-(2-Allyloxy-ethyl)-3-chloro-6-cyclopentyl-4-hydroxy-5,6-dihydro-pyran-2-one (0.333 g, 0.11 mmol) from step 3 above was dissolved in DMF (1 mL). 5,7-Dimethyl-[1,2,4]triazolo[1,5-a]pyrimidine-2-thiol (0.06 g, 0.11 mmol) and TEA (0.015 mL, 0.11 mmol) were added successively. The reaction mixture was then stirred at 55° C. for 2 hours. DMF was completely removed via rotary evaporator, and the residue was purified via preparative HPLC. The solvent was evaporated to give the title compound (0.030 g, 75%) as white foam. $^1$H NMR (CDCl$_3$-d$_6$): δ 1.33–1.88 (m, 8H), 2.15–2.19 (m, 1H), 2.28 (t, J=6.4 Hz, 2H), 2.64 (s, 3H), 2.72 (s, 3H), 2.95 (s, 2H), 3.60 (t, J=6.4 Hz, 2H) 3.93 (d, J=1.3 Hz, 2H), 5.20 (dd, J=15.6, 10.4 Hz, 2H), 5.79–5.94 (m, 1H), 6.81 (s, 1H), 7.95 (brs, 1H). Anal. Calcd. For C$_{22}$H$_{28}$N$_4$O$_4$S.3TFA: C, 42.75; H, 3.97; N, 7.12. Found: C, 42.87; H, 4.02; N, 7.5. ESIMS (MH+): 445.1.

Example 105

6-[2-(5-Chloro-2,4-dimethoxyphenyl)ethyl]-6-cyclopentyl-4-hydroxy-3-[(4-hydroxy-7H-pyrrolo[2,3-d]pyrimidin-2-yl)thio]-5,6-dihydro-2H-pyran-2-one

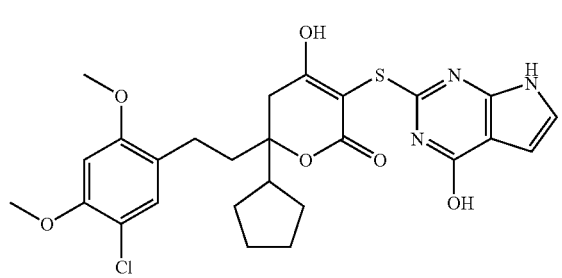

The title compound was prepared as described in Example 91, using 2-mercapto-7H-pyrrolo[2,3-d]pyrimidin-4-ol for 5,7-dimethyl-2-mercapto-s-triazolo[1,5-a]pyrimidine. $^1$H NMR (DMSO-d$_6$) δ 1.36–1.64 (m, 8H), 1.70 (m, 2H), 1.88–2.05 (m, 2H), 2.37 (m, 1H), 2.73 (m, 1H), 2.73 (d, J=15 Hz), 2.93 (d, 1H, J=15 Hz), 3.74 (s, 3H), 3.83 (s, 3H), 6.33 (s, 1H), 6.66 (s, 1H), 6.83 (s, 1H), 7.16 (s, 1H), 11.31 (s, 1H). MS (APCI) calcd for C$_{26}$H$_{28}$ClN$_3$O$_6$S: 545.14. found (M+H$^+$) 546.1.

Example 106

6-[2-(5-Chloro-2,4-dimethoxyphenyl)ethyl]-6-cyclopentyl-3-[(1-ethyl-1H-tetraazol-5-yl)thio]-4-hydroxy-5,6-dihydro-2H-pyran-2-one

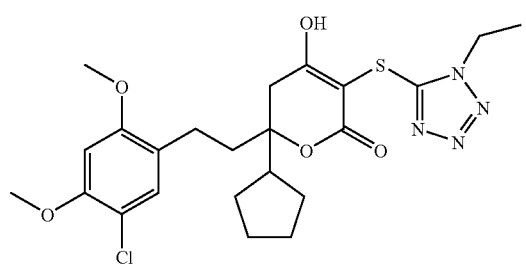

The title compound was prepared as described in Example 91, using 1-ethyl-1H-tetraazole-5-thiol for 5,7-dimethyl-2-mercapto-s-triazolo[1,5-a]pyrimidine. $^1$H NMR (DMSO-d$_6$) δ 1.34 (m, 1H), 1.42 (t, 3H), 1.4–1.7 (m, 7H), 1.68 (m, 2H), 1.93 (m, 2H), 2.38 (m, 1H), 2.70 (d, 1H, J=15 Hz), 2.90 (d, 1H, J=15 Hz), 3.77 (s, 3H), 3.85 (s, 3H), 4.35 (q, 2H), 6.71 (s, 1H), 7.19 (s, 1H). MS (APCI) calcd for C$_{23}$H$_{29}$ClN$_4$O$_5$S: 508.15. found (M+H$^+$) 509.0.

Example 107

6-[2-(5-Chloro-2,4-dimethoxyphenyl)ethyl]-6-cyclopentyl-3-({1-[2-(dimethylamino)ethyl]-1H-tetraazol-5-yl}thio)-4-hydroxy-5,6-dihydro-2H-pyran-2-one

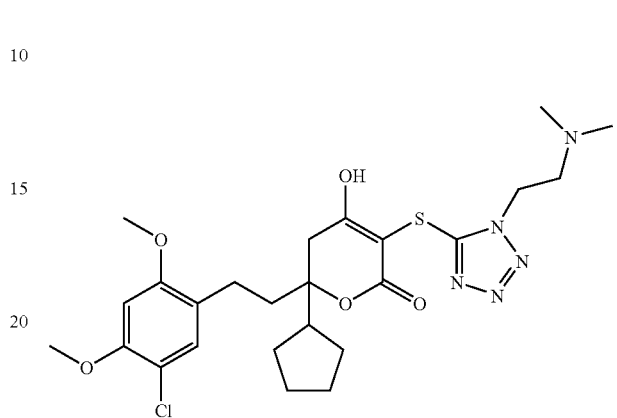

The title compound was prepared as described in Example 91, using 1-[2-(dimethylamino)ethyl]-1H-tetraazole-5-thiol for 5,7-dimethyl-2-mercapto-s-triazolo[1,5-a]pyrimidine. $^1$H NMR (DMSO-d$_6$) δ 1.3–1.7 (m, 8H), 1.8 (m, 2H), 1.9 (m, 2H), 2.38 (m, 1H), 2.65 (m, 1H), 2.83 (m, 1H), 2.85 (s, 6H), 3.61 (t, 2H, J=5 Hz), 3.79 (s, 3H), 3.85 (s, 3H), 4.85 (t, 2H, J=5 Hz), 6.71 (s, 1H), 7.12 (s, 1H). MS (APCI) calcd for C$_{25}$H$_{34}$ClN$_5$O$_5$S: 551.20. found (M+H$^+$) 552.1.

Example 108

6-[2-(5-Chloro-2,4-dimethoxyphenyl)ethyl]-6-cyclopentyl-4-hydroxy-3-(pyrazin-2-ylthio)-5,6-dihydro-2H-pyran-2-one

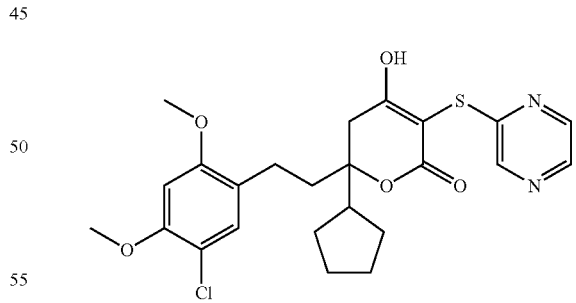

The title compound was prepared as described in Example 91, using ethyl 2-mercaptopyrazine for 5,7-dimethyl-2-mercapto-s-triazolo[1,5-a]pyrimidine. $^1$H NMR (DMSO-d$_6$) δ 1.48 (m, 1H), 1.58–1.73 (m, 7H), 1.8 (m, 2H), 2.02–2.15 (m, 2H), 2.50 (m, 1H), 2.86 (d, 1H, J=17 Hz), 3.12 (d, 1H, J=17 Hz), 3.85 (s, 3H), 3.94 (s, 3H), 6.81 (s, 1H), 7.23 (s, 1H), 8.32 (dd, 1H, J=2.5, 1.3 Hz), 8.35 (d, 1H, J=2.5 Hz), 8.44 (d, 1H, J=1.3 Hz). MS (APCI) calcd for C$_{24}$H$_{27}$ClN$_2$O$_5$S: 490.13; found (M+H$^+$) 491.0.

Example 109

6-[2-(5-Chloro-2,4-dimethoxyphenyl)ethyl]-6-cyclopentyl-4-hydroxy-3-(1,3-thiazol-2-ylthio)-5,6-dihydro-2H-pyran-2-one

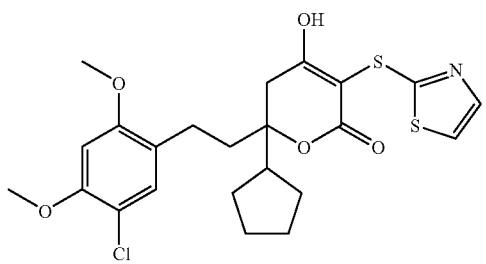

The title compound was prepared as described in Example 91, using 2-mercaptothiazole for 5,7-dimethyl-2-mercapto-s-triazolo[1,5-a]pyrimidine. $^1$H MNR (DMSO-d$_6$) δ 1.46 (m, 1H), 1.57–1.72 (m, 7H), 1.80 (m, 2H), 1.98–2.11 (m, 2H), 2.49 (m, 1H), 2.86 (d, 1H, J=17 Hz), 3.04 (d, 1H, J=17 Hz), 3.85 (s, 3H), 3.94 (s, 3H), 6.80 (s, 1H), 7.23 (s, 1H), 7.54 (d, 1H, J=3.5 Hz), 7.65 (d, 1H, J=3.5 Hz). MS (APCI) calcd for C$_{23}$H$_{26}$ClNO$_5$S$_2$: 495.09. found (M+H$^+$) 496.0.

Example 110

6-[2-(5-Chloro-2,4-dimethoxyphenyl)ethyl]-6-cyclopentyl-4-hydroxy-3-(1,4,5,6-tetrahydropyrimidin-2-ylthio)-5,6-dihydro-2H-pyran-2-one

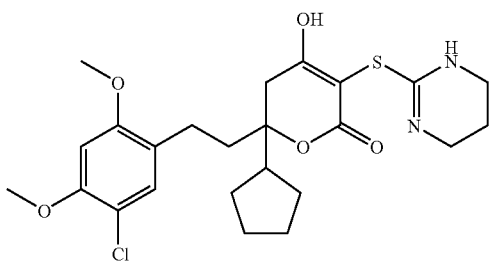

The title compound was prepared as described in Example 91, using 3,4,5,6-tetrahydro-2-pyrimidinethiol for 5,7-dimethyl-2-mercapto-s-triazolo[1,5-a]pyrimidine. $^1$H NMR (DMSO-d$_6$) δ 1.43–1.68 (m, 8H), 1.73 (m, 2H), 1.84–1.92 (m, 4H), 2.4 (m, 1H), 2.8 (m, 2H), 3.2–3.3 (m, 4H, overlap with H$_2$O peak), 3.90 (s, 3H), 3.92 (s, 3H), 6.80 (s, 1H), 7.17 (s, 1H), 8.89 (br s, 2H). MS (APCI) calcd for C$_{24}$H$_{31}$ClN$_2$O$_5$S: 494.16. found (M+H$^+$) 495.1.

Example 111

6-Cyclopentyl-4-hydroxy-6-[2-(4-methoxyphenyl)ethyl]-3-[(5-pyridin-4-yl-1H-1,2,4-triazol-3-yl)thio]-5,6-dihydro-2H-pyran-2-one

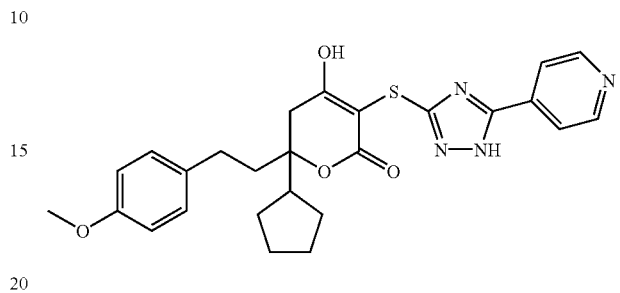

The title compound was prepared as described in Example 91, using 5-(4-pyridyl)-1H-1,2,4-triazole-3-thiolfor 5,7-dimethyl-2-mercapto-s-triazolo[1,5-a]pyrimidine and 3-chloro-6-[2-(4-methoxyphenyl)ethyl]-6-cyclopentyl-4-hydroxy-5,6-dihydro-2H-pyran-2-one (from Example B(5)) for 3-chloro-6-[2-(5-chloro-2,4-dimethoxyphenyl)ethyl]-6-cyclopentyl-4-hydroxy-5,6-dihydro-2-dihydro-2H-pyran-2-one). $^1$H NMR (DMSO-d$_6$) δ 1.4–1.6 (m, 8H), 1.7 (m, 2H), 1.95–2.15 (m, 2H), 2.57 (m, 1H), 2.81 (d, 1H, J=18 Hz), 2.99 (M, 1H), 3.68 (s, 3H), 6.78 (d, 2H, J=8 Hz), 7.09 (d, 2H, J=8 Hz), 7.75 (m, 2H), 8.57 (m, 2H). MS (APCI) calcd for C$_{26}$H$_{28}$N$_4$O$_4$S: 492.18. found (M+H$^+$) 493.1.

Example 112

[2-({6-Cyclopentyl-4-hydroxy-6-[2-(4-methoxyphenyl)ethyl]-2-oxo-5,6-dihydro-2H-pyran-3-yl}thio)-4-methyl-1,3-thiazol-5-yl]acetic acid

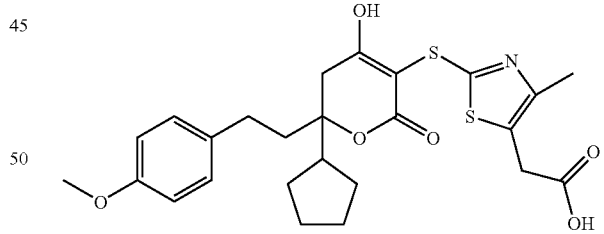

The title compound was prepared as described in Example, 91, using 2-mercapto-4-methyl-5-thiazoleacetic acid for 5,7-dimethyl-2-mercapto-s-triazolo[1,5-a]pyrimidine and 3-chloro-6-[2-(4-methoxyphenyl)ethyl]-6-cyclopentyl-4-hydroxy-5,6-dihydro-2H-pyran-2-one (Example B(5)) for 3-chloro-6-[2-(5-chloro-2,4-dimethoxyphenyl)ethyl]-6-cyclopentyl-4-hydroxy-5,6-dihydro-2H-pyran-2-one. $^1$H NMR (DMSO-d$_6$) δ 1.36 (m, 1H), 1.46–1.55 (m, 7H), 1.68 (m, 2H), 2.04 (m, 2H), 2.13 (s, 3H), 2.5 (m, 1H, overlap with DMSO-d$_5$), 2.78 (d, 1H, J=18 Hz), 2.95 (d, 1H, J=18 Hz), 3.2 (s, 2H, overlap with H$_2$O peak), 3.70 (s, 3H), 6.83 (d, 2H), 7.11 (d, 2H). MS (APCI) calcd for C$_{25}$H$_{29}$NO$_6$S$_2$: 503.14. found (M+H$^+$) 504.1.

Example 113

6-Cyclopentyl-4-hydroxy-3-[(4-hydroxy-7H-pyrrolo[2,3-d]pyrimidin-2-yl)thio]-6-[2-(4-methoxyphenyl)ethyl]-5,6-dihydro-2H-pyran-2-one

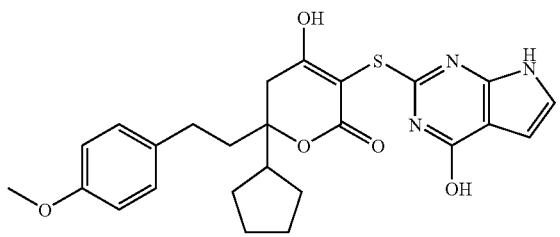

The title compound was prepared as described in Example 91, using 2-mercapto-7H-pyrrolo[2,3-d]pyrimidin-4-ol for 5,7-dimethyl-2-mercapto-s-triazolo[1,5-a]pyrimidine and 3-chloro-6-[2-(4-methoxyphenyl)ethyl]-6-cyclopentyl-4-hydroxy-5,6-dihydro-2H-pyran-2-one (from Example B(5)) for 3-chloro-6-[2-(5-chloro-2,4-dimethoxyphenyl)ethyl]-6-cyclopentyl-4-hydroxy-5,6-dihydro-2H-pyran-2-one. $^1$H NMR (DMSO-$d_6$) δ 1.38–1.62 (m, 8H), 1.68 (m, 2H), 2.05 (m, 2H), 2.50 (m, 1H, overlap with DMSO-$d_5$ peak), 2.74 (d, 1H, J=17 Hz), 2.90 (d, 1H, J=17 Hz), 3.70 (s, 3H), 6.34 (s, 1H), 6.8 (d, J=8 Hz), 6.68 (s, 1H), 7.11 (d, 2H, J=8 Hz), 11.26 (s, 1H). MS (APCI) calcd for $C_{25}H_{27}N_3O_5S$: 481.17. found (M+H$^+$) 482.0.

Example 114

6-Cyclopentyl-4-hydroxy-3-([1-(4-hydroxyphenyl)-1H-tetraazol-5-yl]thio)-6-[2-(4-methoxyphenyl)ethyl]-5,6-dihydro-2H-pyran-2-one

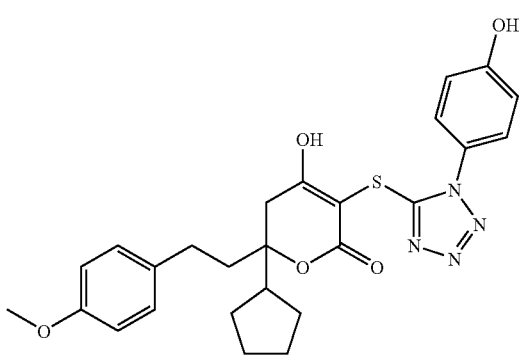

The title compound was prepared as described in Example 91, using 1-(4-hydroxyphenyl)-1H-tetrazole-5-thiol for 5,7-dimethyl-2-mercapto-s-triazolo[1,5-a]pyrimidine and 3-chloro-6-[2-(4-methoxyphenyl)ethyl]-6-cyclopentyl-4-hydroxy-5,6-dihydro-2H-pyran-2-one (from Example B(5)) for 3-chloro-6-[2-(5-chloro-2,4-dimethoxyphenyl)ethyl]-6-cyclopentyl-4-hydroxy-5,6-dihydro-2H-pyran-2-one. $^1$H NMR (DMSO-$d_6$) δ 1.43 (m, 1H), 1.55–1.72 (m, 7H), 1.76 (m, 2H), 2.08–2.23 (m, 2H), 2.52 (quintet, 1H, J=7.8 Hz), 2.76 (d, 1H, J=16 Hz), 2.97 (d, 1H, J=16 Hz), 3.80 (s, 3H), 6.92 (d, 2H, J=8.5 Hz), 7.07 (d, 2H, J=8.5 Hz), 7.28 (d, 2H, J=8.5 Hz), 7.53 (d, 2H, J=8.5 Hz). MS (APCI) calcd for $C_{26}H_{28}N_4O_5S$: 508.18. found (M+H$^+$) 509.0.

Example 115

3-[(3-Amino-1H-1,2,4-triazol-5-yl)thio]-6-cyclopentyl-4-hydroxy-6-[2-(4-methoxyphenyl)ethyl]-5,6-dihydro-2H-pyran-2-one

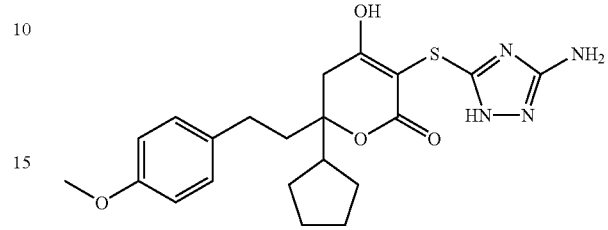

The title compound was prepared as described in Example 91, using 3-amino-5-mercapto-1,2,4-triazole for 5,7-dimethyl-2-mercapto-s-triazolo[1,5-a]pyrimidine and 3-chloro-6-[2-(4-methoxyphenyl)ethyl]-6-cyclopentyl-4-hydroxy-5,6-dihydro-2H-pyran-2-one (from Example B(5)) for 3-chloro-6-[2-(5-chloro-2,4-dimethoxyphenyl)ethyl]-6-cyclopentyl-4-hydroxy-5,6-dihydro-2H-pyran-2-one. $^1$H NMR (DMSO-$d_6$) δ 1.41 (m, 1H), 1.49–1.64 (m, 7H), 1.7 (m, 2H), 2.03 (m, 2H), 2.42 (m, 1H), 2.84 (d, 1H, J=18.4 Hz), 2.9 (d, 1H, J=18.4 Hz), 3.75 (s, 3H), 6.88 (d, 2H), 7.14 (d, 2H). MS (APCI) calcd for $C_{21}H_{36}N_4O_4S$: 430.17. found (M+H$^+$) 431.0.

Example 116

6-Cyclopentyl-3-({1-[2-(dimethylamino)ethyl]-1H-tetraazol-5-yl}thio)-4-hydroxy-6-[2-(4-methoxyphenyl)ethyl]-5,6-dihydro-2H-pyran-2-one

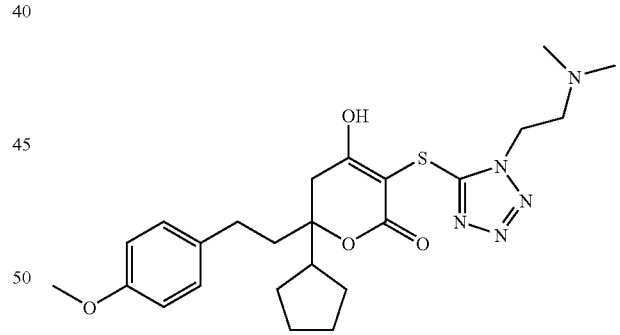

The title compound was prepared as described in Example 91, using 1-[2-(dimethylamino)ethyl]-1H-tetraazole-5-thiol for 5,7-dimethyl-2-mercapto-s-triazolo[1,5-a]pyrimidine and 3-chloro-6-[2-(4-methoxyphenyl)ethyl]-6-cyclopentyl-4-hydroxy-5,6-dihydro-2H-pyran-2-one (from Example B(5)) for 3-chloro-6-[2-(5-chloro-2,4-dimethoxyphenyl)ethyl]-6-cyclopentyl-4-hydroxy-5,6-dihydro-2H-pyran-2-one. $^1$H NMR (DMSO-$d_6$) δ 1.39 (m, 1H), 1.5–1.65 (m, 7H), 1.71 (m, 2H), 2.05 (m, 2H), 2.44 (m, 1H), 2.7 (m, 1H), 2.94 (s, 6H, overlap with m, 1H), 3.77 (s, 3H overlap with t, 2H), 4.89 (t, 2H, J=6.2 Hz), 6.88 (d, 2H, J=8.7 Hz), 7.2 (d, 2H, J=8.7 Hz). MS (APCI) calcd for $C_{24}H_{33}N_5O_4S$: 487.23. found (M+H$^+$) 488.2.

Example 117

6-Cyclopentyl-4-hydroxy-3-[(5-hydroxy-4-methyl-4H-1,2,4-triazol-3-yl)thio]-6-[2-(4-methoxyphenyl)ethyl]-5,6-dihydro-2H-pyran-2-one

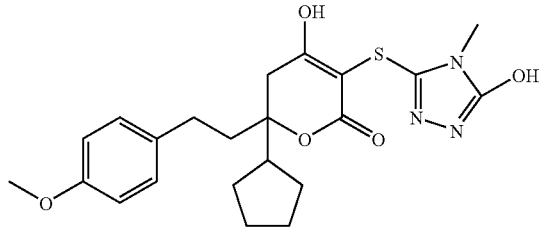

The title compound was prepared as described in Example 91, using 5-hydroxy-4-methyl-4H-1,2,4-triazole-3-thiol for 5,7-dimethyl-2-mercapto-s-triazolo[1,5-a]pyrimidine and 3-chloro-6-[2-(4-methoxyphenyl)ethyl]-6-cyclopentyl-4-hydroxy-5,6-dihydro-2H-pyran-2-one (from Example B(5)) for 3-chloro-6-[2-(5-chloro-2,4-dimethoxyphenyl)ethyl]-6-cyclopentyl-4-hydroxy-5,6-dihydro-2H-pyran-2-one. $^1$H NMR (DMSO-d$_6$) δ 1.37 (m, 1H), 1.5–1.63 (m, 7H), 1.69 (m, 2H), 1.98 (m, 2H), 2.42 (quintet, 1H), 2.77 (d, 1H, J=17.4 Hz), 2.95 (d, 1H, J=17.4 Hz), 3.16 (s, 3H), 3.76 (s, 3H), 6.90 (d, J=8.4 Hz), 7.11 (d, 1H, J=8.4 Hz), 11.75 (s, 1H). MS (APCI) calcd for $C_{22}H_{27}N_3O_5S$: 445.17. found (M+H$^+$) 446.0

Example 118

2-((6-Cyclopentyl-4-hydroxy-6-[2-(4-methoxyphenyl)ethyl]-2-oxo-5,6-dihydro-2H-pyran-3-yl}thio)-1,7-dihydro-6H-purin-6-one

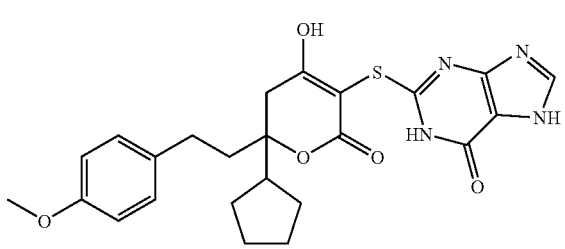

The title compound was prepared as described in Example 91, using 6-hydroxy-2-mercaptopurine for 5,7-dimethyl-2-mercapto-s-triazolo[1,5-a]pyrimidine and 3-chloro-6-[2-(4-methoxyphenyl)ethyl]-6-cyclopentyl-4-hydroxy-5,6-dihydro-2H-pyran-2-one (from Example B(5)) for 3-chloro-6-[2-(5-chloro-2,4-dimethoxyphenyl)ethyl]-6-cyclopentyl-4-hydroxy-5,6-dihydro-2H-pyran-2-one. $^1$H NMR (DMSO-d$_6$) δ 1.47 (m, 1H), 1.52–1.69 (m, 7H), 1.74 (m, 2H), 2.04–2.22 (m, 2H), 2.63 (m, 1H), 2.86 (d, 1H, J=18 Hz), 2.98 (d, 1H, J=18 Hz), 3.75 (s, 3H), 6.86 (d, 2H, J=8.4 Hz), 7.24 (d, 2H, J=8.4 Hz), 8.14 (s, 1H). MS (APCI) calcd for $C_{24}H_{26}N_4O_5S$: 482.16. found (M+H$^+$) 483.1.

Example 119

Ethyl 2-({6-cyclopentyl-4-hydroxy-6-[2-(4-methoxyphenyl)ethyl]-2-oxo-5,6-dihydro-2H-pyran-3-yl}thio)-1H-imidazole-4-carboxylate

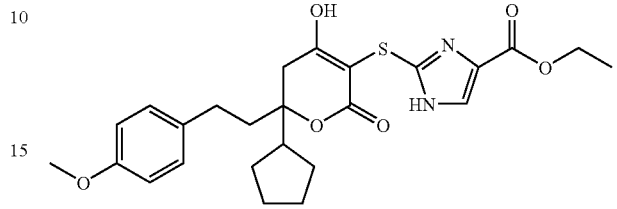

The title compound was prepared as described in Example 91, using ethyl 2-mercapto-1H-imidazole-4-carboxylate for 5,7-dimethyl-2-mercapto-s-triazolo[1,5-a]pyrimidine, and 3-chloro-6-[2-(4-methoxyphenyl)ethyl]-6-cyclopentyl-4-hydroxy-5,6-dihydro-2H-pyran-2-one (from Example B(5)) for 3-chloro-6-[2-(5-chloro-2,4-dimethoxyphenyl)ethyl]-6-cyclopentyl-4-hydroxy-5,6-dihydro-2H-pyran-2-one. $^1$H NMR (DMSO-d$_6$) δ 1.28 (t, 3H, J=6.8 Hz), 1.42 (m, 1H), 1.51–1.66 (m, 7H), 1.7 (m, 2H), 2.0 (m, 2H), 2.44 (m, 1H), 2.76 (d, 1H, J=17.7 Hz), 2.94 (d, 1H, J=17.7 Hz), 3.75 (s, 3H), 4.24 (q, 2H, J=6.8 Hz), 6.86 (d, 2H, J=8.8 Hz), 7.14 (d, 2H, J=8.8 Hz), 7.74 (s, 1H). MS (APCI) calcd for $C_{25}H_{30}N_2O_6S$: 486.18. found (M+H$^+$) 487.1.

Example 120

3-[(4-Amino-1H-pyrazolo[3,4-d]pyrimidin-6-yl)thio]-6-cyclopentyl-4-hydroxy-6-[2-(4-methoxyphenyl)ethyl]-5,6-dihydro-2H-pyran-2-one

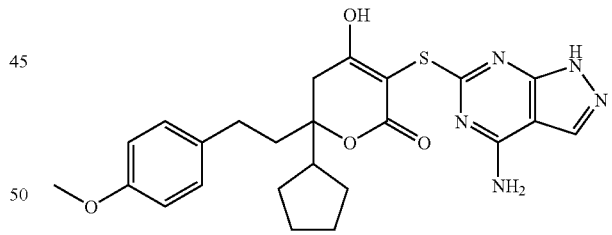

The title compound was prepared as described in Example 91, using 4-amino-6-mercaptopyrazolo[3,4-d]pyrimidine for 5,7-dimethyl-2-mercapto-s-triazolo[1,5-a]pyrimidine, and 3-chloro-6-[2-(4-methoxyphenyl)ethyl]-6-cyclopentyl-4-hydroxy-5,6-dihydro-2H-pyran-2-one (from Example B(5)) for 3-chloro-6-[2-(5-chloro-2,4-dimethoxyphenyl)ethyl]-6-cyclopentyl-4-hydroxy-5,6-dihydro-2H-pyran-2-one. $^1$H NMR (DMSO-d$_6$) δ 1.50 (m, 1H), 1.56–1.69 (m, 7H), 1.77 (m, 2H), 2.15 (m, 1H), 2.28 (m, 1H), 2.49 (m, 1H), 2.82 (d, 1H, J=17.6 Hz), 2.95 (d, 1H, J=17.6 Hz), 3.77 (s, 3H), 6.88 (d, 2H, J=8.7 Hz), 7.20 (d, 2H, J=8.7 Hz), 8.05 (br s). MS (APCI) calcd for $C_{24}H_{27}N_5O_4S$: 481.18. found (M+H$^+$) 482.2.

Example 121

6-Cyclopentyl-3-[(1-ethyl-1H-tetraazol-5-yl)thio]-4-hydroxy-6-[2-(4-methoxyphenyl)ethyl]-5,6-dihydro-2H-pyran-2-one

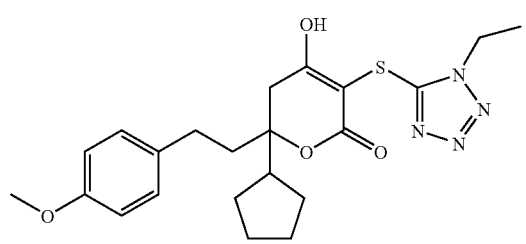

The title compound was prepared as described in Example 91, using 1-ethyl-1H-tetraazole-5-thiol for 5,7-dimethyl-2-mercapto-s-triazolo[1,5-a]pyrimidine, and 3-chloro-6-[2-(4-methoxyphenyl)ethyl]-6-cyclopentyl-4-hydroxy-5,6-dihydro-2H-pyran-2-one (from Example B(5)) for3-chloro-6-[2-(5-chloro-2,4-dimethoxyphenyl)ethyl]-6-cyclopentyl-4-hydroxy-5,6-dihydro-2H-pyran-2-one. $^1$H NMR (DMSO-$d_6$) δ 1.42 (m, 1H), 1.52 (t, 3H, J=6.8 Hz), 1.56–1.70 (m, 7H), 1.75 (m, 2H), 2.05–2.17 (m, 2H), 2.51 (quintet, 1H, J=7.3 Hz), 2.80 (d, 1H, J=16.2 Hz), 3.03 (d, 1H, J=16.2 Hz), 3.80 (s, 3H), 4.45 (q, 2H, J=6.8 Hz), 6.92 (d, 2H, J=8.1 Hz). MS (APCI) calcd for $C_{22}H_{28}N_4O_4S$: 444.18. found (M+H$^+$) 445.1.

Example 122

6-{2-[4-(Benzyloxy)phenyl]ethyl}-6-cyclopentyl-3-[(5,7-dimethyl[1,2,4]triazolo[1,5-a]pyrimidin-2-yl)thio]-4-hydroxy-5,6-dihydro-2H-pyran-2-one

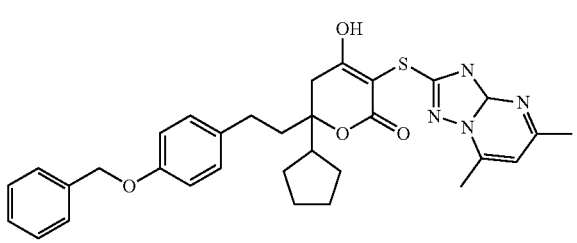

The title compound was prepared as described in Example 91, using 6-{2-[4-(benzyloxy)phenyl]ethyl)-3-chloro-6-cyclopentyl-4-hydroxy-5,6-dihydro-2H-pyran-2-one (described above) for 3-chloro-6-[2-(5-chloro-2,4-dimethoxyphenyl)ethyl]-6-cyclopentyl-4-hydroxy-5,6-dihydro-2H-pyran-2-one. $^1$H NMR (DMSO-$d_6$) δ 1.43 (m, 1H), 1.5–1.65 (m, 7H), 1.71 (m, 2H), 2.12 (m, 1H), 2.25 (m, 1H), 2.34 (s, 6H), 2.59 (m, 1H), 2.71 (m, 1H), 2.90 (m, 1H), 5.07 (s, 2H), 6.90 (d, 2H), 6.99 (s, 1H), 7.19 (d, 2H), 7.32 (t, 1H), 7.39 (t, 2H), 7.43 (d, 2H). MS (APCI) calcd for $C_{32}H_{34}N_4O_4S$: 570.23. found (M+H$^+$) 571.1.

Step 1: 6-{2-[4-(Benzyloxy)phenyl]ethyl}-3-chloro-6-cyclopentyl-4-hydroxy-5,6-dihydro-2H-pyran-2-one

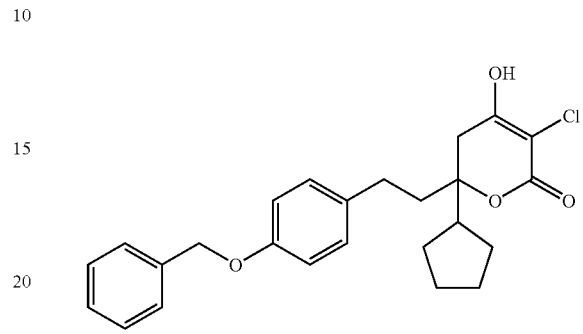

The title compound was prepared as described in Example 87,except 6-[2-(4-benzyloxyphenyl)ethyl]-6-cyclopentyldihydro-2H-pyran-2,4(3H)-dione (from Step 6 of Example A1) was used for 6-[2-(4-methoxyphenyl)ethyl]-6-cyclopentyidihydro-2H-pyran-2,4(3H)-dione. $^1$H NMR (CDCl$_3$, 300 MHz) δ 1.33–1.96 (m, 8H), 2.06 (m, 2H), 2.42 (m, 1H), 2.66 (m, 3H), 2.93 (d, 1H, J=17.8 Hz), 5.07 (s, 2H), 6.92 (d, 2H, J=8.4 Hz), 7.10 (d, 2H, J=8.4 Hz), 7.29–7.46 (m, 5H). MS (APCI) calcd for $C_{25}H_{27}ClO_4$: 426.16. found (M+H$^+$) 427.1.

Example 123

6-{2-[4-(Benzyloxy)phenyl]ethyl}-6-cyclopentyl-4-hydroxy-3-[(4-hydroxy-7H-pyrrolo[2,3-d]pyrimidin-2-yl)thio]-5,6-dihydro-2H-pyran-2-one

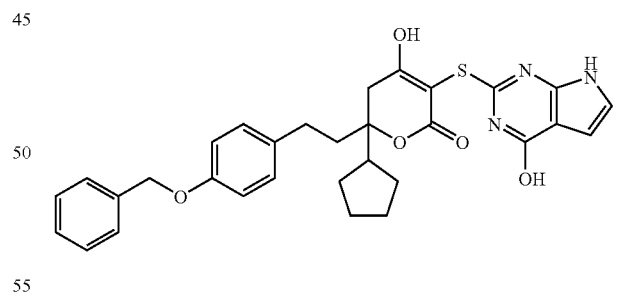

The title compound was prepared as described in Example 91, using 6-{2-[4-(benzyloxy)phenyl]ethyl}-3-chloro-6-cyclopentyl-4-hydroxy-5,6-dihydro-2H-pyran-2-one for 3-chloro-6-[2-(5-chloro-2,4-dimethoxyphenyl)ethyl]-6-cyclopentyl-4-hydroxy-5,6-dihydro-2H-pyran-2-one and using 2-mercapto-7H-pyrrolo[2,3-d]pyrimidin-4-ol for 5,7-dimethyl-2-mercapto-s-triazolo[1,5-a]pyrimidine. $^1$H NMR (DMSO-$d_6$) δ 1.41 (m, 1H), 1.48–1.71 (m, 9 H), 2.04 (m, 2H), 2.38 (m, 1H), 2.73 (m, 1H), 2.88 (m, 1H), 5.05 (s, 2H), 6.34 (s, 1H), 6.85 (s, 1H), 7.11 (d, 2H), 7.3 (m, 1H), 7.38 (t, 2H), 7.42 (d, 2H), 11.27 (s, 1H). MS (APCI) calcd for $C_{31}H_{31}N_3O_5S$: 557.20. found (M+H$^+$) 558.1.

Example 124

6-[2-(3-Chloro-4-methoxy-phenyl)-ethyl]-6-cyclopentyl-4-hydroxy-3-(1 H[1,2,4]triazol-3-ylsulfanyl)-5,6-dihydro-pyran-2-one

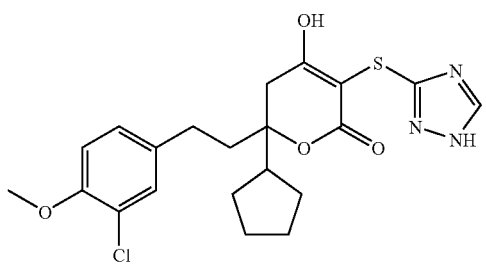

The title compound was prepared as described in Example 101 except 1H-1,2,4-triazole-3-thiol was substituted for 5,7-Dimethyl-[1,2,4]triazolo[1,5-a]pyrimidine-2-thiol. $^1$H (DMSO-d$_6$): δ 1.35–1.66 (br m, 9H), 2.05 (m, 2H), 2.50 (m, 2H), 2.67 (d, 1H, J=17.5 Hz), 2.92 (d, 1H, J=17.5 Hz), 3.80 (s, 3H), 7.05 (d, 1H, J=8.5 Hz), 7.15 (dd, 1H, J=8.5, 2.1 Hz), 7.29 (d, 1H, J=2.1 Hz), 8.21 (s, 1H). Anal. Calcd. For C$_{21}$H$_{24}$N$_3$O$_4$ClS.0.3 H$_2$O: C, 55.39; H, 5.45, N, 9.23. Found: C, 55.26; H, 5.43, N, 9.12.

Example 125

6-[2-(3-Chloro-4-methoxy-phenyl)-ethyl]-6-cyclopentyl-4-hydroxy-3-(5-methyl-[1,3,4]thiadiazol-2-ylsulfanyl)-5,6-dihydro-pyran-2-one

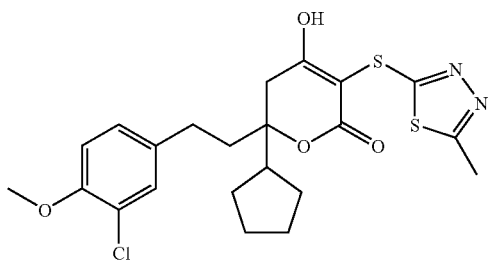

The title compound was prepared as described in Example 101 except 2-mercapto-5-methyl-1,3,4-thiadiazole was substituted for 5,7-Dimethyl-[1,2,4]triazolo[1,5-a]pyrimidine-2-thiol. $^1$H NMR (DMSO-d$_6$): δ 1.17–1.69 (br m, 9H), 2.14 (m, 2H), 2.37 (m, 2H), 2.51 (s, 3H), 2.71 (d, 1H, J=17.7 Hz), 2.91 (d, 1H, J=17.7 Hz), 3.74 (s, 3H), 6.99 (d, 1H, J=8.5 Hz), 7.09 (dd, 1H, J=8.5, 2.1 Hz), 7.23 (d, 1H, J=2.1 Hz). Anal. Calcd. For C$_{22}$H$_{25}$N$_2$O$_4$ClS$_2$.0.4 TFA: C, 52.00; H, 4.86, N, 5.32. Found: C, 51.87; H, 4.94, N, 5.14.

Example 126

6-[2-(3-Chloro-4-methoxy-phenyl)-ethyl]-6-cyclopentyl-4-hydroxy-3-(4-hydroxy-phenylsulfanyl)-5,6-dihydro-pyran-2-one

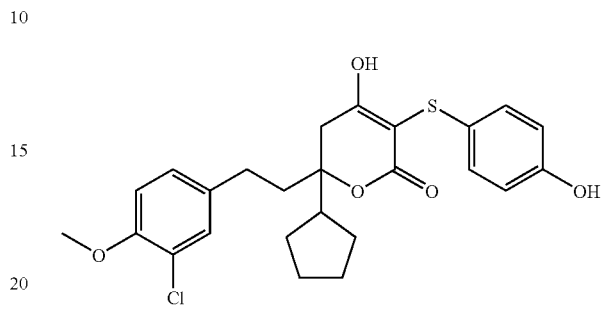

The title compound was prepared as described in Example 101 except 4-mercaptophenol was substituted for 5,7-Dimethyl-[1,2,4]triazolo[1,5-a]pyrimidine-2-thiol. $^1$H NMR (DMSO-d$_6$): δ 1.25–1.65 (br m, 9H), 1.88 (m, 2H), 2.32 (m, 2H), 2.71 (d, 1H, J=17.7 Hz), 2.93 (d, 1H, J=17.7 Hz), 3.81 (s, 3H), 6.64 (d, 2H, J=8.7 Hz), 7.01 (m, 2H), 7.03 (dd, 2H, J=8.7 Hz), 7.21 (s, 1H), 9.42 (br s, 1H), 11.77 (br s, 1H) Anal. Calcd. For C$_{25}$H$_{27}$O$_5$ClS.1.0 H$_2$O: C, 60.90; H, 5.93. Found: C, 60.76; H, 5.77.

Example 127

3-(Benzooxazol-2-ylsulfanyl)-6-[2-(3-chloro-4-methoxy-phenyl)-ethyl]-6-cyclopentyl-4-hydroxy-5,6-dihydro-pyran-2-one

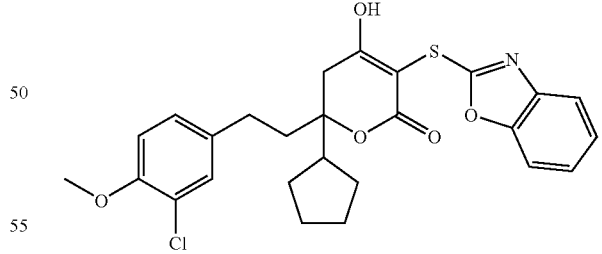

The title compound was prepared as described in Example 101 except 2-mercaptobenzoxazole was substituted for 5,7-Dimethyl-[1,2,4]triazolo[1,5-a]pyrimidine-2-thiol. $^1$H NMR (DMSO-d$_6$): δ 1.40–1.75 (br m, 9H), 2.18 (m, 2H), 2.66 (m, 2H), 2.84 (d, 1H, J=17.7 Hz), 3.04 (d, 1H, J=17.7 Hz) 3.84 (s, 3H), 7.07 (d, 1H, J=8.5 Hz), 7.20 (dd, 1H, J=8.5, 2.3 Hz), 7.27–7.42 (m, 5H).

Example 128

3-(1H-Benzoimidazol-2-ylsulfanyl)-6-[2-(3-chloro-4-methoxy-phenyl)-ethyl]-6-cyclopentyl-4-hydroxy-5,6-dihydro-pyran-2-one

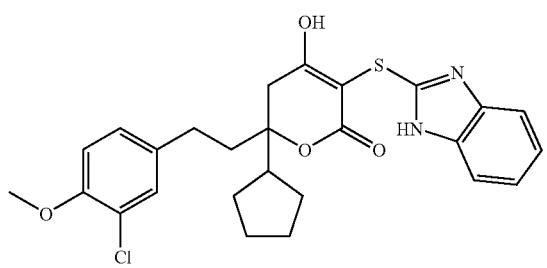

The title compound was prepared as described in Example 101 except 2-mecaptobezimidazole was substituted for 5,7-Dimethyl-[1,2,4]triazolo[1,5-a]pyrimidine-2-thiol. $^1$H NMR (DMSO-d$_6$): δ 1.43–1.69 (br m, 8H), 2.00 (m, 1H), 2.41 (m, 2H), 2.55 (m, 2H), 2.63 (d, 1H, J=17.0 Hz), 2.89 (d, 1H, J=17.0 Hz), 3.80 (s, 3H), 7.02 (d, 1H, J=8.5 Hz), 7.13 (dd, 1H, J=8.5, 1.9 Hz), 7.26 (d, 1H, J=2.1 Hz), 7.34 (m, 2H), 7.53 (m, 2H). Anal. Calcd. For C$_{26}$H$_{27}$N$_2$O$_4$ClS.1.1 TFA: C, 54.24; H, 4.54, N, 4.49. Found: C, 53.94; H, 4.90, N, 4.29.

Example 129

6-[2-(3-Chloro-4-isopropoxy-phenyl)-ethyl]-6-cyclopentyl-3-(5,7-dimethyl-[1,2,4]triazolo[1,5-a]pyrimidin-2-ylsulfanyl)-4-hydroxy-5,6-dihydro-pyran-2-one Step 1: 3-Chloro-6-[2-(3-chloro-4-isopropoxy-phenyl)-ethyl]-6-cyclopentyl-4-hydroxy-5,6-dihydro-pyran-2-one

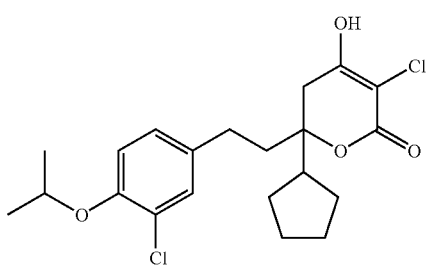

Methyl-2-chloroacetoacetate (2.3 g, 15.3 mmol) was added to a cooled 0° C. suspension of NaH (0.61 g, 15.3 mmol, 60% dispersion in mineral oil) in THF (30 ml). After 15 min the solution was cooled to −40° C. and n-BuLi (9.6 mL, 15.3 mmol, 1.6M in hexanes) was added. The resulting dianion was stirred for an additional 30 min and then treated with a solution of 3-(3-Chloro-4-isopropoxy-phenyl)-1-cyclopentyl-propan-1-one (1.5 g, 5.1 mmol, prepared from Heck route) in THF (10 ml). After stirring for 1 h at −40° C., the reaction mixture was warmed to room temperature. After 4 h the reaction mixture was quenched with saturated NH$_4$Cl and extracted with EtOAc. The organic layers were washed with brine, dried with Na$_2$SO$_4$ and concentrated to an orange oil. The oil was dissolved in toluene (15 mL) and bis(dibutylchlorotin)oxide (1.26 g, 2.3 mmol) was added. The mixture was heated at reflux for 45 mins. The resulting mixture was concentrated and purified by silica gel chromatography to give the title compound (0.49 g, 23% yield, two steps). $^1$H NMR (CDCl$_3$): δ 1.32 (d, 6H, J=6.0), 1.59–1.81 (br m, 8H), 2.03 (m, 1H), 2.40 (m, 2H), 2.61 (m, 2H), 2.65 (d, 1H, J=17.9 Hz), 2.89 (d, 1H, J=17.9 Hz), 4.5 (m, 1H), 6.52 (br s, 1H), 6.86 (d, 1H, J=8.4 Hz), 6.97 (dd, 1H, J=8.4, 2.1 Hz), 7.16 (d, 1H, J=2.1 Hz).

Step 2: 6-[2-(3-Chloro-4-isopropoxy-phenyl)-ethyl]-6-cyclopentyl-3-(5,7-dimethyl-[1,2,4]triazolo[1,5-a]pyrimidin-2-ylsulfanyl)-4-hydroxy-5,6-dihydro-pyran-2-one

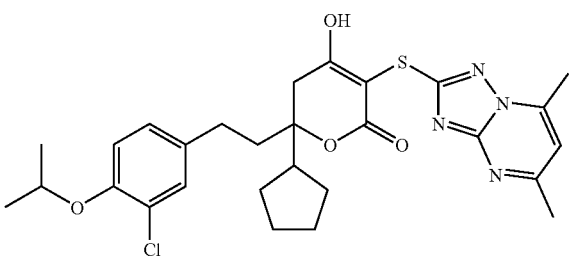

A solution of 3-Chloro-6-[2-(3-chloro-4-isopropoxy-phenyl)-ethyl]-6-cyclopentyl-4-hydroxy-5,6-dihydro-pyran-2-one (110 mg, 0.27 mmol), from step 1 above), 5,7-dimethyl-[1,2,4]triazolo[1,5-a]pyrimidine-2-thiol (49 mg, 0.27 mmol), and triethylamine (38 µL, 0.27 dissolved in DMF (3 mL) was heated to 55° C. under N$_2$ for 4 h. The resulting mixture was concentrated and purified by Prep HPLC to yield the title compound (45 mg, 30%) as a pale yellow solid. $^1$H NMR (DMSO-d$_6$): δ 1.33 (d, 6H, J=5.8), 1.48–1.79 (br m, 9H), 2.27 (m, 2H), 2.44 (s, 3H), 2.60 (s, 3H), 2.67 (m, 2H), 2.86 (d, 1H, J=17.7 Hz), 3.06 (d, 1H, J=17.7 Hz), 4.63 (m, 1H), 7.11 (s, 1H), 7.12 (d, 1H, J=8.3 Hz), 7.28 (dd, 1H, J=8.3, 2.2 Hz), 7.36 (d, 1H, J=2.2 Hz), 12.33 (s, 1H).

Example 130

6-[2-(3-Chloro-4-isopropoxy-phenyl)-ethyl]-6-cyclopentyl-4-hydroxy-3-(4-hydroxy-phenylsulfanyl)-5,6-dihydro-pyran-2-one

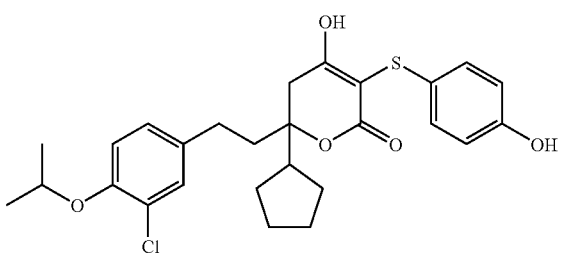

The title compound was prepared as described in Example 129 except 4-mercaptophenol was substituted for 5,7-Dimethyl-[1,2,4]triazolo[1,5-a]pyrimidine-2-thiol. $^1$H NMR (DMSO-d$_6$): δ 1.34 (d, 6H, J=6.0 Hz) 1.52–1.73 (br m, 8H), 1.97 (m, 3H), 2.40 (m, 2H), 2.78 (d, 1H, J=18.0 Hz), 2.97 (d, 1H, J=18.0 Hz), 4.64 (m, 1H), 6.69 (d, 2H, J=8.5 Hz), 6.99 (d, 1H, J=8.5 Hz), 7.13 (m, 3H), 7.27 (s, 1H), 9.47 (s, 1H), 11.85 (s, 1H).

Example 131

6-[2-(3-Chloro-4-isopropoxy-phenyl)-ethyl]-6-cyclopentyl-4-hydroxy-3-(4-methoxy-phenylsulfanyl)-5,6-dihydro-pyran-2-one

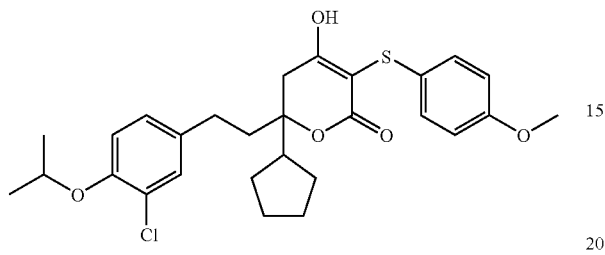

The title compound was prepared as described in Example 129 except 4-methoxybenzenethiol was substituted for 5,7-Dimethyl-[1,2,4]triazolo[1,5-a]pyrimidine-2-thiol. $^1$H NMR (DMSO-$d_6$): δ 1.33 (d, 6H, J=6.0 Hz) 1.52–1.73 (br m, 8H), 1.97 (m, 3H), 2.40 (m, 2H), 2.78 (d, 1H, J=17.7 Hz), 2.97 (d, 1H, J=17.7 Hz), 3.75 (s, 3H), 4.66 (m, 1H), 6.84 (d, 2H, J=8.7 Hz), 7.06 (dd, 1H, J=8.5, 1.7 Hz), 7.13 (d, 1H, J=8.7, Hz), 7.18 (d, 2H, J=8.7, Hz), 7.27 (d, 1H, J=1.7 Hz), 11.96 (s, 1H).

Example 132

6-[2-(3-Chloro-4-isopropoxy-phenyl)-ethyl]-6-cyclopentyl-4-hydroxy-3-(thiazol-2-ylsulfanyl)-5,6-dihydro-pyran-2-one

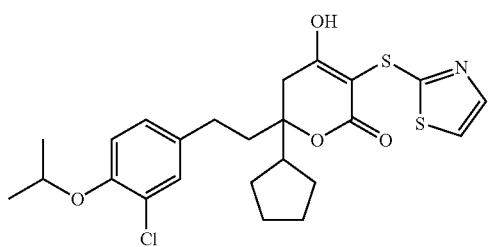

The title compound was prepared as described in Example 129 except 2-mercaptothiazole was substituted for 5,7-Dimethyl-[1,2,4]triazolo[1,5-a]pyrimidine-2-thiol. $^1$H NMR (DMSO-$d_6$): δ 1.18 (d, 6H, J=6.0 Hz) 1.31–1.62 (br m, 9H), 1.97 (m, 2H), 2.53 (m, 2H), 2.76 (d, 1H, J=17.8 Hz), 2.93 (d, 1H, J=17.8 Hz), 4.53 (m, 1H), 7.02 (m, 2H), 7.20 (s, 1H), 7.43 (d, 1H, J=3.4 Hz), 7.53 (d, 1H, J=3.4 Hz). Anal. Calcd. For $C_{24}H_{28}NO_4ClS_2$.0.4 TFA: C, 55.19; H, 5.30, N, 2.60. Found: C, 55.10; H, 5.46, N, 2.36.

Example 133

3-(2-tert-butyl-4-hydroxymethyl-5-methyl-phenylsulfanyl)-6-cyclopentyl-4-hydroxy-6-[2-(4-hydroxyphenyl)-ethyl]-5,6-dihydro-pyran-2-one

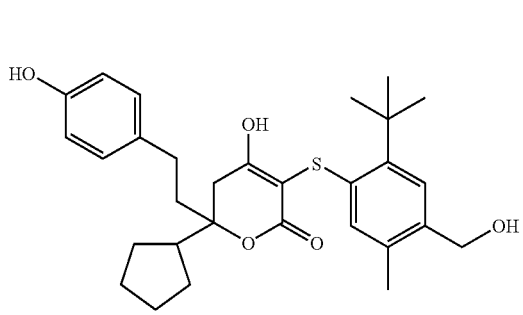

A solution of 6-Cyclopentyl-4-hydroxy-6-[2-(4-hydroxyphenyl)-ethyl]-5,6-dihydro-pyran-2-one (0.2 g, 0.6 mmol; preparation described in Example 1, Toluene-4-thiosulfonic acid S-(2-tert-butyl-4-hydroxymethyl-5-methyl-phenyl) ester (0.2 g, 0.7 mmol; preparation described by; Hagen et al. *J. Med. Chem.* 44(14) 2319–2332 (2000), potassium carbonate (0.4 g, 2.5 mmol) and DMF (2 mL), were stirred for overnight. The resulting mixture was diluted with EtOAc, extracted with 1N HCl, brine, dried with MgSO$_4$, concentrated, and purified by silica gel chromatography (15% i-PrOH:CH$_2$Cl$_2$:hexanes) to yield the purified material. (isolated yield: 63%). Mp: 199–201° C. $^1$H NMR (DMSO-$d_6$): δ 7.63 (s, 1H), 7.34–7.46 (m, 5H), 7.20 (d, 1H), 6.93 (d, 2H), 6.82 (d, 1H), 6.71 (d, 2H), 6.19 (s, 1H), 4.91 (s, 1H), 3.35 (d, 1H), 3.28 (d, 1H), 2.66 (m, 1H), 2.19–2.30 (m, 3H), 1.86 (s, 3H), 1.52 (s, 9H); MS (APCI): 489 (M+H); $C_{30}H_{32}O_4S_1$.0.75H$_2$O: Calc: C71.76, H6.72; Obsd: C71.76; H6.37.

Example 134

3-(2-tert-butyl-4-hydroxymethyl-5-methyl-phenylsufanyl)-6–2-furan-2-yl)-ethyl)4-hyl

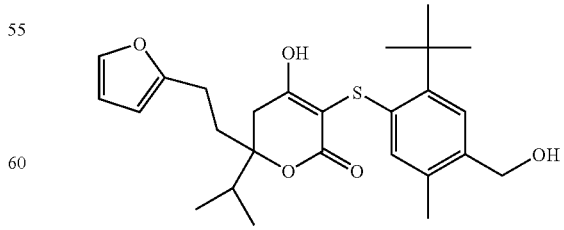

The title compound was prepared as described by: Hagen et al. *J. Med. Chem.*, 44, 2319–2332 (2001). Yield 81%, m.p. 62–70° C. MS (APCI): 457.0 (M–H).

Example 135

5-tert-butyl-4-6-cyclohexyl-4-hydroxy-6-[2-(4-hydroxy-phenyl)-ethyl]-2-oxo-5,6-dihydro-2H-pyran-3-ylsulfanyl}-2-methyl-phenyl ester Step 1: 6-Cyclohexyl-6-[2-(4-hydroxyphenyl)ethyl]dihydropyran-2,4-dione

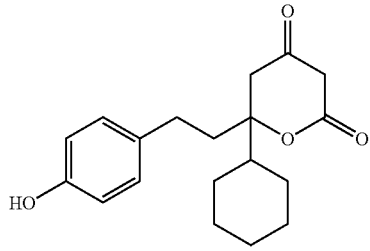

The title compound was prepared as described in Example 1 except cyclohexylmagnesium bromide was used for cyclopentylmagnesium bromide in step 5 of that Example. $^1$H NMR (CDCl$_3$): δ 1.01–1.22 (m, 5H), 1.66–1.89 (m, 7H), 1.95–2.06 (m, 1H), 2.54–2.71 (m, 2H), 2.65 (d, 1H, J=15.9), 2.82 (d, 1H, J=15.9), 3.41 (s, 2H), 5.37 (br s, 1H), 6.72–7.04 (m, 2H); HRMS calcd for C$_{19}$H$_{24}$O$_4$ (M+H$^+$) 317.1753. found 317.1767.

Step 2: Benzenesulfonic acid 5-tert-butyl-4-{6-cyclohexyl-4-hydroxy-6-[2-(4-hydroxy-phenyl)-ethyl]-2-oxo-5,6-dihydro-2H-pyran-3-ylsulfanyl}-2-methyl-phenyl ester

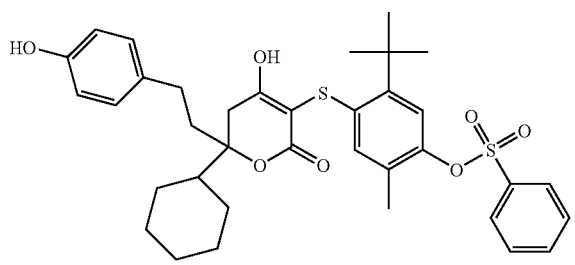

The title compound was prepared as described in Example 133 using 6-Cyclohexyl-4-hydroxy-6-[2-(4-hydroxy-phenyl)-ethyl]-5,6-dihydro-pyran-2-one (preparation described above) instead of 6-Cyclopentyl-4-hydroxy-6-[2-(4-hydroxy-phenyl)-ethyl]-5,6-dihydro-pyran-2-one, and using Benzenesulfonic acid 5-tert-butyl-2-methyl-4-(toluene-4-sulfonylsulfanyl)-phenyl ester (preparation described by Boyer et al., *J. Med Chem.* (2000),) for Toluene-4-thiosulfonic acid S-(2-tert-butyl-4-hydroxymethyl-5-methyl-phenyl) ester. Yield 59%, m.p. 180° C.

Example 136

3-(4-Amino-2-tert-butyl-5-methyl-phenylsulfanyl)-6-cyclopentyl-4-hydroxy-6-[2-(4-hydroxy-phenyl)-ethyl]-5,6-dihydro-pyran-2-one

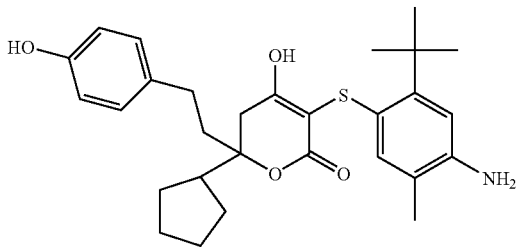

The title compound was prepared as described in Example 133 using 6-Cyclopentyl-4-hydroxy-6-[2-(4-hydroxy-phenyl)-ethyl]-5,6-dihydro-pyran-2-one (0.16 g, 0.53 mmol, preparation described in Example 1), Toluene-4-thiosulfonic acid S-(4-amino-2-tert-butyl-5-methyl-phenyl) ester (0.2 g, 0.53 mmol; preparation described by Boyer et al. *J. Med Chem.* (2000)) for Toluene-4-thiosulfonic acid S-(2-tert-butyl-4-hydroxymethyl-5-methyl-phenyl) ester, anhydrous potassium carbonate (0.20 g) and DMF (2 mL). Isolated yield: 70%. m.p.: 133–135° C.

Example 137

Toluene-4-sulfonic acid 5-tert-butyl-4-(6-Cyclohexyl-4-hydroxy-6-[2-(4-hydroxy-phenyl)-ethyl]-2-oxo-5,6-dihydro-2H-pyran-3-ylsulfanyl)-2-methyl-phenyl ester The title compound was prepared as described in Example 133 using 6-Cyclohexyl-4-hydroxy-6-[2-(4-hydroxy-phenyl)-ethyl]-5,6-dihydro-pyran-2-one (preparation described in step 1 of Example 135 instead of 6-Cyclopentyl-4-hydroxy-6-[2-(4-hydroxy-phenyl)-ethyl]-5,6-dihydro-pyran-2-one, and using Toluene-4-sulfonic acid 5-tert-butyl-2-methyl-4-(toluene-4-sulfonylsulfanyl)-phenyl ester (preparation described by Boyer et al. *J. Med Chem.* (2000), 43(5), 843–858) for Toluene-4-thiosulfonic acid S-(2-tert-butyl-4-hydroxymethyl-5-methyl-phenyl) ester. Yield 58%, m.p. 105° C.

Example 138

3-(4-Amino-2-tert-butyl-5-methyl-phenylsulfanyl)-
6-[2-(4-amino-3,5-dichloro-phenyl)-ethyl]-4-hy-
droxy-6-isopropyl-5,6-dihydro-pyran-2-one:

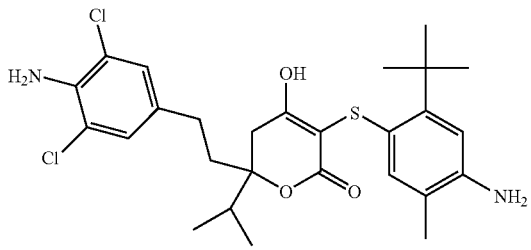

The title compound was prepared as described in Example 133 using Toluene-4-thiosulfonic acid S-(4-amino-2-tert-butyl-5-methyl-phenyl) ester instead of Toluene-4-thiosulfonic acid S-(2-tert-butyl-4-hydroxymethyl-5-methyl-phenyl) ester, and using 6-[2-(4-Amino-3,5-dichloro-phenyl)-ethyl]-4-hydroxy-6-isopropyl-5,6-dihydro-pyran-2-one for 6-Cyclopentyl-4-hydroxy-6-[2-(4-hydroxy-phenyl)-ethyl]-5,6-dihydro-pyran-2-one. m.p. 103–107° C.

Example 139

4-Cyano-benzenesulfonic acid 5-tert-butyl-4-{6-cyclohexyl-4-hydroxy-6-[2-(4-hydroxy-phenyl)-ethyl]-2-oxo-5,6-dihydro-2H-pyran-3-ylsulfanyl}-2-methyl-phenyl ester:

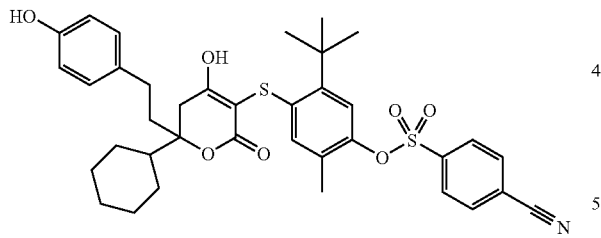

The title compound was prepared as described in Example 133 using 4-Cyano-benzenesulfonic acid 5-tert-butyl-2-methyl-4-(toluene-4-sulfonylsulfanyl)-phenyl ester (preparation described by Boyer et al. *J. Med Chem.* (2000), 43(5), 843–858) instead of Toluene-4-thiosulfonic acid S-(2-tert-butyl-4-hydroxymethyl-5-methyl-phenyl) ester, and using 6-Cyclohexyl-4-hydroxy-6-[2-(4-hydroxy-phenyl)-ethyl]-5,6-dihydro-pyran-2-one (preparation described in step 1 of Example 135) for 6-Cyclopentyl-4-hydroxy-6-[2-(4-hydroxy-phenyl)-ethyl]-5,6-dihydro-pyran-2-one. Isolated yield: 75%. m.p. 112° C.

Example 140

(+/−)N-(5-tert-butyl-4-{6-cyclopentyl-4-hydroxy-6-[2-(4-hydroxy-phenyl)-ethyl]-2-oxo-5,6-dihydro-2H-pyran-3-ylsulfanyl}-2-methyl-phenyl)-acetamide:

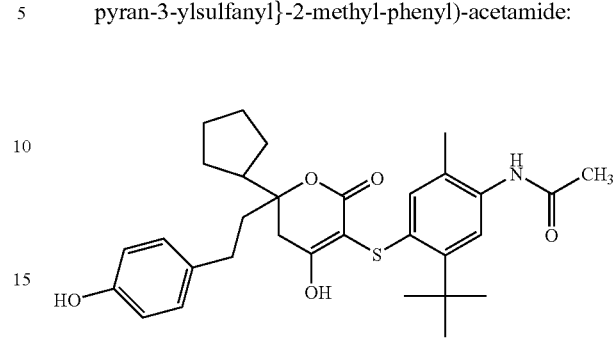

The title compound was prepared as described in Example 133 using 6-Cyclopentyl-4-hydroxy-6-[2-(4-hydroxy-phenyl)-ethyl]-5,6-dihydro-pyran-2-one (0.16 g, 0.53 mmol; preparation described in Example 1), Toluene-4-thiosulfonic acid S-(4-acetylamino-2-tert-butyl-5-methyl-phenyl) ester (0.29 g, 0.73 mmol; preparation described by Prasad et al. *Bioorganic & Medicinal Chemistry Letters* 7 (1999) 2775–2800) for Toluene-4-thiosulfonic acid S-(2-tert-butyl-4-hydroxymethyl-5-methyl-phenyl) ester, anhydrous potassium carbonate (0.25 g) and DMF (2.0 mL). Isolated yield: 63%. m.p.: 181° C.

Example 141

(+/−)N-(5-tert-butyl-{6-cyclopentyl-4-hydroxy-6-[2-(4-hydroxy-phenyl)-ethyl]-2-oxo-5,6-dihydro-2H-pyran-3-ylsulfanyl}-2-methyl-phenyl)-benzene-sulfonamide:

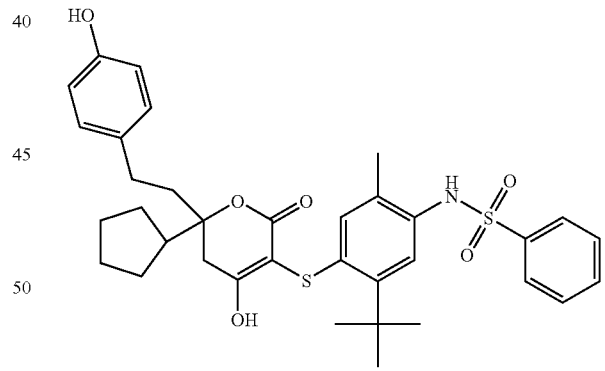

The title compound was prepared as described in Example 133 using 6-Cyclopentyl-4-hydroxy-6-[2-(4-hydroxy-phenyl)-ethyl]-5,6-dihydro-pyran-2-one (0.13 g, 0.42 mmol; preparation described in Example 1), Toluene-4-thiosulfonic acid S-(4-benzenesulfonylamino-2-tert-butyl-5-methyl-phenyl) ester (0.2 g, 0.42 mmol; preparation described by Boyer et al. *J. Med Chem.* (2000), 43(5), 843–858) for Toluene-4-thiosulfonic acid S-(2-tert-butyl4-hydroxymethyl-5-methyl-phenyl) ester, anhydrous potassium carbonate (0.15 g) and DMF (2 mL). Isolated yield: 62%.%. m.p. 125–127° C. $^1$H NMR (DMSO-d$_6$) δ: 9.39 (s, 1H), 9.19 (s, 1H), 7.64 (m, 3H), 7.55 (m, 2H), 6.97 (d, 2H), 6.69 (d, 2H), 6.64 (s, 1H), 6.5 (s, 1H), 2.94 (d of ABX, 1H), 2.83 (d of ABX, 1H), 2.53

(m, 2H), 2.36 (m, 1H), 1.95 (m, 2H)) +1.82 (s, 3H), 1.73–1.32 (m, 8H), 1.93 (s, 9H); MS (APCI): 636 (M+H), 592, 257; $C_{35}H_{41}O_6N_1S_2 \cdot 0.4\ H_2O$: Calc: C65.37, H6.55, N2.18. Found: C65.44; H6.54, N2.01. IR (KBr) cm$^{-1}$: 3426, 2955, 1610, 1168.

Example 142

N-(5-tert-butyl4-{6-cyclohexyl-4-hydroxy-6-[2-(4-hydroxy-phenyl)-ethyl]-2-oxo-5,6-dihydro-2H-pyran-3-ylsulfanyl)-2-methyl-phenyl)-acetamide:

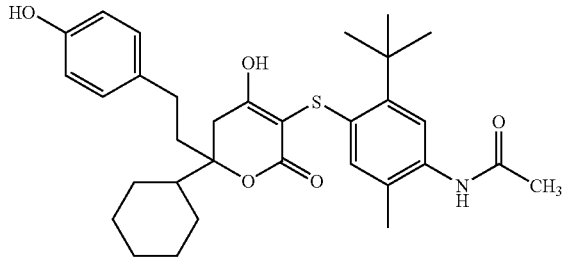

4-hydroxy-6-[2-(4-hydroxy-phenyl)-ethyl]-6-cyclohexyl-5,6-dihydro-pyran-2-one (0.13 g, 0.41 mmol, preparation described in step 1 of Example 135), toluene-4-thiosulfonic acid S-(4-acetamido-2-tert-butyl-5-methyl-phenyl) ester (0.16 g, 0.41 mmol; preparation described by Prasad et al. *Bioorganic & Medicinal Chemistry Letters* 7 (1999) 2775–2800), and anhydrous $K_2CO_3$ (0. 13 g, 0.94 mmol) were dissolved in DMF (5 mL) and stirred at room temperature overnight. The reaction was quenched with saturated citric acid solution and extracted with EtOAc. The organic phase was washed with brine, dried over $MgSO_4$ and concentrated. The crude material was purified by flash silica gel chromatography, eluting with EtOAc, to give afford the title compound as an off-white solid. Isolated yield: 0.11 g (48%) m.p.: >154° C. (effervesces). $^1$H NMR (DMSO-d$_6$) 1.03–1.25 (m, 6H), 1.44 (s, 9H), 1.60–1.74 (m, 6H), 1.84 (s, 3H), 1.91–1.98 (m, 5H), 2.48–2.51 (m, partially obscured by DMSO-d$_6$, 2H), 2.70 (d of ABX q, 1H), 2.95 (d of ABX q, 1H), 6.63 (d, 2H), 6.71 (s, 1H), 6.95 (d, 2H), 7.24 (s, 1H), 9.14 (s, 1H), 9.19 (s, 1H). IR (KBr): 3387, 3026, 2930, 2857, 1669, 1614, 1515, 1479, 1450, 1375, 1263, 1233, 1050, 976, 910, 828, 761 cm$^{-1}$; MS-APCI (m/z+): 552.5. Anal. ($C_{32}H_{41}N_1O_5S_2$ 0.55H$_2$O) C, H, N.

Example 143

3-(4-Amino-2-tert-butyl-5-methyl-phenylsulfanyl)-6-cyclohexyl-4-hydroxy-6-[2-(4-hydroxy-phenyl)-ethyl]-5,6-dihydro-pyran-2-one:

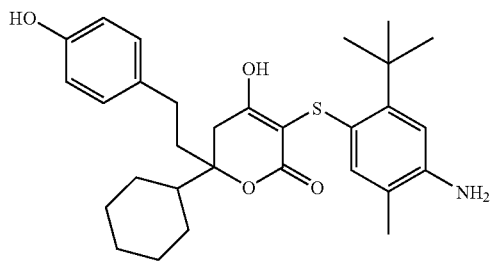

4-hydroxy-6-[2-(4-hydroxy-phenyl)-ethyl]-6-cyclohexyl-5,6-dihydro-pyran-2-one (0.18 g, 0.57 mmol; preparation described in step 1 of Example 135), toluene-4-thiosulfonic acid S-(4-amino-2-tert-butyl-5-methyl-phenyl) ester hydrochloride (0.22 g, 0.57 mmol; preparation described by Boyer et al. *J. Med. Chem.* (2000), 43(5), 843–858), and anhydrous $K_2CO_3$ (0.25 g, 1.81 mmol), were dissolved in DMF (6 mL) and stirred at room temperature overnight. The reaction was quenched with saturated $NH_4Cl$ solution and extracted with EtOAc. The organic phase was washed with brine, dried over $Na_2SO_4$ and concentrated. The crude material was purified by flash silica gel chromatography, eluting with 7% MeOH/CH$_2$Cl$_2$, to give afford the title compound as an off-white solid. Isolated yield: 0.18 g (62%) m.p >133° C. (effervesces). $^1$H NMR (DMSO-d$_6$) 0.98–1.32 (m, 6H), 1.42 (s, 9H), 152–1.80 (m, 9H), 1.88–1.99 (m, 2H), 2.45–2.50 (m, partially obscured by DMSO-d$_6$, 2H), 2.68 (d of ABX q, 1H), 2.90 (d of ABX q, 1H), 6.57 (s, 1h), 6.63(d+s, 3H), 6.64 (d, 2H), 6.93 (d, 2H), 9.13 (br s, 1H). IR (KBr): 3374, 2930, 2857, 2604, 1670, 1613, 1515, 1483, 1450, 1375, 1268, 1240, 1050, 910, 827, 763 cm$^{-1}$; MS-APCI (m/z+): 510.5. Anal. ($C_{30}H_{30}N_1O_4S_2 \cdot 0.59H_2O$) C, H, N.

Example 144

3-(2-tert-butyl-4-hydroxymethyl-5-methyl-phenyl-sulfanyl)-6-cyclopentyl-4-hydroxy-6-(3-methyl-butyl)-5,6-dihydro-pyran-2-one:

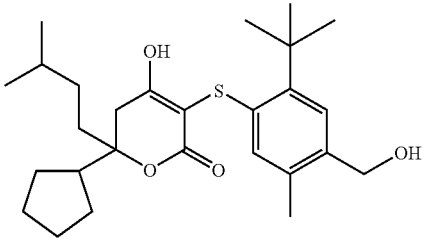

The title compound was prepared as described in Example 133 using 6-Cyclopentyl-4-hydroxy-6-(3-methyl-butyl)-5,6-dihydro-pyran-2-one (preparation described in Example C(19)) instead of 6-Cyclopentyl-4-hydroxy-6-[2-(4-hydroxy-phenyl)-ethyl]-5,6-dihydro-pyran-2-one in the final step of the that Example. Yield 50%, m.p. 74–77° C.

Example 145

3-(2-tert-butyl-4-hydroxymethyl-5-methyl-phenyl-sulfanyl)-6-cyclopentyl-6-(2-cyclopentyl-ethyl)-4-hydroxy-5,6-dihydro-pyran-2-one:

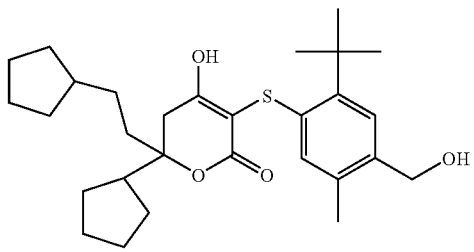

The title compound was prepared as described in Example 133 using 6-Cyclopentyl-6-(2-cyclopentyl-ethyl)-4-hydroxy-5,6-dihydro-pyran-2-one (preparation described in Example C(18)) instead of 6-Cyclopentyl-4-hydroxy-6-[2-(4-hydroxy-phenyl)-ethyl]-5,6-dihydro-pyran-2-one in the final step of the that Example. Yield 100%. m.p. 68–71° C.

Example 146

5-tert-butyl-4-{6-Cyclopentyl-4-hydroxy-6-[2-(4-hydroxy-phenyl)-ethyl]-2-oxo-5,6-dihydro-2H-pyran-3-ylsulfanyl}-2-methyl-benzamide:

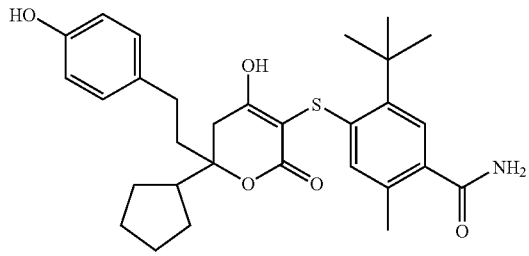

The title compound was prepared as described in Example 133 using 6-Cyclopentyl-4-hydroxy-6-[2-(4-hydroxy-phenyl)-ethyl]-5,6-dihydro-pyran-2-one (0.16 g, 0.53 mmol, preparation described in Example 1), Toluene-4-thiosulfonic acid S-(2-tert-butyl-4-carbamoyl-5-methyl-phenyl) ester (0.2 g, 0.53 mmol) for Toluene-4-thiosulfonic acid S-(2-tert-butyl-4-hydroxymethyl-5-methyl-phenyl) ester, anhydrous potassium carbonate (0.20 g) and DMF (2 mL).

Example 147

4-methyl-piperazine-1-sulfonic acid 5-tert-butyl-4-6-cyclopentyl-4-hydroxy-6-[2-(4-hydroxy-phenyl)-ethyl]-2-oxo-5,6-dihydro-2H-pyran-3-ylsulfanyl}-2-methyl-phenyl ester:

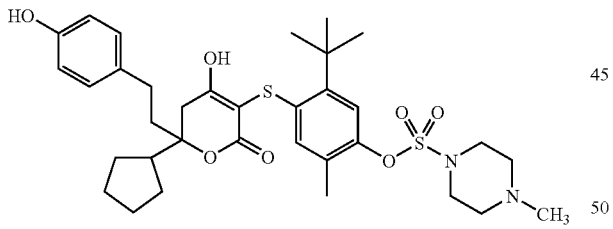

The title compound was prepared as described in Example 133 using 4-Methyl-piperazine-1-sulfonic acid 5-tert-butyl-2-methyl-4-(toluene-4-sulfonylsulfanyl)-phenyl ester (0.37 g, 0.73 mmol) for toluene-4-thiosulfonic acid S-(2-tert-butyl-4-hydroxymethyl-5-methyl-phenyl) ester, 6-Cyclopentyl-4-hydroxy-6-[2-(4-hydroxy-phenyl)-ethyl]-5,6-dihydro-pyran-2-one (0.12 g, 0.39 mmol), anhydrous potassium carbonate (0.15 g) and DMF (2 mL). Isolated yield: 42%. M.p. 163–165° C. $^1$H NMR (DMSO-$d_6$) δ: 9.14 (s, 1H), 7.08 (s, 1H), 6.97 (d, 2H), 6.86 (s, 1H), 6.66 (d, 2H), 3.44 (m, 4H), 2.31–2.77 (m, 12H), 1.94 (s)+1.97 (m) 5H, 1.72–1.31 (m)+1.47 (s), 17H; MS (APCI): 659 (+H), 615, 541; $C_{34}H_{46}O_7N_2S_2 \cdot 0.7$ $H_2O$: Calc: C60.81, H7.12, N4.17. Found: C60.55; H6.99, N4.32. IR (KBr) cm$^{-1}$; 3402, 2953, 1515, 1376, 1187, 826.

Example 148

3-[2-tert-butyl-4-(2-hydroxy-ethoxy)-5-methyl-phenylsulfanyl]-6-cyclopentyl-hydroxy-6-[2-(4-hydroxy-phenyl)-ethyl]-5,6-dihydro-pyran-2-one:

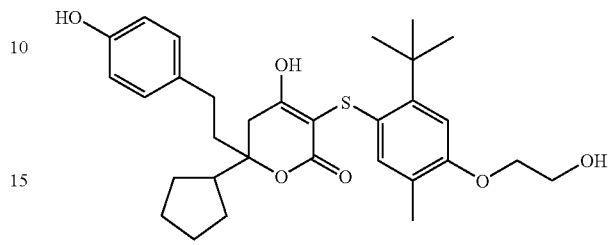

The title compound was prepared as described in Example 133 using Toluene-4-thiosulfonic acid S-[2-tert-butyl-4-(2-hydroxy-ethoxy)-5-methyl-phenyl] ester (0.37 g, 0.73 mmol) for Toluene-4-thiosulfonic acid S-(2-tert-butyl-4-hydroxymethyl-5-methyl-phenyl) ester, 6-Cyclopentyl-4-hydroxy-6-[2-(4-hydroxy-phenyl)-ethyl]-5,6-dihydro-pyran-2-one (0.2 g, 0.66 mmol), anhydrous potassium carbonate (0.2 g) and DMF (2 mL). Isolated yield: 56%. m.p.: 113–115° C. $^1$H NMR (DMSO-$d_6$) δ: 9.14 (s, 1H), 6.97 (d, 2H), 6.81 (s, 1H), 6.75 (s, 1H), 6.66 (d, 2H), 4.81 (brs, 1H), 3.97 (t, 2H), 3.69 (brd, 2H), 2.92 (d of ABX, 1H), 2.81 (d of ABX, 1H), 2.55 (m, 2H, obscured by DMSO peak), 2.36 (m, 1H), 1.94 (m, 2H), 1.81 (s, 3H), 1.47 (s, 9H); MS (APCI): 541 (M+H), 497, 423, 259; $C_{31}H_{40}O_6S_1$: Calc: C68.86, H7.46. Found: C68.51; H7.18. IR (KBr) cm$^{-1}$: 3406, 2954, 1608, 1515, 1253, 1050.

Example 149

Ethyl-sulfamic acid 5-tert-butyl-4-{6-cyclopentyl-4-hydroxy-6-[2-(3-hydroxy-phenyl)-ethyl]-2-oxo-5,6-dihydro-2H-pyran-3-ylsulfanyl}-2-methyl-phenyl ester:

Step 1: 3-(3-Benzyloxy-phenyl)-propionic acid benzyl ester

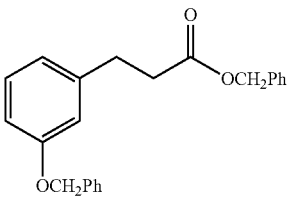

A mixture of 3-(3-hydroxyphenylpropionic acid) (15 g, 0.09 mole), and $K_2CO_3$ (48.9 g, 0.35 mol), dissolved in acetone (200 ml) was treated dropwise with benzyl bromide (22.5 ml, 0.19 mole). The reaction was stirred overnight at reflux, and concentrated after cooling. The residue was diluted with water and then acidified with conc. HCl. After extracting with EtOAc, the organic layer was washed with brine, dried over $Na_2SO_4$, and concentrated to yield 34.49 g of the product as a liquid. $^1$H NMR (CDCl$_3$): δ: 2.68(2H, t), 2.95 (2H, t), 5.02(2H, s), 5.11(2H, s), 6.74–6.83 (3H, m), 7.17–7.21 (1H, m), 7.29–7.44 (10H, m). CI+Mass Spec: m/e 346 (M+).

Step 2: 3-(3-Benzyloxy-phenyl)-propionic acid

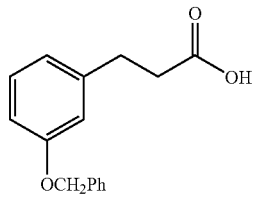

A mixture of 3-(3-Benzyloxy-phenyl)-propionic acid benzyl ester (34.4 g, 0.1 mol; described above), and LiOH (5.95 g, 0.25 mole) were dissolved in THF (140 ml) and MeOH (70 ml), then stirred at room temperature for 2 hours. The reaction was concentrated, acidified to pH~3 with conc. HCl, extracted with EtOAc, washed with brine, dried over $Na_2SO_4$, and concentrated to yield 31.62 g of a solid. The solid was taken up in 150 ml of 1 N NaOH and washed with ether. The aqueous layer was acidified to pH~3 with conc. HCl and extracted with EtOAc. The organic layer was washed with brine, dried over $Na_2SO_4$, and concentrated to yield 25.59 g of the product as a white solid, which was used without further purification. $^1$H NMR (CDCl$_3$): δ: 2.68 (2H, t), 2.94 (2H, t), 5.05 (2H, s), 6.81–6.84 (3H, m), 7.19–7.23 (1H, m), 7.30–7.45 (5H, m). CI+Mass Spec: m/e 256 (M+).

Step 3: 3-(3-Benzyloxy-phenyl)-N-methoxy-N-methyl-propionamide

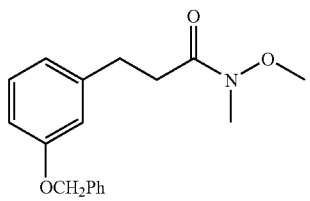

A mixture of 3-(3-Benzyloxy-phenyl)-propionic acid (5.0 g, 19.5 mmol; described above) dissolved in thionyl chloride (20 ml, 0.27 mole) was stirred at reflux for 4 hours, then cooled and concentrated. The residue was taken up in 40 ml of dichloromethane and added slowly to an ice cold solution of N,O-dimethylhydroxylamine hydrochloride (2.43 g, 24.4 mmol) and 12 ml (0.15 mole) of pyridine in 150 ml of $CH_2Cl_2$. After stirring overnight at room temperature, the reaction was washed with water, 10% citric acid, saturated sodium bicarbonate, and brine. The organic layer was dried over $Na_2SO_4$ and concentrated. The resulting oil was chromatographed on silica gel (4.6×25.5 cm) eluting with EtOAc/Hex (1:2 then 1:1), yielding 4.74 g of yellow colored oil. $^1$H NMR (CDCl$_3$): δ:2.73 (2H, m), 2.94 (2H, t), 3.18 (3H, s), 3.61 (3H, s), 5.05 (2H, s), 6.81–6.87 (3H, m), 7.19–7.23 (1H, m), 7.31–7.45 (5H, m). CI+Mass Spec: m/e 300 (M+1).

Step 4: 3-(3-Benzyloxy-phenyl)-1-cyclopentyl-propan-1-one

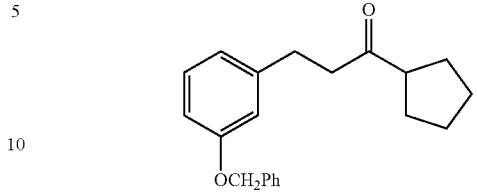

A solution of 3-(3-Benzyloxy-phenyl)-N-methoxy-N-methyl-propionamide (10 g, 33.4 mmol), dissolved in THF (150 ml), under a nitrogen atmosphere, was treated with cyclopentylmagnesium chloride (25 mL, 50 mmol; 2M in ether), and stirred at reflux for 2 hours. The reaction was not complete and was treated with another 3 ml (6 mmol) of cyclopentylmagnesium chloride and refluxed for 1 hour. The reaction was cooled, diluted with water, and acidified with 1N HCl to pH-3, extracted with EtOAc, and dried over $Na_2SO_4$. The resulting oil was chromatographed on silica gel (6.0×31.0 cm) eluted with EtOAc/Hex (1:2), yielding 3.5 g of the product as an oil. $^1$H NMR (CDCl$_3$): δ: 1.51–1.82 (8H, m), 2.74–2.89 (5H, m), 5.05 (2H, s), 6.78–6.82 (3H, m), 7.17–7.23 (1H, m), 7.29–7.44 (5H, m). CI+Mass Spec: m/e 309 (M+1).

Step 5: 6-[2-(3-Benzyloxy-phenyl)-ethyl]-6-cyclopentyl-4-hydroxy-5,6-dihydro-pyran-2-one

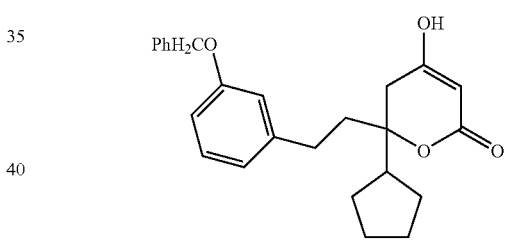

An ice cold suspension of NaH (0.93 g, 23.2 mmol) in THF (85 ml) was treated with methyl acetoacetate (2.45 ml, 22.7 mmol) in THF (40 ml), stirred for 15 minutes and then treated with n-BuLi (14.5 ml, 23.2 mmol, 1.6M in hexanes). After stirring for 15 minutes, the reaction was treated with a solution of 3-(3-Benzyloxy-phenyl)-1-cyclopentyl-propan-1-one (3.5 g, 11.3 mmol; described above), dissolved in THF (85 ml). Reaction was allowed to warm to room temperature and stir for 4.5 hours, at which time it was quenched with HOAc (5 ml), and concentrated. The residue was taken up in EtOAc/water and the aqueous layer was extracted with EtOAc. The organic layer was washed with brine, dried over $Na_2SO_4$, and concentrated to yield 6.71 g of oil. The oil was taken up in THF (85 ml) and treated with 600 ml of 0.1N NaOH and stirred overnight at room temperature. The resulting mixture was acidified to pH~3 with conc. HCl and extracted with EtOAc. The organic layer was washed with brine, dried over $Na_2SO_4$, and concentrated to yield 5.85 g of and oil, which was chromatographed on silica gel (54.×24 cm) eluting with EtOAc/Hex/CH$_2$Cl$_2$ (1:1:1), yielding 2.93 g of product. $^1$H NMR (DMSO-d$_6$) δ: 1.25–1.75 (8H, m), 1.88–1.92 (2H, m), 2.32 (1H, m), 2.42–2.60 (3H, m), 4.95 (1H, s, ex), 5.07 (2H, s), 6.75–6.83

Step 6: 6-Cyclopentyl-4-hydroxy-6-[2-(3-hydroxy-phenyl)-ethyl]-5,6-dihydro-pyran-2-one

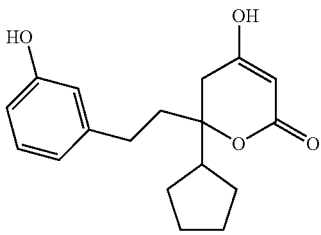

A solution of 6-[2-(3-Benzyloxy-phenyl)-ethyl]-6-cyclopentyl-4-hydroxy-5,6-dihydro-pyran-2-one (2.92 g, 7.4 mmol, described above) in THF (100 ml) was treated with 0.5 g of 20% Pd/C and hydrogenated overnight. After filtering, the solution was concentrated to yield 2.63 g of the product that was used without further purification. 1H NMR (DMSO-$d_6$) δ: 1.36 (2H, broad), 1.40–1.70 (8H, m, broad), 1.86–1.91 (2H, m), 2.30 (1H, m), 2.40–2.60 (2H, m), 4.98 (1H, s, ex), 6.55–6.59 (3H, m), 7.03–7.07 (1H, m), 9.25 (1H, s, ex), 11.35 (1H, s, ex). CI+Mass Spec: m/e 303 (M+1).

Step 7: Ethyl-sulfamic acid 5-tert-butyl-4-6-cyclopentyl-4-hydroxy-6-[2-(3-hydroxy-phenyl)-ethyl]-2-oxo-5,6-dihydro-2H-pyran-3-ylsulfanyl)-2-methyl-phenyl ester

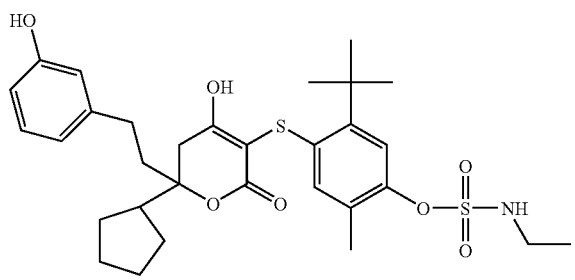

A mixture of 6-Cyclopentyl-4-hydroxy-6-[2-(3-hydroxy-phenyl)-ethyl]-5,6-dihydro-pyran-2-one (0.23 g, 0.75 mmol; described above), toluene-4-thiosulfonic acid S-(2-tert-butyl-4-ethylsulfamoyloxy-5-methyl-phenyl) ester (0.38 g, 0.83 mmol; described by Boyer et al. *J. Med. Chem.* (2000), 43(5), 843–858), $K_2CO_3$ (0.46 g, 3.3 mmol), were dissolved in DMF (10 ml) and stirred overnight at room temperature. The reaction was quenched with 1N HCl to pH~3, then extracted with EtOAc, washed with brine, dried over $Na_2SO_4$, and concentrated to yield 0.69 g of an oil. The oil was chromatographed on silica gel (2.4×38 cm) eluted with EtOAc/Hex/$CH_2Cl_2$ (1:1:1), yielding 0.289 g of the product as a foam. m.p. 69–72° C. $^1$H NMR (DMSO-$d_6$) δ: 1.05–1.15 (5H, m), 1.35–1.45 (1H, broad), 1.48 (9H, s), 1.50–1.75 (7H, m), 1.93 (3H, s), 1.94–2.05 (2H, m), 2.37–2.45 (1H, m), 2.50–2.60 (2H, m), 2.85–3.02 (2H, q), 3.11–3.14 (2H, m), 6.57–6.61 (3H, m), 6.79 (1H, s), 7.04–7.08 (1H, m), 7.11 (1H, s), 8.36 (1H, m, ex), 9.27 (1H, s, ex), 12.19 (1H, broad, ex); APCI+Mass Spec: m/e 604.2 (M+1); CHN Calc. With 0.5 $H_2O$: C, 60.75; H, 6.91; N, 2.29. Found: C, 60.77; H, 6.89; N, 2.68.

Example 150

6-Cyclopentyl-6-(2-cyclopentyl-ethyl)-4-hydroxy-5,6-dihydro-pyran-2-one

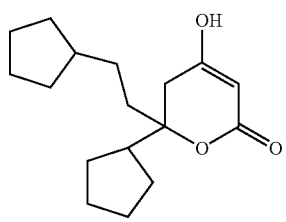

The title compound was prepared as described in step 5 of Example 149, except 1,3-Dicyclopentyl-propan-1-one was used instead of 3-(3-Benzyloxy-phenyl)-1-cyclopentyl-propan-1-one. Isolated yield: 45%. m.p.: 130–132° C.

Example 151

6-Cyclopentyl-4-hydroxy-6-(3-methyl-butyl)-5,6-dihydro-pyran-2-one

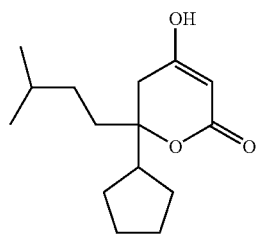

The title compound was prepared as described in Example 133 using 1-Cyclopentyl-4-methyl-pentan-1-one (prepared as described in *J. Amer. Chem. Soc.*, 1973, 1961–1968) instead of 1-cyclopentyl-5-trimethylsilanyl-pent-4-yn-1-one.

Example 152

(S)-3-(2-tert-butyl-4-hydroxymethyl-5-methyl-phenylsulfanyl)-6-cyclopentyl-4-hydroxy-6-[2-(3-hydroxy-phenyl)-ethyl]-5,6-dihydro-pyran-2-one

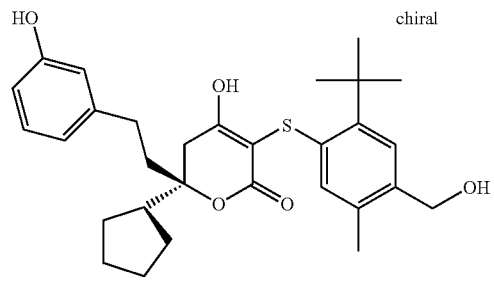

The title compound was prepared as described in Example 133, except (S)-6-cyclopentyl-4-hydroxy-6-[2-(3-hydroxy-phenyl)-ethyl]-5,6-dihydro-pyran-2-one (0.44 g, 1.47 described in step 2 of Example C(24)) was used instead of 6-Cyclopentyl-4-hydroxy-6-[2-(4-hydroxy-phenyl)-ethyl]-

5,6-dihydro-pyran-2-one. Also toluene-4-thiosulfonic acid S-(2-tert-butyl-4-hydroxymethyl-5-methyl-phenyl) ester (0.59 g, 1.62 mmol), prepared as described in *J. Med. Chem.* 2001; 2319–2332), potassium carbonate (0.81 mmol, 5.86 mmol) and DMF (5 mL) were used in the amounts indicated. m.p. 128–132° C. ¹H NMR (DMSO-d₆): 1.47 (s, 9H), 1.4–1.7 (m, 8H), 1.9 (s, 3H), 1.95–2.1 (m, 2H), 2.35 (t, 1H), 2.5–2.6 (m, 2H, partially obscured by DMSO peak), 2.7 (s, 2H), 3.35 (bs, 1H), 4.35 (s, 2H), 4.95 (bs, 1H), 6.55 (t, 3H), 6.65 (s, 1H), 7.05 (t, 1H), 7.25 (s, 1H), 9.25 (s, 1H).

Example 153

(R)-3-(2-tert-butyl-4-hydroxymethyl-5-methyl-phenylsulfanyl)-6-cyclopentyl-4-hydroxy-6-[2-(3-hydroxy-phenyl)-ethyl]-5,6-dihydro-pyran-2-one Step 1: (R)-6-Cyclopentyl-6-[2-(3-hydroxy-phenyl)-ethyl]-dihydro-pyran-2,4-dione

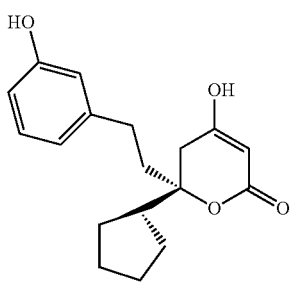

The title compound was prepared as described in *J. Med. Chem.*, 43, 843–858 using 3-(3-benzyloxy-phenyl)-1-cyclopentyl-propan-1-one instead of 1-cyclopentyl-3-(4-hydroxyphenyl)-propan-1-one.

Step 2: (R)-3-(2-tert-butyl-4-hydroxymethyl-5-methyl-phenylsulfanyl)-6-cyclopentyl-4-hydroxy-6-[2-(3-hydroxy-phenyl)-ethyl]-5,6-dihydro-pyran-2-one

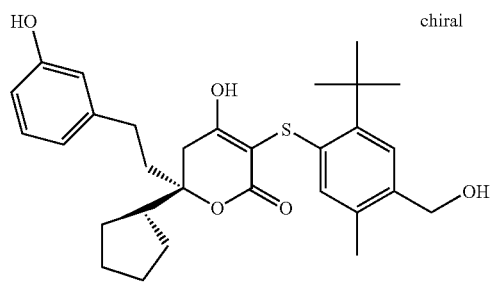

The title compound was prepared as described in Example 133 using (R)-6-cyclopentyl-4-hydroxy-6-[2-(3-hydroxy-phenyl)-ethyl]-5,6-dihydro-pyran-2-one described in step 1 above instead of 6-Cyclopentyl-4-hydroxy-6-[2-(4-hydroxy-phenyl)-ethyl]-5,6-dihydro-pyran-2-one, tolune-4-thiosulfonic acid S-(2-tert-butyl-4-hydroxymethyl-5-methyl-phenyl) ester, prepared as described in *J. Med. Chem.* 2001; 2319–2332), potassium carbonate and DMF.

Example 154

3-(2-tert-butyl-4-hydroxymethyl-5-methyl-phenyl-sulfanyl)-4-hydroxy-6-[2-(4-hydroxy-phenyl)-ethyl]-6-phenyl-5,6-dihydro-pyran-2-one

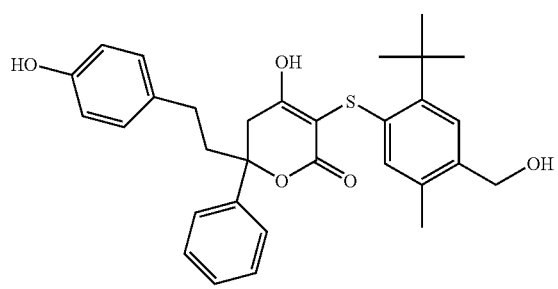

The title compound was prepared as described in Example 133 using 4-hydroxy-6-[2-(4-hydroxyphenyl)ethyl]-6-phenyl-dihydropyran-2-one (0.2 g, 0.6 mmol, prepared as described in *Bioorg. Med. Chem.*, 1999; 2775–2800), 2-tert-butyl-5-methylphenyl-p-toluenethiosulfonate (0.2 g, 0.7 mmol, prepared as described in J. Med. Chem 2001; 2319–2332), potassium carbonate (0.4g, 2.5 mmol) and DMF (2 mL). Isolated yield: 63%. mp: 199–201° C. ¹H NMR (DMSO-d₆) δ: 7.63 (s, 1H), 7.34–7.46 (m, 5H), 7.20 (d, 1H), 6.93 (d, 2H), 6.82 (d, 1H), 6.71 (d, 2H), 6.19 (s, 1H), 4.91 (s, 1H), 3.35 (d, 1H), 3.28 (d, 1H), 2.66 (m, 1H), 2.19–2.30 (m, 3H), 1.86 (s, 3H), 1.52 (s, 9H); MS (APCI): 489 (M+H); C₃₀H₃₂O₄S₁.0.75H₂O: Calc: C71.76, H6.72. Found: C71.76; H6.37.

Example 155

6-(S)-Cyclopentyl-4-hydroxy-6-[2-(3-hydroxy-phenyl)-ethyl]-3-(phenyl-propyl-amino)-5,6-dihydro-pyran-2-one Step 1: (S)-6-Cyclopentyl-6-[2-(3-hydroxy-phenyl)-ethyl]-dihydro-pyran-2,4-dione

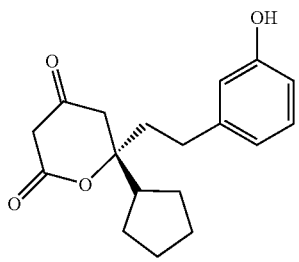

The title compound was prepared as described in *J. Med. Chem.*, 43, 843–858 with 3-(3-benzyloxy-phenyl)-1-cyclopentyl-propan-1-one instead of 1-cyclopentyl-3-(4-hydroxy-phenyl)-propan-1-one.

Step 2: (S)-6-Cyclopentyl-3-diazo-6-[2-(3-hydroxy-phenyl)-ethyl]-dihydro-pyran-2,4-dione

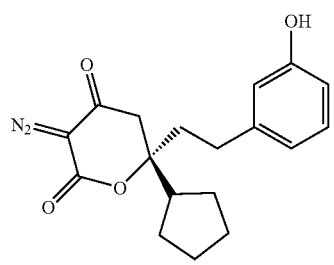

The title compound was prepared as described in step 1 of Example 187 using (S)-6-cyclopentyl-6-[2-(3-hydroxy-phenyl)-ethyl]-dihydro-pyran-2,4-dione from step 1 above for 6,6-dicyclopentyl-3-diazo-dihydro-pyran-2,4-dione.

Step 3: 6-(S)-Cyclopentyl-4-hydroxy-6-[2-(3-hydroxy-phenyl)-ethyl]-3-(phenyl-propyl-amino)-5,6-dihydro-pyran-2-one

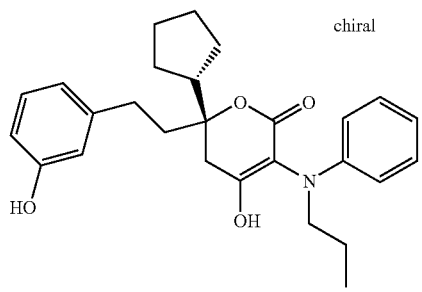

The title compound was prepared analogously to Example 187 using (S)-6-cyclopentyl-3-diazo-6-[2-(3-hydroxy-phenyl)-ethyl]-dihydro-pyran-2,4-dione (0.3 g, 0.91 mmol) described in step 2 above instead of 6,6-Dicyclopentyl-3-diazo-dihydro-pyran-2,4-dione,and N-propylaniline (0.5 g, 3.6 mmol) instead of N-propyl(3-nitro)aniline, rhodium acetate (0.04 g, 0.091 mmol) and benzene (5 mL). Isolated yield: 73%. m.p.: 74–76° C. $^1$H NMR (DMSO-$d_6$) δ: 9.28 (brs, 1H), 7.03–7.17 (m, 3H), 6.39–6.60 (m, 6H), 2.77–3.07 (dd, 2H), 2.52–2.69 (m, 2H), 2.42 (m, 2H), 1.89–2.19 (m, 2H), 1.2–1.8 (m, 11H), 0.83 (brt, 3H); MS (APCI): 436 (M+H), 392; $C_{27}H_{33}O_4N_1 \cdot 0.36H_2O$: Calc: C73.36, H7.69, N3.17. Found: C73.32; H7.55, N3.17. IR (KBr) cm$^{-1}$: 3376, 2958, 1645, 1598, 1498.

Example 156

(S)-6-Cyclopentyl-3-diphenylamino-4-hydroxy-6-[2-(3-hydroxy-phenyl)-ethyl]-5,6-dihydro-pyran-2-one

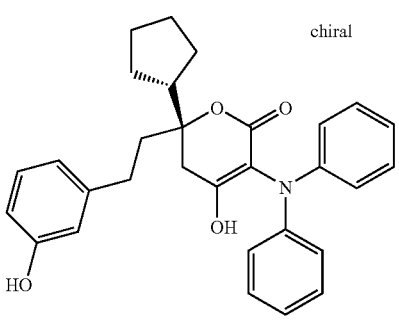

The title compound was prepared as described in Example 187, using (S)-6-Cyclopentyl-3-diazo-6-[2-(3-hydroxy-phenyl)-ethyl]-dihydro-pyran-2,4-dione (0.3 g, 0.91 mmol) (from step 2 of Example C(23)) for 6,6-Dicyclopentyl-3-diazo-dihydro-pyran-2,4-dione, diphenylamine (0.611 g, 3.64 mmol), rhodium acetate (0.04 g, 0.091 mmol) and benzene (5 mL). Isolated yield: 70%. m.p.: 90–92° C. $^1$H NMR (DMSO-$d_6$) δ: 9.28+9.2 (d, 1H), 6.83–7.69 (m, 12H), 6.33–6.64 (m, 2H), 2.94–3.28 (dd, 2H), 2.19–2.72 (m, 4H), 1.89–2.08 (m, 1H), 1.2–1.8 (m, 8H); MS (APCI): 436 (M+H), 392; $C_{30}H_{31}O_4N_1 \cdot 0.68H_2O$: Calc: C74.78, H6.77, N2.91. Found: C75.18; H6.43, N2.11. IR (KBr) cm$^{-1}$: 3419, 2952, 1650, 1590, 1492, 697.

Example 157

(S)-3-(butyl-phenyl-amino)-6-Cyclopentyl-4-hydroxy-6-[2-(3-hydroxy-phenyl)-ethyl]-5,6-dihydro-pyran-2-one

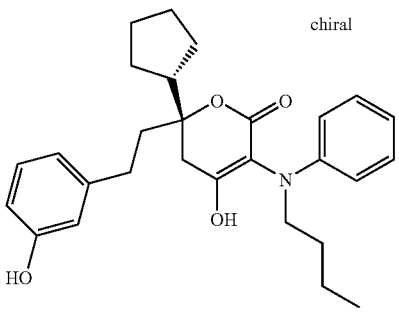

The title compound was prepared as described in step 2 of Example 187 using (S)-6-cyclopentyl-3-diazo-6-[2-(3-hydroxy-phenyl)-ethyl]-dihydro-pyran-2,4-dione (0.3 g, 0.91 mmol) from step 2 of Example C(23) instead of 6,6-dicyclopentyl-3-diazo-dihydro-pyran-2,4-dione, N-butylaniline (0.5 g, 3.6 mmol), rhodium acetate (0.04 g, 0.091 mmol) and benzene (5 mL). Isolated yield: 65%, m.p.: 64–66° C.

Example 158

3-[2-tert-butyl-4-(2-hydroxy-ethoxy)-5-methyl-phenylsulfanyl]-6,6-dicyclopentyl-4-hydroxy-5,6-dihydro-pyran-2-one Step 1: (S)-6-Cyclopentyl-6-[2-(4-hydroxy-phenyl)-ethyl]-dihydro-pyran-2,4-dione

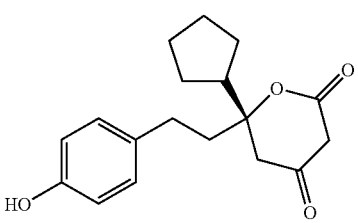

The title compound was prepared as described in the following reference: *J. Med. Chem.* 43:8,43–858.

Step 2: 3-[2-tert-butyl-4-(2-hydroxy-ethoxy)-5-methyl-phenylsulfanyl]-6,6-dicyclopentyl-4-hydroxy-5,6-dihydro-pyran-2-one

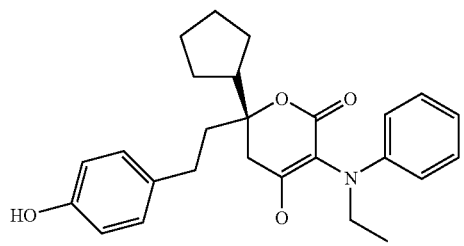

The title compound was prepared as described in step 2 of Example 187 using (S)-6-Cyclopentyl-6-[2-(4-hydroxy-phenyl)-ethyl]-dihydro-pyran-2,4-dione (0.3 g, 0.91 mmol, prepared as described in *J. Med. Chem.*, 43, 843–858) instead of 6,6-dicyclopentyl-3-diazo-dihydro-pyran-2,4-dione, N-ethylaniline (0.44 g, 3.6 mmol) and rhodium acetate (0.04 g, 0.091 mmol) in benzene (5 mL). m.p.: 90–92° C. $^1$H-NMR (DMSO-d$_6$) δ: 9.28 (brs, 1H), 7.07–7.11 (m, 3H), 6.39–6.64 (m, 6H), 2.77–3.07 (dd, 2H), 2.52–2.69 (m, 2H), 2.36–2.44 (m, 2H), 1.94–2.07 (m, 2H), 1.31–1.66 (m, 9H), 107 (t, 3H); MS (APCI): 422 (M+H), 378; $C_{26}H_{31}O_4N_1$: Calc: C74.08, H7.41, N3.32; Obsd: C73.93; H7.25, N3.47. IR (KBr) cm$^{-1}$: 3383, 2955, 1642, 1599, 1498, 1383, 1266.

Example 159

6-Cyclopentyl-4-hydroxy-6-[2-(4-hydroxy-phenyl)-ethyl]-3-(phenyl-propyl-amino)-5,6-dihydro-pyran-2-one

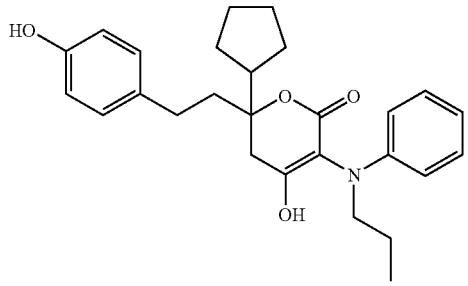

The title compound was prepared as described in Example 187 except 6-Cyclopentyl-3-diazo-6-[2-(4-hydroxy-phenyl)-ethyl]-dihydro-pyran-2,4-dione (0.3 g, 0.91 mmol) was used for 6,6-Dicyclopentyl-3-diazo-dihydro-pyran-2,4-dione, and N-propylaniline (0.49 g, 3.6 mmol) was used instead of N-propyl(3-nitro)aniline. Isolated yield: 63%. m.p.: 95° C. $^1$H NMR (DMSO-d$_6$) δ: 9.12 (d,1H), 7.14–6.89 (m, 4H), 6.75–6.53 (m, 5H), 3.07 (d, 1H), 2.86 (d, 1H), 2.72–2.17 (m, 6H), 2.14–1.17 (m, 10H), 0.86 (m, 3H); MS (APCI): 436 (M+H), 390; $C_{27}H_{33}O_4N_1.0.2H_2O$: Calc: C73.84, H7.67, N3.19. Found: C73.74; H7.64, N2.94. IR (KBr) cm$^{-1}$: 3377, 2957, 1645, 1515, 1223, 749.

Example 160

Cyclopentyl-(ethyl-phenyl-amino)-hydroxy-[2-(4-hydroxy-phenyl)-ethyl]-5,6-dihydro-pyran-2-one The title compound was prepared as described in Example 187 except 6-Cyclopentyl-3-diazo-6-[2-(4-hydroxy-phenyl)-ethyl]-dihydro-pyran-2,4-dione (0.3 g, 0.91 mmol), was used for 6,6-Dicyclopentyl-3-diazo-dihydro-pyran-2,4-dione, and N-ethylaniline (0.49 g, 3.6 mmol) was used place of N-propyl(3-nitro)aniline. Isolated yield: 70%. m.p.: 83–85° C. $^1$H NMR (DMSO-d$_6$) δ: 9.12 (d, 1H), 7.17–6.89 (m, 4H), 6.75–6.53 (m, 5H), 3.0 (d, 1H), 2.87 (d, 1H), 2.69–2.33 (m, 6H), 2.14–1.33 (m, 10H), 1.07 (t, 3H); MS (APCI): 422 (M+H), 404, 376; $C_{26}H_{31}O_4N_1.0.6H_2O$: Calc: C72.23, H7.51, N3.24. Found: C71.91; H7.36, N3.18. IR (KBr) cm$^{-1}$: 3377, 2954, 1643, 1515, 1223, 751.

Example 161

Cyclopentyl-diphenylamino-hydroxy-[2-(4-hydroxy-phenyl)-ethyl]-5,6-dihydro-pyran-2-one

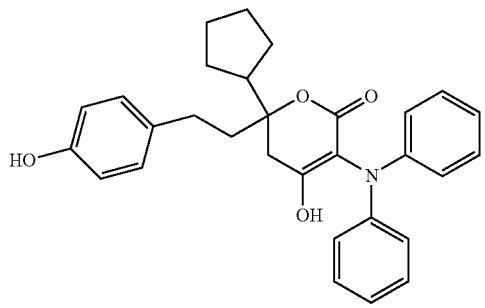

The title compound was prepared as described in Example 187 except 6-Cyclopentyl-3-diazo-6-[2-(4-hydroxy-phenyl)-ethyl]-dihydro-pyran-2,4-dione (0.3 g, 0.91 mmol), was used for 6,6-Dicyclopentyl-3-diazo-dihydro-pyran-2,4-dione, and), diphenylamine (0.62 g, 3.66 mmol) was used place of N-propyl(3-nitro)aniline. Isolated yield: 52%; mp.: 93–94° C. $^1$H NMR (DMSO-$d_6$) δ: 9.12 (d, 1H), 7.19–7.07 (m, 12H), 6.66 (m, 2H), 2.94–3.28 (dd, 2H), 2.25–2.47 (m, 4H), 1.2–2.07 (m, 9H); MS (APCI): 470 (M+H), 452, 426, 257, 210, 170; $C_{30}H_{31}O_4N_1 \cdot 0.75H_2O$: Calc: C74.59, H6.78, N2.90. Found: C74.59; H6.69, N2.54. IR (KBr) cm$^{-1}$: 3418, 2953, 1646, 1591, 1492, 1235, 697.

Example 162

6-Cyclopentyl-6-[2-(2,4-dimethoxy-phenyl)-ethyl]-3-(3-methoxy-benzyl)-dihydro-pyran-2,4-dione

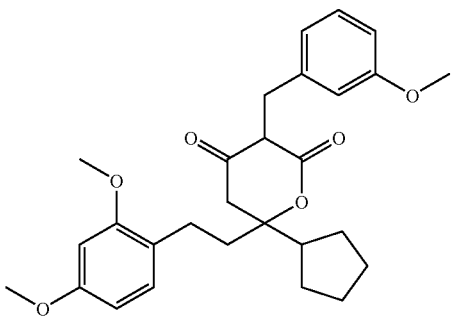

The title compound was prepared as described in Example 88 except 6-cyclopentyl-6-[2-(2,4-dimethoxy-phenyl)-ethyl]-dihydro-pyran-2,4-dione (described in Example 38) was used for 6-cyclopentyl-6-[2-(phenyl)-ethyl]-dihydro-pyran-2,4-dione in step 1, and except m-anisaldehyde was used for benzaldehyde in the final step of that Example. $^1$H NMR (CD$_3$OD) δ 1.3–1.87 (m, 10H), 2.3–2.37 (m, 1H), 2.38–2.4 (m, 2H), 2.42 (d, J=17.6 Hz, 1H), 2.74 (d, J=17.6 Hz, 1H), 3.44 (d, J 14.4 Hz, 1H), 3.53 (d, J=14.4 Hz, 1H), 3.54 (s, 3H), 3.56 (s, 3H), 3.66 (s, 3H), 6.27 (dd, J=8.3, 2.2 Hz, 1H), 6.32 (d, J=2.2 Hz, 1H), 6.56 (dd, J=8.3, 2.2 Hz, 1H), 6.6–6.76 (m, 3H), 6.95–7 (m, 1H). APCI; M+H=467.2 & M−H=465.2.

Example 163

6-Cyclopentyl-6-[2-(2,4-dimethoxy-phenyl)-ethyl]-3-phenoxy-dihydro-pyran-2,4-dione Step 1: 6-Cyclopentyl-3-diazo-6-[2-(2,4-dimethoxy-phenyl)-ethyl]-dihydro-pyran-2,4-dione

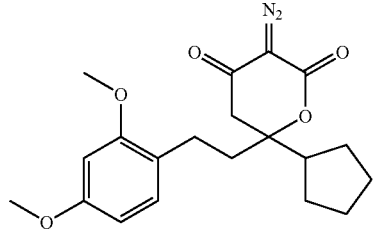

To a solution of 6-Cyclopentyl-6-[2-(2,4-dimethoxy-phenyl)-ethyl]-dihydro-pyran-2,4-dione (0.5 g, 1.44 mmol; preparation described in Example 38, and sodium hydrogen phoshate (monobasic) (0.26 g, 2.16 mmol), dissolved in 6 ml of DMF at room temperature, under Argon, was added 4-acetamido benzenesulfonyl azide (0.52 g, 2.16 mmol). The resulting mixture was stirred for 4 hours, during which time starting material disappearance was monitored via TLC. The reaction was quenched at this time by adding sodium hydrogen phosphate (dibasic) (40 ml). The resulting mixture was extracted with EtOAc (3×30 ml), water (20 ml), and dried over anhydrous Na$_2$SO$_4$. The result material was purified by column chromatography using Hexanes: EtOAc (1:1) yielding the product in quantitative yield. $^1$H NMR (CDCl$_3$): δ 1.17–1.87 (m, 8H), 1.9–1.98 (m, 2H), 2.3–2.44 (m, 1H), (m, 2H), 2.69–2.7 (d, J=2.3 Hz, 2H), 3.71 (s, 3H), 3.72 (s, 3H), 6.31–6.39 (m, 3H), 6.91 (d, J=8.1 Hz, 1H). API-ES; M+H=373.1.

Step 2: 6-Cyclopentyl-6-[2-(2,4-dimethoxy-phenyl)-ethyl]-3-phenoxy-dihydro-pyran-2,4-dione

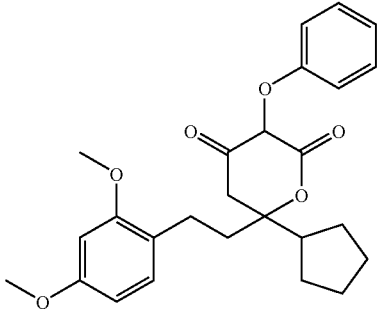

A solution of 6-Cyclopentyl-3-diazo-6-[2-(2,4-dimethoxy-phenyl)-ethyl]-dihydro-pyran-2,4-dione (from step 1 above), and phenol (25.3 mg, 2.68 mmol), were dissolved in benzene (1 ml), purged with argon for 10 minutes, then treated with Rh(OAc)$_2$ (6 mg, 0.134 mmol). The resulting mixture was refluxed for 12 h, then cooled to room temperature and concentrated on a rotary evaporator. The residue was treated with 3 N HCl (10 ml), extracted, with EtOAc (2×25 ml), water (15 ml), brine (25 ml), then dried over anhydrous Na$_2$SO$_4$ filtered, and concentrated. The resulting oil was purified via preparative HPLC to afford the desired compound (2 mg) in 3.4% yield. ¹H NMR (CD₃OD) δ 1.54–2.04 (m, 10H), 2.6–2.87 (m, 4H), 3.78 (s, 3H), 3.79 (s, 3H), 5.96 (s, 1H), 6.42 (dd, J=8.15, 2.45 Hz, 1H), 6.48 (d, J=2.2 Hz, 1H), 7.03–7.1 (m, 3H), 7.25–7.28 (m, 1H), 7.39–7.28 (m, 1H), 7.39–7.45 (m, 2H). APCI; M–H=437.2.

Step 3: 6-Cyclopentyl-6-[2-(2,4-dimethoxy-phenyl)-ethyl]-3-phenoxy-dihydro-pyran-2,4-dione

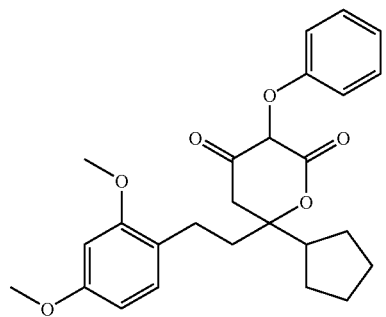

A solution of 6-Cyclopentyl-3-diazo-6-[2-(2,4-dimethoxy-phenyl)-ethyl]-dihydro-pyran-2,4-dione (from step 1 above), and phenol (25.3 mg, 2.68 mmol), were dissolved in benzene (1 ml), purged with argon for 10 minutes, then treated with Rh(OAc)₂ (6 mg, 0.134 mmol). The resulting mixture was refluxed for 12 h, then cooled to room temperature and concentrated on a rotary evaporator. The residue was treated with 3 N HCl (10 ml), extracted with EtOAc (2×25 ml), water (15 ml), brine (25 ml), then dried over anhydrous Na₂SO₄ filtered, and concentrated. The resulting oil was purified via preparative HPLC to afford the desired compound (2 mg) in 3.4% yield. ¹H NMR (CD₃OD) δ 1.54–2.04 (m, 10H), 2.6–2.87 (m, 4H), 3.78 (s, 3H), 3.79 (s, 3H), 5.96 (s, 1H), 6.42 (dd, J=8.15, 2.45 Hz, 1H), 6.48 (d, J=2.2 Hz, 1H), 7.03–7.1 (m, 3H), 7.25–7.28 (m, 1H), 7.39–7.45 (m, 2H). APCI; M–H=437.2.

Example 164

3-(4-Chloro-phenoxy)-6-cyclopentyl-6-[2-(2,4-dimethoxy-phenyl)-ethyl]-dihydro-pyran-2,4-dione

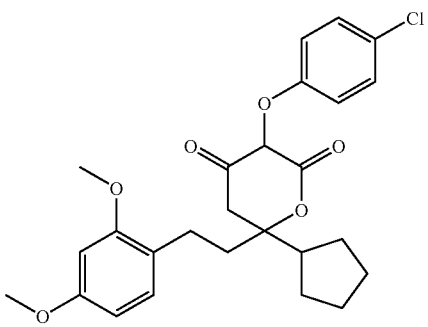

The title compound was prepared as described in Example 162, except ortho-chlorophenol was substituted for phenol. ¹H NMR (CD₃OD) δ 1.1–1.8 (m, 18H), 1.9–2.05 (m, 2H), 2.2–2.3 (m, 1H), 2.35–2.6 (m, 2H), 2.37 (d, J=17.6 Hz, 1H), 2.77 (d, J=17.6 Hz, 1H), 6.24 (dd, J=8.3, 2.45 Hz, 1H), 6.32 (d, J=2.2 Hz, 1H), 6.72 (d, J=6.7 Hz, 2H), 6.83 (d, J=8.3 Hz, 1H), 7.01 (d, J=6.7 Hz, 2H), 7.29 (s, 1H). APCI; M+H=473.1.

Example 165

6-Cyclopentyl-6-[2-(4-methoxy-phenyl)-ethyl]-3-[2-(3-methyl-isoxazol-5-yl)-acetyl]-dihydro-pyran-2,4-dione

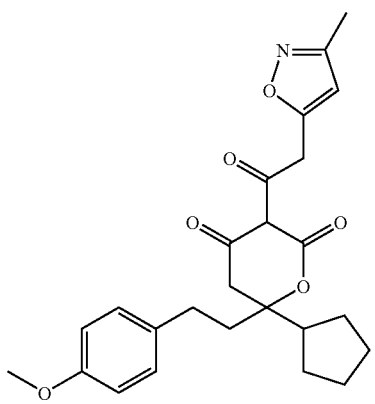

To a mixture of 6-Cyclopentyl-6-[2-(4-methoxy-phenyl)-ethyl]-dihydro-pyran-2,4-dione (60 mg, 0.189 mmol; described in Example 3, 3-methyl-5-isoxazoleacetic acid (35 mg, 0.24 mmol), triethylamine (73 μl, 0.66 mmol), and DMAP (cat), dissolved in CH₂Cl₂, under argon, was added EDC.HCl (47.3 mg, 0.24 mmol) in one portion. The resulting solution was stirred overnight, then quenched with 0.5N HCl (10 ml), extracted with EtOAc (3×15 ml), water (15 ml), brine (15 ml), dried over anhydrous Na₂SO₄, filtered and concentrated. The resulting mixture was purified via preparative HPLC, yielding the 23.5 mg of the product (0.053 mmol, 28%). ¹H NMR (CD₃OD) δ 1.44–1.79 (m, 8H), 1.82–2.04 (m, 2H), 2.25 (s, 3H), 2.38–2.5 (m, 1H), 2.6–2.66 (m, 2H), 2.87 (d, J=18 Hz), 3.06 (d, J=18 Hz, 1H), 6.19 (s, 1H), 6.83 (d, J=8.6 Hz, 2H), 7.07 (d, J 8.6 Hz, 2H). APCI; M+H=440.2 & M–H=438.1.

Example 166

3-Acetyl-6-cyclopentyl-6-[2-(2,4-dimethoxy-phenyl)-ethyl]-dihydro-pyran-2,4-dione

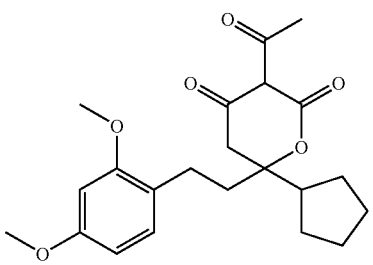

The title compound was prepared as described in Example 165 using acetic acid for 3-methyl-5-isoxazoleacetic acid, and 6-Cyclopentyl-6-[2-(2,4-dimethoxy-phenyl)-ethyl]-dihydro-pyran-2,4-dione (preparation described in Example 38) for 6-Cyclopentyl-6-[2-(4-methoxy-phenyl)-ethyl]-dihydro-pyran-2,4-dione. $^1$H NMR (CDCl$_3$): δ 1.18–2 (m, 11H), 2.2–2.4 (m 2H), 2.56 (s, 3H), 2.66 (d, J=17.6 Hz, 1H), 2.79 (d, J=17.6 Hz, 1H), 3.69 (s, 3H), 3.71 (s, 3H), 6.3–6.38 (m, 2H), 6.91 (d, J=8.1 Hz, 1H 16.09 (s, 1H). APCI; M+H=389.3 & M–H=387.

Example 167

3-Acetyl-6-[2-(3-chloro-phenyl)-ethyl]-6-cyclopentyl-dihydro-pyran-2,4-dione

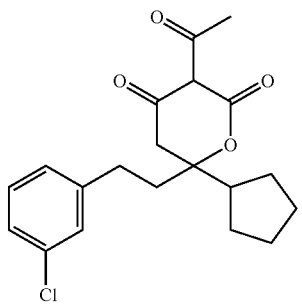

The title compound was prepared as described in Example 165 using acetic acid for 3-methyl-5-isoxazoleacetic acid, and 6-[2-(3-Chloro-phenyl)-ethyl]-6-cyclopentyl-dihydro-pyran-2,4-dione (preparation described in Example 26) instead of 6-cyclopentyl-6-(2,4-dimethoxyphenethyl)dihydro-2H-pyran-2,4(3H)-dione. $^1$H NMR (CDCl$_3$): δ 1.18–1.8 (m, 11H), 1.88–1.97 (m 2H), 2.24–2.35 (m 1H), 2.57 (s, 3H), 2.56–2.61 (m, 2H), 2.63 (d, J=17.6 Hz, 1H), 2.81 (d, J=17.6 Hz, 1H), 6.95–7.0 (m, 1H), 7.05–7.22 (3H), 16.0 (s, 0.5 H, enolic proton), 17.71 (s, 0.5 H, other enolic form). APCI; M+H=363.1 & M–H 361.1.

Example 168

3-Acetyl-6-cyclopentyl-6-[2-(4-methoxy-phenyl)-ethyl]-dihydro-pyran-2,4-dione

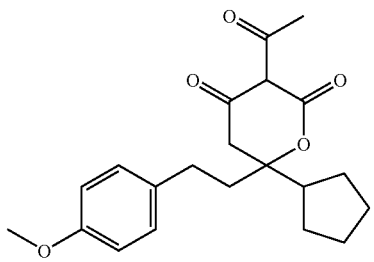

The title compound was prepared as described in Example 165 using acetic acid for 3-methyl-5-isoxazoleacetic. $^1$H NMR (CD$_3$OD) δ 1.3–1.75 (m, 8H), 1.85–1.9 (m, 2H), 2.25–2.4 (m, 1H), 2.46 (s, 3H), 2.49–2.55 (m, 2H), 2.7 d, J=17.6 Hz, 1H), 2.87 (d, J=17.6 Hz, 1H), 3.64 (s, 3H), 6.71 (d, J=8.6 Hz, 2H), 6.96 (d, J=8.6 Hz, 2H). APCI; M+H=359.2 & M–H=357.2.

Example 169

6-Cyclopentyl-6-[2-(2,4-dimethoxy-phenyl)-ethyl]-3-phenylacetyl-dihydro-pyran-2,4-dione

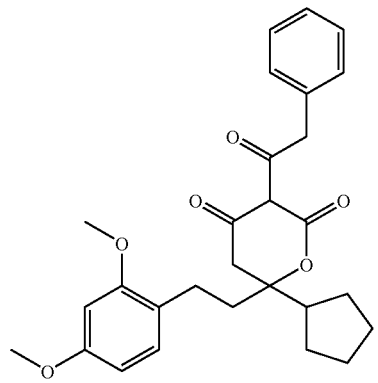

The title compound was prepared as described in Example 165 using phenylacetic acid for 3-methyl-5-isoxazoleacetic acid, and using 6-Cyclopentyl-6-[2-(2,4-dimethoxy-phenyl)-ethyl]-dihydro-pyran-2,4-dione instead of 6-Cyclopentyl-6-[2-(4-methoxy-phenyl)-ethyl]-dihydro-pyran-2,4-dione. $^1$H NMR (DMSO-d$_6$) δ 1.09–2.0 (m, 9H), 2.2–2.3 (m, 2H), 2.53–2.57 (m, 2H), 2.89 (d, J=18.9 Hz, 1H), 3.15 (d, J=18.9 Hz, 1H), 3.75 (s, 3H), 3.78 (s, 3H), 4.39 (s, 2H), 6.47 (dd, J=8.15, 2.45 Hz, 1H), 6.54 (d, J=2.4 Hz, 1H), 7.15 (d, J=8.3 Hz, 1H), 7.29–7.34 (m, 5H), 17.62 (br, 1H). APCI; M+H=456.1 & M–H=463.2.

Example 170

6-[2-(3-Chloro-phenyl)-ethyl]-6-cyclopentyl-3-phenylacetyl-dihydro-pyran-2,4-dione

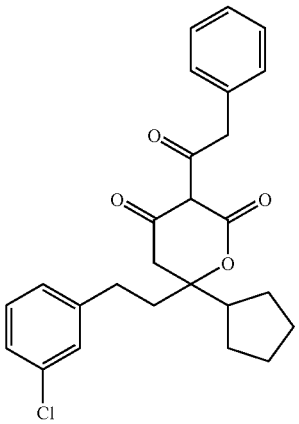

The title compound was prepared as described in Example 165 using phenylacetic acid for 3-methyl-5-isoxazoleacetic acid, and 6-[2-(3-Chloro-phenyl)-ethyl]-6-cyclopentyl-dihydro-pyran-2,4-dione (preparation described in Example 26) for 6-cyclopentyl-6-(2,4-dimethoxyphenethyl)dihydro-2H-pyran-2,4(3H)-dione. $^1$H NMR (CDCl$_3$): δ 1.18–1.8 (m, 9H), 1.83–1.91 (m 2H), 2.25–2.32 (m, 1H), 2.51–2.63 (m, 1H), 2.58 (d, J=17.6 Hz, 1H), 2.81 (d, J=17.6 Hz, 1H), 4.28

(d, J=14.8 Hz, 1H), 4.37 (d, J=14.8 Hz, 1H), 6.87–7.3 (m, 9H), 16.27 (s, 0.5H, enolic proton), 17.62 (s, 0.5H, other enolic form). APCI: M+H=439.2.

Example 171

6-Cyclopentyl-6-[2-(4-methoxy-phenyl)-ethyl]-3-phenylacetyl-dihydro-pyran-2,4-dione

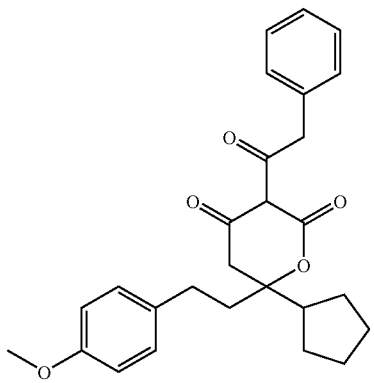

The title compound was prepared as described in Example 165 using phenylacetic acid for 3-methyl-5-isoxazoleacetic acid. $^1$H NMR (CD$_3$OD) δ 1.35–1.75 (m, 10H), 1.89–1.94 (m, 2H), 2.32–2.4g, 1H), 2.54–2.59 (m, 2H), 2.58 (d, J=17.6 Hz, 1), 2.99 (d, J=17.6 Hz, 1H), 3.77 (s, 3H), 4.3 (d, J=14.2 Hz, 1H), 4.41 (d, J=14.2 Hz, 1H), 6.81, (d, J=8.6 Hz, 1H), 6.99 (d, J=8.6 Hz, 1H), 7.21–7.32 (m, 5H). APCI: M+H=435.2 & M−H=433.1.

Example 172

6-Cyclopentyl-6-[2-(2,4-dimethoxy-phenyl)-ethyl]-3-(2-pyridin-3-yl-acetyl)-dihydro-pyran-2,4-dione

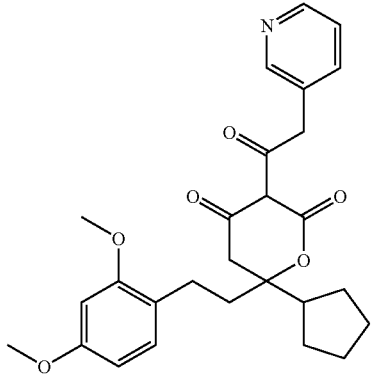

The title compound was prepared as described in Example 165 using 3-pyridylacetic acid for 3-methyl-5-isoxazoleacetic acid, and 6-Cyclopentyl-6-[2-(2,4-dimethoxy-phenyl)-ethyl]-dihydro-pyran-2,4-dione (preparation described in Example 38) for 6-Cyclopentyl-6-[2-(4-methoxy-phenyl)-ethyl]-dihydro-pyran-2,4-dione. $^1$H NMR (CD$_3$OD) (approx. 1:1 mixture of tautomers) δ 1.31–2.1 (m, 10H), 2.4–2.51 (M, 1H), 2.51–2.61 (m, 2H), 2.79 (d, J=18.6 Hz, 1H), 3.03 (d, J=18.6 Hz, 1H), 3.76 (s, 3H), 3.77 (s, 3H), 6.4–6.43 (m, 1H), 6.47 (s, 1H), 6.92–7.0 (d, J=8, 8.3 Hz, 1H), 7.4 & 7.6 (dd, J=7.5, 5.3 Hz, J=7.6, 5.1 Hz, 1H), 7.83 & 7.92 (d, J=7.7 & 7.7 Hz, 1H), 8.42–8.56 (m, 2H).

Example 173

6-Cyclopentyl-6-[2-(4-methoxy-phenyl)-ethyl]-3-(2-pyridin-3-yl-acetyl)-dihydro-pyran-2,4-dione

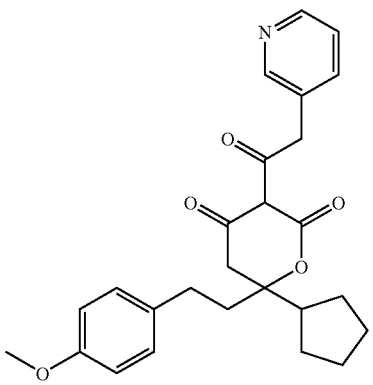

The title compound was prepared as described in Example 165 using 3-pyridylacetic acid for 3-methyl-5-isoxazoleacetic acid. $^1$H NNR (CD$_3$OD) δ 1.19–1.56 (m, 8H), 1.82–1.9 (m, 2H), 2.26–2.4 (m, 1H), 2.4–2.6 (m, 2H), 2.7 (d, J=17.6 Hz, 1H), 2.76 (d, J=17.6 Hz, 1H), 3.63 (s, 3H), 6.69 (d, J=8.6 Hz, 1H), 6.91 (d, J=8.6 Hz, 1H), 7.32–7.45 (m, 1H), 7.79 (d, J=7.7 Hz, 1H), 8.36 (m, 1H), 8.43 (m, 1H). APCI: M+H=436.2 & M−H=434.1.

Example 174

6-[2-(3-Chloro-phenyl)-ethyl]-6-cyclopentyl-3-(2-pyridin-3-yl-acetyl)-dihydro-pyran-2,4-dione

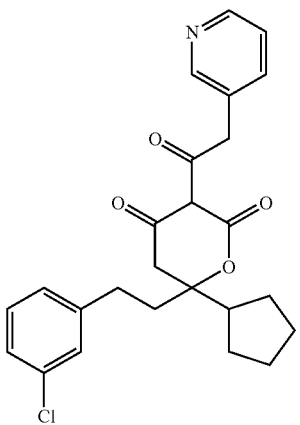

The title compound was prepared as described in Example 165 using 3-pyridylacetic acid for 3-methyl-5-isoxazoleacetic acid, and 6-[2-(3-Chloro-phenyl)-ethyl]-6-cyclopentyl-dihydro-pyran-2,4-dione (preparation described in Example 26) for 6-cyclopentyl-6-(2,4-dimethoxyphenethyl)dihydro-2H-pyran-2,4(3H)-dione. $^1$H NMR (CD$_3$OD) δ 1.18–1.57 (m, 8H), 8H), 1.85–1.93 (m, 2H), 2.25–2.37 (m, 1H), 2.5–2.6 (m, 2H), 2.71 (d, J=17.7 Hz, 1H), 2.89 (d, J=17.7 Hz, 1H), 6.96 (d, J=7.3 Hz, 1H), 7.06–7.17 (m, 3H), 7.29–7.34 (dd, J=7.7, 2.9 Hz, 1H), 7.75 (d, J=7.7 Hz, 1H), 8.3–8.38 (s, 1H), 8.38–8.48 (s, 1H). APCI: M+H=438.1 & M−H=440.2.

Example 175

3-Benzoyl-6-cyclopentyl-6-[2-(2,4-dimethoxy-phenyl)-ethyl]-dihydro-pyran-2,4-dione

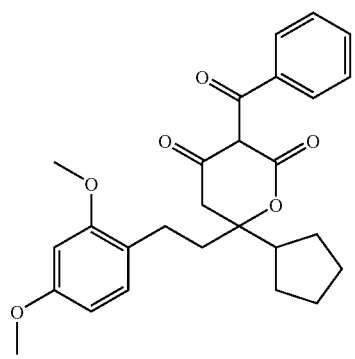

The title compound was prepared as described in Example 165 using benzoic acid place of 3-methyl-5-isoxazoleacetic acid, 6-Cyclopentyl-6-[2-(2,4-dimethoxy-phenyl)-ethyl]-dihydro-pyran-2,4-dione (preparation described in Example 38) for 6-Cyclopentyl-6-[2-(4-methoxy-phenyl)-ethyl]-dihydro-pyran-2,4-dione. $^1$H NMR (CD$_3$OD) δ 1.4–2.0 (m, 8H), 2.1–2.2 (m, 2H), 2.45–2.6 (m, 1H), 2.63–2.85 (m, 2H), 2.74 (d, J=17.9 Hz, 1H), 3.88 (d, J=17.9 Hz, 1H), 3.76 (s, 3H), 3.78 (s, 3H), 6.4–6.48 (dd, J=8.3, 2.45 Hz, 1H), 6.51 (br, 1H), 7.04 (d, J=8.3 Hz, 1H), 7.42–7.47 (m, 2H), 7.57–7.62 (m, 3H). APCI; M+H=451.2 & M−H=449.1.

Example 176

3-Benzoyl-6-cyclopentyl-6-[2-(2,4-dimethoxy-phenyl)-ethyl]-dihydro-pyran-2,4-dione

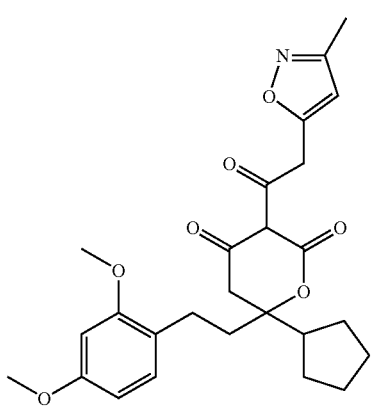

The title compound was prepared as described in Example 165 using 6-cyclopentyl-6-(2,4-dimethoxyphenethyl)dihydro-2H-pyran-2,4(3H)-dione (preparation described in Example 38) for 6-Cyclopentyl-6-[2-(4-methoxy-phenyl)-ethyl]-dihydro-pyran-2,4-dione. $^1$H NMR (CDCl$_3$): δ1.35–1.85 (m, 8H), 1.88–1.94 (m, 2H), 2.21 (s, 3H), 2.24–2.36 (m, 1H), 2.42–2.55 (m, 2H), 2.71 (d, J=17.9 Hz, 1H), 2.86 (d, J=17.9 Hz, 1H), 3.69 (s, 3H), 3.71 (s, 3H), 4.43 (d, J=17.6 Hz, 1H), 4.54 (d, J=17.6 Hz, 1H), 5.96 & 6.9 (d, J=8.0 Hz, 1H), 16.59 & 17.6 (tautomeric enolic 'H').

Example 177

3-Benzyl-6-cyclopentyl-6-[2-(4-methoxy-phenyl)-ethyl]-dihydro-pyran-2,4-dione

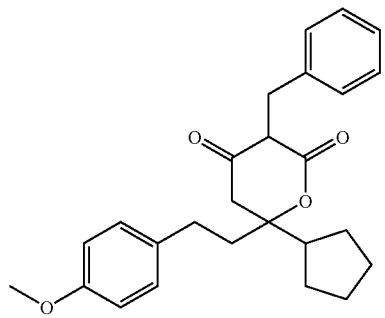

To 6-Cyclopentyl-6-[2-(4-methoxy-phenyl)-ethyl]-dihydro-pyran-2,4-dione (60 mg, 0.189 mmol, described in Example 3, in benzene (1.9 ml) was added DBU (28 μl, 0.19 mmol) and the resulting homogenous mixture was stirred at room temperature for 10 minutes. Benzyl bromide (21 μl, 0.174 mmol) was added followed by a catalytic amount of NaI. The reaction was stirred overnight at room temperature. The reaction was then filtered through celite and the filtrate concentrated to yield a crude product, which was purified by preparative HPLC. The appropriate fractions were then combined and concentrated to yield the desired product (9 mg, 0.022 mmol, 15%) after azeotroping twice with benzene (3 ml). $^1$H NMR (CDCl$_3$): δ 1.1–1.75 (m, 9H), 1.85–2.05 (m, 2H), 2.15–2.73 (m, 4H), 3.14 3.53 (m, 2H), 3.56 (s, 1H), 3.7–3.73 (s, 3H), 6.72 (d, J=8.6 Hz, 1H), 6.77 (d, J=8.7 Hz, 1H), 6.91 (d, J=8.6 Hz, 1H), 7.00 (d, J=8.7 Hz, 1H), 7.01–7.29 (m, 5H).

Example 178

3-Benzyl-6-[2-(3-chloro-4-methoxy-phenyl)-ethyl]-6-cyclopentyl-dihydro-pyran-2,4-dione

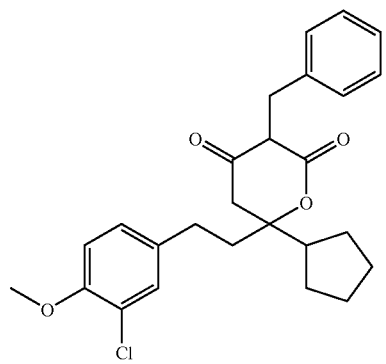

The title compound was prepared as described in Example 177 using 6-[2-(3-Chloro-4-methoxy-phenyl)-ethyl]-6-cyclopentyl-dihydro-pyran-2,4-dione (described in Example 27) for 6-Cyclopentyl-6-[2-(4-methoxy-phenyl)-ethyl]-dihydro-pyran-2,4-dione. $^1$H NMR (CDCl$_3$): δ 1.0–2.83 (m, 15H), 3.19–3.6 (m, 2H), 3.87–3.89 (s, 3H), 6.77–6.9 (m, 1H), 6.93–7.09 (m, 1H), 7.12–7.36 (m, 6H).

Example 179

3-(4-Amino-2-tert-butyl-5-methyl-phenylsulfanyl)-6,6-dicyclopentyl-4-hydroxy-5,6-dihydro-pyran-2-one

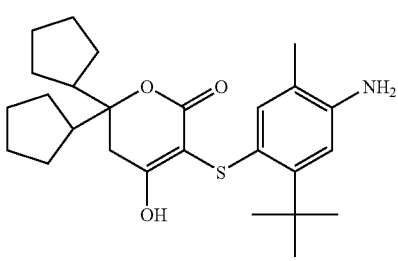

The title compound was prepared as described in Example 133 using Toluene-4-thiosulfonic acid S-(4-amino-2-tert-butyl-5-methyl-phenyl) ester (preparation described by Boyer et al. *J. Med. Chem.* (2000), 43(5)) for Toluene-4-thiosulfonic acid S-(2-tert-butyl-4-hydroxymethyl-5-methyl-phenyl) ester, and using 6-Cyclopentyl-4-hydroxy-6-[2-(4-hydroxy-phenyl)-ethyl]-5,6-dihydro-pyran-2-one instead of of 6-Cyclopentyl-4-hydroxy-6-[2-(4-hydroxy-phenyl)-ethyl]-5,6-dihydro-pyran-2-one in the final srep of that Example.). Isolated yield: 42%, m.p. 163–165° C. $^1$H NMR (DMSO-d$_6$) δ: 6.61 (s, 1H), 6.57 (s, 1H), 2.75 (s, 2H), 2.11–2.25 (m, 2H), 1.17–1.61 (m)+1.42 (s) 25H; MS (APCI): 444 (M+H), 400, 237, 205, 194, 164; C$_{26}$H$_{37}$O$_3$S$_1$N$_1$. 0.6H$_2$O: Calc: C68.71, H8.47, N3.08. Found: C68.47; H8.08, N3.04. IR (KBr) cm$^{-1}$: 3370, 2954, 1619, 1483, 1396, 1271.

Example 180

3-(2-tert-butyl-4-hydroxymethyl-5-methyl-phenyl-sulfanyl)-6,6-dicyclopentyl-4-hydroxy-5,6-dihydro-pyran-2-one

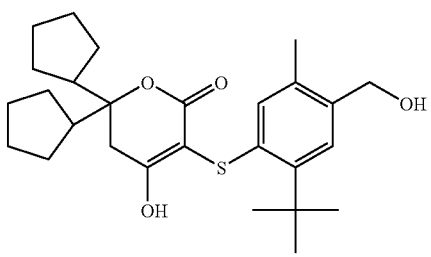

The title compound was prepared as described in Example 133 using 6,6-Dicyclopentyl-4-hydroxy-5,6-dihydro-pyran-2-one (preparation described in step 1 of Example D(3)) instead of 6-Cyclopentyl-4-hydroxy-6-[2-(4-hydroxy-phenyl)-ethyl]-5,6-dihydro-pyran-2-on in the final step of the that Example. Yield: 72%, m.p.: 158–160° C. $^1$H NMR (DMSO-d$_6$) δ: 7.28 (s, 1H), 6.75 (s, 1H), 4.96 (brs, 1H), 4.4 (s, 2H), 2.81 (s, 2H), 2.17–2.27 (m, 2H), 2.08 (s, 3H), 1.37–1.18 (m)+1.48 (s) 25H; MS (APCI): 459 (M+H), 441, 415; C$_{27}$H$_{38}$O$_4$S$_1$. 0.2H$_2$O: Calc: C70.15, H8.37; Found: C70.01; H8.38. IR (KBr) cm$^{-1}$: 3422, 2955, 1621, 1385, 1052.

Example 181

3-[2-tert-butyl-4-(2-hydroxy-ethoxy)-5-methyl-phenylsulfanyl]-6,6-dicyclopentyl-4-hydroxy-5,6-dihydro-pyran-2-one Step 1: 4-(6,6-dicyclopentyl-4-hydroxy-2-oxo-5,6-dihydro-2H-pyranone

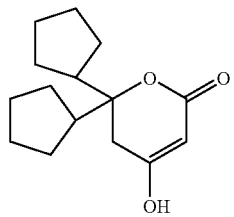

The title compound was prepared as described in Example 149 using dicyclopentylketone (30 g, 168.5 mmol) instead of 3-(3-Benzyloxy-phenyl)-1-cyclopentyl-propan-1-one in step 5 of that Example. $^1$H NMR (DMSO-d$_6$) δ: 4.89 (s, 1H), 2.33 (s, 2H), 2.00–2.14 (m, 2H), 1.11–1.64 (m, 16H; MS (APCI): 251 (M+H), 207, 196.

Step 2: 3-[2-tert-butyl-4-(2-hydroxy-ethoxy)-5-methyl-phenylsulfanyl]-6,6-dicyclopentyl-4-hydroxy-5,6-dihydro-pyran-2-one

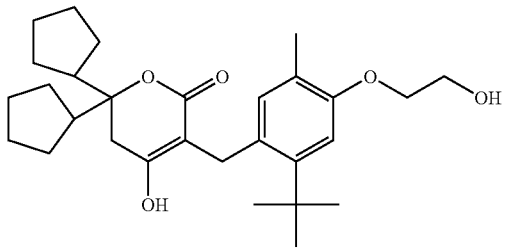

The title compound was prepared as described in Example 133 using 6,6-Dicyclopentyl-4-hydroxy-5,6-dihydro-pyran-2-one (preparation described in step 1 of Example D(3)) instead of 6-Cyclopentyl-4-hydroxy-6-[2-(4-hydroxy-phenyl)-ethyl]-5,6-dihydro-pyran-2-on, and using Toluene4-thiosulfonic acid S-[2-tert-butyl-4-(2-hydroxy-ethoxy)-5-methyl-phenyl]ester for Toluene-4-thiosulfonic acid S-(2-tert-butyl-4-hydroxymethyl-5-methyl-phenyl) ester in the final step of the that Example. The product was obtained in 62% overall yield. m.p.: 100–102° C. $^1$H NMR (DMSO-d$_6$) δ: 6.83 (s, 1H), 6.75 (s, 1H), 4.8 (brs, 1H), 3.97 (t, 2H), 3.69 (brs, 2H), 2.77 (s, 2H), 2.11–2.25 (m, 2H), 2.0 (s, 3H), 1.17–1.63 (m)+1.35 (s) 25H; MS (APCI): 489 (M+H), 445, 251, 237; $C_{28}H_{40}O_5S_1$. 1.1H$_2$O: Calc: C66.13, H8.37. Found: C65.93; H8.06. IR (KBr) cm$^{-1}$: 3426, 2954, 1608, 1383, 1253, 1171, 1052.

Example 182

1-methyl-1H-imidazole-4-sulfonic acid 5-tert-butyl-4-(6,6-dicyclopentyl-4-hydroxy-2-oxo-5,6-dihydro-2H-pyran-3-ylsulfanyl)-2-methyl-phenyl ester

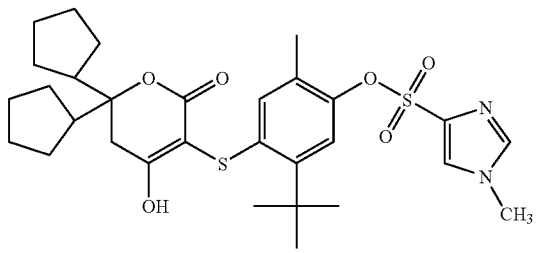

The title compound was prepared as described in Example 133 using 4-(6,6-dicyclopentyl-4-hydroxy-2-oxo-5,6-dihydro-2H-pyranone (0.2 g, 0.8 mmol) described in step 1 of Example D(3) instead of 6-Cyclopentyl-4-hydroxy-6-[2-(4-hydroxy-phenyl)-ethyl]-5,6-dihydro-pyran-2-one, 1-methyl-1H-imidazole-4-sulfonic acid 5-tert-butyl-2-methyl-4-(toluene-4-sulfonylsulfanyl)-phenyl ester (0.8 mmol; preparation described by Boyer et al. *J. Med. Chem.* (2000), 43(5), 843–858) and anhydrous potassium carbonate (0.2 g) and DMF (3 mL). Isolated yield: 69%. m.p.: 143–145° C. $^1$H NMR (DMSO-d$_6$) δ: 8.04 (s, 2H), 6.78 (s, 1H), 6.66 (s, 1H), 3.72 (s, 3H), 2.81 (s, 2H), 2.28–2.14 (m, 2H), 2.06 (s, 3H), 1.75–1.17 (m)+1.33 (s) 25H; MS (APCI): 589 (M+H), 545, 341, 251, 205; $C_{30}H_{40}O_6S_1N_2$. 0.3H$_2$O: Calc: C60.64, B6.89, N4.72. Found: C60.32; H6.69, N4.60. IR (KBr) cm$^{-1}$: 3431, 2955, 1619, 1376, 1181, 830, 627.

Example 183

3-(2-Amino-5-tert-butyl-benzothiazol-6-ylsulfanyl)-6,6-dicyclopentyl-4-hydroxy-5,6-dihydro-pyran-2-one

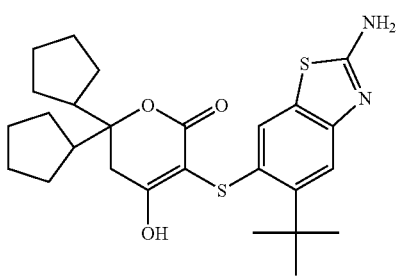

The title compound was prepared as described in Example 133 using 4-(6,6-dicyclopentyl-4-hydroxy-2-oxo-5,6-dihydro-2H-pyranone (0.25 g, 1 mmol; described in step 1 of Example 182, instead of 6-cyclopentyl-4-hydroxy-6-[2-(4-hydroxy-phenyl)-ethyl]-5,6-dihydro-pyran-2-one, and toluene-4-thiosulfonic acid S-(2-amino-6-tert-butyl-benzothiazol-5-yl) ester (0.8 mmol, prepared as described in *Tetrahedron. Letters*. 41, 2000; 4065–4068) and anhydrous, potassium carbonate (0.2 g ) in DMF (3 mL).

Example 184

Pyridine-2-sulfonic acid {3-[(6,6-dicyclopentyl-4-hydroxy-2-oxo-5,6-dihydro-2H-pyran-3-yl)-propyl-amino]-phenyl}-amide

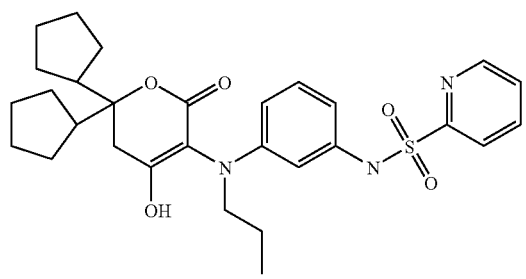

A solution of 3-[(3-Amino-phenyl)-propyl-amino]-6,6-dicyclopentyl-4-hydroxy-5,6-dihydro-pyran-2-one (0.2 g, 0.5 mmol; preparation described in Example 187), pyridine-2-sulfonyl chloride (0.18 g, 0.55 mmol), pyridine (0.2 mL) and dichloromethane (4 mL) were stirred at room temperature overnight. The resulting mixture was quenched with saturated ammonium chloride solution; extracted with ethyl acetate (3×25 mL), and dried over magnesium sulfate. The crude product was purified by flash silica gel chromatography giving the product in yield: 41%. m.p.: 105–107° C. $^1$H NMR (DMSO-d$_6$) δ: 10.8 (brs, 1H), 10.25 (s, 1H), 8.69 (d, 1H), 8.07 (t, 1H),m 7.97 (t, 1H), 7.64 (m, 1H), 6.89 (m, 1H), 6.42(m, 1H), 6.33(d, 1H), 6.14 (tm 1H), 3.08 (m, 2H), 2.72 (dd, ABX, 2H), 2.36–2.07 (m, 2H), 1.17–1.83 (m, 18H), 0.86 (t, 3H); MS (APCI): 540 (M+H), 516, 496, 292; $C_{29}H_{37}O_5N_3S_1$. 0.6H$_2$O: Calc: C63.27, H6.99, N7.64. Found: C63.01; H6.89, N7.63. IR (KBr) cm$^{-1}$: 2957, 1655, 1605, 1173, 593.

Example 185

5-Trifluoromethyl-pyridine-2-sulfonic acid[5-tert-butyl-4-(6,6-dicyclopentyl-4-hydroxy-2-oxo-5,6-dihydro-2H-pyran-3-ylsulfanyl)-2-methyl-phenyl]-amide

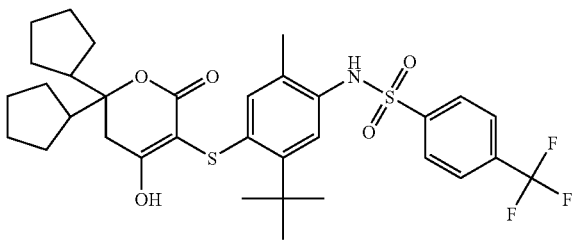

The title compound was prepared as described in Example 133 using 4-(6,6-dicyclopentyl-4-hydroxy-2-oxo-5,6-dihydro-2H-pyranone (0.25 g, 1 mmol described in step 1 in Example 182, instead of 6-Cyclopentyl-4-hydroxy-6-[2-(4-hydroxy-phenyl)-ethyl]-5,6-dihydro-pyran-2-one, toluene-4-thiosulfonic acid S-[2-tert-butyl-5-methyl-4-(5-trifluoromethyl-pyridine-2-sulfonylamino)-phenyl]ester (0.8 mmol, prepared as described in *J. Med Chem.*, 2000; 843–858) and anhydrous potassium carbonate (0.2 g) in DMF (3 mL). Isolated yield: 55%. m.p.: 127–129° C. $^1$H NMR (DMSO-d$_6$) δ: 9.29 (s, 1H), 8.5 (dd, 1H), 8.0 (d, 1H), 6.75 (s, 1H), 6.58 )s, 1H), 2.77 (s, 2H), 2.28–2.14 (m, 2H), 2.02 (s, 3H), 1.75–1.17 (m)+1.23 (s) 25H; MS (APCI): 653 (M+H), 609, 399, 373, 251, 237, 205; $C_{32}H_{39}O_5S_2N_2F_3$. 0.3H$_2$O: Calc: C58.39, H6.06, N4.26. Found: C58.14; H6.09, N4.06. IR (KBr) cm$^{-1}$: 3439, 2957, 1616, 1327, 1179, 1146, 1073.

Example 186

Thiophene-2-sulfonic acid {3-[(6,6-dicyclopentyl-4-hydroxy-2-oxo-5,6-dihydro-2H-pyran-3-yl)-propyl-amino]-phenyl}-amide

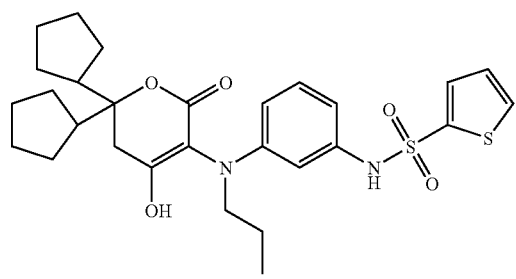

The tile compound was prepared using 3-[(3-Amino-phenyl)-propyl-amino]-6,6-dicyclopentyl-4-hydroxy-5,6-dihydro-pyran-2-one (0.2 g, 0.5 mmol) described in Example 187, thiophene-2-sulfonyl chloride (0.1 g, 0.55 mmol), pyridine (0.2 mL) and dichloromethane (4 mL). The reaction was stirred at room temperature overnight, then was quenched with saturated ammonium chloride. It was extracted with ethyl acetate (3×25 mL); dried over magnesium sulfate. The crude product was purified by flash silica gel chromatography to obtain the title compound. Isolated yield: 5 45%; m.p.: 92–95° C. $^1$H NMR (DMSO-d$_6$) δ: 10.8 (s, 1H), 10.2 (s, 1H), 7.89 (d, 1H),m 7.5 (d, 1H), 7.08 (m, 1H), 6.94 (m, 1H), 6.47 (m, 1H), 6.39 (d, 1H), 6.22 (dd, 1H), 3.19–3.07 (m, 2H), 2.77 (dd, ABX, 2H), 2.37–2.08 (m, 2H), 1.2–1.8 (m, 18H), 0.86 (t, 3H); MS (APCI): 545 (M+H), 521, 338, 297; $C_{28}H_{36}O_5N_2S_2$. 0.5H$_2$O: Calc: C60.73, H6.74, H5.06. Found: C60.41; H6.61, N4.71. IR (KBr) cm$^{-1}$: 344, 2957, 1605, 1158, 591.

Example 187

3-[(3-Amino-phenyl)-propyl-amino]-6,6-dicyclopentyl-4-hydroxy-5,6-dihydro-pyran-2-one Step 1: 6,6-Dicyclopentyl-3-diazo-dihydro-pyran-2,4-dione

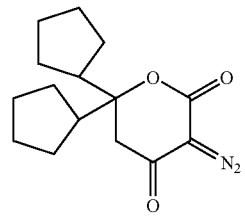

To a solution of 6,6-dicyclopentyl-dihydro-pyran-2,4-dione described in step 1 of Example 182 (1 equivalent), Na$_2$HPO$_4$(1 equivalent), and DMF (0.8 M), was added 4-acetylamino-benzenesulfonyl azide(1 equivalent), at 0 degrees C. The reaction was stirred for 2.5 hours, and then poured into 1 N HCl. The layers were separated, and the aqueous was extracted with EtOAc. The organic was dried with MgSO$_4$ and concentrated. It was then chromatographed. Isolated yield: 69%.

Step 2: 6-Dicyclopentyl-4-hydroxy-3-[(3-nitro-phenyl)-propyl-amino]-5,6-dihydro-pyran-2-one

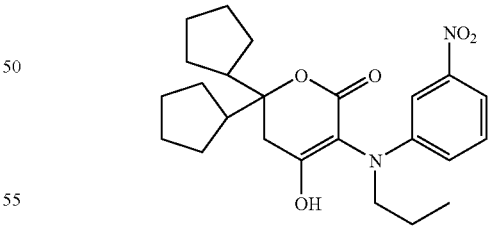

A solution of 6,6-dicyclopentyl-3-diazo-dihydro-pyran-2, 4-dione (0.5 g, 1.81 mmol) from step 1 above, and N-propyl (3-nitro)aniline (1.3 g, 7.24 mmol) in benzene (10 mL) was heated at 85 degrees C. for one minute. Rhodium acetate (0,08 g, 0.181 mmol) was then added and the reaction was stirred for 3 hours. It was diluted with ethyl ether, and extracted with 1N NaOH. The basic extracts were acidified with 1N HCl and extracted with EtOAc. The crude product was purified by flash silica gel chromatography to yield 90% of the product.

Step 3: 3-[(3-Amino-phenyl)-propyl-amino]-6,6-dicyclopentyl-4-hydroxy-5,6-dihydro-pyran-2-one

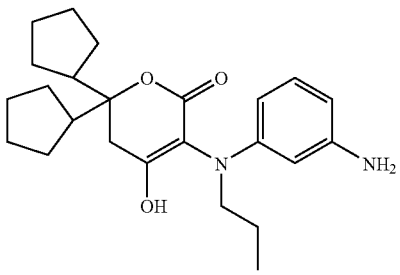

The 6,6-dicyclopentyl-4-hydroxy-3-[(3-nitro-phenyl)-propyl-amino]-5,6-dihydro-pyran-2-one from step 2 above was subjected to hydrogenation using 0.5 g of Raney nickel and 75 mL of methanol and THF (1:1 ratio). Isolated yield: 73%. m.p.: 173–175° C. $^1$H NMR (DMSO-$d_6$) δ: 6.89 (m, 1H), 5.9 m, 2H), 5.77 (t, 1H), 4.77–3.98 (m, 2H), 2.75 (t, 1H), 2.55 (t, 1H), 2.44–2.08 (m, 2H), 1.75–1.83 (m, 18H), 0.89 (m, 3H); MS (APCI): 399 (M+H), 375; $C_{24}H_{34}O_3N_2 \cdot 0.6H_2O$: Calc: C70.42, H8.67, N6.85; Found: C70.70; H8.65, N6.38. IR (KBr) cm$^{-1}$: 2956, 1654, 1613, 1499, 1388, 1213.

HCV Polymerase Inhibition Assay

The above-described compounds were tested for activity with HCV polymerase. Recombinant HCV polymerase was tested for its ability to perform primer/template-directed transcription in assays that contained 30 mM tris-HCl pH 7.2, 10 mM $MgCl_2$, 20 mM NaCl, 1 mM Dithiothreitol (DTT), 0.05% Tween-20, 1% glycerol, 5 pmoles biotin-$dG_{12}$ (primer), 0.5 pmoles poly(rC)$_{300}$ (template), 1 μM GTP, 0.1–0.3 uCi α-$^{32}$P-GTP, and 2.5 pmoles (0.15 μg) HCV polymerase protein in a final volume of 75 μL. Reactions were initiated by addition of enzyme and incubated 30 minutes at 30° C. Reactions were stopped by addition of 33 mM EDTA, and polynucleotide products were collected by filtration through Diethylaminoethyl (DE) Filtermat papers (Wallac). Unincorporated triphosphate was removed by washing the filters with 5% dibasic sodium phosphate. The filters were counted in a Packard Tri-Lux Microbeta scintillation counter (Packard Bioscience, Meriden, Conn.). Compounds to be tested were added at various concentrations, e.g., 1 μm to 50 μm, from stocks in 10% DMSO-water (final DMSO is 1% in reaction).

$IC_{50}$ values were estimated from the primary cpm data (collected in triplicate) using the formula: cpm (I)=cpm (no inhibitor)(1−([I]/([I]+$IC_{50}$))). An $IC_{50}$ value represents the concentration (in μM) of a compound that provides 50% inhibition of polymerase-directed transcription in the above assay. A percent inhibition value is expressed for a compound where it was impractical to calculate an $IC_{50}$ value with available data. If the $IC_{50}$ estimated by the above equation was less than 200 nM, it was recalculated using the following equation, which takes into account the enzyme concentration (30 nM) in the assay: cpm(I)=cpm(no inhibitor)(1−((((I+$IC_{50}$+30e−9)−sqrt(((I+$IC_{50}$+30e−9)$^2$)−4×30e−9×I)))/((2) (30e−9))). Curve fitting was performed using the program KaleidaGraph (Synergy Software, Reading, Pa.).

Inhibition concentration ($IC_{50}$) data as determined for exemplary compounds of the invention are presented in Table 1 below. The $IC_{50}$ values were divided into four categories based on the following μM ranges:
A: less than about 1.0 μM
B: from about 1.0 to about 10 μM
C: from about 10 to about 50 μM
D: greater than about 50 μM.

TABLE 1

HCV Polymerase Inhibition Assay

| Example Number | Structure | $IC_{50}$(μM) Category |
|---|---|---|
| 1 | 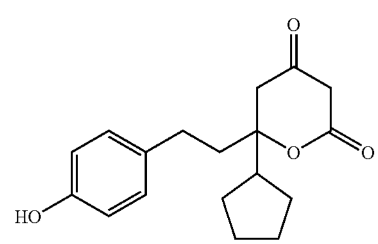 | C |
| 2 | 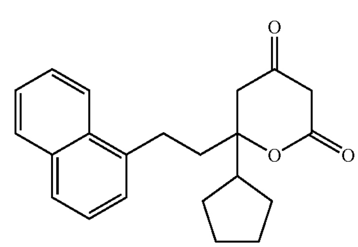 | D |

TABLE 1-continued

HCV Polymerase Inhibition Assay

| Example Number | Structure | IC$_{50}$(μM) Category |
|---|---|---|
| 3 | 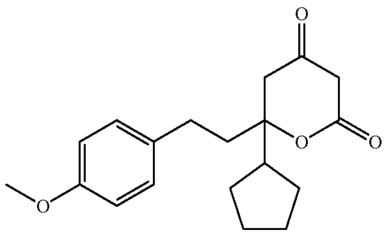 | B |
| 4 | 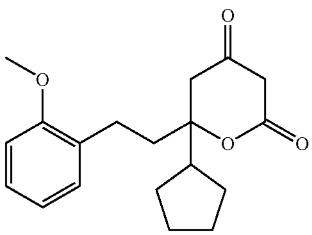 | C |
| 5 | 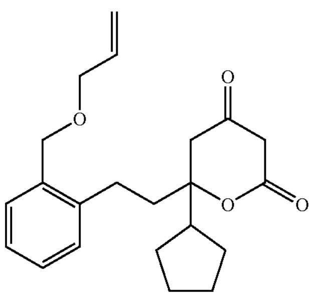 | C |
| 6 | 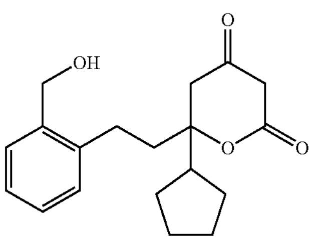 | C |
| 7 | 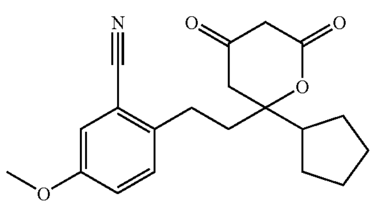 | C |
| 8 | 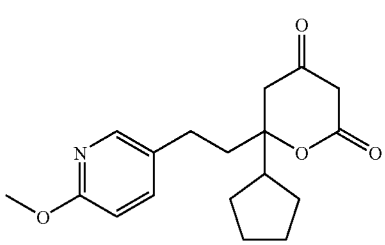 | C |

TABLE 1-continued
HCV Polymerase Inhibition Assay
| Example Number | Structure | IC$_{50}$(μM) Category |
|---|---|---|
| 9 | 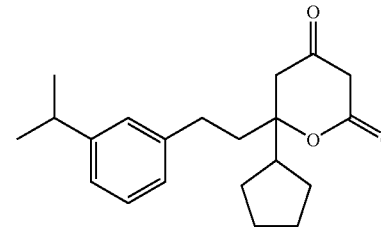 | B |
| 10 | 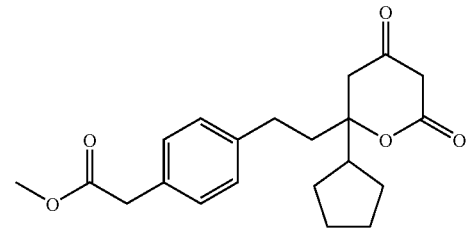 | C |
| 11 | 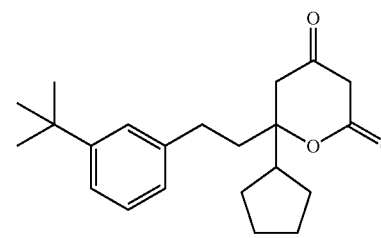 | B |
| 12 | 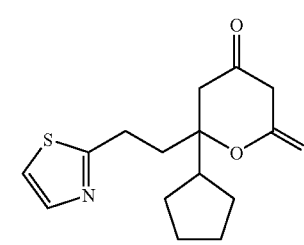 | D |
| 13 | 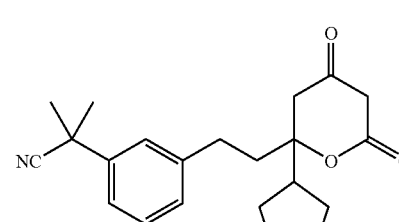 | B |
| 14 | 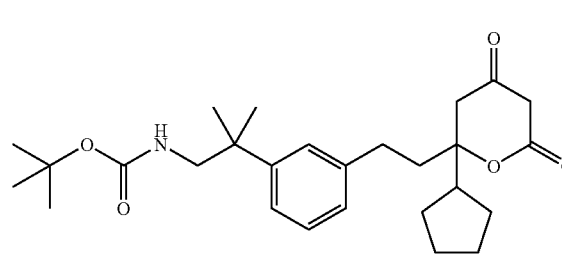 | C |

TABLE 1-continued

HCV Polymerase Inhibition Assay

| Example Number | Structure | IC$_{50}$(μM) Category |
|---|---|---|
| 15 | 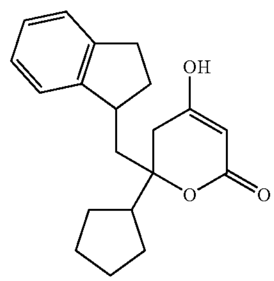 | D |
| 16 | 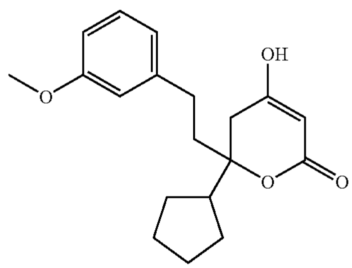 | C |
| 17 | 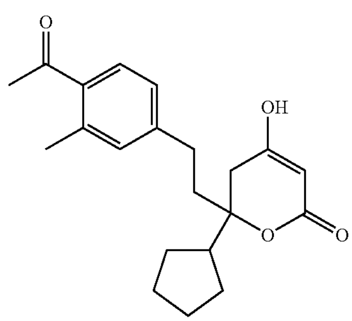 | B |
| 18 | 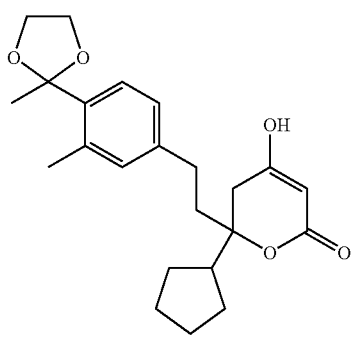 | B |
| 19 | 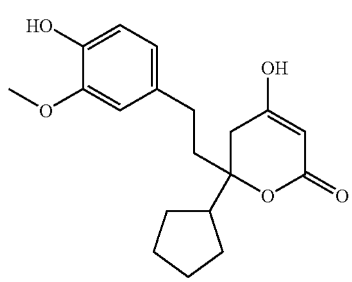 | B |

TABLE 1-continued

HCV Polymerase Inhibition Assay

| Example Number | Structure | IC$_{50}$(μM) Category |
|---|---|---|
| 20 | 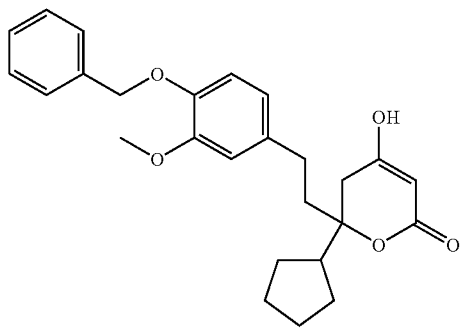 | B |
| 21 | 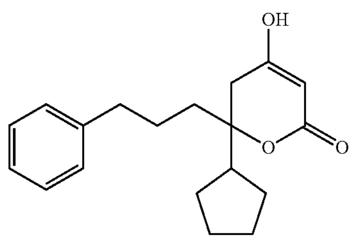 | D |
| 22 | 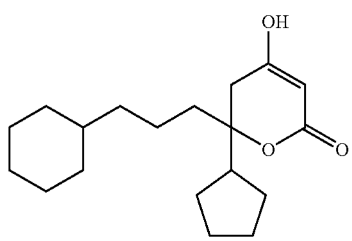 | C |
| 23 | 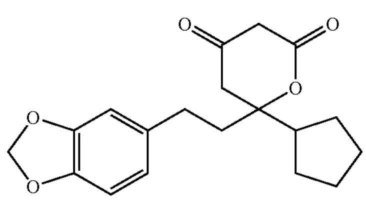 | C |
| 24 | 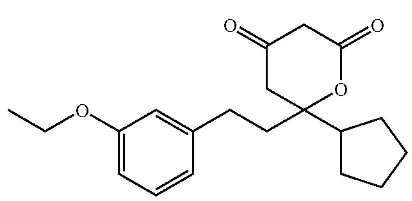 | B |
| 25 | 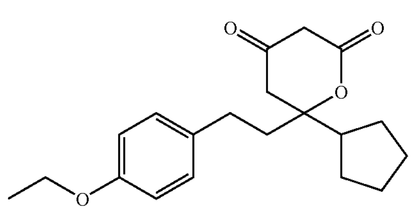 | B |

TABLE 1-continued

HCV Polymerase Inhibition Assay

| Example Number | Structure | IC$_{50}$(μM) Category |
|---|---|---|
| 26 | 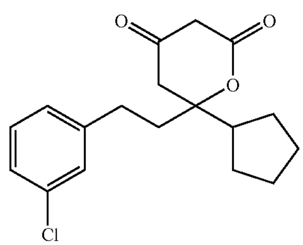 | B |
| 27 | 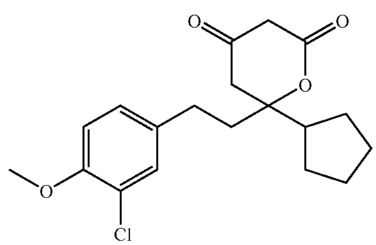 | B |
| 28 | 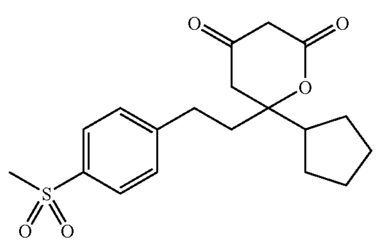 | B |
| 29 | 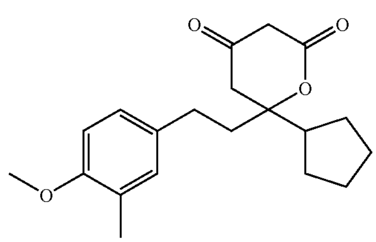 | B |
| 30 | 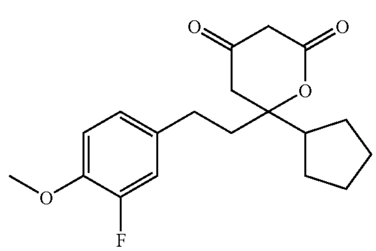 | A |
| 31 | 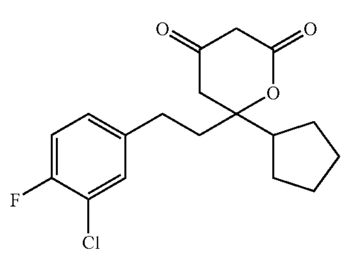 | B |

TABLE 1-continued

HCV Polymerase Inhibition Assay

| Example Number | Structure | IC$_{50}$(μM) Category |
|---|---|---|
| 32 | 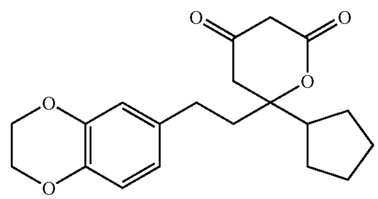 | B |
| 33 | 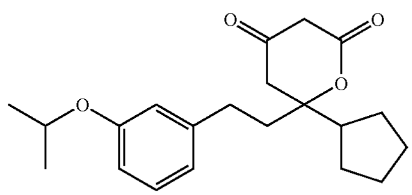 | B |
| 34 | 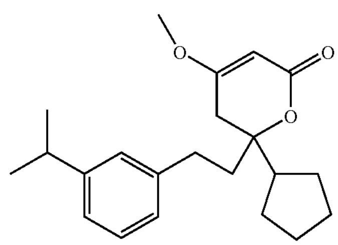 | C |
| 35 | 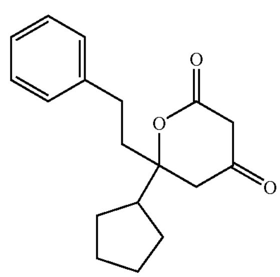 | C |
| 36 | 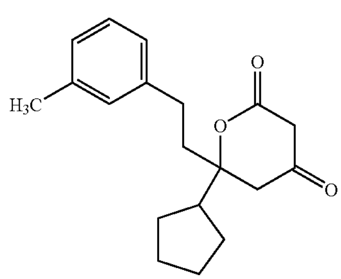 | C |
| 37 | 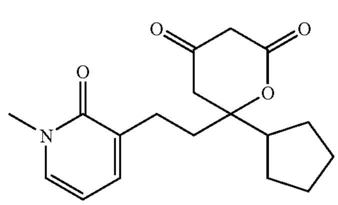 | D |

TABLE 1-continued

HCV Polymerase Inhibition Assay

| Example Number | Structure | IC$_{50}$(μM) Category |
|---|---|---|
| 38 | 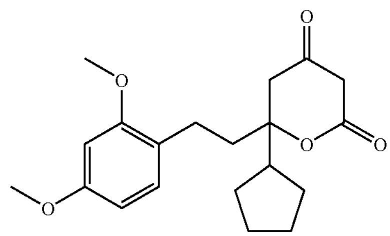 | C |
| 39 | 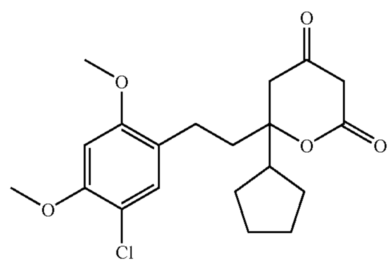 | A |
| 40 | 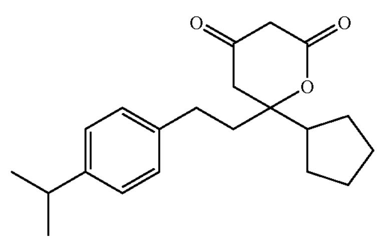 | B |
| 41 | 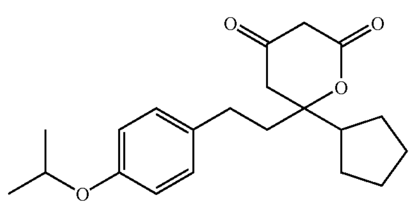 | B |
| 42 | 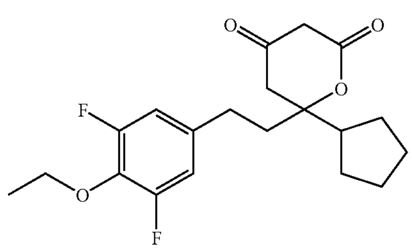 | B |
| 43 | 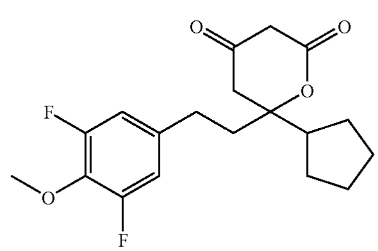 | B |

TABLE 1-continued

HCV Polymerase Inhibition Assay

| Example Number | Structure | IC$_{50}$(μM) Category |
|---|---|---|
| 44 | 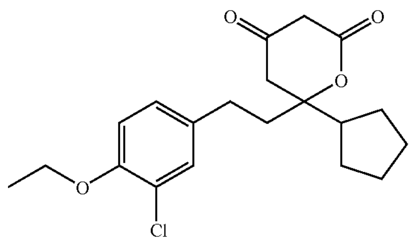 | A |
| 45 | 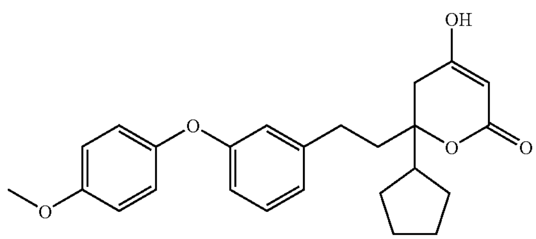 | C |
| 46 | 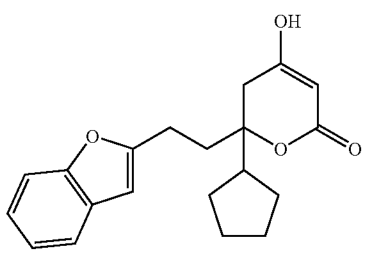 | C |
| 47 | 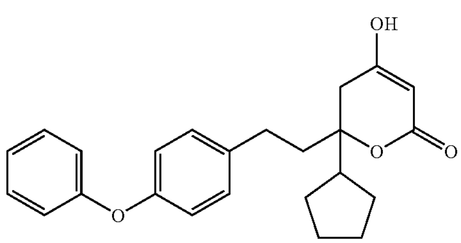 | C |
| 48 | 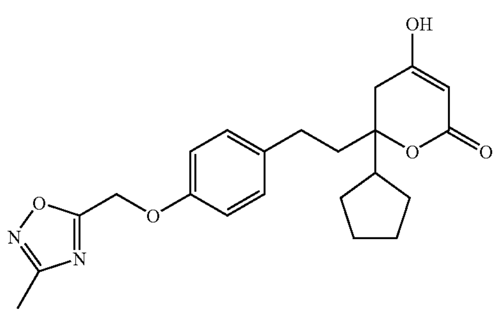 | C |

TABLE 1-continued

HCV Polymerase Inhibition Assay

| Example Number | Structure | IC$_{50}$(μM) Category |
|---|---|---|
| 49 | 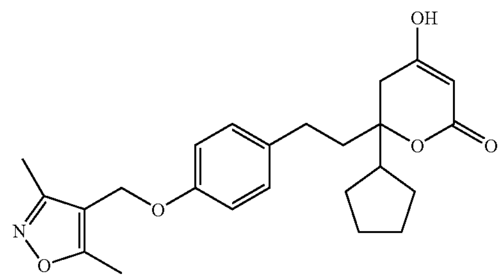 | C |
| 50 | 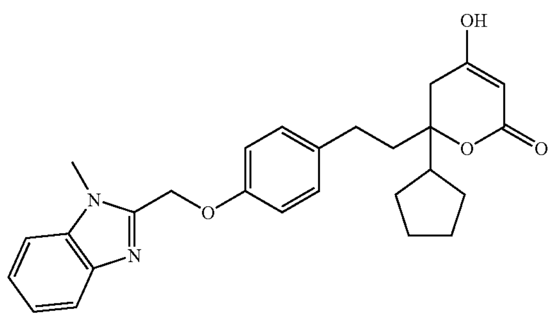 | C |
| 51 | 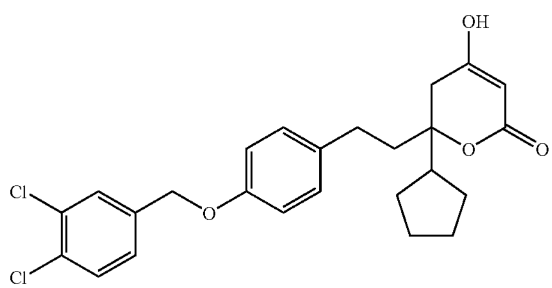 | C |
| 52 | 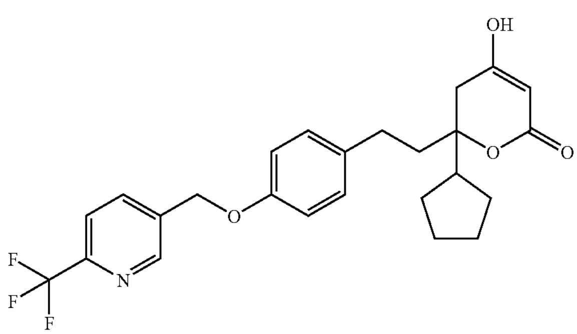 | C |
| 53 | 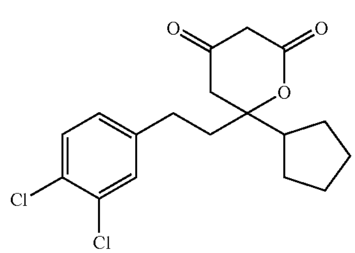 | B |

TABLE 1-continued

HCV Polymerase Inhibition Assay

| Example Number | Structure | IC$_{50}$(µM) Category |
|---|---|---|
| 54 | | C |
| 55 | | B |
| 56 | | B |
| 57 | | B |
| 58 | | D |
| 59 | | B |

TABLE 1-continued
HCV Polymerase Inhibition Assay
| Example Number | Structure | IC$_{50}$(μM) Category |
|---|---|---|
| 60 | 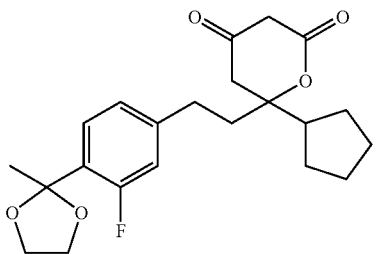 | B |
| 61 | 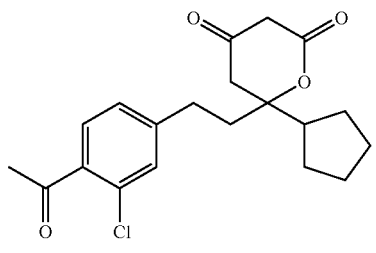 | B |
| 62 | 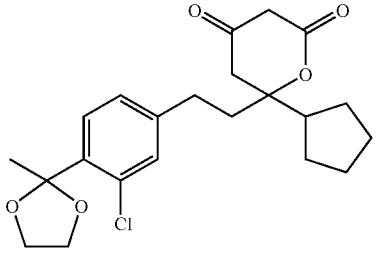 | A |
| 63 | 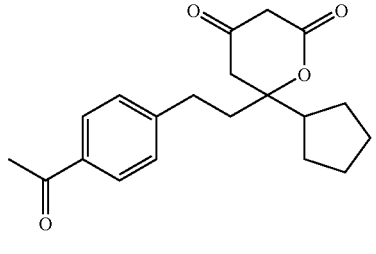 | B |
| 64 | 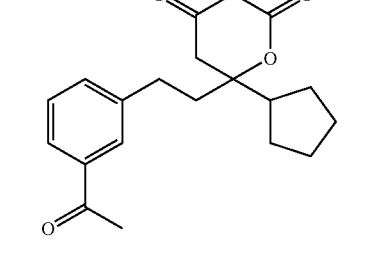 | B |

TABLE 1-continued

HCV Polymerase Inhibition Assay

| Example Number | Structure | IC$_{50}$(μM) Category |
|---|---|---|
| 65 | | B |
| 66 | | A |
| 67 | | D |
| 68 | | D |

TABLE 1-continued

HCV Polymerase Inhibition Assay

| Example Number | Structure | IC$_{50}$(μM) Category |
|---|---|---|
| 69 | 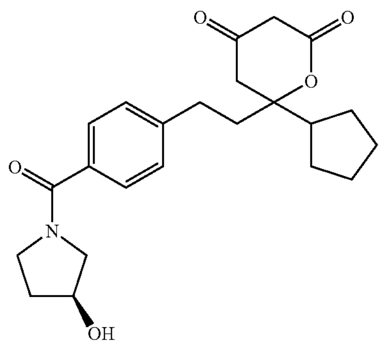 | C |
| 70 | 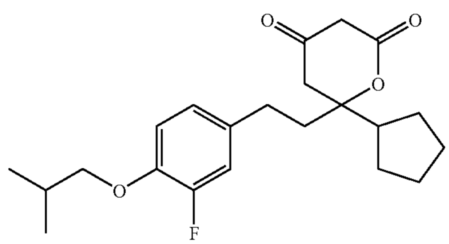 | B |
| 71 | 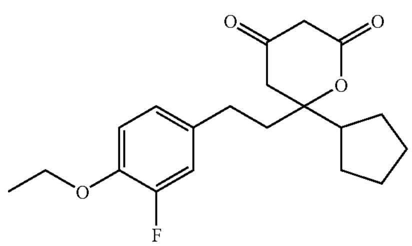 | A |
| 72 | 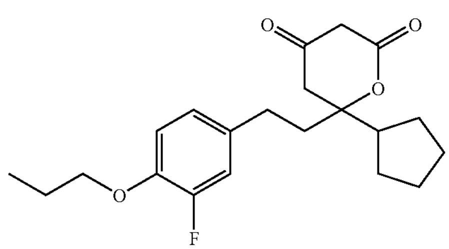 | B |
| 73 | 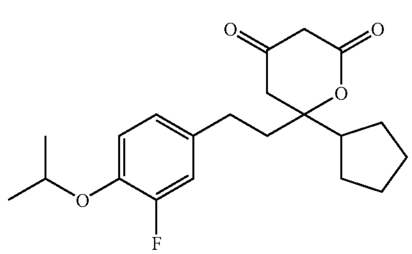 | A |

TABLE 1-continued

HCV Polymerase Inhibition Assay

| Example Number | Structure | IC$_{50}$(μM) Category |
|---|---|---|
| 74 | 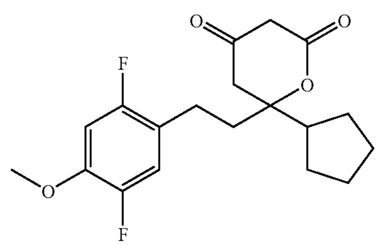 | B |
| 75 | 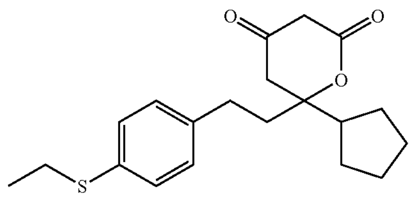 | B |
| 76 | 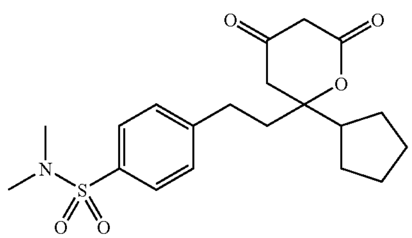 | C |
| 77 | 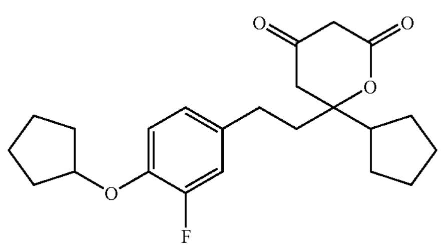 | B |
| 78 | 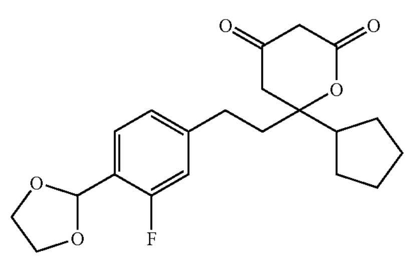 | B |
| 79 | 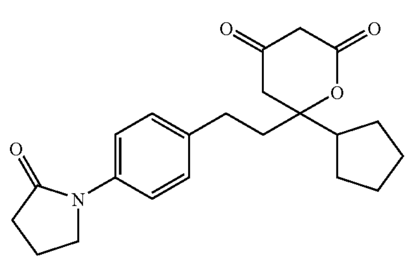 | B |

TABLE 1-continued

HCV Polymerase Inhibition Assay

| Example Number | Structure | IC$_{50}$(μM) Category |
|---|---|---|
| 80 | | B |
| 81 | | A |
| 82 | | A |
| 83 | | B |
| 84 | | B |

TABLE 1-continued

HCV Polymerase Inhibition Assay

| Example Number | Structure | IC$_{50}$(μM) Category |
|---|---|---|
| 85 | 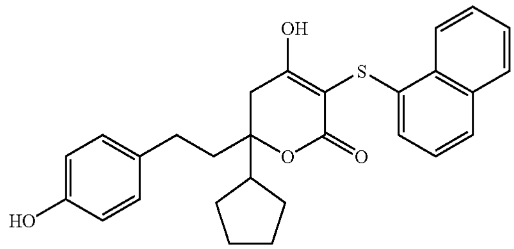 | B |
| 86 | 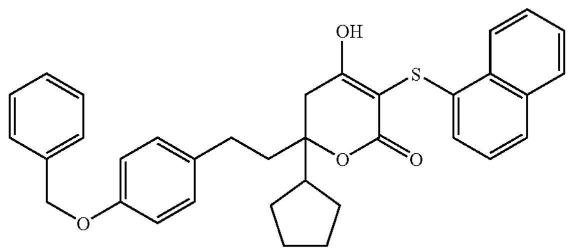 | B |
| 87 | 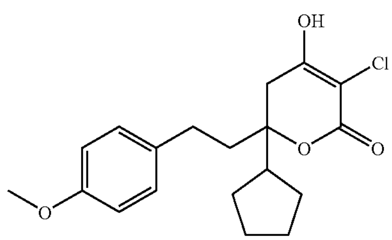 | C |
| 88 | 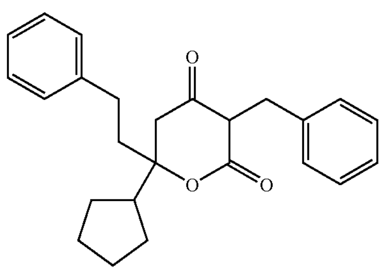 | C |
| 89 | 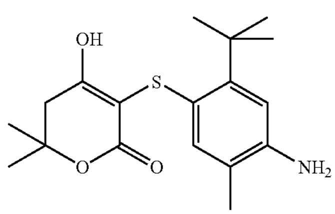 | D |
| 90 | 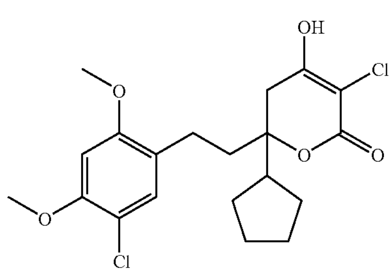 | A |

TABLE 1-continued
HCV Polymerase Inhibition Assay
| Example Number | Structure | IC$_{50}$(μM) Category |
|---|---|---|
| 91 | 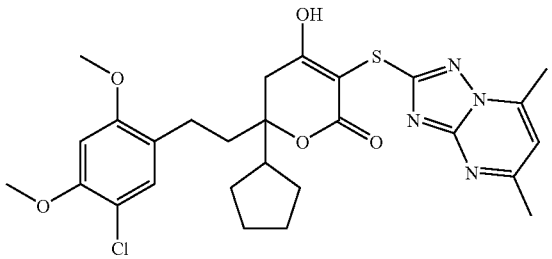 | A |
| 92 | 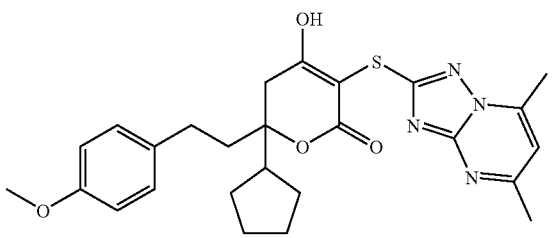 | A |
| 93 | 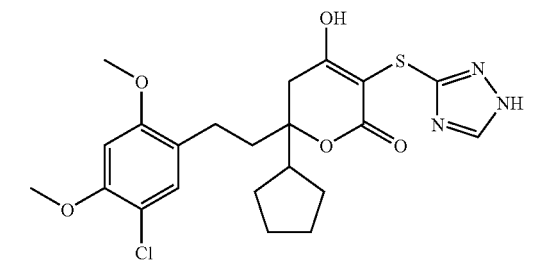 | A |
| 94 | 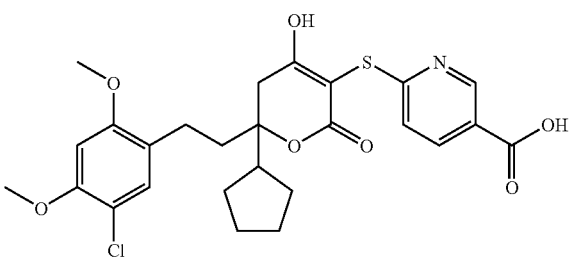 | A |
| 95 | 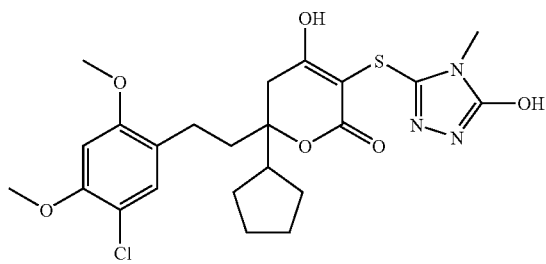 | A |

TABLE 1-continued

HCV Polymerase Inhibition Assay

| Example Number | Structure | IC$_{50}$(μM) Category |
|---|---|---|
| 96 | 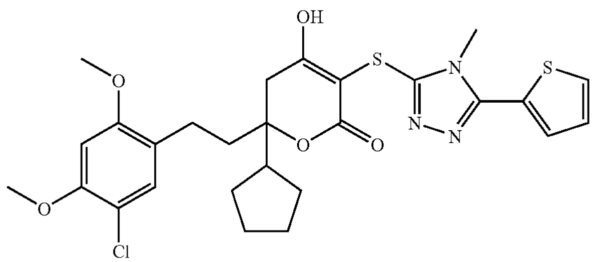 | A |
| 97 | 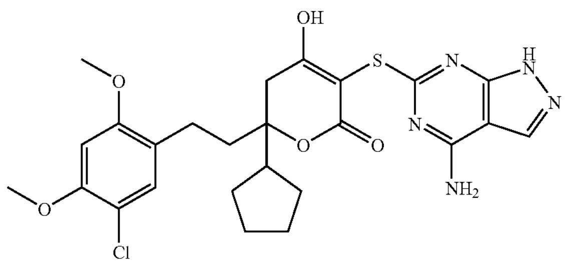 | A |
| 98 | 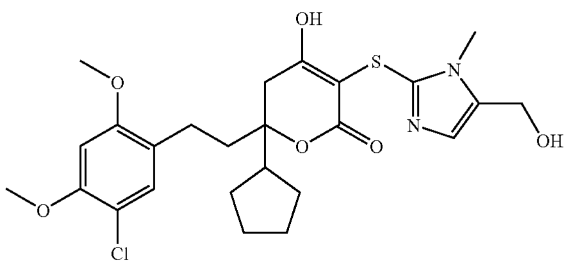 | A |
| 99 | 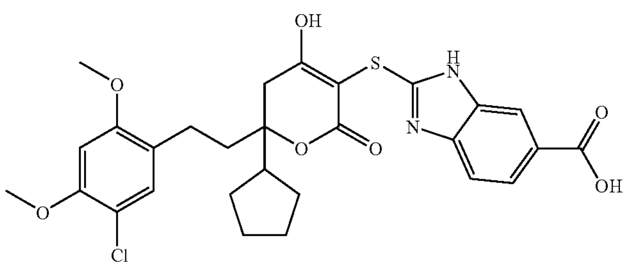 | A |
| 100 | 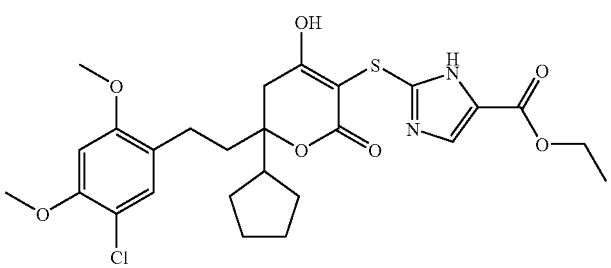 | A |

TABLE 1-continued

HCV Polymerase Inhibition Assay

| Example Number | Structure | IC$_{50}$(µM) Category |
|---|---|---|
| 101 | | A |
| 102 | | A |
| 103 | | D |
| 104 | | C |
| 105 | | A |

TABLE 1-continued

HCV Polymerase Inhibition Assay

| Example Number | Structure | IC$_{50}$(μM) Category |
|---|---|---|
| 106 | 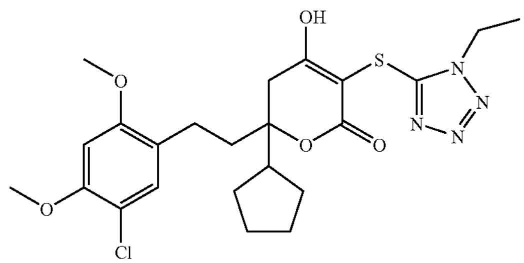 | A |
| 107 | 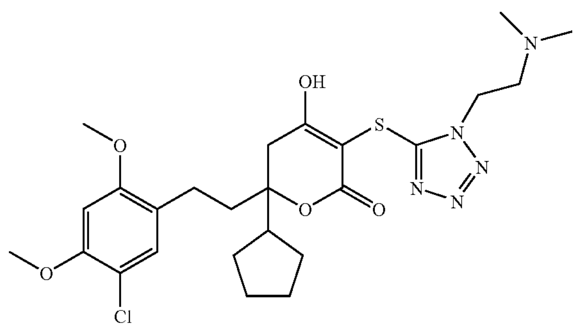 | A |
| 108 | 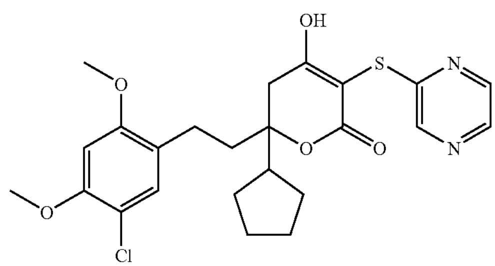 | A |
| 109 | 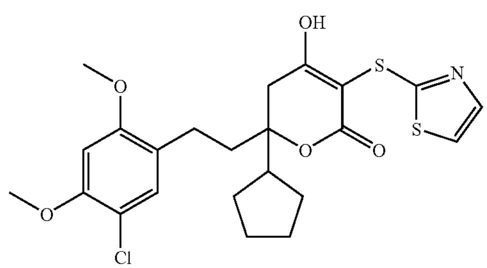 | A |
| 110 | 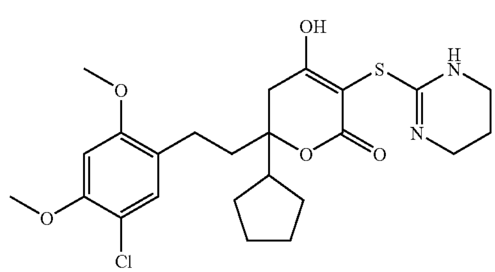 | A |

TABLE 1-continued
HCV Polymerase Inhibition Assay
| Example Number | Structure | IC$_{50}$(μM) Category |
|---|---|---|
| 111 | 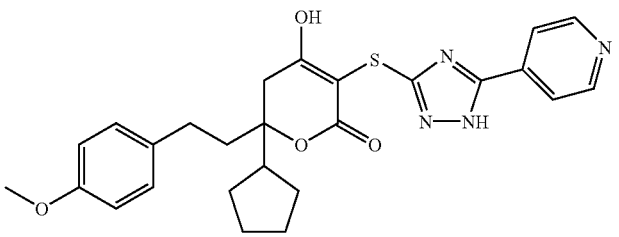 | A |
| 112 | 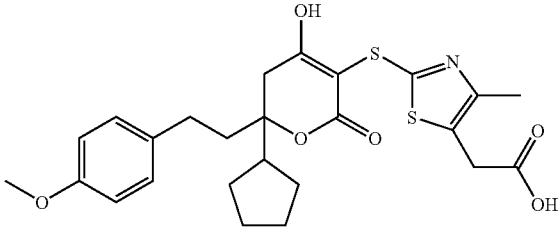 | A |
| 113 | 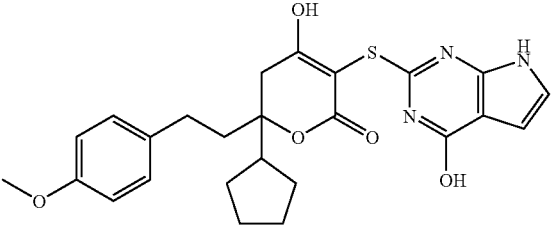 | A |
| 114 | 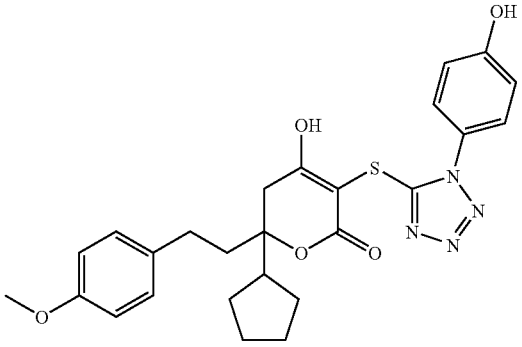 | A |
| 115 | 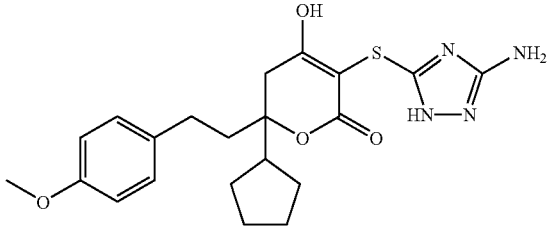 | B |

TABLE 1-continued
HCV Polymerase Inhibition Assay
| Example Number | Structure | $IC_{50}(\mu M)$ Category |
|---|---|---|
| 116 | 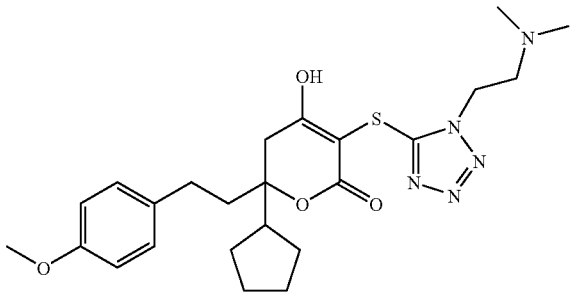 | B |
| 117 | 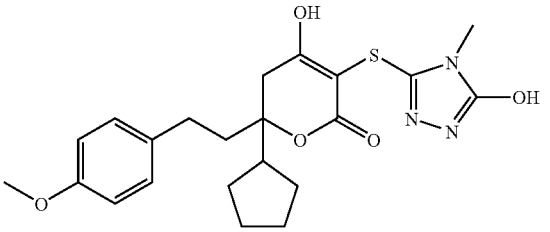 | B |
| 118 | 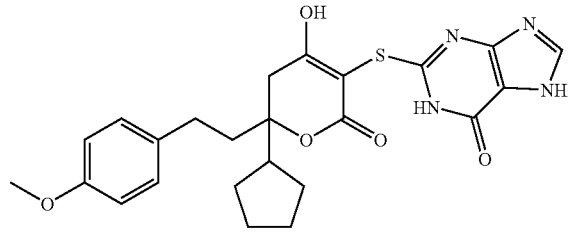 | A |
| 119 | 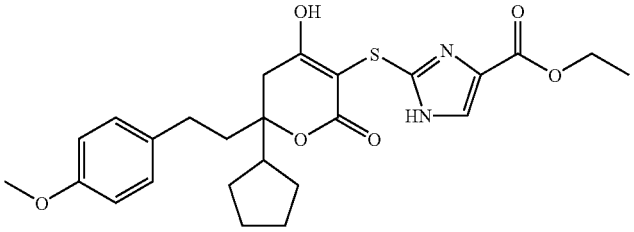 | B |
| 120 | 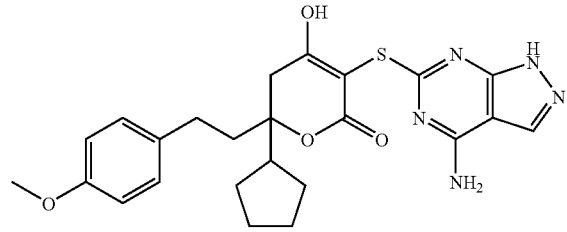 | A |
| 121 | 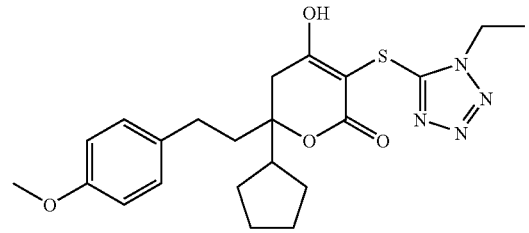 | A |

TABLE 1-continued
HCV Polymerase Inhibition Assay
| Example Number | Structure | IC$_{50}$(µM) Category |
|---|---|---|
| 122 | 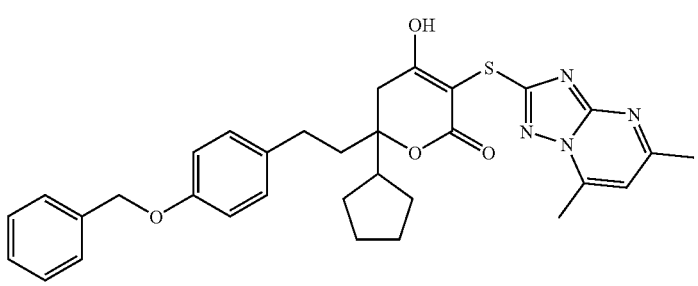 | A |
| 123 | 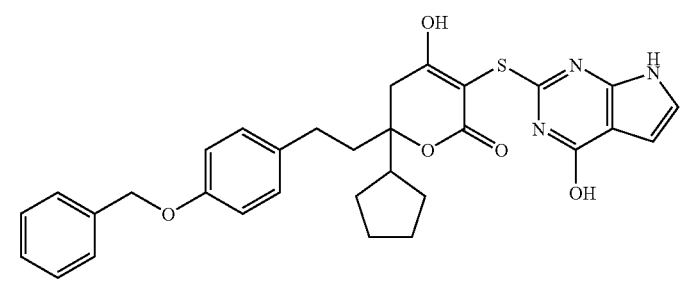 | A |
| 124 | 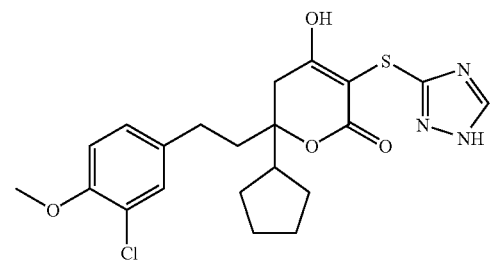 | A |
| 125 | 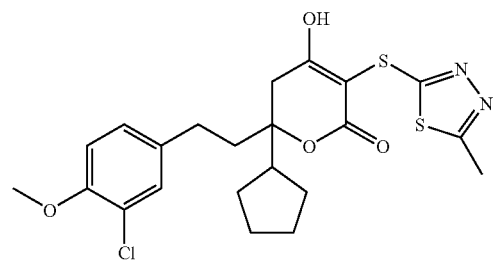 | A |
| 126 | 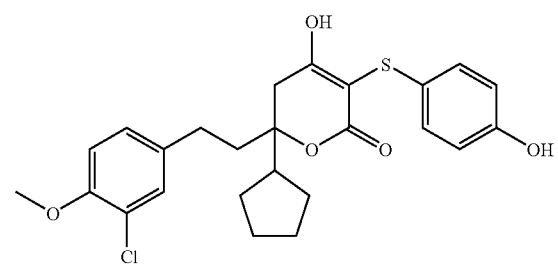 | A |

TABLE 1-continued

HCV Polymerase Inhibition Assay

| Example Number | Structure | IC$_{50}$(μM) Category |
|---|---|---|
| 127 | 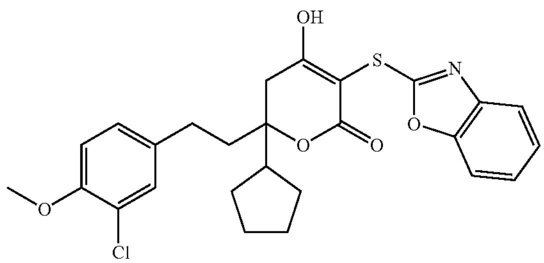 | A |
| 128 | 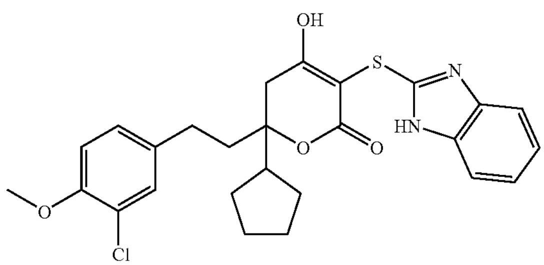 | A |
| 129 | 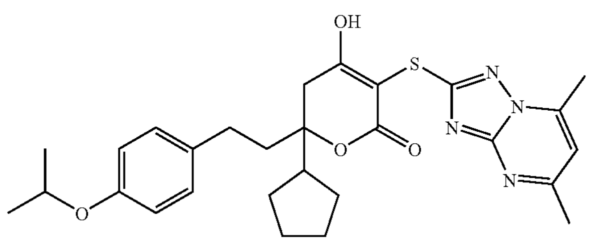 | A |
| 130 | 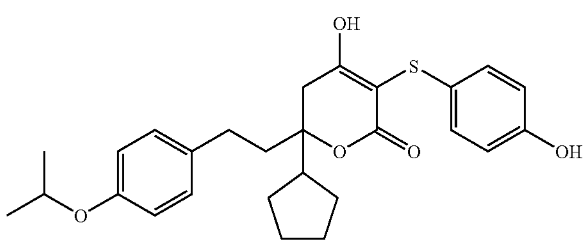 | A |
| 131 | 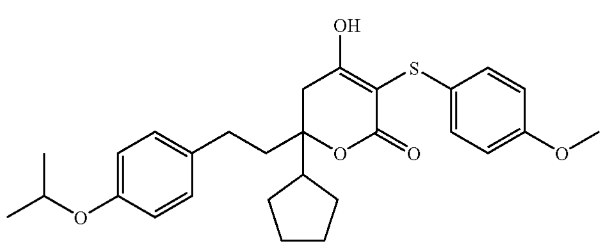 | A |
| 132 | 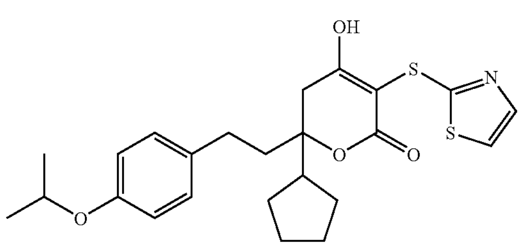 | A |

TABLE 1-continued

HCV Polymerase Inhibition Assay

| Example Number | Structure | IC$_{50}$(μM) Category |
|---|---|---|
| 133 | 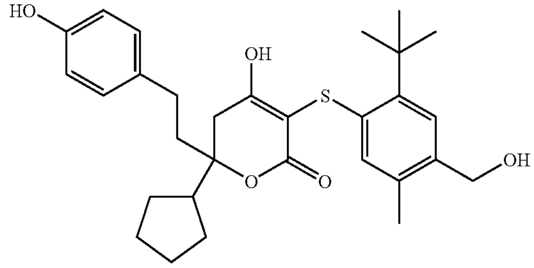 | A |
| 134 | 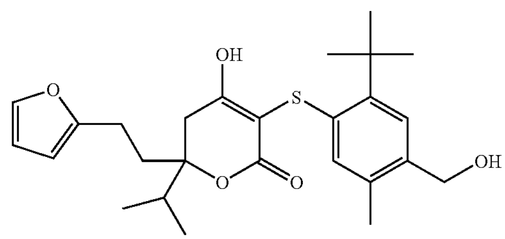 | B |
| 135 | 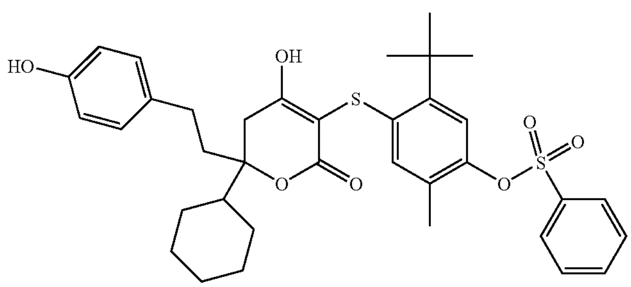 | C |
| 136 | 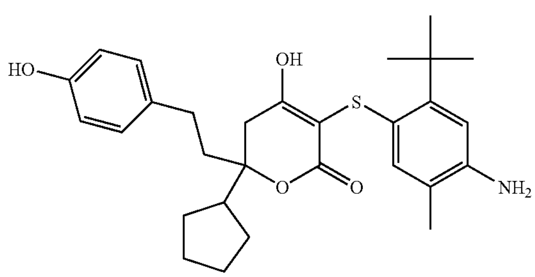 | A |
| 137 | 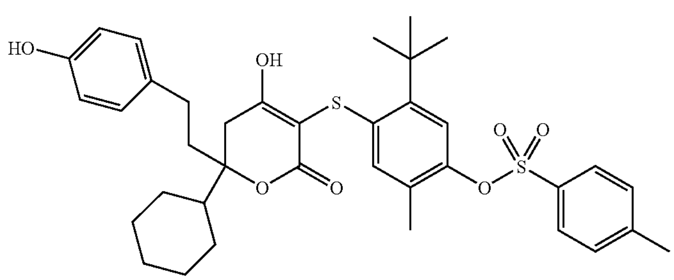 | C |

TABLE 1-continued

HCV Polymerase Inhibition Assay

| Example Number | Structure | IC$_{50}$(μM) Category |
|---|---|---|
| 138 | 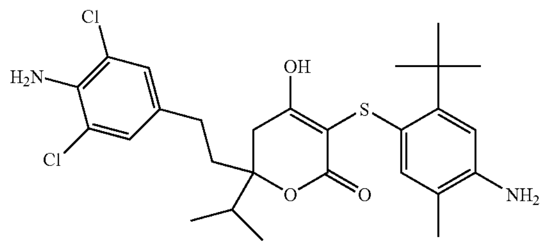 | C |
| 139 | 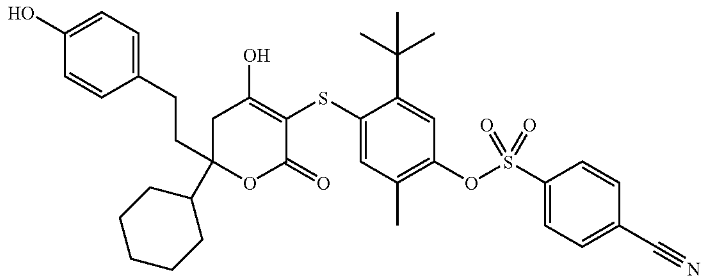 | B |
| 140 | 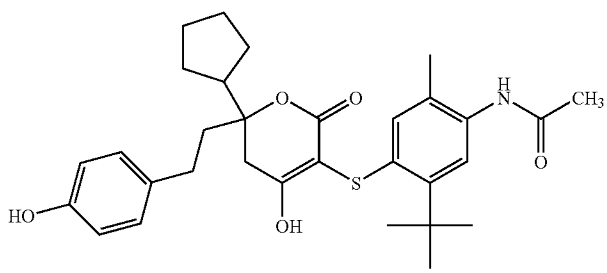 | B |
| 141 | 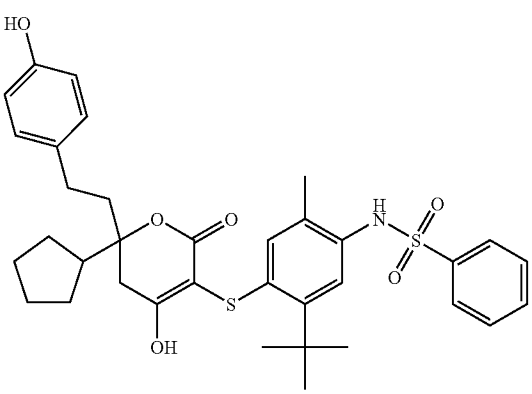 | B |
| 142 | 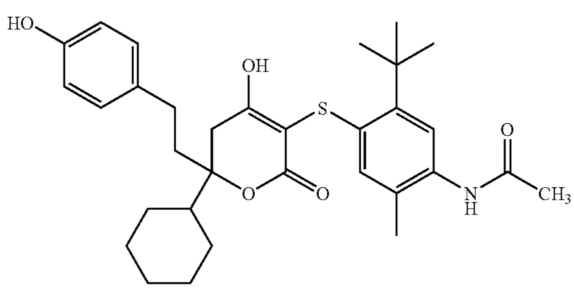 | D |

TABLE 1-continued

HCV Polymerase Inhibition Assay

| Example Number | Structure | IC$_{50}$(μM) Category |
|---|---|---|
| 143 | | B |
| 144 | | D |
| 145 | | C |
| 146 | | B |
| 147 | | B |

TABLE 1-continued

HCV Polymerase Inhibition Assay

| Example Number | Structure | IC$_{50}$(μM) Category |
|---|---|---|
| 148 | 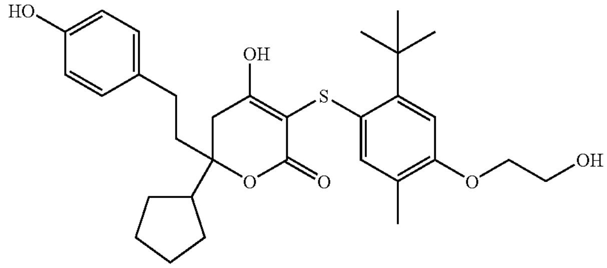 | B |
| 149 | 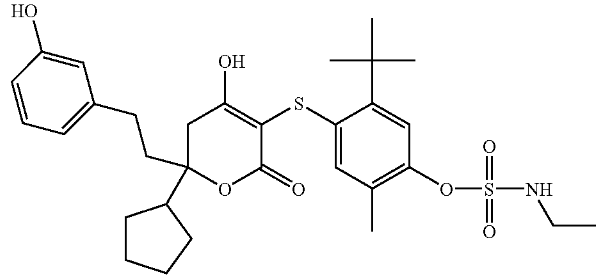 | D |
| 150 | 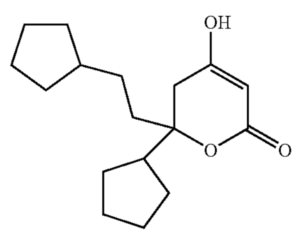 | C |
| 151 | 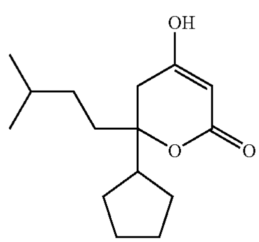 | D |
| 152 | (chiral) | B |

TABLE 1-continued
HCV Polymerase Inhibition Assay
| Example Number | Structure | IC$_{50}$(μM) Category |
|---|---|---|
| 153 | 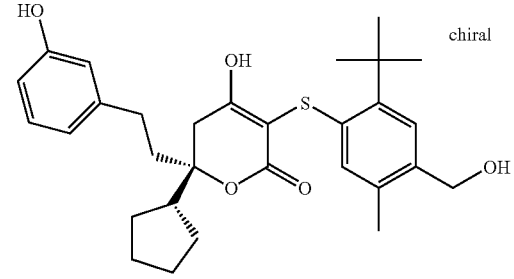 | A |
| 154 | 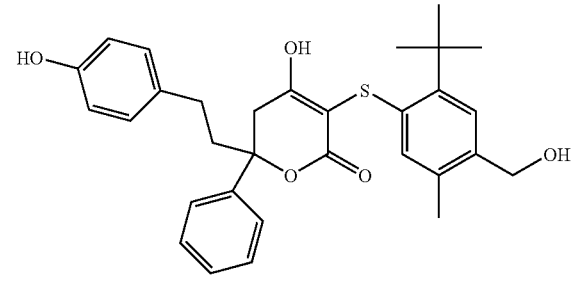 | D |
| 155 | 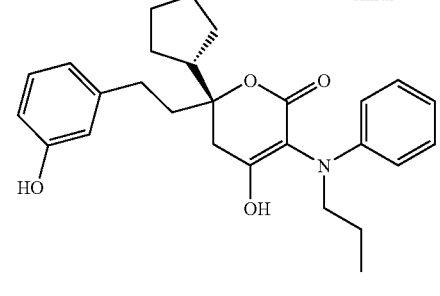 | B |
| 156 | 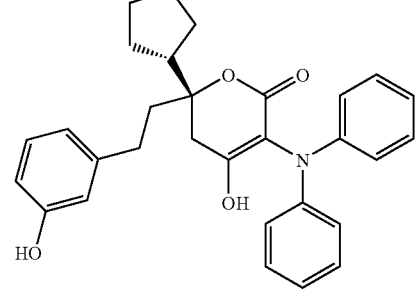 | C |

TABLE 1-continued
HCV Polymerase Inhibition Assay
| Example Number | Structure | IC$_{50}$(μM) Category |
|---|---|---|
| 157 | 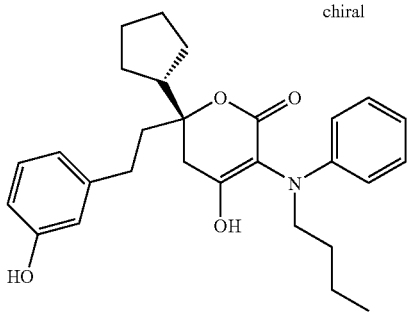 chiral | B |
| 158 | 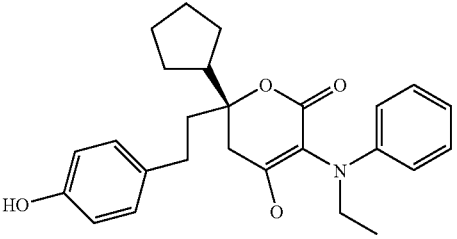 | B |
| 159 | 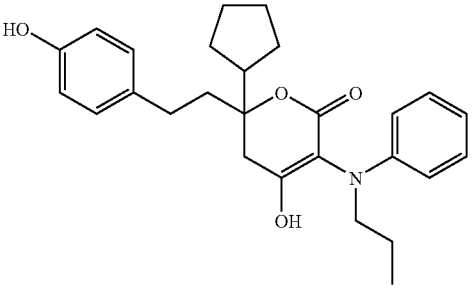 | B |
| 160 | 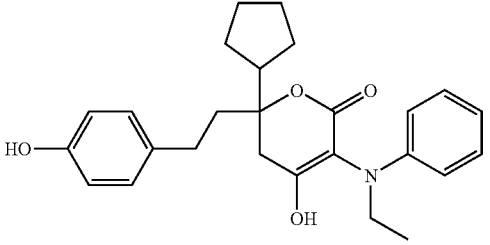 | B |
| 161 | 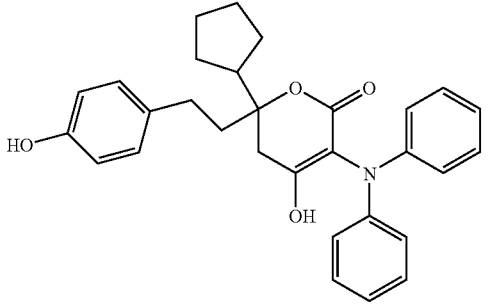 | B |

TABLE 1-continued

HCV Polymerase Inhibition Assay

| Example Number | Structure | IC$_{50}$(µM) Category |
|---|---|---|
| 162 | 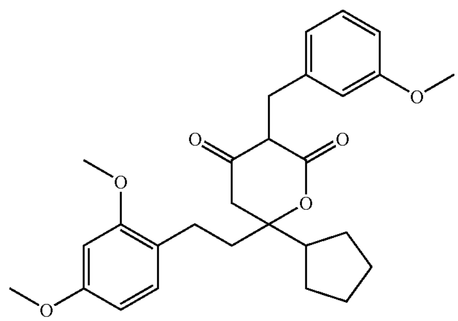 | B |
| 163 | 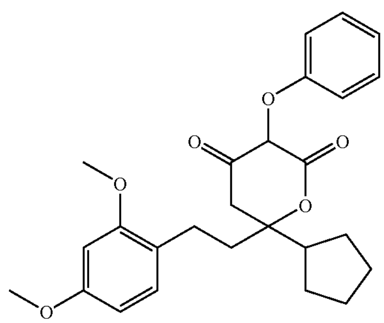 | C |
| 164 | 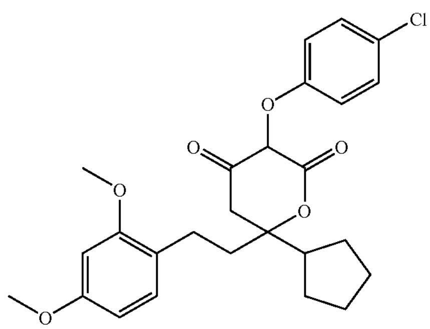 | C |
| 165 | 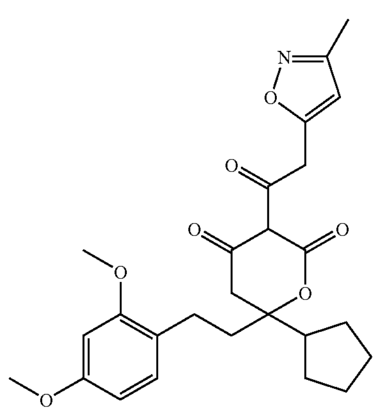 | C |

TABLE 1-continued

HCV Polymerase Inhibition Assay

| Example Number | Structure | IC$_{50}$(μM) Category |
|---|---|---|
| 166 | 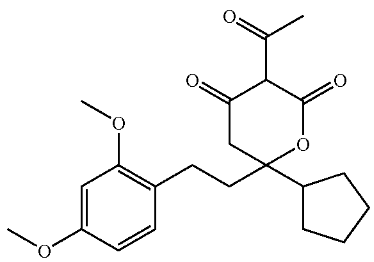 | C |
| 167 | 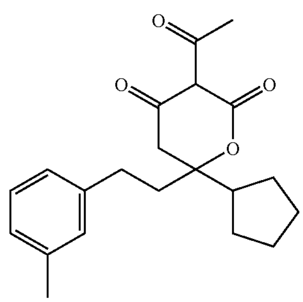 | C |
| 168 | 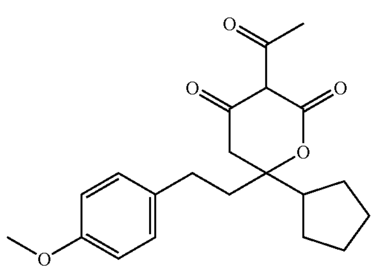 | C |
| 169 | 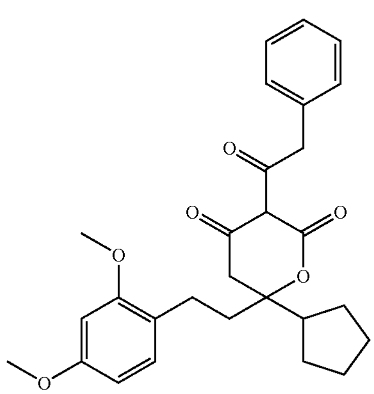 | C |

TABLE 1-continued
HCV Polymerase Inhibition Assay
| Example Number | Structure | IC$_{50}$(μM) Category |
|---|---|---|
| 170 | 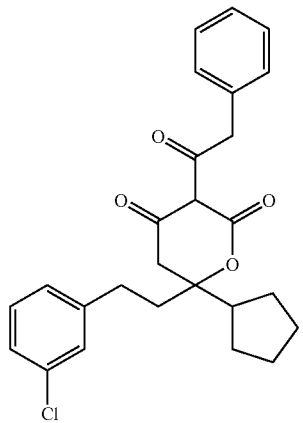 | C |
| 171 | 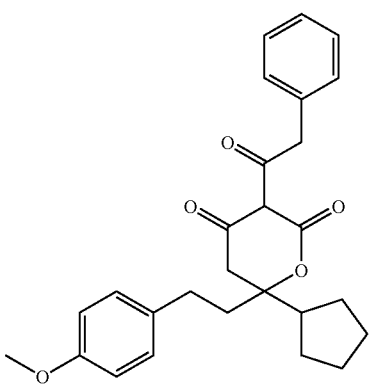 | C |
| 172 | 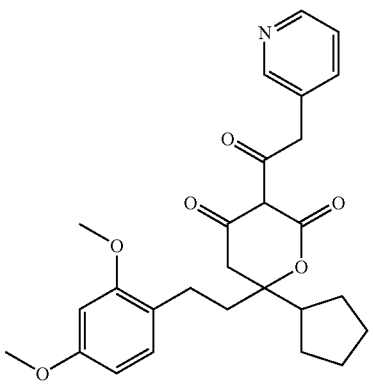 | B |

TABLE 1-continued
HCV Polymerase Inhibition Assay
| Example Number | Structure | IC$_{50}$(μM) Category |
|---|---|---|
| 173 | 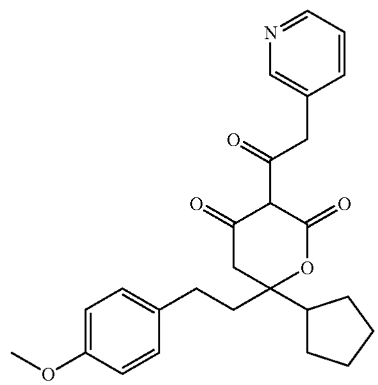 | B |
| 174 | 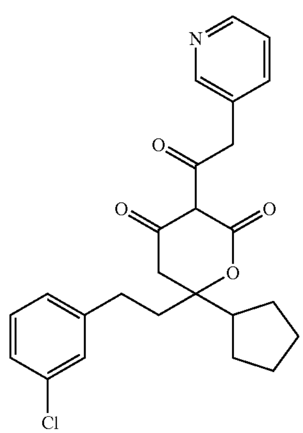 | B |
| 175 | 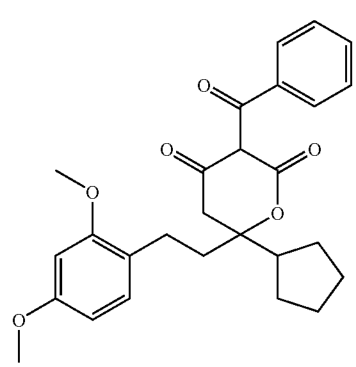 | C |
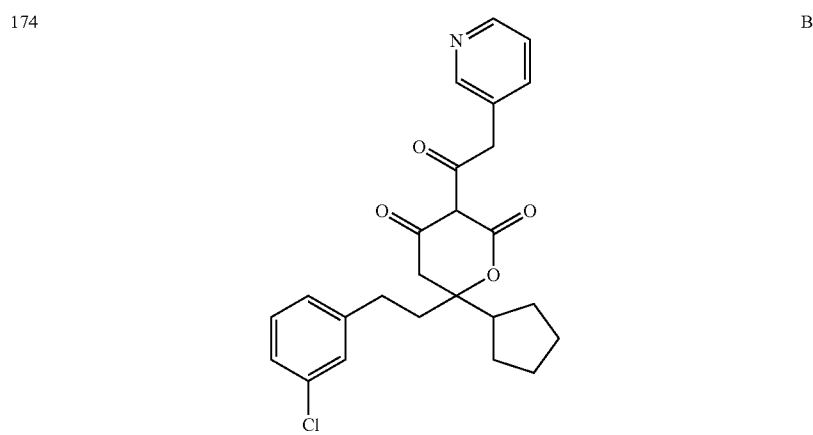
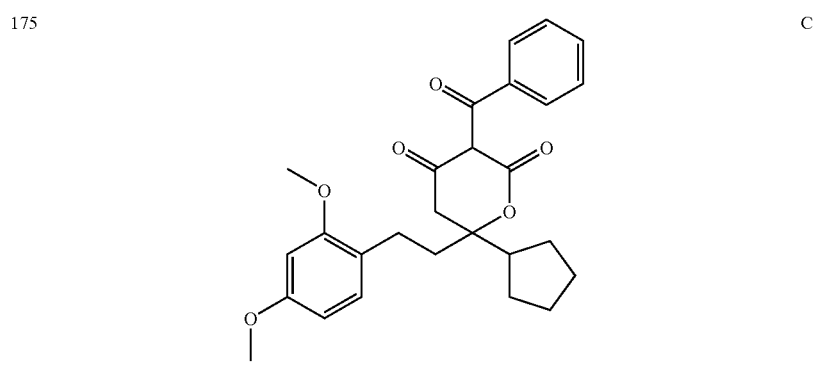

TABLE 1-continued

HCV Polymerase Inhibition Assay

| Example Number | Structure | IC$_{50}$(µM) Category |
|---|---|---|
| 176 | | C |
| 177 | | 5.5 |
| 178 | | 0.6 |
| 179 | | 15.5 |

TABLE 1-continued

HCV Polymerase Inhibition Assay

| Example Number | Structure | IC$_{50}$(μM) Category |
|---|---|---|
| 180 | 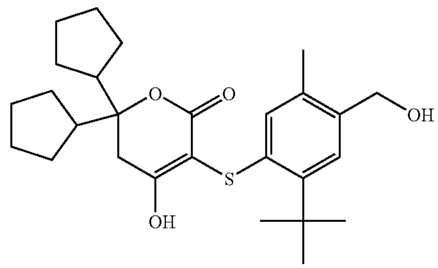 | 15 |
| 181 | 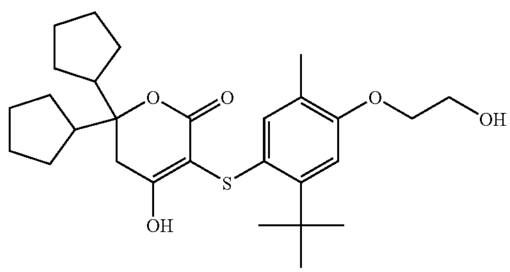 | 36 |
| 182 | 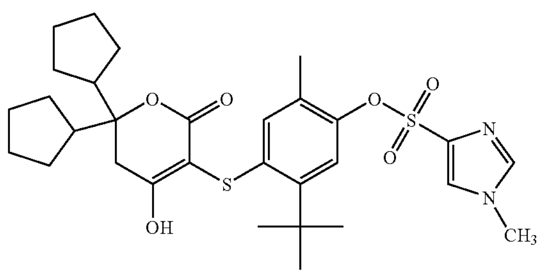 | C |
| 183 | 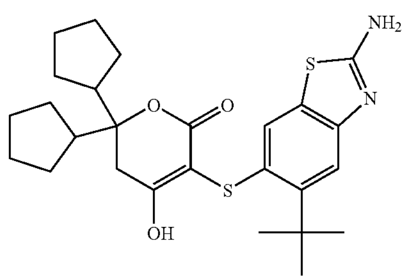 | C |
| 184 | 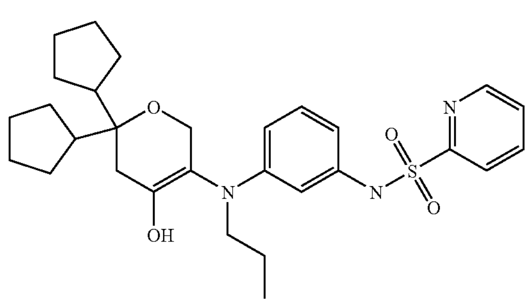 | C |

TABLE 1-continued

HCV Polymerase Inhibition Assay

| Example Number | Structure | IC$_{50}$(μM) Category |
|---|---|---|
| 185 | 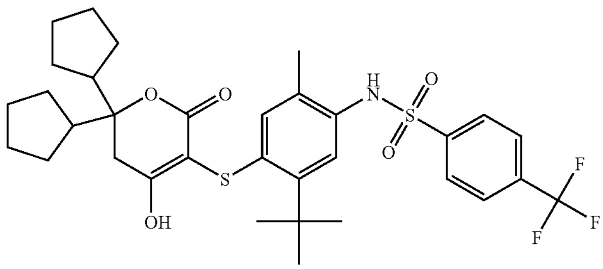 | C |
| 186 | 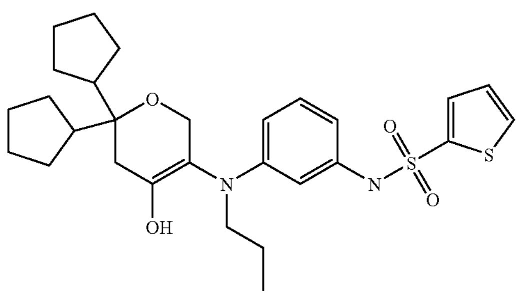 | C |
| 187 | 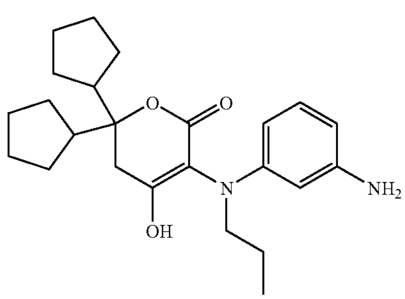 | D |

While the invention has been described in terms of various preferred embodiments and specific Examples, the invention should be understood as not being limited by the foregoing detailed description, but as being defined by the appended claims and their equivalents.

What is claimed is:

1. A method of inhibiting HCV polymerase activity, comprising contacting an HCV polymerase with an effective amount of a compound selected from the group consisting of:

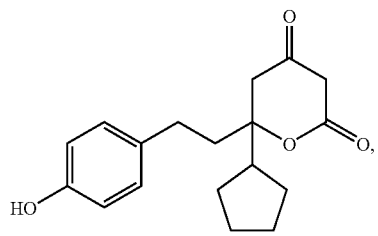

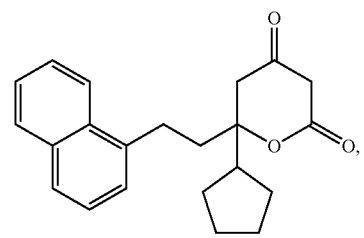

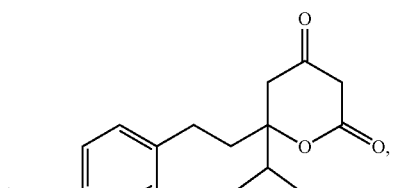

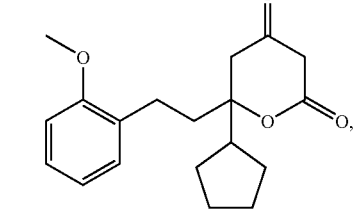

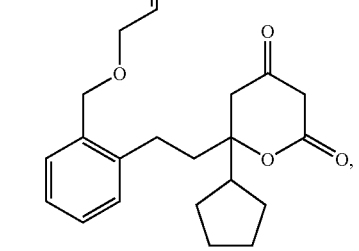

-continued

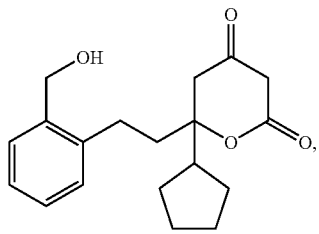

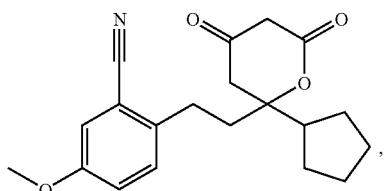

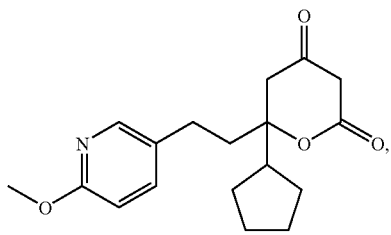

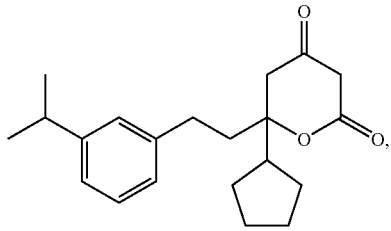

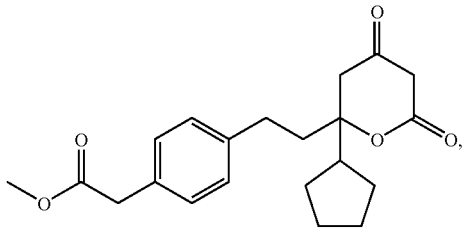

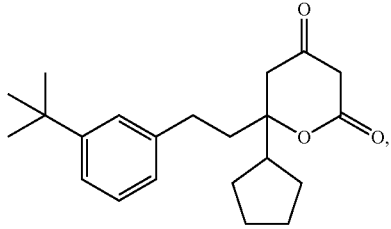

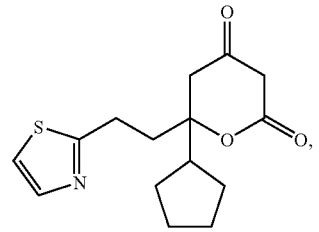

-continued
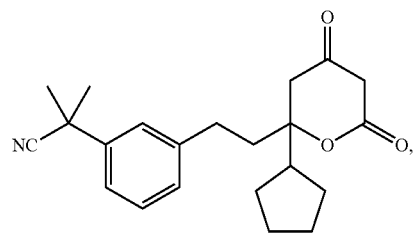
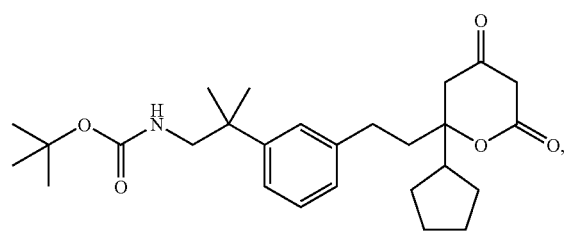
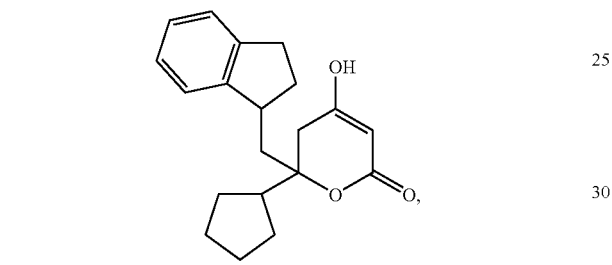
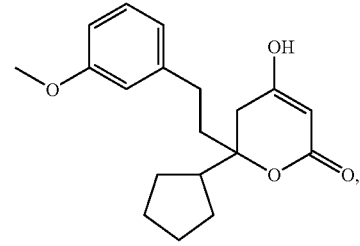
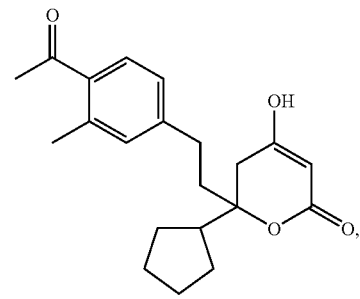
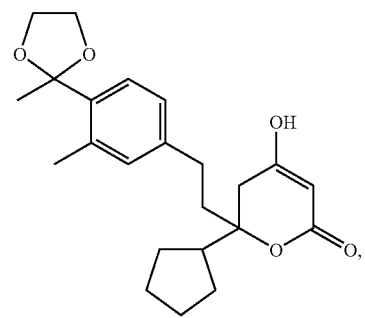
-continued
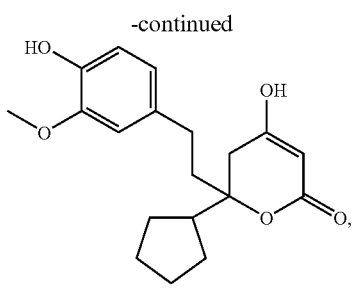
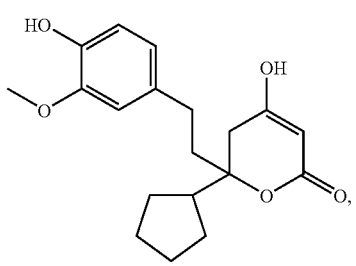
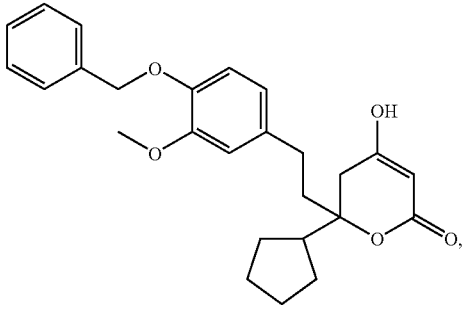
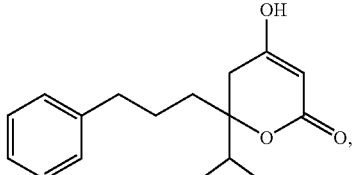
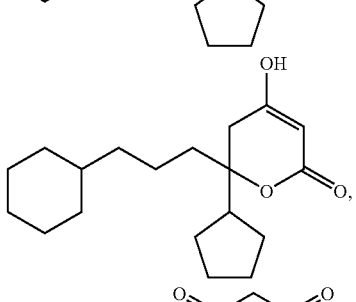
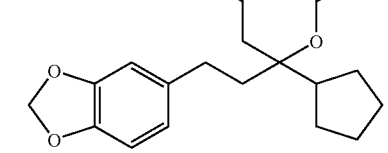
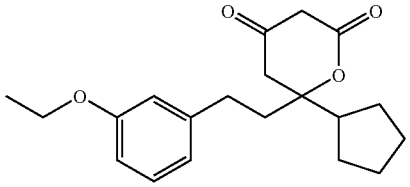

-continued
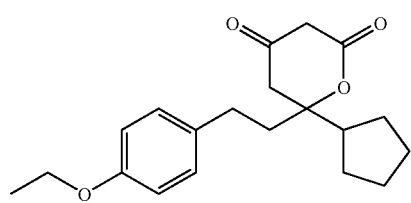
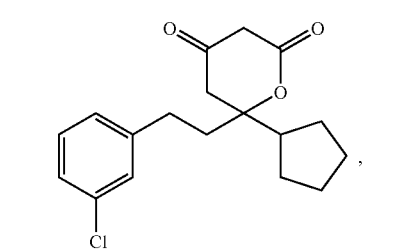
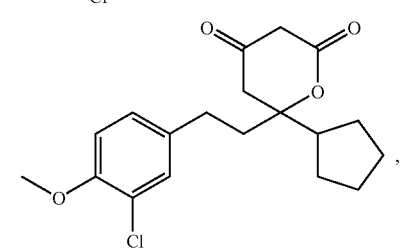
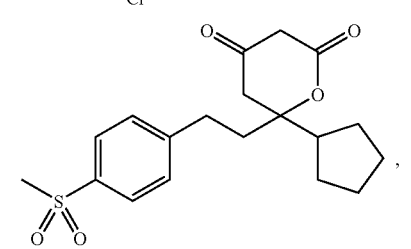
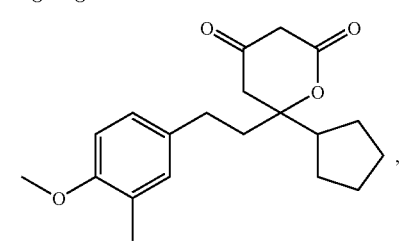
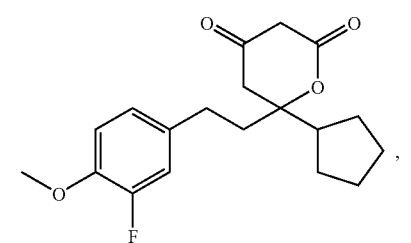
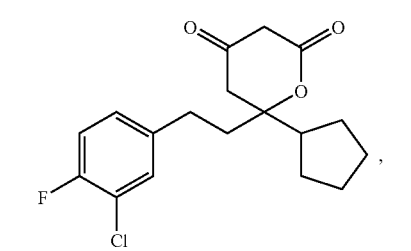
-continued
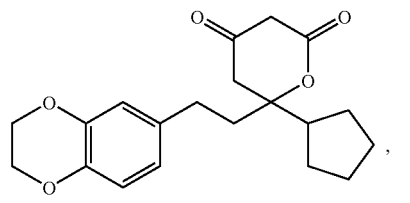,
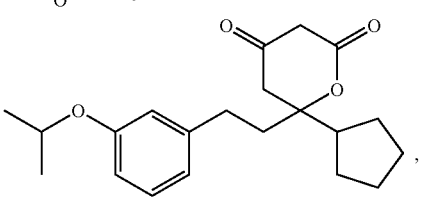,
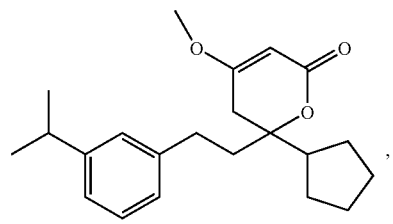,
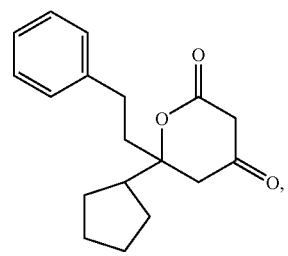,
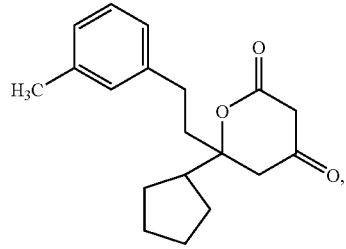,
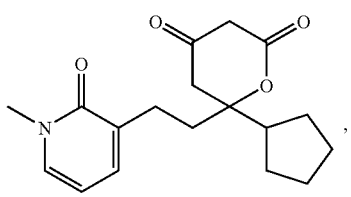,
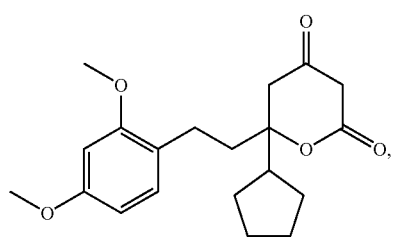, 227
-continued
228
-continued
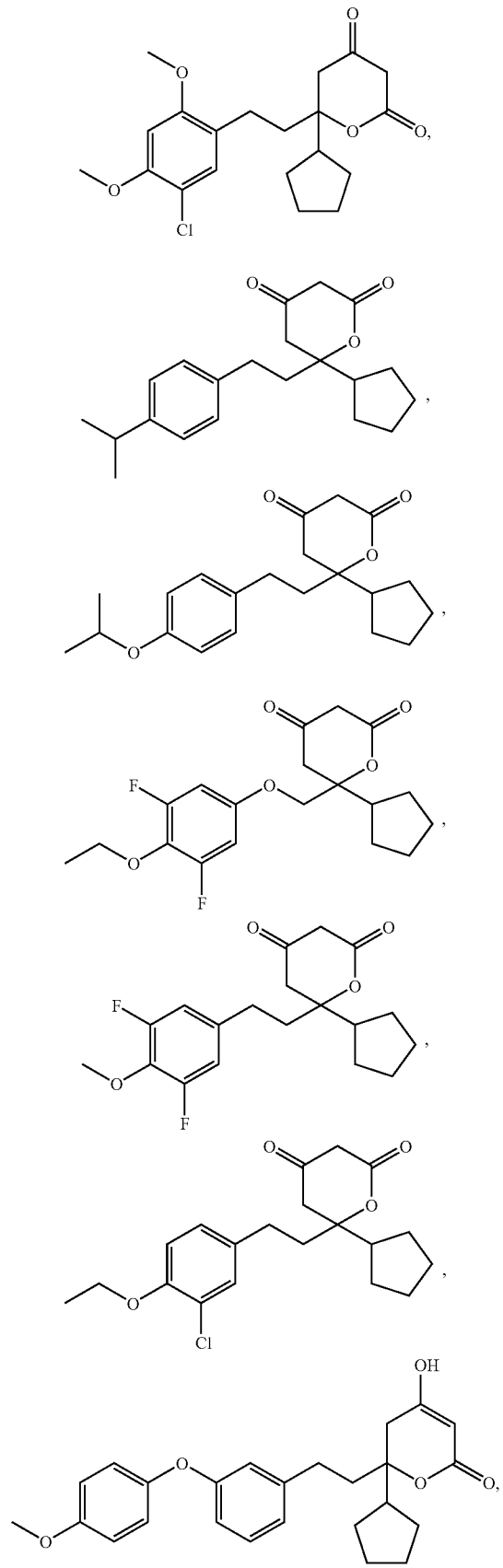
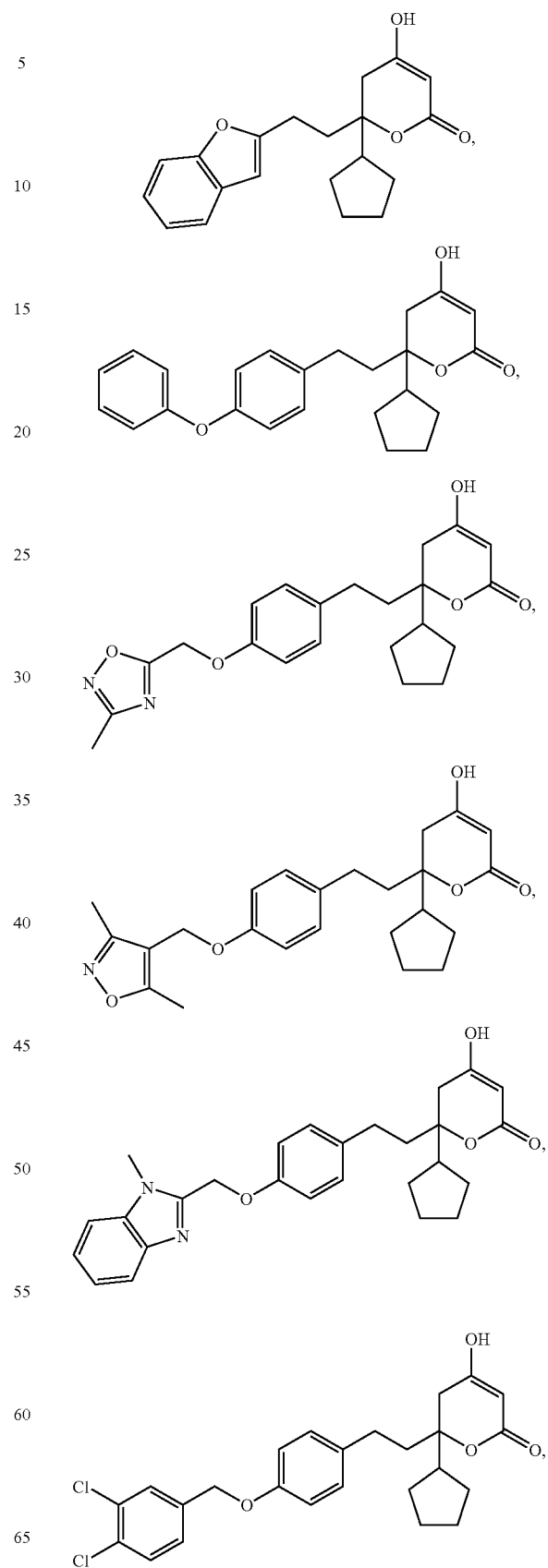

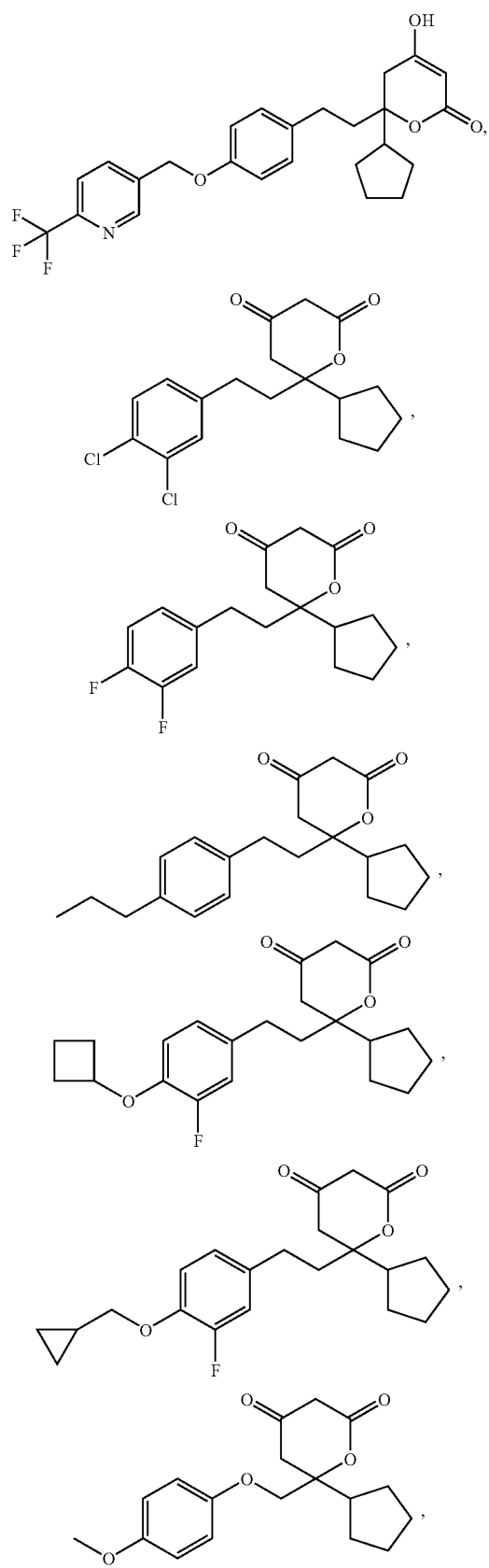
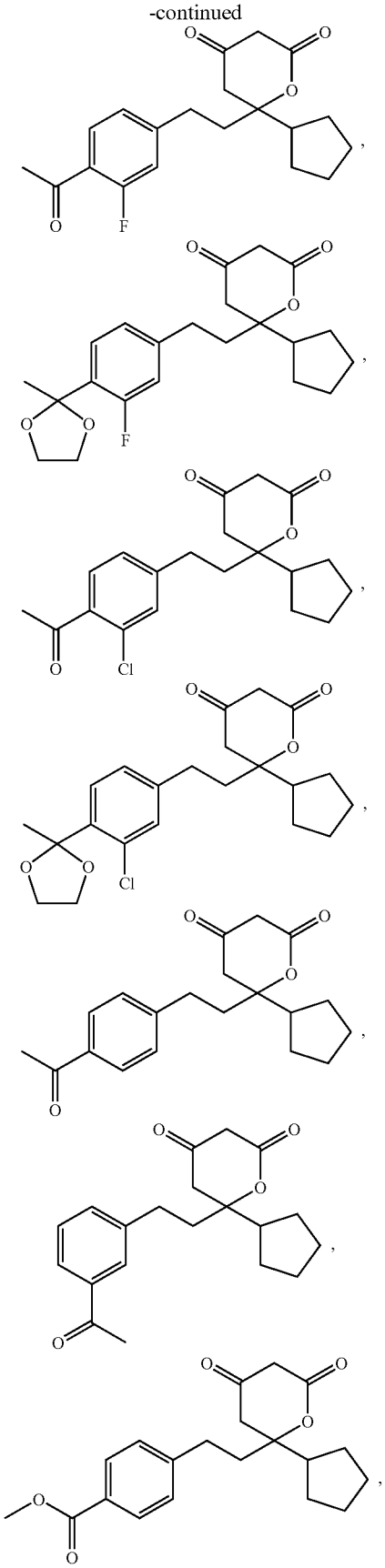

231
-continued
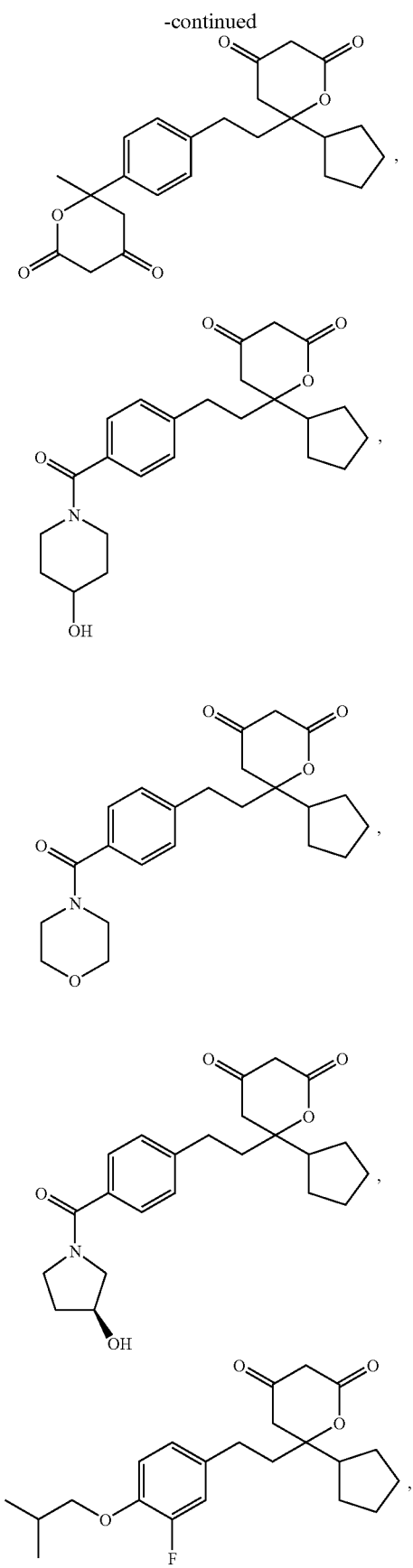
232
-continued
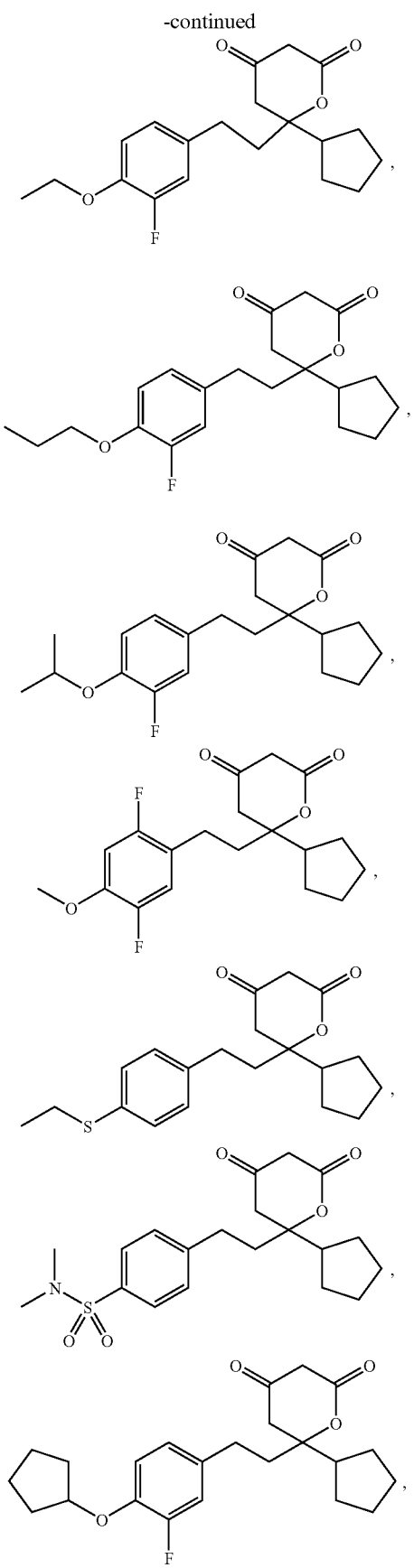

-continued
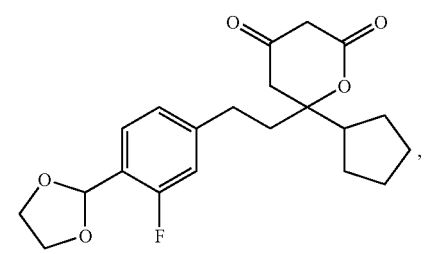
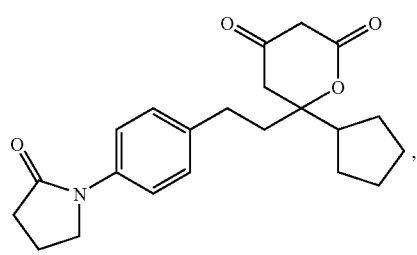
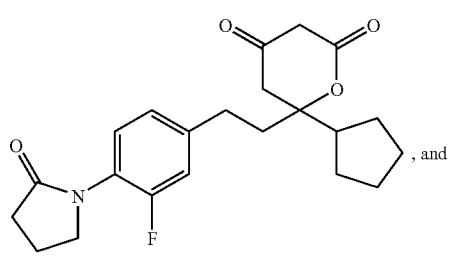, and
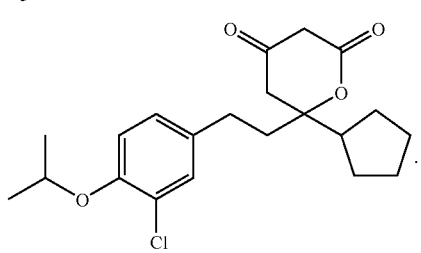.
2. A method of inhibiting HCV polymerase activity, comprising contacting an HCV polymerase with an effective amount of a compound selected from the group consisting of:
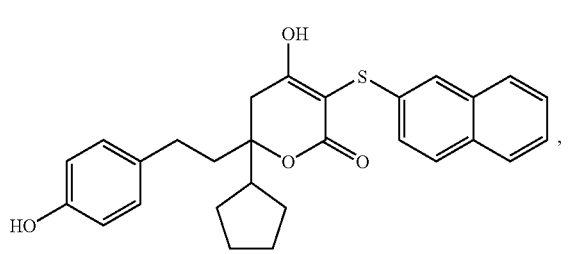,
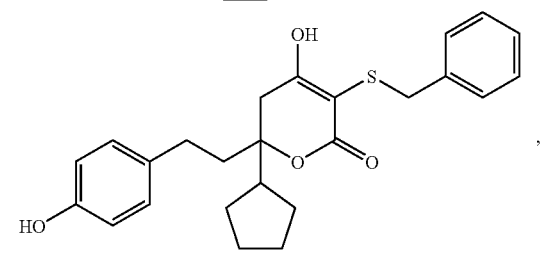,
-continued
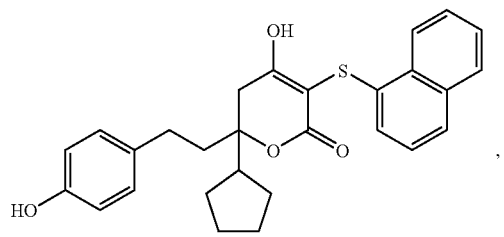,
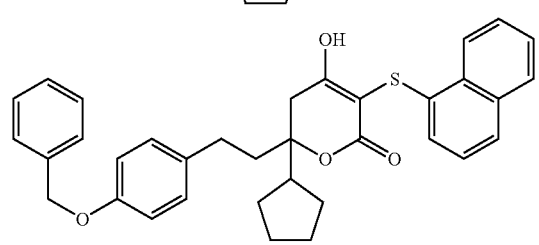,
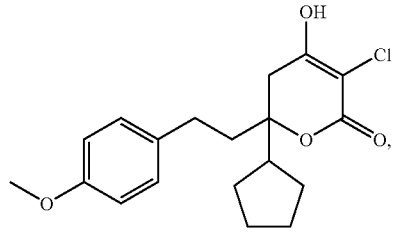,
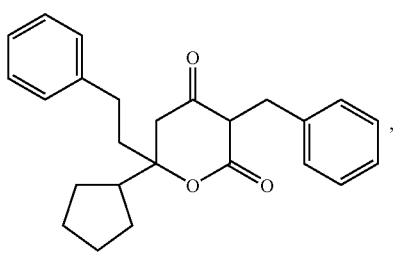,
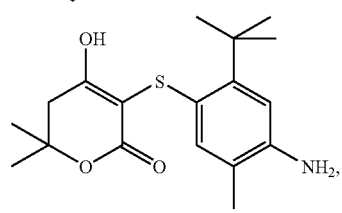,
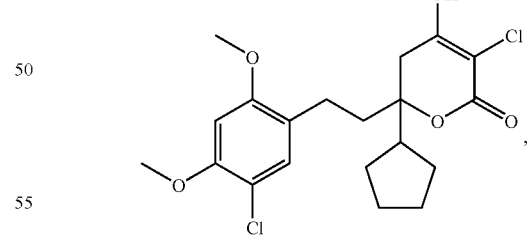,
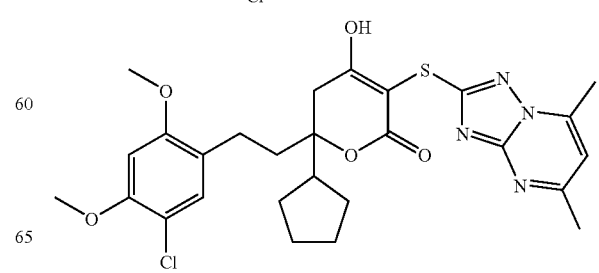, -continued
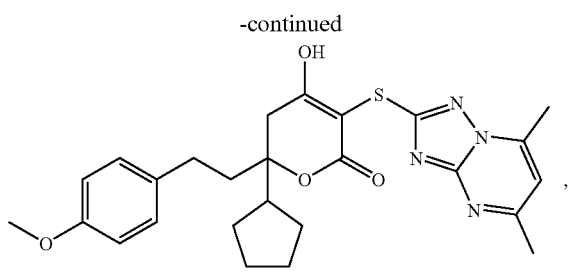
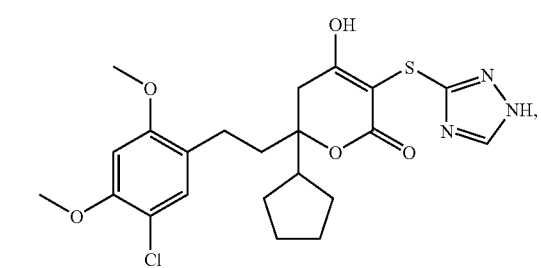
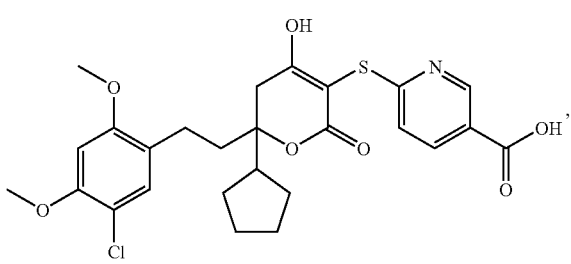
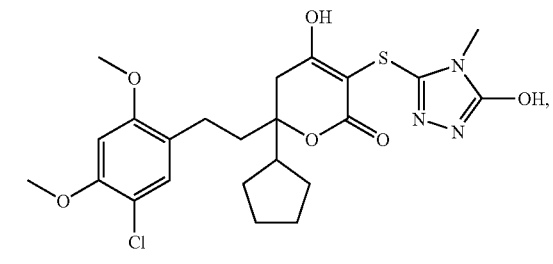
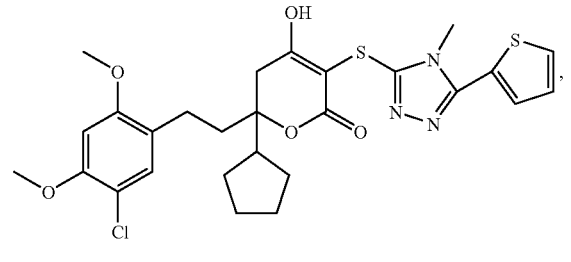
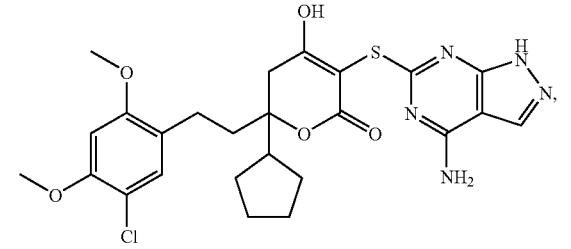
-continued
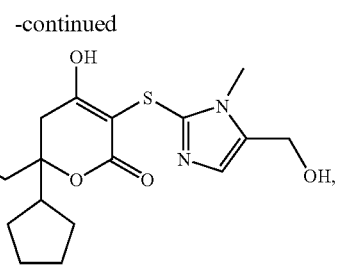
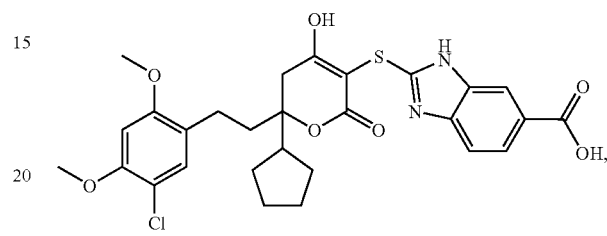
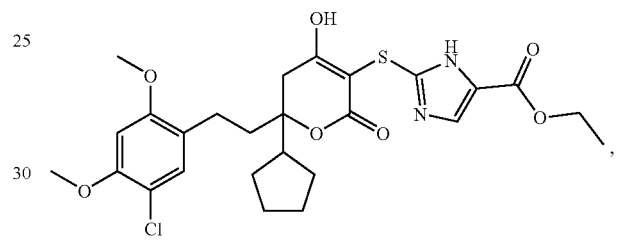
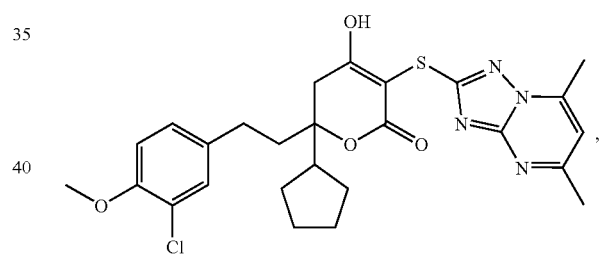
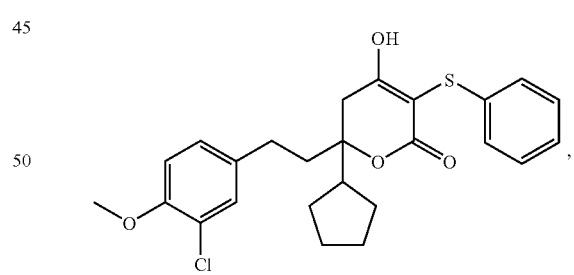
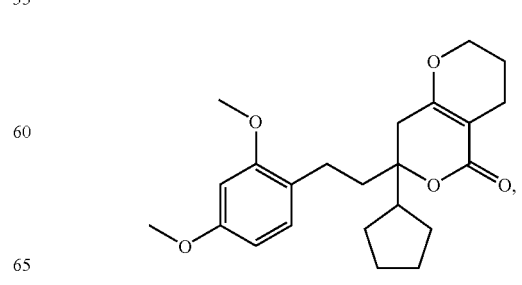

-continued
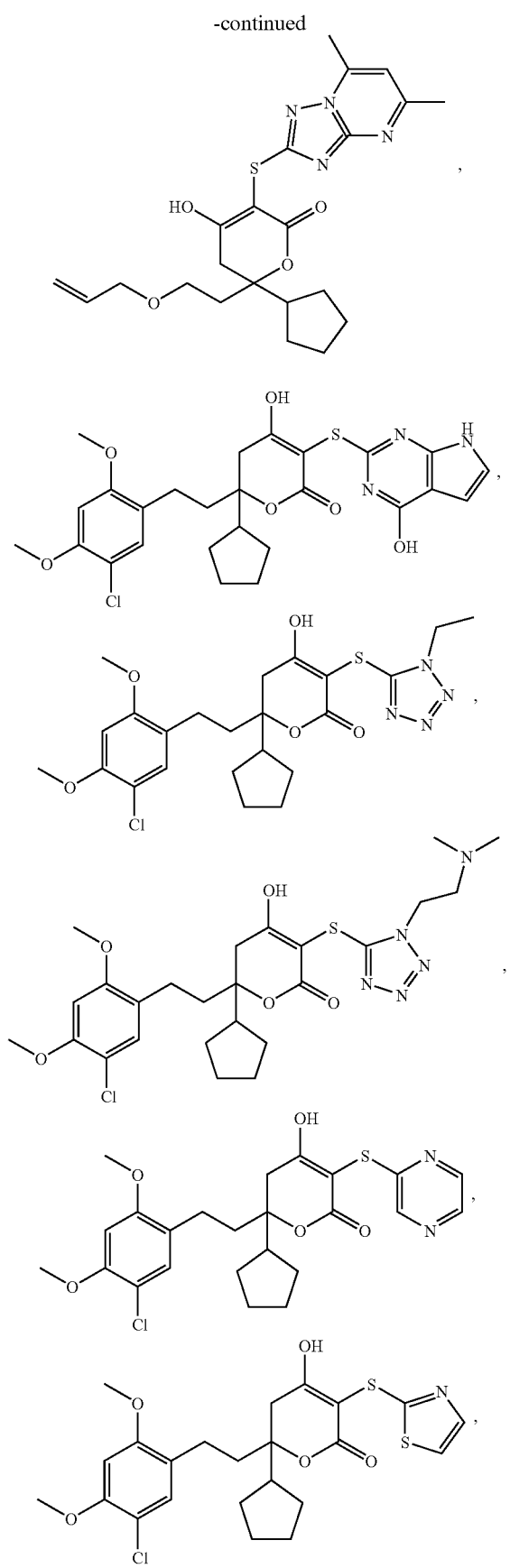
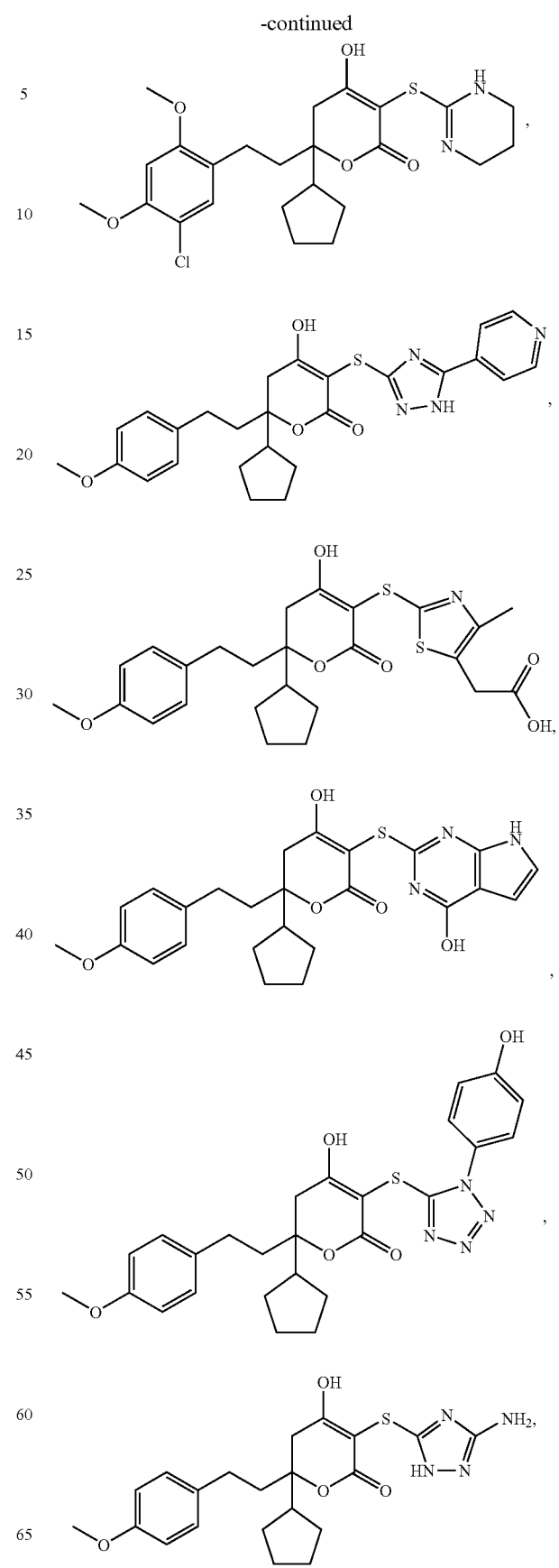

-continued
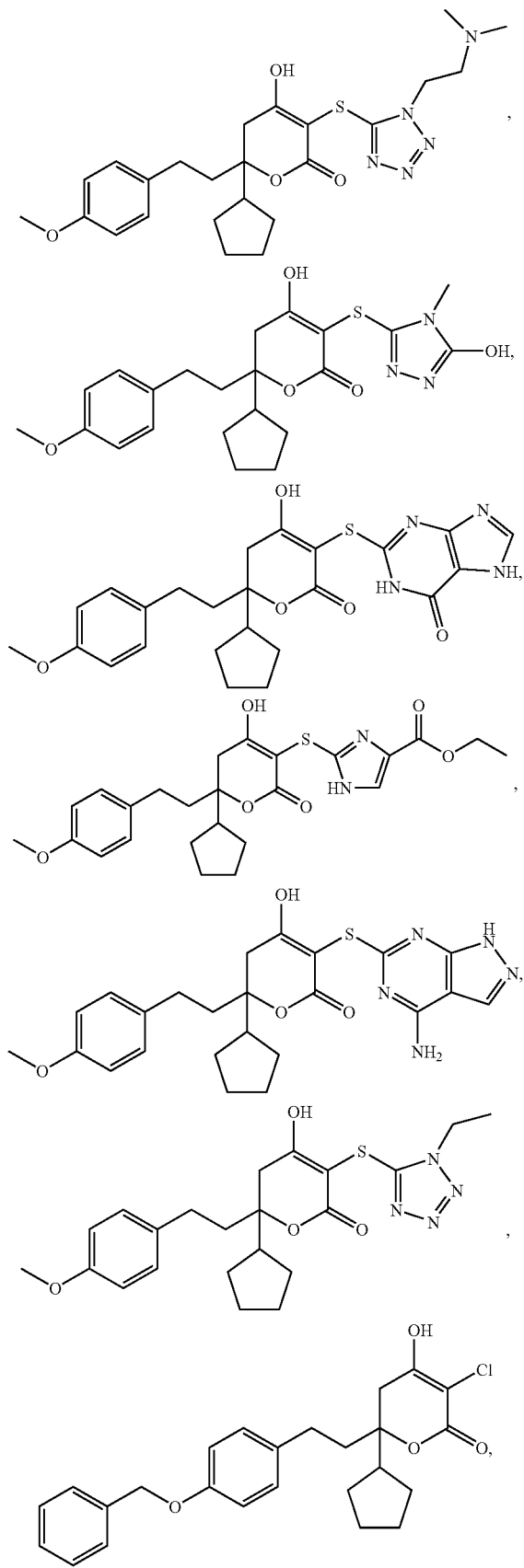
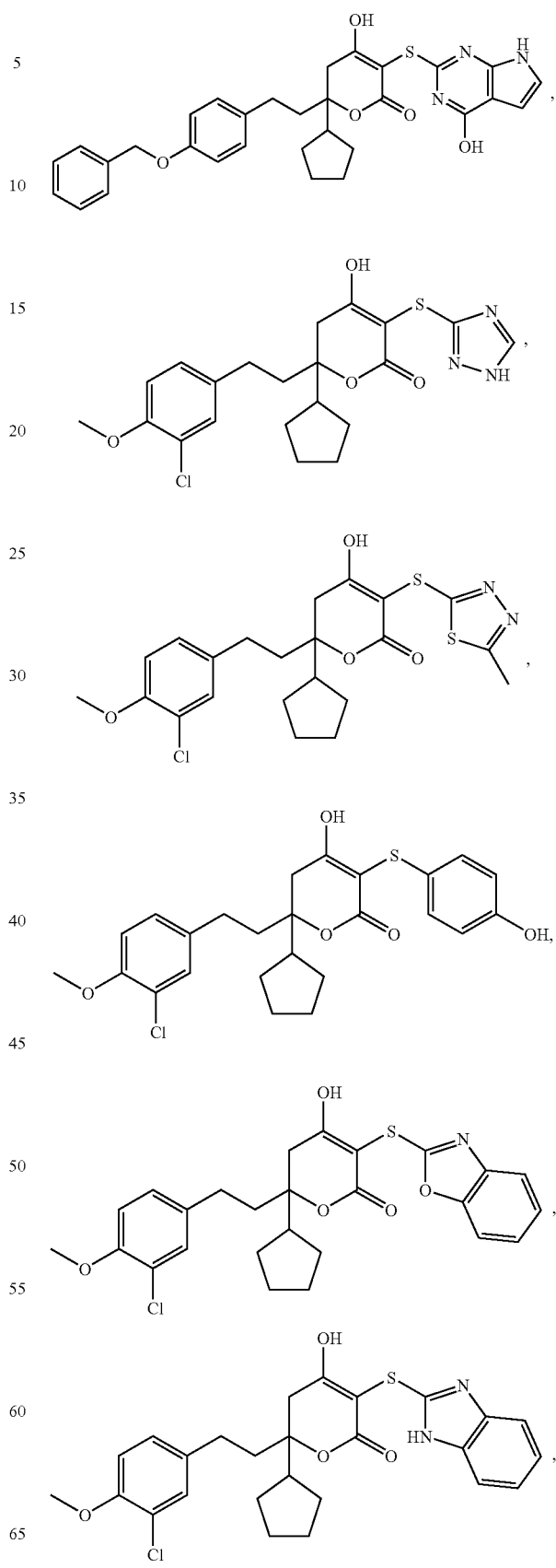

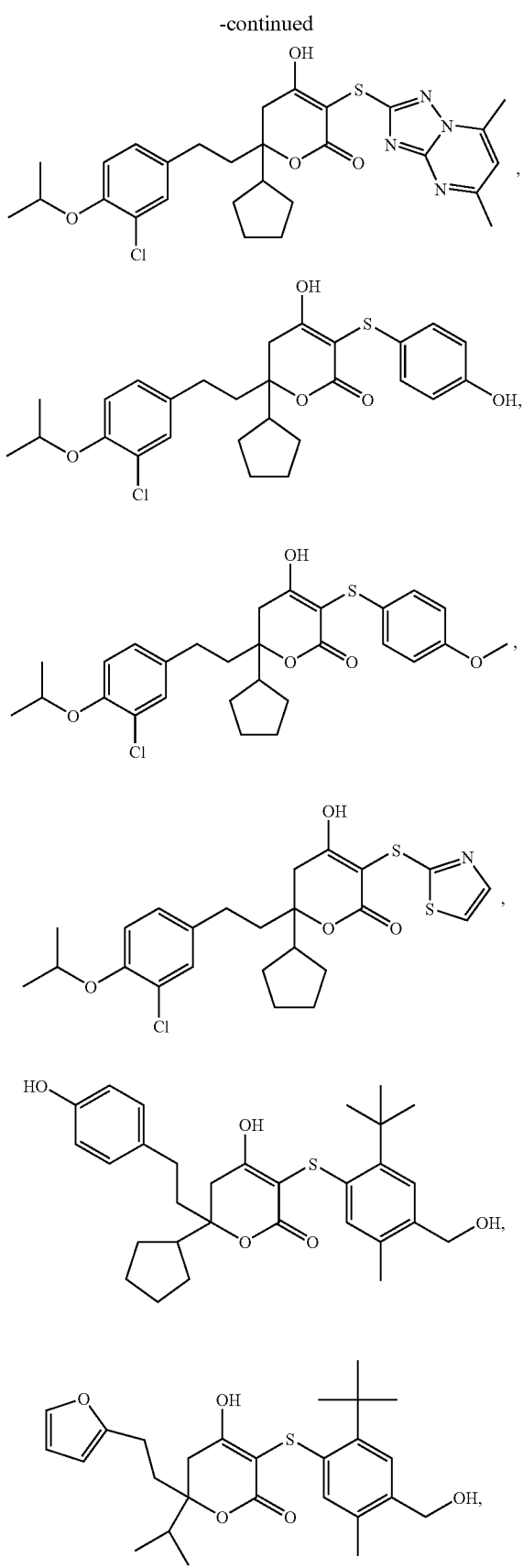
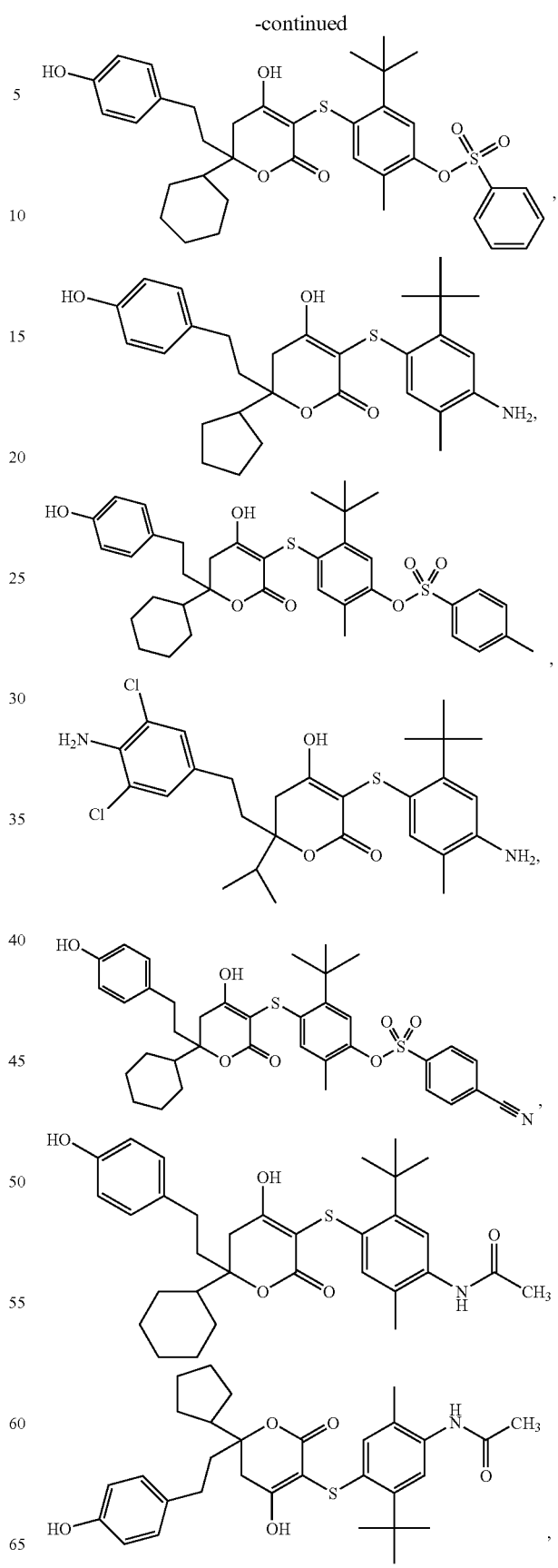

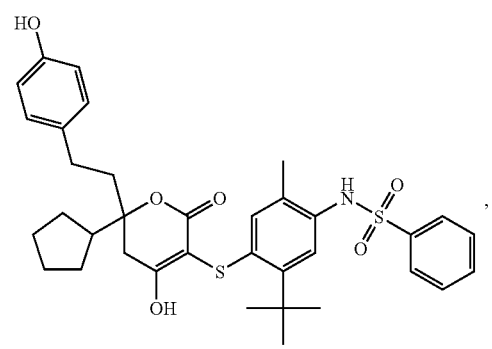
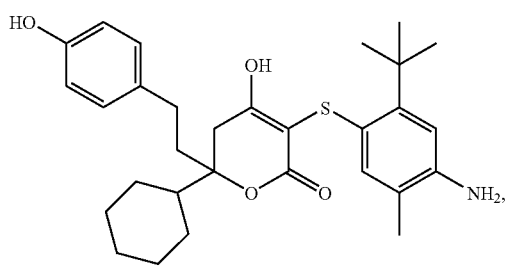
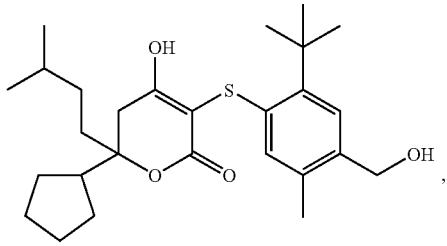
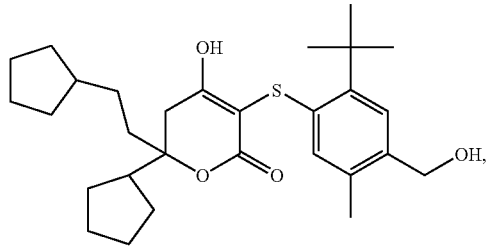
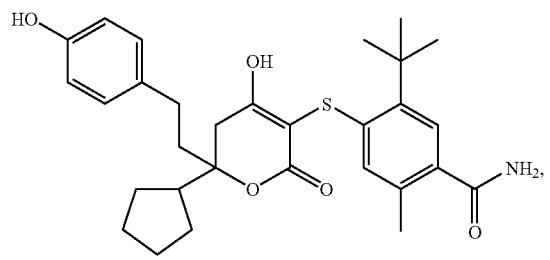
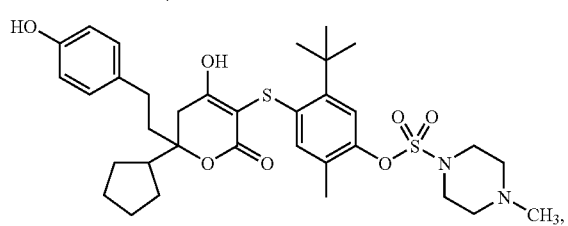
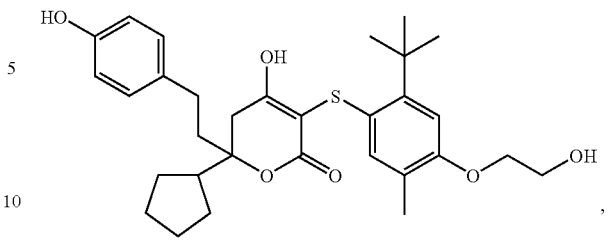
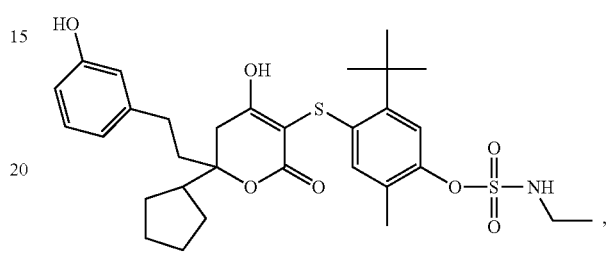
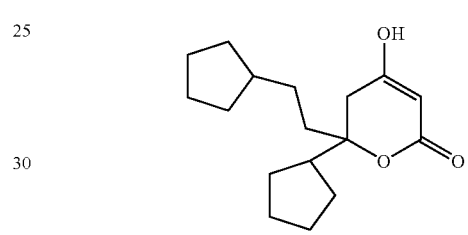
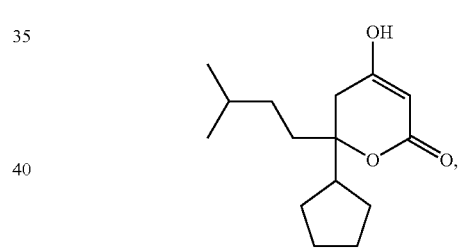
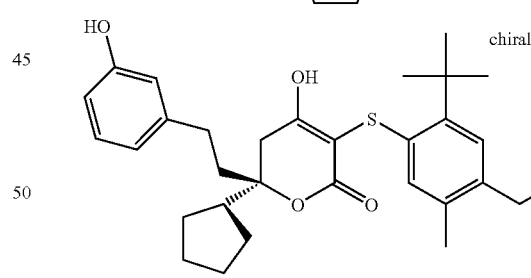
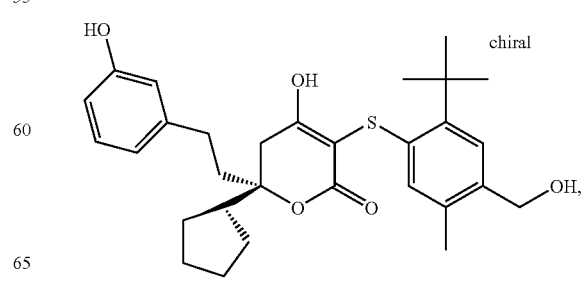

245
-continued
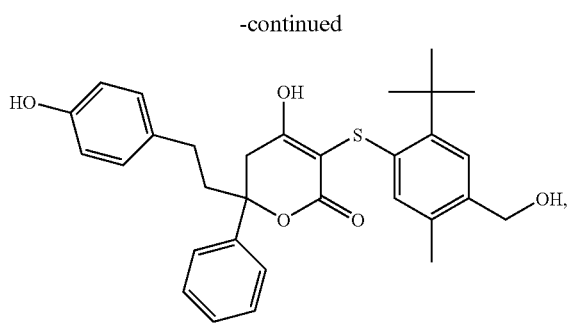
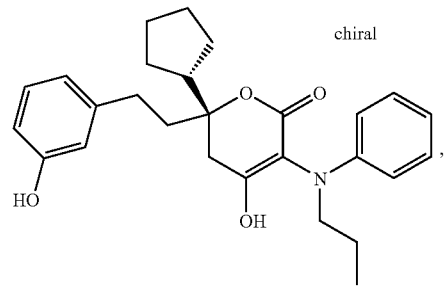
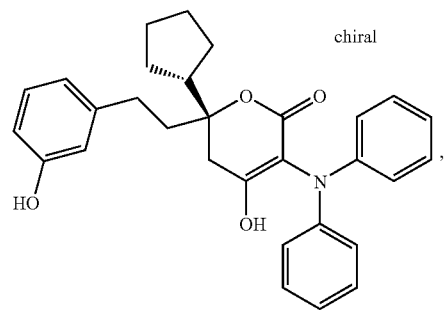
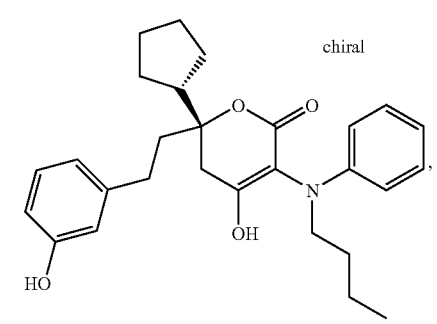
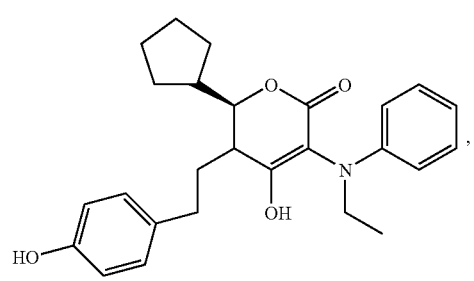
246
-continued
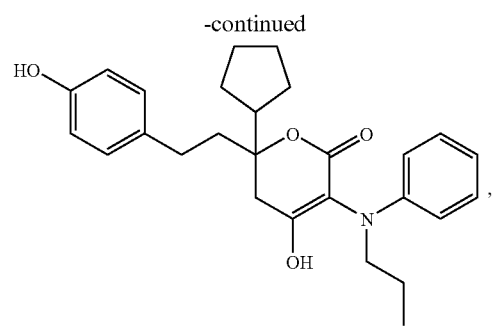
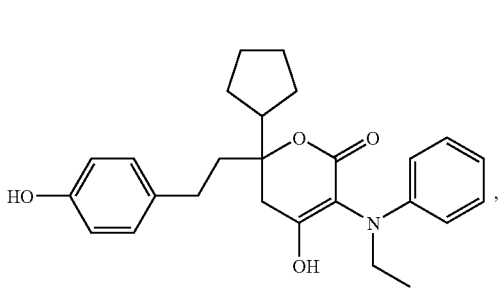
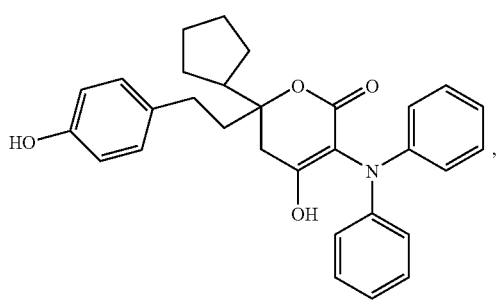
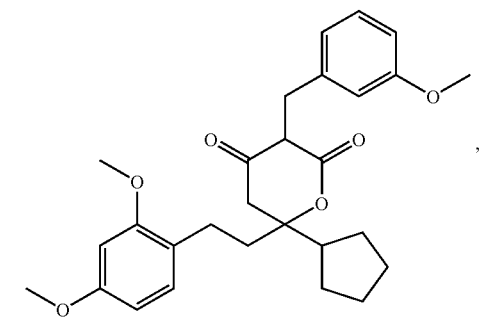
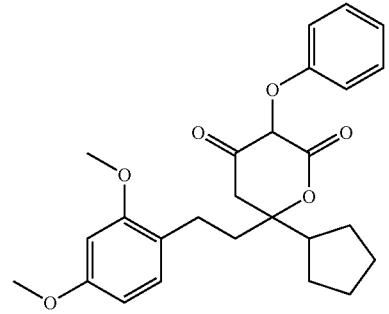

247
-continued
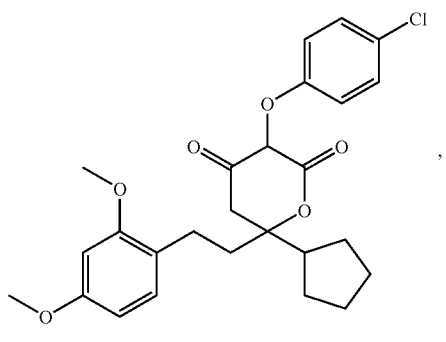
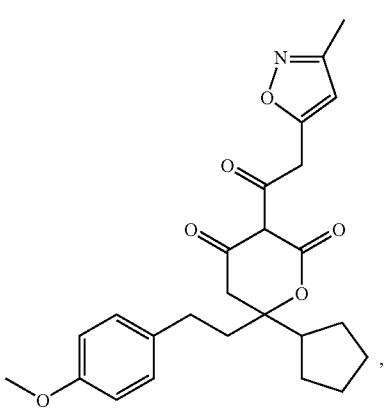
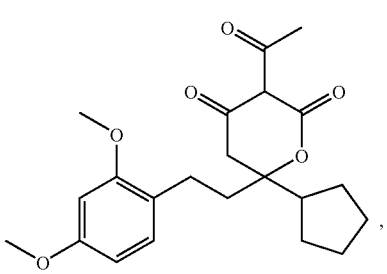
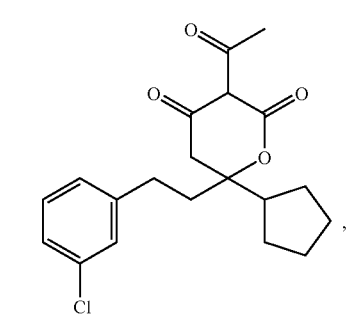
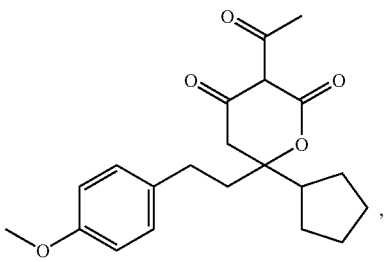
248
-continued
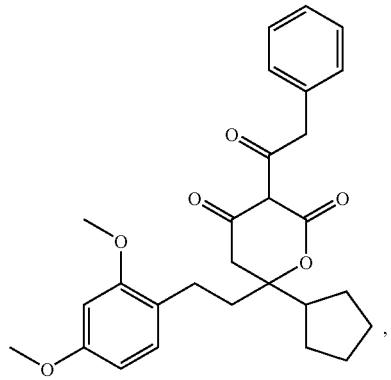
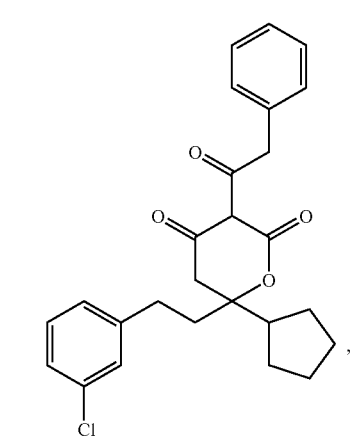
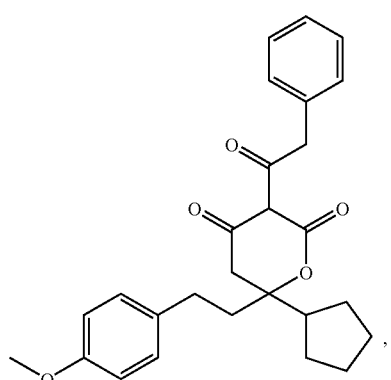
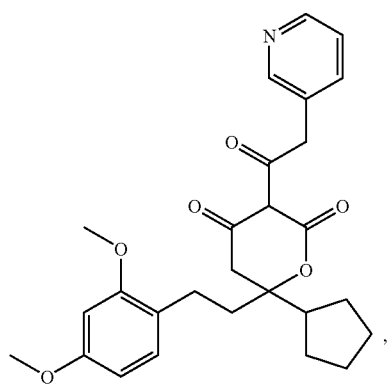

249
-continued
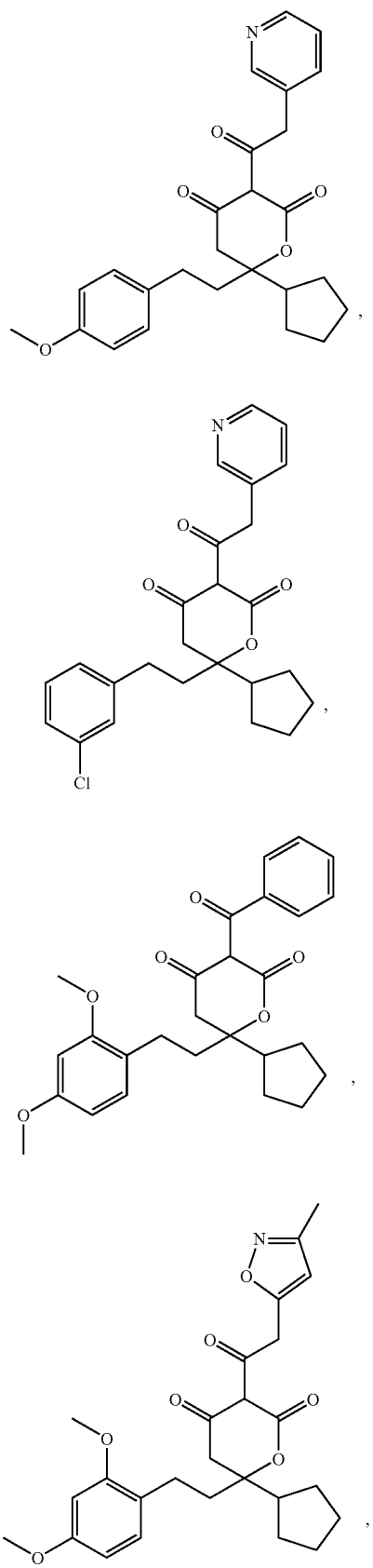
250
-continued
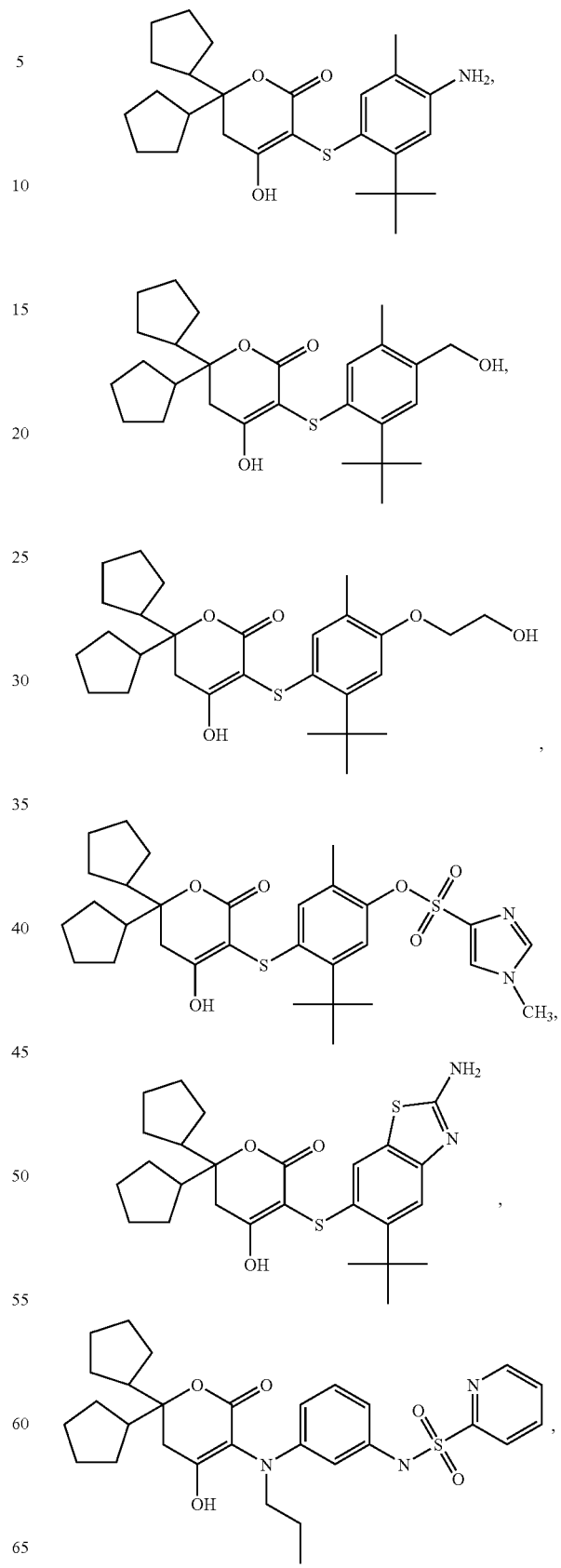

251
-continued
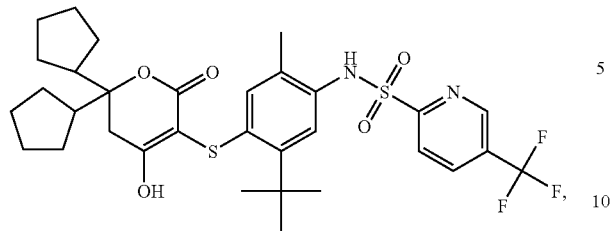
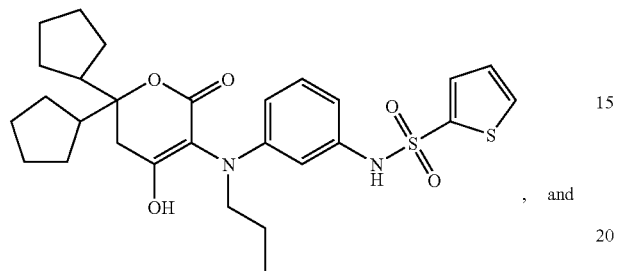
, and
252
-continued
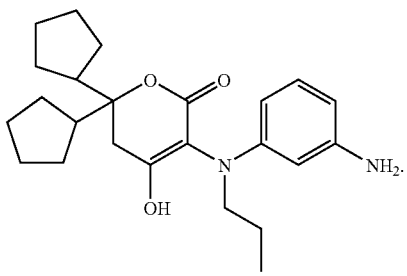
* * * * *